(12) United States Patent
Dietrich et al.

(10) Patent No.: US 10,472,653 B2
(45) Date of Patent: *Nov. 12, 2019

(54) RECOMBINANT HOST CELLS FOR THE PRODUCTION OF MALONATE

(71) Applicant: Lygos, Inc., Berkeley, CA (US)

(72) Inventors: Jeffrey A. Dietrich, Berkeley, CA (US); Jeffrey L. Fortman, Berkeley, CA (US); Eric J. Steen, Berkeley, CA (US)

(73) Assignee: Lygos, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/627,191

(22) Filed: Jun. 19, 2017

(65) Prior Publication Data

US 2017/0362614 A1 Dec. 21, 2017

Related U.S. Application Data

(62) Division of application No. 14/386,272, filed as application No. PCT/US2013/029441 on Mar. 6, 2013, now Pat. No. 9,816,114.

(60) Provisional application No. 61/607,479, filed on Mar. 6, 2012, provisional application No. 61/619,112, filed on Apr. 2, 2012.

(51) Int. Cl.
| | |
|---|---|
| *C12N 9/16* | (2006.01) |
| *C12N 15/00* | (2006.01) |
| *C12N 1/20* | (2006.01) |
| *C07H 21/04* | (2006.01) |
| *C12P 7/46* | (2006.01) |
| *C07C 67/31* | (2006.01) |
| *C07C 67/08* | (2006.01) |
| *C07C 51/38* | (2006.01) |

(52) U.S. Cl.
CPC .............. *C12P 7/46* (2013.01); *C07C 51/38* (2013.01); *C07C 67/08* (2013.01); *C07C 67/31* (2013.01); *C12N 9/16* (2013.01); *C12Y 301/02004* (2013.01)

(58) Field of Classification Search
None
See application file for complete search history.

(56) References Cited

U.S. PATENT DOCUMENTS

2010/0323418 A1 12/2010 Burgard

FOREIGN PATENT DOCUMENTS

EP 0808822 A1 11/1997

OTHER PUBLICATIONS

Supplemental Partial European Search issued by the European Patent Office (The Hague), dated Sep. 17, 2015, for related application EP13758501; 6 pages.
Lee, Sunhee et al., "Improvement of Fatty Acid Biosynthesis by Engineered Recombinant *Escherichia coli*," Biotechnology and Bioprocess Engineering, vol. 16, No. 4, Aug. 2011, pp. 706-713.
Oefner, Christian et al., "Mapping the active site of *Escherichia coli* malonyl-CoA-acyl carrier protein transacylase (FabD) by protein crystallography," Acta Crystallographica Section D, Biological Crystallography, vol. 62, Part 6, Jun. 2006, pp. 613-618.
Lee, Sang-Hyun et al., "Biosynthesis of enantiopure (S)-3-hydroxybutyric acid in metabolically engineered *Escherichia coli*," Applied Microbiology and Biotechnology, vol. 79, No. 4, Jun. 2008, pp. 633-641.
Examination report issued by the Australian Government, IP Australia, dated Oct. 9, 2017, for related Application No. 2013230930; 4 pages.
Rangan, Vangipuram S. et al., "Alteration of the Substrate Specificity of the Malonyl-CoA/Acetyl-CoA:Acyl Carrier Protein S-Acyltransferase Domain of the Multifunctional Fatty Acid Synthase by Mutation of a Single Arginine Residue," The Journal of Biological Chemistry, vol. 272, No. 18, May 2, 1997 issue; pp. 11975-11978.
Rouhier, Matthew F., Dissertation "Characterization of YDR036C From *Saccharomyces cerevisiae*," Miami University; 68 pages.
Han, Seong Jun et al., "Ab initio MO study on model compounds of malonyl-CoA: malonic acid and malonyl methyl sulfide", Journal of Molecular Structure (THEOCHEM), Sep. 30, 1996, vol. 369. Issues 1-3, pp. 145-156.
Kim, Yu Sam, "Malonate Metabolism: Biochemistry, Molecular Biology, Physiology, and Industrial Application", Journal of Biochemistry and Molecular Biology, Sep. 2002, vol. 35, No. 5, pp. 443-451.
Riley, Kathy M. et al., "The Origin of Free Brain Malonate", Neurochemical Research, 1991, vol. 16, No. 2, pp. 117-122.
Koo, Jae Hyung et al., "The Malonate Decarboxylase Operon of *Acinetobacter calcoaceticus* KCCM 40902 is Regulated by Malonate and the Transcriptional Repressor MdcY", Journal of Bacteriology, Nov. 2000, vol. 182, No. 22, pp. 6382-6390.
Stumpf, David K. et al., "Biosynthesis of Malonate in Roots of Soybean Seedlings", Plant Physiology, 1981, vol. 68, No. 5, pp. 992-995.
International Search Report and Written Opinion issued by the Korean Intellectual Property Office, dated Jul. 25, 2013, for International Application No. PCT/US2013/029441; 14 pages.
International Preliminary Report on Patentability issued by the International Bureau of WIPO, dated Sep. 9, 2014, for International Application No. PCT/US2013/029441; 10 pages.
Claxton, Heather B., et al., "Structure and Functional Analysis of RifR, the Type II Thioesterase from the Rifamycin Biosynthetic Pathway", Journal of Biological Chemistry, Feb. 20, 2009, 284(8); 5021-5029.

(Continued)

*Primary Examiner* — Yong D Pak
(74) *Attorney, Agent, or Firm* — Faegre Baker Daniels LLP

(57) ABSTRACT

Systems and methods for the production of malonate in recombinant host cells.

5 Claims, 2 Drawing Sheets

Specification includes a Sequence Listing.

(56) References Cited

OTHER PUBLICATIONS

Hunt, Mary C., et al., "Characterization of an Acyl-CoA Thioesterase That Functions as a Major Regulator of Peroxisomal Lipid Metabolism," Journal of Biological Chemistry, Jan. 11, 2002, 277(2); 45 pages.
Cao, Jian, et al., "The Mechanisms of Human Hotdog-fold Thioesterase 2 (hTHEM2) Substrate Recognition and Catalysis Illuminated by a Structure and Function Based Analysis," Biochemistry, Feb. 17, 2009, 48(6);1293-1304.
Zhuang, Zhihao, et al., "Divergence of Function in the Hot Dog Fold Enzyme Superfamily: The Bacterial Thioesterase YciA," Biochemistry, Mar. 4, 2008, 47(9), 2789-2796.
Examination Report issued by the Australian Government IP Australia, dated Jul. 2, 2018, for related Application No. 2013230930; 5 pages.

```
SEQUENCE LISTING

<160> NUMBER OF SEQ ID NOS: 53

<210> SEQ ID NO 1
<211> LENGTH: 500
<212> TYPE: PRT
<213> ORGANISM: Saccharomyces cerevisiae

<400> SEQUENCE: 1

Met Leu Arg Asn Thr Leu Lys Cys Ala Gln Leu Ser Ser Lys Tyr Gly
1               5                   10                  15

Phe Lys Thr Thr Thr Arg Thr Phe Met Thr Thr Gln Pro Gln Leu Asn
            20                  25                  30

Val Thr Asp Ala Pro Pro Val Leu Phe Thr Val Gln Asp Thr Ala Arg
        35                  40                  45

Val Ile Thr Leu Asn Arg Pro Lys Lys Leu Asn Ala Leu Asn Ala Glu
    50                  55                  60

Met Ser Glu Ser Met Phe Lys Thr Leu Asn Glu Tyr Ala Lys Ser Asp
65                  70                  75                  80

Thr Thr Asn Leu Val Ile Leu Lys Ser Ser Asn Arg Pro Arg Ser Phe
                85                  90                  95

Cys Ala Gly Gly Asp Val Ala Thr Val Ala Ile Phe Asn Phe Asn Lys
            100                 105                 110

Glu Phe Ala Lys Ser Ile Lys Phe Phe Thr Asp Glu Tyr Ser Leu Asn
        115                 120                 125

Phe Gln Ile Ala Thr Tyr Leu Lys Pro Ile Val Thr Phe Met Asp Gly
    130                 135                 140

Ile Thr Met Gly Gly Gly Val Gly Leu Ser Ile His Thr Pro Phe Arg
145                 150                 155                 160

Ile Ala Thr Glu Asn Thr Lys Trp Ala Met Pro Glu Met Asp Ile Gly
                165                 170                 175

Phe Phe Pro Asp Val Gly Ser Thr Phe Ala Leu Pro Arg Ile Val Thr
            180                 185                 190

Leu Ala Asn Ser Asn Ser Gln Met Ala Leu Tyr Leu Cys Leu Thr Gly
        195                 200                 205

Glu Val Val Thr Gly Ala Asp Ala Tyr Met Leu Gly Leu Ala Ser His
    210                 215                 220

Tyr Val Ser Ser Glu Asn Leu Asp Ala Leu Gln Lys Arg Leu Gly Glu
225                 230                 235                 240

Ile Ser Pro Pro Phe Asn Asn Asp Pro Gln Ser Ala Tyr Phe Phe Gly
                245                 250                 255

Met Val Asn Glu Ser Ile Asp Glu Phe Val Ser Pro Leu Pro Lys Asp
            260                 265                 270

Tyr Val Phe Lys Tyr Ser Asn Glu Lys Leu Asn Val Ile Glu Ala Cys
        275                 280                 285

Phe Asn Leu Ser Lys Asn Gly Thr Ile Glu Asp Ile Met Asn Asn Leu
    290                 295                 300
```

| Arg | Gln | Tyr | Glu | Gly | Ser | Ala | Glu | Gly | Lys | Ala | Phe | Ala | Gln | Glu | Ile |
|---|---|---|---|---|---|---|---|---|---|---|---|---|---|---|---|
| 305 | | | | 310 | | | | 315 | | | | | | | 320 |

Lys Thr Lys Leu Leu Thr Lys Ser Pro Ser Ser Leu Gln Ile Ala Leu
325 330 335

Arg Leu Val Gln Glu Asn Ser Arg Asp His Ile Glu Ser Ala Ile Lys
340 345 350

Arg Asp Leu Tyr Thr Ala Ala Asn Met Cys Met Asn Gln Asp Ser Leu
355 360 365

Val Glu Phe Ser Glu Ala Thr Lys His Lys Leu Ile Asp Lys Gln Arg
370 375 380

Val Pro Tyr Pro Trp Thr Lys Lys Glu Gln Leu Phe Val Ser Gln Leu
385 390 395 400

Thr Ser Ile Thr Ser Pro Lys Pro Ser Leu Pro Met Ser Leu Leu Arg
405 410 415

Asn Thr Ser Asn Val Thr Trp Thr Gln Tyr Pro Tyr His Ser Lys Tyr
420 425 430

Gln Leu Pro Thr Glu Gln Glu Ile Ala Ala Tyr Ile Glu Lys Arg Thr
435 440 445

Asn Asp Asp Thr Gly Ala Lys Val Thr Glu Arg Glu Val Leu Asn His
450 455 460

Phe Ala Asn Val Ile Pro Ser Arg Arg Gly Lys Leu Gly Ile Gln Ser
465 470 475 480

Leu Cys Lys Ile Val Cys Glu Arg Lys Cys Glu Glu Val Asn Asp Gly
485 490 495

Leu Arg Trp Lys
500

<210> SEQ ID NO 2
<211> LENGTH: 1000
<212> TYPE: DNA
<213> ORGANISM: Haemophilus influenzae

<400> SEQUENCE: 2

```
atgttttaca ctgaaactta tgatgtgatt gtgatcggtg gtggtcatgc gggtacagaa      60
gccgcacttg caccagctcg tatgggattt aaaacccttt tattaacaca taatgtagat     120
actttagggc aaatgtcttg taaccctgca attggtggga tcggtaaagg tcatttagta     180
aaagaagtag atgcaatggg cggtttaatg gcgcatgctg cagataaagc agggatccaa     240
tttcgtactt taaatagcag taaaggccca gcagtgcgtg ctactcgagc tcaagctgac     300
agagttctat atcgtcaagc tgttcgtact gcattagaaa atcaacctaa tttagatatt     360
ttccaacaag aagcgaccga tattctgatt aagcaagatc gagttacagg cgttagcaca     420
aaaatgggat taacttttcg tgctaaatca gtggtattaa ctgcgggtac tttcttagct     480
ggtaaaattc atattggttt ggaaaattat gaaggtggcc gtgcagggga tcctgcttct     540
gtaaatcttt cacatcgatt aagagatctc ggattacgtg tagatcgcct taaaacaggt     600
acaccgccgc gtattgatgc acgtacgatc aatttttgata ttttagctaa caacacggt     660
gatgctgttt acctgtgtt ttcttttatg ggatcagttg atgatcaccc tcaacaaatt     720
ccttgttata taactcatac caatgaacaa acccatgaag tgatccgtaa taacttggat     780
cgcagtccaa tgtatactgg tgtgattgaa gggatcggtc cacgttattg cccatccatt     840
gaagataaag tgatgcgttt ctcggatcgt aattcacatc aaatttattt agaaccagaa     900
ggcttaacca gtaatgaagt gtatccaaac gggatctcta ccagtttacc gtttgacgtg     960
```
caaatgggca ttgtgaattc tatgaaaggt ttagaaaacg        1000

<210> SEQ ID NO 3
<211> LENGTH: 224
<212> TYPE: PRT
<213> ORGANISM: Acinetobacter calcoaceticus

<400> SEQUENCE: 3

```
Met Asn Ser Ile Ala Glu Leu Pro Leu Ser Ile Gln Ile Ser Lys Lys
1               5                   10                  15

Leu Glu Asp Asp Ile Ile Tyr Gly Phe Tyr Leu Pro Gly Thr Lys Leu
                20                  25                  30

Asp Glu Gln Glu Leu Cys Glu Arg Tyr Gly Ala Ser Arg Thr Pro Ile
            35                  40                  45

Arg Glu Ala Leu Lys Leu Leu Ala Ala Glu Gly Leu Val Glu Ile Arg
        50                  55                  60

Pro Arg Arg Gly Ala Ile Ile Pro Thr Ile Asn Pro Leu Thr Leu Cys
65                  70                  75                  80

Glu Met Phe Glu Val Met Ala Glu Leu Glu Ala Met Cys Gly Arg Leu
                85                  90                  95

Ala Ala Arg Arg Ile Gln Pro Glu Glu Lys Leu Glu Leu Gln Arg Leu
            100                 105                 110

His Gln Leu Cys Gln Asp Tyr Leu Asn Gln Asn Asp Ser Glu Asn Tyr
        115                 120                 125

Tyr Glu Ala Asn Arg Leu Phe His Phe Ala Ile Tyr Gln Ala Ser His
    130                 135                 140

Asn Ala Phe Leu Ile Glu Gln Ala Cys Thr Leu His Lys Arg Leu His
145                 150                 155                 160

Pro Tyr Arg Arg Leu Gln Leu Arg Val Asn Asn Arg Met Asn Asn Ser
                165                 170                 175

Phe Thr Glu His Asn Glu Ile Leu Glu Ala Ile Phe Ala Gly Asn Glu
            180                 185                 190

Gln Gln Ala Glu Ala Leu Leu Lys Ala His Val Val Ile Gln Gly Gln
        195                 200                 205

Lys Phe Thr Asp Phe Ile Ser Thr Ile Glu Ser Leu Gln Pro Lys Ser
    210                 215                 220
```

<210> SEQ ID NO 4
<211> LENGTH: 222
<212> TYPE: PRT
<213> ORGANISM: Rhizobium leguminosarum

<400> SEQUENCE: 4

```
Met Arg Lys Val Lys Arg Met Ser Glu Asn Val Gly Arg Trp Leu Arg
1               5                   10                  15

Asp Glu Ile Glu Asn Ser Ile Leu Ser Asn Glu Phe Ser Pro Gly Glu
                20                  25                  30

Arg Leu Asp Glu Thr Val Leu Ala Thr Arg Phe Gly Val Ser Arg Thr
            35                  40                  45

Pro Val Arg Glu Ala Leu Met Gln Leu Asp Ala Ile Gly Leu Ile Glu
        50                  55                  60

Ile Arg Pro Arg Arg Gly Ala Ile Val Ile Asp Pro Gly Pro His Arg
65                  70                  75                  80

Val Tyr Glu Met Phe Glu Val Met Ala Glu Leu Glu Gly Leu Ala Gly
                85                  90                  95

Ser Leu Ala Ala Arg Arg Leu Asp Lys Thr Ser Arg Glu Ala Ile Thr
```

```
            100                 105                 110
Ala Thr His Gly Arg Cys Glu Lys Ser Ala Ala Gly Asp Ser Asp
        115                 120                 125
Ala Tyr Tyr Asp Asn Glu Glu Phe His Lys Ala Ile Tyr Ala Ala
        130                 135                 140
Gly Arg Ser Asp Phe Leu Glu Glu Gln Cys Leu Gln Leu His Arg Arg
145                 150                 155                 160
Leu Arg Pro Asp Arg Arg Leu Gln Leu Arg Val Arg Asn Arg Leu Ser
                165                 170                 175
Thr Ser Phe Leu Glu His Cys Ala Ile Val Asp Ala Ile Phe Ala Gly
            180                 185                 190
Asp Gly Asp Glu Ala Arg Arg Leu Leu Arg Gly His Val Gly Ile Gln
        195                 200                 205
Gly Glu Arg Phe Ser Asp Leu Val Ala Ser Met Ala Ala Arg
    210                 215                 220

<210> SEQ ID NO 5
<211> LENGTH: 308
<212> TYPE: PRT
<213> ORGANISM: Klebsiella pneumoniae

<400> SEQUENCE: 5

Met Lys Asp Asp Ile Asn Gln Glu Ile Thr Phe Arg Lys Leu Ser Val
1               5                   10                  15
Phe Met Met Phe Met Ala Lys Gly Asn Ile Ala Arg Thr Ala Glu Ala
                20                  25                  30
Met Lys Leu Ser Ser Val Ser His Arg Ala Leu His Thr Leu Glu
        35                  40                  45
Glu Gly Val Gly Cys Pro Leu Phe Val His Lys Gly Arg Asn Leu Leu
    50                  55                  60
Pro Leu Gln Ala Ala Trp Thr Leu Leu Glu Tyr Cys Gln Asp Val Ile
65                  70                  75                  80
Ser Leu Met Asn Arg Gly Leu Glu Ala Thr Arg Lys Val Ala Gly Val
                85                  90                  95
Gly Gln Gly Arg Leu Arg Ile Gly Thr Leu Tyr Ser Leu Thr Leu Glu
            100                 105                 110
Thr Val Pro Arg Ile Ile Met Gly Met Lys Leu Arg Arg Pro Glu Leu
        115                 120                 125
Glu Leu Asp Leu Thr Met Gly Ser Asn Gln Met Leu Leu Asp Met Leu
    130                 135                 140
Glu Asp Asp Ala Leu Asp Ala Ile Leu Ile Ala Thr Asn Glu Gly Glu
145                 150                 155                 160
Phe Asn Asn Thr Ala Phe Asp Val Val Pro Leu Phe Glu Asp Ile
                165                 170                 175
Phe Leu Ala Ala Pro Ala Thr Glu Arg Leu Asp Ala Ser Arg Leu Ala
            180                 185                 190
Asp Leu Arg Asp Tyr Ala Asp Arg Lys Phe Val Ser Leu Ala Glu Gly
        195                 200                 205
Phe Ala Thr Tyr Ala Gly Phe Arg Glu Ala Phe His Ile Ala Gly Phe
    210                 215                 220
Glu Pro Glu Ile Val Thr Arg Val Asn Asp Ile Phe Ser Met Ile Ser
225                 230                 235                 240
Leu Val Gln Ala Gly Val Gly Phe Ala Leu Leu Pro Gly Arg Met Lys
                245                 250                 255
```

```
Lys Val Tyr Glu Lys Asp Val Gln Leu Leu Lys Leu Ala Glu Pro Tyr
            260                 265                 270

Gln Met Arg Gln Leu Ile Ser Ile Val Tyr Ser His His Arg Glu Arg
        275                 280                 285

Asp Ala Asp Leu Leu Ala Leu Ala Ala Glu Gly Arg Met Tyr Ala Arg
    290                 295                 300

Ser Ile Asn Arg
305

<210> SEQ ID NO 6
<211> LENGTH: 77
<212> TYPE: DNA
<213> ORGANISM: Acinetobacter calcoaceticus

<400> SEQUENCE: 6
aaaaaaattg tatacaattt atgtttattt gagtacaaag cattgtacac tgaatacaga    60
taggctataa ctatacc                                                  77

<210> SEQ ID NO 7
<211> LENGTH: 598
<212> TYPE: PRT
<213> ORGANISM: Artificial Sequence
<220> FEATURE:
<223> OTHER INFORMATION: EHD3 EC 3.1.2.4 malonyl-CoA hydrolase consensus
      sequence
<220> FEATURE:
<221> NAME/KEY: VARIANT
<222> LOCATION: (1)..(16)
<223> OTHER INFORMATION: Xaa can be any naturally occurring amino acid
      or absent
<220> FEATURE:
<221> NAME/KEY: VARIANT
<222> LOCATION: (18)..(18)
<223> OTHER INFORMATION: Ile, Leu or Val
<220> FEATURE:
<221> NAME/KEY: VARIANT
<222> LOCATION: (19)..(19)
<223> OTHER INFORMATION: Arg, Lys or His
<220> FEATURE:
<221> NAME/KEY: VARIANT
<222> LOCATION: (20)..(21)
<223> OTHER INFORMATION: Ser or Thr
<220> FEATURE:
<221> NAME/KEY: VARIANT
<222> LOCATION: (22)..(22)
<223> OTHER INFORMATION: Ile, Leu or Val
<220> FEATURE:
<221> NAME/KEY: VARIANT
<222> LOCATION: (23)..(23)
<223> OTHER INFORMATION: Arg, Lys or His
<220> FEATURE:
<221> NAME/KEY: VARIANT
<222> LOCATION: (24)..(24)
<223> OTHER INFORMATION: Xaa can be any naturally occurring amino acid
<220> FEATURE:
<221> NAME/KEY: VARIANT
<222> LOCATION: (27)..(27)
<223> OTHER INFORMATION: Xaa can be any naturally occurring amino acid
<220> FEATURE:
<221> NAME/KEY: VARIANT
<222> LOCATION: (28)..(28)
<223> OTHER INFORMATION: Ser or Thr
<220> FEATURE:
<221> NAME/KEY: VARIANT
<222> LOCATION: (29)..(30)
<223> OTHER INFORMATION: Arg, Lys or His
<220> FEATURE:
<221> NAME/KEY: VARIANT
<222> LOCATION: (31)..(31)
<223> OTHER INFORMATION: Xaa can be any naturally occurring amino acid
<220> FEATURE:
<221> NAME/KEY: VARIANT
```

```
<222> LOCATION: (32)..(35)
<223> OTHER INFORMATION: Xaa can be any naturally occurring amino acid
      or absent
<220> FEATURE:
<221> NAME/KEY: VARIANT
<222> LOCATION: (36)..(36)
<223> OTHER INFORMATION: Xaa can be any naturally occurring amino acid
<220> FEATURE:
<221> NAME/KEY: VARIANT
<222> LOCATION: (37)..(40)
<223> OTHER INFORMATION: Xaa can be any naturally occurring amino acid
      or absent
<220> FEATURE:
<221> NAME/KEY: VARIANT
<222> LOCATION: (41)..(41)
<223> OTHER INFORMATION: Xaa can be any naturally occurring amino acid
<220> FEATURE:
<221> NAME/KEY: VARIANT
<222> LOCATION: (44)..(44)
<223> OTHER INFORMATION: Ile, Leu or Val
<220> FEATURE:
<221> NAME/KEY: VARIANT
<222> LOCATION: (45)..(46)
<223> OTHER INFORMATION: Arg, Lys or His
<220> FEATURE:
<221> NAME/KEY: VARIANT
<222> LOCATION: (47)..(47)
<223> OTHER INFORMATION: Ile, Leu or Val
<220> FEATURE:
<221> NAME/KEY: VARIANT
<222> LOCATION: (48)..(48)
<223> OTHER INFORMATION: Arg, Lys or His
<220> FEATURE:
<221> NAME/KEY: VARIANT
<222> LOCATION: (49)..(52)
<223> OTHER INFORMATION: Xaa can be any naturally occurring amino acid
      or absent
<220> FEATURE:
<221> NAME/KEY: VARIANT
<222> LOCATION: (53)..(53)
<223> OTHER INFORMATION: Xaa can be any naturally occurring amino acid
<220> FEATURE:
<221> NAME/KEY: VARIANT
<222> LOCATION: (54)..(58)
<223> OTHER INFORMATION: Xaa can be any naturally occurring amino acid
      or absent
<220> FEATURE:
<221> NAME/KEY: VARIANT
<222> LOCATION: (59)..(59)
<223> OTHER INFORMATION: Xaa can be any naturally occurring amino acid
<220> FEATURE:
<221> NAME/KEY: VARIANT
<222> LOCATION: (60)..(60)
<223> OTHER INFORMATION: Arg, Lys or His
<220> FEATURE:
<221> NAME/KEY: VARIANT
<222> LOCATION: (61)..(61)
<223> OTHER INFORMATION: Ser or Thr
<220> FEATURE:
<221> NAME/KEY: VARIANT
<222> LOCATION: (62)..(62)
<223> OTHER INFORMATION: Ile, Leu or Val
<220> FEATURE:
<221> NAME/KEY: VARIANT
<222> LOCATION: (63)..(65)
<223> OTHER INFORMATION: Ser or Thr
<220> FEATURE:
<221> NAME/KEY: VARIANT
<222> LOCATION: (66)..(90)
<223> OTHER INFORMATION: Xaa can be any naturally occurring amino acid
      or absent
<220> FEATURE:
<221> NAME/KEY: VARIANT
<222> LOCATION: (93)..(93)
<223> OTHER INFORMATION: Ile, Leu or Val
<220> FEATURE:
<221> NAME/KEY: VARIANT
<222> LOCATION: (95)..(97)
<223> OTHER INFORMATION: Xaa can be any naturally occurring amino acid
```

-continued

```
<220> FEATURE:
<221> NAME/KEY: VARIANT
<222> LOCATION: (98)..(100)
<223> OTHER INFORMATION: Ser or Thr
<220> FEATURE:
<221> NAME/KEY: VARIANT
<222> LOCATION: (102)..(102)
<223> OTHER INFORMATION: Ile, Leu or Val
<220> FEATURE:
<221> NAME/KEY: VARIANT
<222> LOCATION: (104)..(104)
<223> OTHER INFORMATION: Ser or Thr
<220> FEATURE:
<221> NAME/KEY: VARIANT
<222> LOCATION: (105)..(105)
<223> OTHER INFORMATION: Ile, Leu or Val
<220> FEATURE:
<221> NAME/KEY: VARIANT
<222> LOCATION: (107)..(107)
<223> OTHER INFORMATION: Asp or Glu
<220> FEATURE:
<221> NAME/KEY: VARIANT
<222> LOCATION: (108)..(108)
<223> OTHER INFORMATION: Ser or Thr
<220> FEATURE:
<221> NAME/KEY: VARIANT
<222> LOCATION: (111)..(112)
<223> OTHER INFORMATION: Ile, Leu or Val
<220> FEATURE:
<221> NAME/KEY: VARIANT
<222> LOCATION: (113)..(113)
<223> OTHER INFORMATION: Ser or Thr
<220> FEATURE:
<221> NAME/KEY: VARIANT
<222> LOCATION: (118)..(118)
<223> OTHER INFORMATION: Arg, Lys or His
<220> FEATURE:
<221> NAME/KEY: VARIANT
<222> LOCATION: (125)..(125)
<223> OTHER INFORMATION: Ser or Thr
<220> FEATURE:
<221> NAME/KEY: VARIANT
<222> LOCATION: (126)..(126)
<223> OTHER INFORMATION: Asp or Glu
<220> FEATURE:
<221> NAME/KEY: VARIANT
<222> LOCATION: (128)..(128)
<223> OTHER INFORMATION: Ser or Thr
<220> FEATURE:
<221> NAME/KEY: VARIANT
<222> LOCATION: (129)..(129)
<223> OTHER INFORMATION: Asp or Glu
<220> FEATURE:
<221> NAME/KEY: VARIANT
<222> LOCATION: (130)..(130)
<223> OTHER INFORMATION: Ser or Thr
<220> FEATURE:
<221> NAME/KEY: VARIANT
<222> LOCATION: (131)..(131)
<223> OTHER INFORMATION: Ile, Leu or Val
<220> FEATURE:
<221> NAME/KEY: VARIANT
<222> LOCATION: (133)..(133)
<223> OTHER INFORMATION: Arg, Lys or His
<220> FEATURE:
<221> NAME/KEY: VARIANT
<222> LOCATION: (134)..(134)
<223> OTHER INFORMATION: Ser or Thr
<220> FEATURE:
<221> NAME/KEY: VARIANT
<222> LOCATION: (139)..(139)
<223> OTHER INFORMATION: Ser or Thr
<220> FEATURE:
<221> NAME/KEY: VARIANT
<222> LOCATION: (142)..(142)
<223> OTHER INFORMATION: Asp or Glu
<220> FEATURE:
<221> NAME/KEY: VARIANT
<222> LOCATION: (143)..(144)
```

```
<223> OTHER INFORMATION: Ser or Thr
<220> FEATURE:
<221> NAME/KEY: VARIANT
<222> LOCATION: (146)..(149)
<223> OTHER INFORMATION: Ile, Leu or Val
<220> FEATURE:
<221> NAME/KEY: VARIANT
<222> LOCATION: (150)..(150)
<223> OTHER INFORMATION: Arg, Lys or His
<220> FEATURE:
<221> NAME/KEY: VARIANT
<222> LOCATION: (152)..(152)
<223> OTHER INFORMATION: Ser or Thr
<220> FEATURE:
<221> NAME/KEY: VARIANT
<222> LOCATION: (157)..(157)
<223> OTHER INFORMATION: Ser or Thr
<220> FEATURE:
<221> NAME/KEY: VARIANT
<222> LOCATION: (158)..(158)
<223> OTHER INFORMATION: Ile, Leu or Val
<220> FEATURE:
<221> NAME/KEY: VARIANT
<222> LOCATION: (166)..(166)
<223> OTHER INFORMATION: Ser or Thr
<220> FEATURE:
<221> NAME/KEY: VARIANT
<222> LOCATION: (167)..(167)
<223> OTHER INFORMATION: Ile, Leu or Val
<220> FEATURE:
<221> NAME/KEY: VARIANT
<222> LOCATION: (169)..(169)
<223> OTHER INFORMATION: Ile, Leu or Val
<220> FEATURE:
<221> NAME/KEY: VARIANT
<222> LOCATION: (170)..(170)
<223> OTHER INFORMATION: Xaa can be any naturally occurring amino acid
<220> FEATURE:
<221> NAME/KEY: VARIANT
<222> LOCATION: (172)..(172)
<223> OTHER INFORMATION: Ile, Leu or Val
<220> FEATURE:
<221> NAME/KEY: VARIANT
<222> LOCATION: (173)..(173)
<223> OTHER INFORMATION: Asp or Glu
<220> FEATURE:
<221> NAME/KEY: VARIANT
<222> LOCATION: (174)..(175)
<223> OTHER INFORMATION: Arg, Lys or His
<220> FEATURE:
<221> NAME/KEY: VARIANT
<222> LOCATION: (177)..(178)
<223> OTHER INFORMATION: Xaa can be any naturally occurring amino acid
      or absent
<220> FEATURE:
<221> NAME/KEY: VARIANT
<222> LOCATION: (179)..(180)
<223> OTHER INFORMATION: Arg, Lys or His
<220> FEATURE:
<221> NAME/KEY: VARIANT
<222> LOCATION: (181)..(181)
<223> OTHER INFORMATION: Ser or Thr
<220> FEATURE:
<221> NAME/KEY: VARIANT
<222> LOCATION: (182)..(182)
<223> OTHER INFORMATION: Ile, Leu or Val
<220> FEATURE:
<221> NAME/KEY: VARIANT
<222> LOCATION: (183)..(183)
<223> OTHER INFORMATION: Asp or Glu
<220> FEATURE:
<221> NAME/KEY: VARIANT
<222> LOCATION: (186)..(186)
<223> OTHER INFORMATION: Arg, Lys or His
<220> FEATURE:
<221> NAME/KEY: VARIANT
<222> LOCATION: (187)..(187)
<223> OTHER INFORMATION: Ser or Thr
<220> FEATURE:
```

```
<221> NAME/KEY: VARIANT
<222> LOCATION: (188)..(188)
<223> OTHER INFORMATION: Ala, Asp, Arg, His, Lys, Ser, Thr, Asn, Gln,
      Tyr
<220> FEATURE:
<221> NAME/KEY: VARIANT
<222> LOCATION: (191)..(191)
<223> OTHER INFORMATION: Ile, Leu or Val
<220> FEATURE:
<221> NAME/KEY: VARIANT
<222> LOCATION: (195)..(195)
<223> OTHER INFORMATION: Ile, Leu or Val
<220> FEATURE:
<221> NAME/KEY: VARIANT
<222> LOCATION: (199)..(199)
<223> OTHER INFORMATION: Ile, Leu or Val
<220> FEATURE:
<221> NAME/KEY: VARIANT
<222> LOCATION: (202)..(205)
<223> OTHER INFORMATION: Ile, Leu or Val
<220> FEATURE:
<221> NAME/KEY: VARIANT
<222> LOCATION: (207)..(207)
<223> OTHER INFORMATION: Asp or Glu
<220> FEATURE:
<221> NAME/KEY: VARIANT
<222> LOCATION: (217)..(217)
<223> OTHER INFORMATION: Ile, Leu or Val
<220> FEATURE:
<221> NAME/KEY: VARIANT
<222> LOCATION: (218)..(218)
<223> OTHER INFORMATION: Ser or Thr
<220> FEATURE:
<221> NAME/KEY: VARIANT
<222> LOCATION: (219)..(219)
<223> OTHER INFORMATION: Ile, Leu or Val
<220> FEATURE:
<221> NAME/KEY: VARIANT
<222> LOCATION: (221)..(221)
<223> OTHER INFORMATION: Ser or Thr
<220> FEATURE:
<221> NAME/KEY: VARIANT
<222> LOCATION: (225)..(225)
<223> OTHER INFORMATION: Ile, Leu or Val
<220> FEATURE:
<221> NAME/KEY: VARIANT
<222> LOCATION: (231)..(231)
<223> OTHER INFORMATION: Arg, Lys or His
<220> FEATURE:
<221> NAME/KEY: VARIANT
<222> LOCATION: (247)..(248)
<223> OTHER INFORMATION: Ser or Thr
<220> FEATURE:
<221> NAME/KEY: VARIANT
<222> LOCATION: (251)..(251)
<223> OTHER INFORMATION: Ile, Leu or Val
<220> FEATURE:
<221> NAME/KEY: VARIANT
<222> LOCATION: (253)..(253)
<223> OTHER INFORMATION: Arg, Lys or His
<220> FEATURE:
<221> NAME/KEY: VARIANT
<222> LOCATION: (254)..(255)
<223> OTHER INFORMATION: Ile, Leu or Val
<220> FEATURE:
<221> NAME/KEY: VARIANT
<222> LOCATION: (256)..(256)
<223> OTHER INFORMATION: Ser or Thr
<220> FEATURE:
<221> NAME/KEY: VARIANT
<222> LOCATION: (257)..(257)
<223> OTHER INFORMATION: Ile, Leu or Val
<220> FEATURE:
<221> NAME/KEY: VARIANT
<222> LOCATION: (260)..(260)
<223> OTHER INFORMATION: Ser or Thr
<220> FEATURE:
<221> NAME/KEY: VARIANT
<222> LOCATION: (261)..(261)
```

```
<223> OTHER INFORMATION: Arg, Lys or His
<220> FEATURE:
<221> NAME/KEY: VARIANT
<222> LOCATION: (262)..(262)
<223> OTHER INFORMATION: Ser or Thr
<220> FEATURE:
<221> NAME/KEY: VARIANT
<222> LOCATION: (264)..(264)
<223> OTHER INFORMATION: Ile, Leu or Val
<220> FEATURE:
<221> NAME/KEY: VARIANT
<222> LOCATION: (266)..(266)
<223> OTHER INFORMATION: Ile, Leu or Val
<220> FEATURE:
<221> NAME/KEY: VARIANT
<222> LOCATION: (270)..(270)
<223> OTHER INFORMATION: Ile, Leu or Val
<220> FEATURE:
<221> NAME/KEY: VARIANT
<222> LOCATION: (273)..(273)
<223> OTHER INFORMATION: Asp or Glu
<220> FEATURE:
<221> NAME/KEY: VARIANT
<222> LOCATION: (274)..(275)
<223> OTHER INFORMATION: Ile, Leu or Val
<220> FEATURE:
<221> NAME/KEY: VARIANT
<222> LOCATION: (276)..(276)
<223> OTHER INFORMATION: Ser or Thr
<220> FEATURE:
<221> NAME/KEY: VARIANT
<222> LOCATION: (278)..(279)
<223> OTHER INFORMATION: Asp or Glu
<220> FEATURE:
<221> NAME/KEY: VARIANT
<222> LOCATION: (282)..(283)
<223> OTHER INFORMATION: Ile, Leu or Val
<220> FEATURE:
<221> NAME/KEY: VARIANT
<222> LOCATION: (285)..(285)
<223> OTHER INFORMATION: Ile, Leu or Val
<220> FEATURE:
<221> NAME/KEY: VARIANT
<222> LOCATION: (290)..(290)
<223> OTHER INFORMATION: Ile, Leu or Val
<220> FEATURE:
<221> NAME/KEY: VARIANT
<222> LOCATION: (291)..(291)
<223> OTHER INFORMATION: Ser or Thr
<220> FEATURE:
<221> NAME/KEY: VARIANT
<222> LOCATION: (292)..(292)
<223> OTHER INFORMATION: Arg, Lys or His
<220> FEATURE:
<221> NAME/KEY: VARIANT
<222> LOCATION: (293)..(293)
<223> OTHER INFORMATION: Asp or Glu
<220> FEATURE:
<221> NAME/KEY: VARIANT
<222> LOCATION: (295)..(295)
<223> OTHER INFORMATION: Ile, Leu or Val
<220> FEATURE:
<221> NAME/KEY: VARIANT
<222> LOCATION: (296)..(297)
<223> OTHER INFORMATION: Asp or Glu
<220> FEATURE:
<221> NAME/KEY: VARIANT
<222> LOCATION: (299)..(299)
<223> OTHER INFORMATION: Asp or Glu
<220> FEATURE:
<221> NAME/KEY: VARIANT
<222> LOCATION: (300)..(300)
<223> OTHER INFORMATION: Arg, Lys or His
<220> FEATURE:
<221> NAME/KEY: VARIANT
<222> LOCATION: (305)..(305)
<223> OTHER INFORMATION: Ile, Leu or Val
<220> FEATURE:
<221> NAME/KEY: VARIANT
```

```
<222> LOCATION: (306)..(306)
<223> OTHER INFORMATION: Arg, Lys or His
<220> FEATURE:
<221> NAME/KEY: VARIANT
<222> LOCATION: (308)..(308)
<223> OTHER INFORMATION: Ser or Thr
<220> FEATURE:
<221> NAME/KEY: VARIANT
<222> LOCATION: (309)..(309)
<223> OTHER INFORMATION: Asp or Glu
<220> FEATURE:
<221> NAME/KEY: VARIANT
<222> LOCATION: (310)..(310)
<223> OTHER INFORMATION: Xaa can be any naturally occurring amino acid
<220> FEATURE:
<221> NAME/KEY: VARIANT
<222> LOCATION: (311)..(311)
<223> OTHER INFORMATION: Ile, Leu or Val
<220> FEATURE:
<221> NAME/KEY: VARIANT
<222> LOCATION: (312)..(312)
<223> OTHER INFORMATION: Asp or Glu
<220> FEATURE:
<221> NAME/KEY: VARIANT
<222> LOCATION: (313)..(313)
<223> OTHER INFORMATION: Xaa can be any naturally occurring amino acid
<220> FEATURE:
<221> NAME/KEY: VARIANT
<222> LOCATION: (314)..(314)
<223> OTHER INFORMATION: Xaa can be any naturally occurring amino acid
    or absent
<220> FEATURE:
<221> NAME/KEY: VARIANT
<222> LOCATION: (315)..(317)
<223> OTHER INFORMATION: Xaa can be any naturally occurring amino acid
<220> FEATURE:
<221> NAME/KEY: VARIANT
<222> LOCATION: (318)..(318)
<223> OTHER INFORMATION: Ser or Thr
<220> FEATURE:
<221> NAME/KEY: VARIANT
<222> LOCATION: (320)..(320)
<223> OTHER INFORMATION: Ser or Thr
<220> FEATURE:
<221> NAME/KEY: VARIANT
<222> LOCATION: (321)..(322)
<223> OTHER INFORMATION: Asp or Glu
<220> FEATURE:
<221> NAME/KEY: VARIANT
<222> LOCATION: (325)..(325)
<223> OTHER INFORMATION: Asp or Glu
<220> FEATURE:
<221> NAME/KEY: VARIANT
<222> LOCATION: (326)..(327)
<223> OTHER INFORMATION: Ile, Leu or Val
<220> FEATURE:
<221> NAME/KEY: VARIANT
<222> LOCATION: (329)..(329)
<223> OTHER INFORMATION: Asp or Glu
<220> FEATURE:
<221> NAME/KEY: VARIANT
<222> LOCATION: (330)..(330)
<223> OTHER INFORMATION: Ser or Thr
<220> FEATURE:
<221> NAME/KEY: VARIANT
<222> LOCATION: (331)..(331)
<223> OTHER INFORMATION: Ile, Leu or Val
<220> FEATURE:
<221> NAME/KEY: VARIANT
<222> LOCATION: (332)..(332)
<223> OTHER INFORMATION: Asp or Glu
<220> FEATURE:
<221> NAME/KEY: VARIANT
<222> LOCATION: (335)..(336)
<223> OTHER INFORMATION: Ser or Thr
<220> FEATURE:
<221> NAME/KEY: VARIANT
<222> LOCATION: (338)..(338)
<223> OTHER INFORMATION: Xaa can be any naturally occurring amino acid
```

```
           or absent
<220> FEATURE:
<221> NAME/KEY: VARIANT
<222> LOCATION: (339)..(339)
<223> OTHER INFORMATION: Ile, Leu or Val
<220> FEATURE:
<221> NAME/KEY: VARIANT
<222> LOCATION: (341)..(341)
<223> OTHER INFORMATION: Arg, Lys or His
<220> FEATURE:
<221> NAME/KEY: VARIANT
<222> LOCATION: (342)..(342)
<223> OTHER INFORMATION: Asp or Glu
<220> FEATURE:
<221> NAME/KEY: VARIANT
<222> LOCATION: (344)..(344)
<223> OTHER INFORMATION: Arg, Lys or His
<220> FEATURE:
<221> NAME/KEY: VARIANT
<222> LOCATION: (346)..(346)
<223> OTHER INFORMATION: Arg, Lys or His
<220> FEATURE:
<221> NAME/KEY: VARIANT
<222> LOCATION: (348)..(348)
<223> OTHER INFORMATION: Ser or Thr
<220> FEATURE:
<221> NAME/KEY: VARIANT
<222> LOCATION: (350)..(350)
<223> OTHER INFORMATION: Asp or Glu
<220> FEATURE:
<221> NAME/KEY: VARIANT
<222> LOCATION: (351)..(351)
<223> OTHER INFORMATION: Arg, Lys or His
<220> FEATURE:
<221> NAME/KEY: VARIANT
<222> LOCATION: (353)..(353)
<223> OTHER INFORMATION: Asp or Glu
<220> FEATURE:
<221> NAME/KEY: VARIANT
<222> LOCATION: (356)..(356)
<223> OTHER INFORMATION: Asp or Glu
<220> FEATURE:
<221> NAME/KEY: VARIANT
<222> LOCATION: (357)..(357)
<223> OTHER INFORMATION: Arg, Lys or His
<220> FEATURE:
<221> NAME/KEY: VARIANT
<222> LOCATION: (360)..(360)
<223> OTHER INFORMATION: Asp or Glu
<220> FEATURE:
<221> NAME/KEY: VARIANT
<222> LOCATION: (361)..(361)
<223> OTHER INFORMATION: Ile, Leu or Val
<220> FEATURE:
<221> NAME/KEY: VARIANT
<222> LOCATION: (362)..(362)
<223> OTHER INFORMATION: Ser or Thr
<220> FEATURE:
<221> NAME/KEY: VARIANT
<222> LOCATION: (363)..(363)
<223> OTHER INFORMATION: Arg, Lys or His
<220> FEATURE:
<221> NAME/KEY: VARIANT
<222> LOCATION: (364)..(364)
<223> OTHER INFORMATION: Ile, Leu or Val
<220> FEATURE:
<221> NAME/KEY: VARIANT
<222> LOCATION: (365)..(366)
<223> OTHER INFORMATION: Ser or Thr
<220> FEATURE:
<221> NAME/KEY: VARIANT
<222> LOCATION: (367)..(367)
<223> OTHER INFORMATION: Ile, Leu or Val
<220> FEATURE:
<221> NAME/KEY: VARIANT
<222> LOCATION: (368)..(368)
<223> OTHER INFORMATION: Arg, Lys or His
<220> FEATURE:
<221> NAME/KEY: VARIANT
```

```
<222> LOCATION: (369)..(369)
<223> OTHER INFORMATION: Asp or Glu
<220> FEATURE:
<221> NAME/KEY: VARIANT
<222> LOCATION: (370)..(371)
<223> OTHER INFORMATION: Ile, Leu or Val
<220> FEATURE:
<221> NAME/KEY: VARIANT
<222> LOCATION: (372)..(373)
<223> OTHER INFORMATION: Arg, Lys or His
<220> FEATURE:
<221> NAME/KEY: VARIANT
<222> LOCATION: (375)..(376)
<223> OTHER INFORMATION: Asp or Glu
<220> FEATURE:
<221> NAME/KEY: VARIANT
<222> LOCATION: (377)..(377)
<223> OTHER INFORMATION: Ile, Leu or Val
<220> FEATURE:
<221> NAME/KEY: VARIANT
<222> LOCATION: (378)..(378)
<223> OTHER INFORMATION: Xaa can be any naturally occurring amino acid
      or absent
<220> FEATURE:
<221> NAME/KEY: VARIANT
<222> LOCATION: (379)..(380)
<223> OTHER INFORMATION: Xaa can be any naturally occurring amino acid
<220> FEATURE:
<221> NAME/KEY: VARIANT
<222> LOCATION: (381)..(381)
<223> OTHER INFORMATION: Xaa can be any naturally occurring amino acid
      or absent
<220> FEATURE:
<221> NAME/KEY: VARIANT
<222> LOCATION: (383)..(383)
<223> OTHER INFORMATION: Asp or Glu
<220> FEATURE:
<221> NAME/KEY: VARIANT
<222> LOCATION: (385)..(385)
<223> OTHER INFORMATION: Ser or Thr
<220> FEATURE:
<221> NAME/KEY: VARIANT
<222> LOCATION: (386)..(387)
<223> OTHER INFORMATION: Asp or Glu
<220> FEATURE:
<221> NAME/KEY: VARIANT
<222> LOCATION: (389)..(389)
<223> OTHER INFORMATION: Arg, Lys or His
<220> FEATURE:
<221> NAME/KEY: VARIANT
<222> LOCATION: (390)..(390)
<223> OTHER INFORMATION: Asp or Glu
<220> FEATURE:
<221> NAME/KEY: VARIANT
<222> LOCATION: (393)..(393)
<223> OTHER INFORMATION: Arg, Lys or His
<220> FEATURE:
<221> NAME/KEY: VARIANT
<222> LOCATION: (394)..(394)
<223> OTHER INFORMATION: Asp or Glu
<220> FEATURE:
<221> NAME/KEY: VARIANT
<222> LOCATION: (395)..(395)
<223> OTHER INFORMATION: Ile, Leu or Val
<220> FEATURE:
<221> NAME/KEY: VARIANT
<222> LOCATION: (396)..(396)
<223> OTHER INFORMATION: Arg, Lys or His
<220> FEATURE:
<221> NAME/KEY: VARIANT
<222> LOCATION: (397)..(397)
<223> OTHER INFORMATION: Asp or Glu
<220> FEATURE:
<221> NAME/KEY: VARIANT
<222> LOCATION: (398)..(398)
<223> OTHER INFORMATION: Arg, Lys or His
<220> FEATURE:
<221> NAME/KEY: VARIANT
<222> LOCATION: (400)..(400)
```

```
<223> OTHER INFORMATION: Ile, Leu or Val
<220> FEATURE:
<221> NAME/KEY: VARIANT
<222> LOCATION: (401)..(401)
<223> OTHER INFORMATION: Ser or Thr
<220> FEATURE:
<221> NAME/KEY: VARIANT
<222> LOCATION: (405)..(405)
<223> OTHER INFORMATION: Ser or Thr
<220> FEATURE:
<221> NAME/KEY: VARIANT
<222> LOCATION: (407)..(407)
<223> OTHER INFORMATION: Ile, Leu or Val
<220> FEATURE:
<221> NAME/KEY: VARIANT
<222> LOCATION: (409)..(409)
<223> OTHER INFORMATION: Ile, Leu or Val
<220> FEATURE:
<221> NAME/KEY: VARIANT
<222> LOCATION: (411)..(411)
<223> OTHER INFORMATION: Ile, Leu or Val
<220> FEATURE:
<221> NAME/KEY: VARIANT
<222> LOCATION: (412)..(412)
<223> OTHER INFORMATION: Arg, Lys or His
<220> FEATURE:
<221> NAME/KEY: VARIANT
<222> LOCATION: (413)..(414)
<223> OTHER INFORMATION: Ile, Leu or Val
<220> FEATURE:
<221> NAME/KEY: VARIANT
<222> LOCATION: (415)..(415)
<223> OTHER INFORMATION: Arg, Lys or His
<220> FEATURE:
<221> NAME/KEY: VARIANT
<222> LOCATION: (416)..(416)
<223> OTHER INFORMATION: Asp or Glu
<220> FEATURE:
<221> NAME/KEY: VARIANT
<222> LOCATION: (418)..(418)
<223> OTHER INFORMATION: Ser or Thr
<220> FEATURE:
<221> NAME/KEY: VARIANT
<222> LOCATION: (419)..(419)
<223> OTHER INFORMATION: Arg, Lys or His
<220> FEATURE:
<221> NAME/KEY: VARIANT
<222> LOCATION: (420)..(420)
<223> OTHER INFORMATION: Asp or Glu
<220> FEATURE:
<221> NAME/KEY: VARIANT
<222> LOCATION: (421)..(421)
<223> OTHER INFORMATION: Arg, Lys or His
<220> FEATURE:
<221> NAME/KEY: VARIANT
<222> LOCATION: (422)..(422)
<223> OTHER INFORMATION: Ile, Leu or Val
<220> FEATURE:
<221> NAME/KEY: VARIANT
<222> LOCATION: (423)..(423)
<223> OTHER INFORMATION: Asp or Glu
<220> FEATURE:
<221> NAME/KEY: VARIANT
<222> LOCATION: (424)..(424)
<223> OTHER INFORMATION: Ser or Thr
<220> FEATURE:
<221> NAME/KEY: VARIANT
<222> LOCATION: (426)..(426)
<223> OTHER INFORMATION: Ile, Leu or Val
<220> FEATURE:
<221> NAME/KEY: VARIANT
<222> LOCATION: (427)..(428)
<223> OTHER INFORMATION: Arg, Lys or His
<220> FEATURE:
<221> NAME/KEY: VARIANT
<222> LOCATION: (431)..(431)
<223> OTHER INFORMATION: Ile, Leu or Val
<220> FEATURE:
<221> NAME/KEY: VARIANT
```

```
<222> LOCATION: (434)..(434)
<223> OTHER INFORMATION: Ser or Thr
<220> FEATURE:
<221> NAME/KEY: VARIANT
<222> LOCATION: (438)..(438)
<223> OTHER INFORMATION: Ile, Leu or Val
<220> FEATURE:
<221> NAME/KEY: VARIANT
<222> LOCATION: (440)..(440)
<223> OTHER INFORMATION: Xaa can be any naturally occurring amino acid
      or absent
<220> FEATURE:
<221> NAME/KEY: VARIANT
<222> LOCATION: (441)..(443)
<223> OTHER INFORMATION: Xaa can be any naturally occurring amino acid
<220> FEATURE:
<221> NAME/KEY: VARIANT
<222> LOCATION: (445)..(445)
<223> OTHER INFORMATION: Asp or Glu
<220> FEATURE:
<221> NAME/KEY: VARIANT
<222> LOCATION: (446)..(446)
<223> OTHER INFORMATION: Ser or Thr
<220> FEATURE:
<221> NAME/KEY: VARIANT
<222> LOCATION: (447)..(448)
<223> OTHER INFORMATION: Ile, Leu or Val
<220> FEATURE:
<221> NAME/KEY: VARIANT
<222> LOCATION: (451)..(451)
<223> OTHER INFORMATION: Ser or Thr
<220> FEATURE:
<221> NAME/KEY: VARIANT
<222> LOCATION: (452)..(452)
<223> OTHER INFORMATION: Asp or Glu
<220> FEATURE:
<221> NAME/KEY: VARIANT
<222> LOCATION: (454)..(454)
<223> OTHER INFORMATION: Ser or Thr
<220> FEATURE:
<221> NAME/KEY: VARIANT
<222> LOCATION: (455)..(456)
<223> OTHER INFORMATION: Arg, Lys or His
<220> FEATURE:
<221> NAME/KEY: VARIANT
<222> LOCATION: (459)..(459)
<223> OTHER INFORMATION: Ile, Leu or Val
<220> FEATURE:
<221> NAME/KEY: VARIANT
<222> LOCATION: (460)..(460)
<223> OTHER INFORMATION: Asp or Glu
<220> FEATURE:
<221> NAME/KEY: VARIANT
<222> LOCATION: (463)..(463)
<223> OTHER INFORMATION: Arg, Lys or His
<220> FEATURE:
<221> NAME/KEY: VARIANT
<222> LOCATION: (464)..(464)
<223> OTHER INFORMATION: Ile, Leu or Val
<220> FEATURE:
<221> NAME/KEY: VARIANT
<222> LOCATION: (464)..(464)
<223> OTHER INFORMATION: Ile, Leu or Val
<220> FEATURE:
<221> NAME/KEY: VARIANT
<222> LOCATION: (469)..(471)
<223> OTHER INFORMATION: Arg, Lys or His
<220> FEATURE:
<221> NAME/KEY: VARIANT
<222> LOCATION: (472)..(472)
<223> OTHER INFORMATION: Xaa can be any naturally occurring amino acid
<220> FEATURE:
<221> NAME/KEY: VARIANT
<222> LOCATION: (473)..(474)
<223> OTHER INFORMATION: Asp or Glu
<220> FEATURE:
<221> NAME/KEY: VARIANT
<222> LOCATION: (475)..(475)
<223> OTHER INFORMATION: Ile, Leu or Val
```

-continued

```
<220> FEATURE:
<221> NAME/KEY: VARIANT
<222> LOCATION: (476)..(476)
<223> OTHER INFORMATION: Ser or Thr
<220> FEATURE:
<221> NAME/KEY: VARIANT
<222> LOCATION: (477)..(477)
<223> OTHER INFORMATION: Ile, Leu or Val
<220> FEATURE:
<221> NAME/KEY: VARIANT
<222> LOCATION: (478)..(478)
<223> OTHER INFORMATION: Ser or Thr
<220> FEATURE:
<221> NAME/KEY: VARIANT
<222> LOCATION: (480)..(480)
<223> OTHER INFORMATION: Ile, Leu or Val
<220> FEATURE:
<221> NAME/KEY: VARIANT
<222> LOCATION: (481)..(482)
<223> OTHER INFORMATION: Ser or Thr
<220> FEATURE:
<221> NAME/KEY: VARIANT
<222> LOCATION: (483)..(484)
<223> OTHER INFORMATION: Ile, Leu or Val
<220> FEATURE:
<221> NAME/KEY: VARIANT
<222> LOCATION: (485)..(485)
<223> OTHER INFORMATION: Ser or Thr
<220> FEATURE:
<221> NAME/KEY: VARIANT
<222> LOCATION: (487)..(487)
<223> OTHER INFORMATION: Arg, Lys or His
<220> FEATURE:
<221> NAME/KEY: VARIANT
<222> LOCATION: (489)..(489)
<223> OTHER INFORMATION: Ser or Thr
<220> FEATURE:
<221> NAME/KEY: VARIANT
<222> LOCATION: (490)..(490)
<223> OTHER INFORMATION: Ile, Leu or Val
<220> FEATURE:
<221> NAME/KEY: VARIANT
<222> LOCATION: (492)..(492)
<223> OTHER INFORMATION: Ile, Leu or Val
<220> FEATURE:
<221> NAME/KEY: VARIANT
<222> LOCATION: (493)..(493)
<223> OTHER INFORMATION: Ser or Thr
<220> FEATURE:
<221> NAME/KEY: VARIANT
<222> LOCATION: (495)..(495)
<223> OTHER INFORMATION: Ile, Leu or Val
<220> FEATURE:
<221> NAME/KEY: VARIANT
<222> LOCATION: (496)..(496)
<223> OTHER INFORMATION: Arg, Lys or His
<220> FEATURE:
<221> NAME/KEY: VARIANT
<222> LOCATION: (498)..(499)
<223> OTHER INFORMATION: Ser or Thr
<220> FEATURE:
<221> NAME/KEY: VARIANT
<222> LOCATION: (501)..(501)
<223> OTHER INFORMATION: Ile, Leu or Val
<220> FEATURE:
<221> NAME/KEY: VARIANT
<222> LOCATION: (504)..(504)
<223> OTHER INFORMATION: Arg, Lys or His
<220> FEATURE:
<221> NAME/KEY: VARIANT
<222> LOCATION: (505)..(505)
<223> OTHER INFORMATION: Asp or Glu
<220> FEATURE:
<221> NAME/KEY: VARIANT
<222> LOCATION: (508)..(509)
<223> OTHER INFORMATION: Arg, Lys or His
<220> FEATURE:
<221> NAME/KEY: VARIANT
<222> LOCATION: (510)..(510)
```

```
<223> OTHER INFORMATION: Ile, Leu or Val
<220> FEATURE:
<221> NAME/KEY: VARIANT
<222> LOCATION: (511)..(511)
<223> OTHER INFORMATION: Arg, Lys or His
<220> FEATURE:
<221> NAME/KEY: VARIANT
<222> LOCATION: (516)..(516)
<223> OTHER INFORMATION: Ser or Thr
<220> FEATURE:
<221> NAME/KEY: VARIANT
<222> LOCATION: (517)..(517)
<223> OTHER INFORMATION: Asp or Glu
<220> FEATURE:
<221> NAME/KEY: VARIANT
<222> LOCATION: (518)..(518)
<223> OTHER INFORMATION: Ser or Thr
<220> FEATURE:
<221> NAME/KEY: VARIANT
<222> LOCATION: (519)..(519)
<223> OTHER INFORMATION: Asp or Glu
<220> FEATURE:
<221> NAME/KEY: VARIANT
<222> LOCATION: (520)..(520)
<223> OTHER INFORMATION: Ile, Leu or Val
<220> FEATURE:
<221> NAME/KEY: VARIANT
<222> LOCATION: (521)..(521)
<223> OTHER INFORMATION: Arg, Lys or His
<220> FEATURE:
<221> NAME/KEY: VARIANT
<222> LOCATION: (524)..(524)
<223> OTHER INFORMATION: Ile, Leu or Val
<220> FEATURE:
<221> NAME/KEY: VARIANT
<222> LOCATION: (525)..(527)
<223> OTHER INFORMATION: Arg, Lys or His
<220> FEATURE:
<221> NAME/KEY: VARIANT
<222> LOCATION: (528)..(528)
<223> OTHER INFORMATION: Asp or Glu
<220> FEATURE:
<221> NAME/KEY: VARIANT
<222> LOCATION: (530)..(530)
<223> OTHER INFORMATION: Arg, Lys or His
<220> FEATURE:
<221> NAME/KEY: VARIANT
<222> LOCATION: (532)..(534)
<223> OTHER INFORMATION: Xaa can be any naturally occurring amino acid
      or absent
<220> FEATURE:
<221> NAME/KEY: VARIANT
<222> LOCATION: (535)..(535)
<223> OTHER INFORMATION: Xaa can be any naturally occurring amino acid
<220> FEATURE:
<221> NAME/KEY: VARIANT
<222> LOCATION: (537)..(537)
<223> OTHER INFORMATION: Xaa can be any naturally occurring amino acid
      or absent
<220> FEATURE:
<221> NAME/KEY: VARIANT
<222> LOCATION: (538)..(539)
<223> OTHER INFORMATION: Xaa can be any naturally occurring amino acid
<220> FEATURE:
<221> NAME/KEY: VARIANT
<222> LOCATION: (540)..(540)
<223> OTHER INFORMATION: Ile, Leu or Val
<220> FEATURE:
<221> NAME/KEY: VARIANT
<222> LOCATION: (541)..(541)
<223> OTHER INFORMATION: Arg, Lys or His
<220> FEATURE:
<221> NAME/KEY: VARIANT
<222> LOCATION: (542)..(542)
<223> OTHER INFORMATION: Ile, Leu or Val
<220> FEATURE:
<221> NAME/KEY: VARIANT
<222> LOCATION: (543)..(543)
<223> OTHER INFORMATION: Ser or Thr
```

```
<220> FEATURE:
<221> NAME/KEY: VARIANT
<222> LOCATION: (543)..(543)
<223> OTHER INFORMATION: Ser or Thr
<220> FEATURE:
<221> NAME/KEY: VARIANT
<222> LOCATION: (544)..(545)
<223> OTHER INFORMATION: Arg, Lys, or His
<220> FEATURE:
<221> NAME/KEY: VARIANT
<222> LOCATION: (546)..(546)
<223> OTHER INFORMATION: Asp or Glu
<220> FEATURE:
<221> NAME/KEY: VARIANT
<222> LOCATION: (547)..(548)
<223> OTHER INFORMATION: Ile, Leu or Val
<220> FEATURE:
<221> NAME/KEY: VARIANT
<222> LOCATION: (549)..(550)
<223> OTHER INFORMATION: Arg, Lys or His
<220> FEATURE:
<221> NAME/KEY: VARIANT
<222> LOCATION: (552)..(552)
<223> OTHER INFORMATION: Ser or Thr
<220> FEATURE:
<221> NAME/KEY: VARIANT
<222> LOCATION: (554)..(554)
<223> OTHER INFORMATION: Ile, Leu or Val
<220> FEATURE:
<221> NAME/KEY: VARIANT
<222> LOCATION: (556)..(556)
<223> OTHER INFORMATION: Asp or Glu
<220> FEATURE:
<221> NAME/KEY: VARIANT
<222> LOCATION: (557)..(557)
<223> OTHER INFORMATION: Ser or Thr
<220> FEATURE:
<221> NAME/KEY: VARIANT
<222> LOCATION: (558)..(559)
<223> OTHER INFORMATION: Arg, Lys or His
<220> FEATURE:
<221> NAME/KEY: VARIANT
<222> LOCATION: (560)..(560)
<223> OTHER INFORMATION: Asp or Glu
<220> FEATURE:
<221> NAME/KEY: VARIANT
<222> LOCATION: (562)..(562)
<223> OTHER INFORMATION: Ile, Leu or Val
<220> FEATURE:
<221> NAME/KEY: VARIANT
<222> LOCATION: (564)..(564)
<223> OTHER INFORMATION: Ile, Leu or Val
<220> FEATURE:
<221> NAME/KEY: VARIANT
<222> LOCATION: (565)..(565)
<223> OTHER INFORMATION: Asp or Glu
<220> FEATURE:
<221> NAME/KEY: VARIANT
<222> LOCATION: (566)..(566)
<223> OTHER INFORMATION: Ser or Thr
<220> FEATURE:
<221> NAME/KEY: VARIANT
<222> LOCATION: (567)..(568)
<223> OTHER INFORMATION: Ile, Leu or Val
<220> FEATURE:
<221> NAME/KEY: VARIANT
<222> LOCATION: (569)..(569)
<223> OTHER INFORMATION: Arg, Lys or His
<220> FEATURE:
<221> NAME/KEY: VARIANT
<222> LOCATION: (570)..(572)
<223> OTHER INFORMATION: Ile, Leu or Val
<220> FEATURE:
<221> NAME/KEY: VARIANT
<222> LOCATION: (573)..(573)
<223> OTHER INFORMATION: Asp or Glu
<220> FEATURE:
<221> NAME/KEY: VARIANT
<222> LOCATION: (574)..(575)
```

```
<223> OTHER INFORMATION: Arg, Lys or His
<220> FEATURE:
<221> NAME/KEY: VARIANT
<222> LOCATION: (577)..(577)
<223> OTHER INFORMATION: Ser or Thr
<220> FEATURE:
<221> NAME/KEY: VARIANT
<222> LOCATION: (578)..(580)
<223> OTHER INFORMATION: Asp or Glu
<220> FEATURE:
<221> NAME/KEY: VARIANT
<222> LOCATION: (582)..(582)
<223> OTHER INFORMATION: Xaa can be any naturally occurring amino acid
<220> FEATURE:
<221> NAME/KEY: VARIANT
<222> LOCATION: (585)..(585)
<223> OTHER INFORMATION: Ile, Leu or Val
<220> FEATURE:
<221> NAME/KEY: VARIANT
<222> LOCATION: (586)..(586)
<223> OTHER INFORMATION: Arg, Lys or His
<220> FEATURE:
<221> NAME/KEY: VARIANT
<222> LOCATION: (588)..(588)
<223> OTHER INFORMATION: Arg, Lys or His
<220> FEATURE:
<221> NAME/KEY: VARIANT
<222> LOCATION: (589)..(590)
<223> OTHER INFORMATION: Xaa can be any naturally occurring amino acid
<220> FEATURE:
<221> NAME/KEY: VARIANT
<222> LOCATION: (591)..(591)
<223> OTHER INFORMATION: Xaa can be any naturally occurring amino acid
       or absent
<220> FEATURE:
<221> NAME/KEY: VARIANT
<222> LOCATION: (592)..(592)
<223> OTHER INFORMATION: Xaa can be any naturally occurring amino acid
<220> FEATURE:
<221> NAME/KEY: VARIANT
<222> LOCATION: (593)..(598)
<223> OTHER INFORMATION: Xaa can be any naturally occurring amino acid
       or absent

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Met Xaa Xaa Xaa Xaa Xaa Xaa Xaa Ala Gln Xaa Xaa Xaa Xaa Xaa Xaa
            20                  25                  30

Xaa Xaa Xaa Xaa Xaa Xaa Xaa Xaa Xaa Gly Phe Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Ala Gln Xaa Asn Xaa Xaa
                85                  90                  95

Xaa Xaa Xaa Xaa Val Xaa Phe Xaa Xaa Gln Xaa Xaa Ala Arg Xaa Xaa
            100                 105                 110

Xaa Leu Asn Arg Pro Xaa Lys Leu Asn Ala Leu Asn Xaa Xaa Met Xaa
        115                 120                 125

Xaa Xaa Xaa Phe Xaa Xaa Leu Asn Glu Tyr Xaa Lys Ser Xaa Xaa Xaa
    130                 135                 140

Asn Xaa Xaa Xaa Xaa Xaa Ser Xaa Asn Gln Pro Arg Xaa Xaa Cys Ala
145                 150                 155                 160

Gly Gly Asp Val Ala Xaa Xaa Ala Xaa Xaa Asn Xaa Xaa Xaa Xaa Phe
                165                 170                 175
```

```
Xaa Xaa Xaa Xaa Xaa Xaa Phe Phe Xaa Xaa Xaa Tyr Ser Xaa Asn
            180              185                190

Phe Gln Xaa Ala Thr Tyr Xaa Lys Pro Xaa Xaa Xaa Met Xaa Gly
        195                 200             205

Ile Thr Met Gly Gly Val Gly Xaa Xaa Xaa His Xaa Pro Phe Arg
    210             215                 220

Xaa Ala Thr Glu Asn Thr Xaa Trp Ala Met Pro Glu Met Asp Ile Gly
225             230              235             240

Phe Phe Pro Asp Val Gly Xaa Xaa Phe Ala Xaa Pro Xaa Xaa Xaa
                245             250             255

Xaa Ala Asn Xaa Xaa Xaa Gln Xaa Ala Xaa Tyr Leu Cys Xaa Thr Gly
        260             265                 270

Xaa Xaa Xaa Xaa Gly Xaa Xaa Ala Tyr Xaa Xaa Gly Xaa Ala Ser His
            275             280             285

Tyr Xaa Xaa Xaa Xaa Asn Xaa Xaa Xaa Leu Xaa Xaa Arg Leu Gly Glu
    290             295             300

Xaa Xaa Pro Xaa Xaa Xaa Xaa Xaa Xaa Xaa Xaa Xaa Gln Xaa
305             310             315                 320

Xaa Xaa Phe Phe Xaa Xaa Xaa Asn Xaa Xaa Xaa Xaa Glu Phe Xaa Xaa
            325             330                 335

Pro Xaa Xaa Pro Xaa Xaa Tyr Xaa Phe Xaa Tyr Xaa Asn Xaa Xaa Leu
        340             345             350

Xaa Val Ile Xaa Xaa Cys Phe Xaa Xaa Xaa Xaa Xaa Xaa Xaa
    355             360             365

Xaa Xaa Xaa Xaa Xaa Leu Xaa Xaa Xaa Xaa Xaa Xaa Tyr Xaa Gly
370              375             380

Xaa Xaa Xaa Ala Xaa Xaa Phe Ala Xaa Xaa Xaa Xaa Xaa Leu Xaa
385             390             395             400

Xaa Lys Ser Pro Xaa Ser Xaa Gln Xaa Ala Xaa Xaa Xaa Xaa Xaa
        405             410             415

Asn Xaa Xaa Xaa Xaa Xaa Xaa Ala Xaa Xaa Xaa Asp Leu Xaa Thr
        420             425             430

Ala Xaa Asn Met Cys Xaa Asn Xaa Xaa Xaa Gln Xaa Xaa Xaa Xaa
    435             440             445

Glu Phe Xaa Xaa Ala Xaa Xaa Xaa Lys Leu Xaa Xaa Lys Gln Xaa Xaa
    450             455             460

Pro Tyr Pro Trp Xaa Xaa Xaa Xaa Xaa Xaa Xaa Xaa Gln Xaa
465             470             475             480

Xaa Xaa Xaa Xaa Xaa Pro Xaa Pro Xaa Xaa Pro Xaa Xaa Leu Xaa Xaa
            485             490             495

Asn Xaa Xaa Asn Xaa Thr Trp Xaa Xaa Tyr Pro Xaa Xaa Xaa Tyr
        500             505             510

Gln Leu Pro Xaa Xaa Xaa Xaa Xaa Gln Tyr Xaa Xaa Xaa Xaa
        515             520             525

Asn Xaa Asn Xaa Xaa Xaa Gly Xaa Xaa Xaa Xaa Xaa Xaa Xaa
    530             535             540

Xaa Xaa Xaa Xaa Xaa Xaa Phe Xaa Asn Xaa Asn Xaa Xaa Xaa Xaa
545             550             555             560

Lys Xaa Gly Xaa Xaa Xaa Xaa Xaa Xaa Xaa Xaa Xaa Xaa Xaa Cys
        565             570             575

Xaa Xaa Xaa Xaa Ala Xaa Gly Gly Xaa Xaa Trp Xaa Xaa Xaa Xaa
        580             585             590

Xaa Xaa Xaa Xaa Xaa Xaa
```

```
                595

<210> SEQ ID NO 8
<211> LENGTH: 351
<212> TYPE: PRT
<213> ORGANISM: Artificial Sequence
<220> FEATURE:
<223> OTHER INFORMATION: Bacillus EC 3.1.2.4 malonyl-CoA hydrolase
      consensus sequence
<220> FEATURE:
<221> NAME/KEY: VARIANT
<222> LOCATION: (4)..(4)
<223> OTHER INFORMATION: Arg, Lys or His
<220> FEATURE:
<221> NAME/KEY: VARIANT
<222> LOCATION: (9)..(9)
<223> OTHER INFORMATION: Ile, Leu or Val
<220> FEATURE:
<221> NAME/KEY: VARIANT
<222> LOCATION: (10)..(10)
<223> OTHER INFORMATION: Ser or Thr
<220> FEATURE:
<221> NAME/KEY: VARIANT
<222> LOCATION: (11)..(11)
<223> OTHER INFORMATION: Asp or Glu
<220> FEATURE:
<221> NAME/KEY: VARIANT
<222> LOCATION: (16)..(16)
<223> OTHER INFORMATION: Ser or Thr
<220> FEATURE:
<221> NAME/KEY: VARIANT
<222> LOCATION: (31)..(31)
<223> OTHER INFORMATION: Asp or Glu
<220> FEATURE:
<221> NAME/KEY: VARIANT
<222> LOCATION: (45)..(45)
<223> OTHER INFORMATION: Arg, Lys or His
<220> FEATURE:
<221> NAME/KEY: VARIANT
<222> LOCATION: (46)..(47)
<223> OTHER INFORMATION: Asp or Glu
<220> FEATURE:
<221> NAME/KEY: VARIANT
<222> LOCATION: (48)..(48)
<223> OTHER INFORMATION: Arg, Lys or His
<220> FEATURE:
<221> NAME/KEY: VARIANT
<222> LOCATION: (51)..(51)
<223> OTHER INFORMATION: Ile, Leu or Val
<220> FEATURE:
<221> NAME/KEY: VARIANT
<222> LOCATION: (59)..(59)
<223> OTHER INFORMATION: Ser or Thr
<220> FEATURE:
<221> NAME/KEY: VARIANT
<222> LOCATION: (79)..(79)
<223> OTHER INFORMATION: Ile, Leu or Val
<220> FEATURE:
<221> NAME/KEY: VARIANT
<222> LOCATION: (83)..(83)
<223> OTHER INFORMATION: Arg, Lys or His
<220> FEATURE:
<221> NAME/KEY: VARIANT
<222> LOCATION: (86)..(86)
<223> OTHER INFORMATION: Arg, Lys or His
<220> FEATURE:
<221> NAME/KEY: VARIANT
<222> LOCATION: (89)..(89)
<223> OTHER INFORMATION: Asp or Glu
<220> FEATURE:
<221> NAME/KEY: VARIANT
<222> LOCATION: (91)..(91)
<223> OTHER INFORMATION: Ala, Asp, Arg, His, Lys, Ser, Thr, Asn, Gln,
      Tyr
<220> FEATURE:
<221> NAME/KEY: VARIANT
<222> LOCATION: (93)..(93)
<223> OTHER INFORMATION: Asp or Glu
```

```
<220> FEATURE:
<221> NAME/KEY: VARIANT
<222> LOCATION: (98)..(98)
<223> OTHER INFORMATION: Ile, Leu or Val
<220> FEATURE:
<221> NAME/KEY: VARIANT
<222> LOCATION: (102)..(102)
<223> OTHER INFORMATION: Arg, Lys or His
<220> FEATURE:
<221> NAME/KEY: VARIANT
<222> LOCATION: (125)..(125)
<223> OTHER INFORMATION: Arg, Lys or His
<220> FEATURE:
<221> NAME/KEY: VARIANT
<222> LOCATION: (131)..(131)
<223> OTHER INFORMATION: Asp or Glu
<220> FEATURE:
<221> NAME/KEY: VARIANT
<222> LOCATION: (132)..(132)
<223> OTHER INFORMATION: Arg, Lys or His
<220> FEATURE:
<221> NAME/KEY: VARIANT
<222> LOCATION: (156)..(156)
<223> OTHER INFORMATION: Arg, Lys or His
<220> FEATURE:
<221> NAME/KEY: VARIANT
<222> LOCATION: (161)..(161)
<223> OTHER INFORMATION: Ser or Thr
<220> FEATURE:
<221> NAME/KEY: VARIANT
<222> LOCATION: (163)..(163)
<223> OTHER INFORMATION: Arg, Lys or His
<220> FEATURE:
<221> NAME/KEY: VARIANT
<222> LOCATION: (168)..(168)
<223> OTHER INFORMATION: Ser or Thr
<220> FEATURE:
<221> NAME/KEY: VARIANT
<222> LOCATION: (170)..(170)
<223> OTHER INFORMATION: Ser or Thr
<220> FEATURE:
<221> NAME/KEY: VARIANT
<222> LOCATION: (171)..(171)
<223> OTHER INFORMATION: Ile, Leu or Val
<220> FEATURE:
<221> NAME/KEY: VARIANT
<222> LOCATION: (175)..(175)
<223> OTHER INFORMATION: Ser or Thr
<220> FEATURE:
<221> NAME/KEY: VARIANT
<222> LOCATION: (188)..(189)
<223> OTHER INFORMATION: Ser or Thr
<220> FEATURE:
<221> NAME/KEY: VARIANT
<222> LOCATION: (190)..(190)
<223> OTHER INFORMATION: Asp or Glu
<220> FEATURE:
<221> NAME/KEY: VARIANT
<222> LOCATION: (191)..(191)
<223> OTHER INFORMATION: Ser or Thr
<220> FEATURE:
<221> NAME/KEY: VARIANT
<222> LOCATION: (194)..(194)
<223> OTHER INFORMATION: Arg, Lys or His
<220> FEATURE:
<221> NAME/KEY: VARIANT
<222> LOCATION: (197)..(197)
<223> OTHER INFORMATION: Ser or Thr
<220> FEATURE:
<221> NAME/KEY: VARIANT
<222> LOCATION: (198)..(198)
<223> OTHER INFORMATION: Asp or Glu
<220> FEATURE:
<221> NAME/KEY: VARIANT
<222> LOCATION: (199)..(199)
<223> OTHER INFORMATION: Ile, Leu or Val
<220> FEATURE:
<221> NAME/KEY: VARIANT
<222> LOCATION: (200)..(200)
```

```
<223> OTHER INFORMATION: Asp or Glu
<220> FEATURE:
<221> NAME/KEY: VARIANT
<222> LOCATION: (200)..(200)
<223> OTHER INFORMATION: Ser or Thr
<220> FEATURE:
<221> NAME/KEY: VARIANT
<222> LOCATION: (201)..(201)
<223> OTHER INFORMATION: Ser or Thr
<220> FEATURE:
<221> NAME/KEY: VARIANT
<222> LOCATION: (202)..(202)
<223> OTHER INFORMATION: Ile, Leu or Val
<220> FEATURE:
<221> NAME/KEY: VARIANT
<222> LOCATION: (205)..(206)
<223> OTHER INFORMATION: Arg, Lys or His
<220> FEATURE:
<221> NAME/KEY: VARIANT
<222> LOCATION: (207)..(209)
<223> OTHER INFORMATION: Asp or Glu
<220> FEATURE:
<221> NAME/KEY: VARIANT
<222> LOCATION: (211)..(211)
<223> OTHER INFORMATION: Arg, Lys or His
<220> FEATURE:
<221> NAME/KEY: VARIANT
<222> LOCATION: (212)..(212)
<223> OTHER INFORMATION: Ser or Thr
<220> FEATURE:
<221> NAME/KEY: VARIANT
<222> LOCATION: (213)..(213)
<223> OTHER INFORMATION: Arg, Lys or His
<220> FEATURE:
<221> NAME/KEY: VARIANT
<222> LOCATION: (216)..(216)
<223> OTHER INFORMATION: Asp or Glu
<220> FEATURE:
<221> NAME/KEY: VARIANT
<222> LOCATION: (217)..(218)
<223> OTHER INFORMATION: Ile, Leu or Val
<220> FEATURE:
<221> NAME/KEY: VARIANT
<222> LOCATION: (219)..(219)
<223> OTHER INFORMATION: Arg, Lys or His
<220> FEATURE:
<221> NAME/KEY: VARIANT
<222> LOCATION: (220)..(220)
<223> OTHER INFORMATION: Ser or Thr
<220> FEATURE:
<221> NAME/KEY: VARIANT
<222> LOCATION: (223)..(226)
<223> OTHER INFORMATION: Ser or Thr
<220> FEATURE:
<221> NAME/KEY: VARIANT
<222> LOCATION: (227)..(227)
<223> OTHER INFORMATION: Ile, Leu or Val
<220> FEATURE:
<221> NAME/KEY: VARIANT
<222> LOCATION: (228)..(228)
<223> OTHER INFORMATION: Asp or Glu
<220> FEATURE:
<221> NAME/KEY: VARIANT
<222> LOCATION: (229)..(229)
<223> OTHER INFORMATION: Ser or Thr
<220> FEATURE:
<221> NAME/KEY: VARIANT
<222> LOCATION: (230)..(230)
<223> OTHER INFORMATION: Asp or Glu
<220> FEATURE:
<221> NAME/KEY: VARIANT
<222> LOCATION: (232)..(233)
<223> OTHER INFORMATION: Ser or Thr
<220> FEATURE:
<221> NAME/KEY: VARIANT
<222> LOCATION: (234)..(235)
<223> OTHER INFORMATION: Ile, Leu or Val
<220> FEATURE:
<221> NAME/KEY: VARIANT
```

```
<222> LOCATION: (237)..(237)
<223> OTHER INFORMATION: Asp or Glu
<220> FEATURE:
<221> NAME/KEY: VARIANT
<222> LOCATION: (238)..(238)
<223> OTHER INFORMATION: Ile, Leu or Val
<220> FEATURE:
<221> NAME/KEY: VARIANT
<222> LOCATION: (240)..(240)
<223> OTHER INFORMATION: Ser or Thr
<220> FEATURE:
<221> NAME/KEY: VARIANT
<222> LOCATION: (245)..(245)
<223> OTHER INFORMATION: Asp or Glu
<220> FEATURE:
<221> NAME/KEY: VARIANT
<222> LOCATION: (246)..(246)
<223> OTHER INFORMATION: Ser or Thr
<220> FEATURE:
<221> NAME/KEY: VARIANT
<222> LOCATION: (247)..(247)
<223> OTHER INFORMATION: Ile, Leu or Val
<220> FEATURE:
<221> NAME/KEY: VARIANT
<222> LOCATION: (249)..(249)
<223> OTHER INFORMATION: Asp or Glu
<220> FEATURE:
<221> NAME/KEY: VARIANT
<222> LOCATION: (252)..(252)
<223> OTHER INFORMATION: Arg, Lys or His
<220> FEATURE:
<221> NAME/KEY: VARIANT
<222> LOCATION: (256)..(256)
<223> OTHER INFORMATION: Arg, Lys or His
<220> FEATURE:
<221> NAME/KEY: VARIANT
<222> LOCATION: (257)..(257)
<223> OTHER INFORMATION: Asp or Glu
<220> FEATURE:
<221> NAME/KEY: VARIANT
<222> LOCATION: (259)..(260)
<223> OTHER INFORMATION: Ser or Thr
<220> FEATURE:
<221> NAME/KEY: VARIANT
<222> LOCATION: (263)..(263)
<223> OTHER INFORMATION: Ile, Leu or Val
<220> FEATURE:
<221> NAME/KEY: VARIANT
<222> LOCATION: (264)..(264)
<223> OTHER INFORMATION: Arg, Lys or His
<220> FEATURE:
<221> NAME/KEY: VARIANT
<222> LOCATION: (265)..(265)
<223> OTHER INFORMATION: Ser or Thr
<220> FEATURE:
<221> NAME/KEY: VARIANT
<222> LOCATION: (266)..(266)
<223> OTHER INFORMATION: Arg, Lys or His
<220> FEATURE:
<221> NAME/KEY: VARIANT
<222> LOCATION: (267)..(267)
<223> OTHER INFORMATION: Asp or Glu
<220> FEATURE:
<221> NAME/KEY: VARIANT
<222> LOCATION: (268)..(268)
<223> OTHER INFORMATION: Ser or Thr
<220> FEATURE:
<221> NAME/KEY: VARIANT
<222> LOCATION: (275)..(275)
<223> OTHER INFORMATION: Ile, Leu or Val
<220> FEATURE:
<221> NAME/KEY: VARIANT
<222> LOCATION: (285)..(285)
<223> OTHER INFORMATION: Ile, Leu or Val
<220> FEATURE:
<221> NAME/KEY: VARIANT
<222> LOCATION: (286)..(286)
<223> OTHER INFORMATION: Asp or Glu
<220> FEATURE:
```

```
<221> NAME/KEY: VARIANT
<222> LOCATION: (288)..(288)
<223> OTHER INFORMATION: Arg, Lys or His
<220> FEATURE:
<221> NAME/KEY: VARIANT
<222> LOCATION: (289)..(289)
<223> OTHER INFORMATION: Asp or Glu
<220> FEATURE:
<221> NAME/KEY: VARIANT
<222> LOCATION: (292)..(292)
<223> OTHER INFORMATION: Ile, Leu or Val
<220> FEATURE:
<221> NAME/KEY: VARIANT
<222> LOCATION: (294)..(294)
<223> OTHER INFORMATION: Asp or Glu
<220> FEATURE:
<221> NAME/KEY: VARIANT
<222> LOCATION: (301)..(301)
<223> OTHER INFORMATION: Ile, Leu or Val
<220> FEATURE:
<221> NAME/KEY: VARIANT
<222> LOCATION: (310)..(310)
<223> OTHER INFORMATION: Asp or Glu
<220> FEATURE:
<221> NAME/KEY: VARIANT
<222> LOCATION: (319)..(319)
<223> OTHER INFORMATION: Ile, Leu or Val
<220> FEATURE:
<221> NAME/KEY: VARIANT
<222> LOCATION: (321)..(321)
<223> OTHER INFORMATION: Ile, Leu or Val
<220> FEATURE:
<221> NAME/KEY: VARIANT
<222> LOCATION: (332)..(332)
<223> OTHER INFORMATION: Arg, Lys or His
<220> FEATURE:
<221> NAME/KEY: VARIANT
<222> LOCATION: (334)..(334)
<223> OTHER INFORMATION: Ile, Leu or Val
<220> FEATURE:
<221> NAME/KEY: VARIANT
<222> LOCATION: (335)..(335)
<223> OTHER INFORMATION: Ser or Thr
<220> FEATURE:
<221> NAME/KEY: VARIANT
<222> LOCATION: (338)..(338)
<223> OTHER INFORMATION: Ser or Thr
<220> FEATURE:
<221> NAME/KEY: VARIANT
<222> LOCATION: (339)..(341)
<223> OTHER INFORMATION: Asp or Glu
<220> FEATURE:
<221> NAME/KEY: VARIANT
<222> LOCATION: (344)..(344)
<223> OTHER INFORMATION: Arg, Lys or His

<400> SEQUENCE: 8

Met Thr Glu Xaa Val Leu Phe Ser Xaa Xaa Xaa Asn Gly Val Ala Xaa
1               5                   10                  15

Ile Thr Leu Asn Arg Pro Lys Ala Leu Asn Ser Leu Ser Tyr Xaa Met
            20                  25                  30

Leu Gln Pro Ile Gly Gln Lys Leu Lys Glu Trp Glu Xaa Xaa Xaa Xaa
        35                  40                  45

Ile Ala Xaa Ile Val Leu Lys Gly Ala Gly Xaa Lys Gly Phe Cys Ala
    50                  55                  60

Gly Gly Asp Ile Lys Thr Leu Tyr Glu Ala Arg Ser Asn Glu Xaa Ala
65                  70                  75                  80

Leu Gln Xaa Ala Glu Xaa Phe Phe Xaa Glu Xaa Tyr Xaa Ile Asp Thr
                85                  90                  95

Tyr Xaa Tyr Gln Tyr Xaa Lys Pro Ile Ile Ala Cys Leu Asp Gly Ile
            100                 105                 110
```

```
Val Met Gly Gly Val Gly Leu Thr Asn Gly Ala Xaa Tyr Arg Ile
            115                 120                 125

Val Thr Xaa Xaa Thr Lys Trp Ala Met Pro Glu Met Asn Ile Gly Phe
130                 135                 140

Phe Pro Asp Val Gly Ala Ala Tyr Phe Leu Asn Xaa Ala Pro Gly Tyr
145                 150                 155                 160

Xaa Gly Xaa Tyr Val Ala Leu Xaa Ala Xaa Xaa Leu Lys Ala Xaa Asp
                165                 170                 175

Val Leu Phe Ile Asn Ala Ala Asp Tyr Phe Met Xaa Xaa Xaa Leu
            180                 185                 190

Pro Xaa Phe Leu Xaa Xaa Xaa Xaa Xaa Asn Trp Xaa Xaa Xaa Xaa
        195                 200                 205

Xaa Val Xaa Xaa Xaa Leu Lys Xaa Xaa Xaa Xaa Xaa Phe Ala Xaa Xaa
210                 215                 220

Xaa Xaa Xaa Xaa Xaa Xaa Leu Xaa Xaa Xaa Xaa Glu Xaa Xaa Asn Xaa
225                 230                 235                 240

His Phe Ala Phe Xaa Xaa Xaa Glu Xaa Ile Ile Xaa Ser Leu Glu Xaa
                245                 250                 255

Xaa Gln Xaa Xaa Phe Ala Xaa Xaa Xaa Xaa Xaa Xaa Leu Leu Ser Lys
        260                 265                 270

Ser Pro Xaa Ser Leu Lys Val Thr Leu Lys Gln Phe Xaa Xaa Gly Xaa
            275                 280                 285

Xaa Lys Ser Xaa Glu Xaa Cys Phe Ala Thr Asp Leu Xaa Leu Ala Lys
290                 295                 300

Asn Phe Met Arg His Xaa Asp Phe Phe Glu Gly Val Arg Ser Xaa Val
305                 310                 315                 320

Xaa Asp Lys Asp Gln Asn Pro Asn Tyr Lys Tyr Xaa Gln Xaa Xaa Asp
            325                 330                 335

Val Xaa Xaa Xaa Xaa Val Asn Xaa Phe Phe Asn Leu Leu Asn Ala
            340                 345                 350

<210> SEQ ID NO 9
<211> LENGTH: 370
<212> TYPE: PRT
<213> ORGANISM: Artificial Sequence
<220> FEATURE:
<223> OTHER INFORMATION: Pseudomonas EC 3.1.2.4 malonyl-CoA hydrolase
      consensus sequence
<220> FEATURE:
<221> NAME/KEY: VARIANT
<222> LOCATION: (3)..(3)
<223> OTHER INFORMATION: Ile, Leu or Val
<220> FEATURE:
<221> NAME/KEY: VARIANT
<222> LOCATION: (4)..(4)
<223> OTHER INFORMATION: Arg, Lys or His
<220> FEATURE:
<221> NAME/KEY: VARIANT
<222> LOCATION: (7)..(7)
<223> OTHER INFORMATION: Asp or Glu
<220> FEATURE:
<221> NAME/KEY: VARIANT
<222> LOCATION: (8)..(8)
<223> OTHER INFORMATION: Arg, Lys or His
<220> FEATURE:
<221> NAME/KEY: VARIANT
<222> LOCATION: (9)..(10)
<223> OTHER INFORMATION: Ser or Thr
<220> FEATURE:
<221> NAME/KEY: VARIANT
<222> LOCATION: (11)..(11)
<223> OTHER INFORMATION: Ile, Leu or Val
<220> FEATURE:
<221> NAME/KEY: VARIANT
```

```
<222> LOCATION: (12)..(12)
<223> OTHER INFORMATION: Arg, Lys or His
<220> FEATURE:
<221> NAME/KEY: VARIANT
<222> LOCATION: (18)..(18)
<223> OTHER INFORMATION: Ile, Leu or Val
<220> FEATURE:
<221> NAME/KEY: VARIANT
<222> LOCATION: (20)..(20)
<223> OTHER INFORMATION: Ser or Thr
<220> FEATURE:
<221> NAME/KEY: VARIANT
<222> LOCATION: (24)..(24)
<223> OTHER INFORMATION: Asp or Glu
<220> FEATURE:
<221> NAME/KEY: VARIANT
<222> LOCATION: (25)..(25)
<223> OTHER INFORMATION: Arg, Lys or His
<220> FEATURE:
<221> NAME/KEY: VARIANT
<222> LOCATION: (26)..(26)
<223> OTHER INFORMATION: Ser or Thr
<220> FEATURE:
<221> NAME/KEY: VARIANT
<222> LOCATION: (31)..(31)
<223> OTHER INFORMATION: Ser or Thr
<220> FEATURE:
<221> NAME/KEY: VARIANT
<222> LOCATION: (36)..(36)
<223> OTHER INFORMATION: Asp or Glu
<220> FEATURE:
<221> NAME/KEY: VARIANT
<222> LOCATION: (37)..(37)
<223> OTHER INFORMATION: Ile, Leu or Val
<220> FEATURE:
<221> NAME/KEY: VARIANT
<222> LOCATION: (40)..(40)
<223> OTHER INFORMATION: Asp or Glu
<220> FEATURE:
<221> NAME/KEY: VARIANT
<222> LOCATION: (41)..(41)
<223> OTHER INFORMATION: Arg, Lys or His
<220> FEATURE:
<221> NAME/KEY: VARIANT
<222> LOCATION: (42)..(42)
<223> OTHER INFORMATION: Ile, Leu or Val
<220> FEATURE:
<221> NAME/KEY: VARIANT
<222> LOCATION: (43)..(43)
<223> OTHER INFORMATION: Arg, Lys or His
<220> FEATURE:
<221> NAME/KEY: VARIANT
<222> LOCATION: (47)..(47)
<223> OTHER INFORMATION: Arg, Lys or His
<220> FEATURE:
<221> NAME/KEY: VARIANT
<222> LOCATION: (48)..(48)
<223> OTHER INFORMATION: Asp or Glu
<220> FEATURE:
<221> NAME/KEY: VARIANT
<222> LOCATION: (51)..(52)
<223> OTHER INFORMATION: Ile, Leu or Val
<220> FEATURE:
<221> NAME/KEY: VARIANT
<222> LOCATION: (55)..(55)
<223> OTHER INFORMATION: Ile, Leu or Val
<220> FEATURE:
<221> NAME/KEY: VARIANT
<222> LOCATION: (69)..(69)
<223> OTHER INFORMATION: Asp or Glu
<220> FEATURE:
<221> NAME/KEY: VARIANT
<222> LOCATION: (71)..(72)
<223> OTHER INFORMATION: Arg, Lys or His
<220> FEATURE:
<221> NAME/KEY: VARIANT
<222> LOCATION: (74)..(74)
<223> OTHER INFORMATION: Ile, Leu or Val
<220> FEATURE:
```

```
-continued

<221> NAME/KEY: VARIANT
<222> LOCATION: (75)..(75)
<223> OTHER INFORMATION: Asp or Glu
<220> FEATURE:
<221> NAME/KEY: VARIANT
<222> LOCATION: (78)..(78)
<223> OTHER INFORMATION: Arg, Lys or His
<220> FEATURE:
<221> NAME/KEY: VARIANT
<222> LOCATION: (79)..(79)
<223> OTHER INFORMATION: Asp or Glu
<220> FEATURE:
<221> NAME/KEY: VARIANT
<222> LOCATION: (80)..(80)
<223> OTHER INFORMATION: Arg, Lys or His
<220> FEATURE:
<221> NAME/KEY: VARIANT
<222> LOCATION: (83)..(83)
<223> OTHER INFORMATION: Asp or Glu
<220> FEATURE:
<221> NAME/KEY: VARIANT
<222> LOCATION: (84)..(84)
<223> OTHER INFORMATION: Ile, Leu or Val
<220> FEATURE:
<221> NAME/KEY: VARIANT
<222> LOCATION: (90)..(90)
<223> OTHER INFORMATION: Arg, Lys or His
<220> FEATURE:
<221> NAME/KEY: VARIANT
<222> LOCATION: (94)..(94)
<223> OTHER INFORMATION: Asp or Glu
<220> FEATURE:
<221> NAME/KEY: VARIANT
<222> LOCATION: (95)..(95)
<223> OTHER INFORMATION: Ala, Asp, Arg, His, Lys, Ser, Thr, Asn, Gln, or
      Tyr
<220> FEATURE:
<221> NAME/KEY: VARIANT
<222> LOCATION: (99)..(99)
<223> OTHER INFORMATION: Asp or Glu
<220> FEATURE:
<221> NAME/KEY: VARIANT
<222> LOCATION: (100)..(100)
<223> OTHER INFORMATION: Arg, Lys or His
<220> FEATURE:
<221> NAME/KEY: VARIANT
<222> LOCATION: (101)..(101)
<223> OTHER INFORMATION: Arg, Lys or His
<220> FEATURE:
<221> NAME/KEY: VARIANT
<222> LOCATION: (102)..(102)
<223> OTHER INFORMATION: Ile, Leu or Val
<220> FEATURE:
<221> NAME/KEY: VARIANT
<222> LOCATION: (104)..(104)
<223> OTHER INFORMATION: Ser or Thr
<220> FEATURE:
<221> NAME/KEY: VARIANT
<222> LOCATION: (109)..(110)
<223> OTHER INFORMATION: Ile, Leu or Val
<220> FEATURE:
<221> NAME/KEY: VARIANT
<222> LOCATION: (116)..(116)
<223> OTHER INFORMATION: Arg, Lys or His
<220> FEATURE:
<221> NAME/KEY: VARIANT
<222> LOCATION: (118)..(118)
<223> OTHER INFORMATION: Ile, Leu or Val
<220> FEATURE:
<221> NAME/KEY: VARIANT
<222> LOCATION: (125)..(125)
<223> OTHER INFORMATION: Ile, Leu or Val
<220> FEATURE:
<221> NAME/KEY: VARIANT
<222> LOCATION: (129)..(129)
<223> OTHER INFORMATION: Ser or Thr
<220> FEATURE:
<221> NAME/KEY: VARIANT
<222> LOCATION: (130)..(130)
```

```
<223> OTHER INFORMATION: Ile, Leu or Val
<220> FEATURE:
<221> NAME/KEY: VARIANT
<222> LOCATION: (136)..(137)
<223> OTHER INFORMATION: Ser or Thr
<220> FEATURE:
<221> NAME/KEY: VARIANT
<222> LOCATION: (144)..(144)
<223> OTHER INFORMATION: Ile, Leu or Val
<220> FEATURE:
<221> NAME/KEY: VARIANT
<222> LOCATION: (145)..(145)
<223> OTHER INFORMATION: Ser or Thr
<220> FEATURE:
<221> NAME/KEY: VARIANT
<222> LOCATION: (159)..(159)
<223> OTHER INFORMATION: Ser or Thr
<220> FEATURE:
<221> NAME/KEY: VARIANT
<222> LOCATION: (161)..(161)
<223> OTHER INFORMATION: Ile, Leu or Val
<220> FEATURE:
<221> NAME/KEY: VARIANT
<222> LOCATION: (164)..(164)
<223> OTHER INFORMATION: Arg, Lys or His
<220> FEATURE:
<221> NAME/KEY: VARIANT
<222> LOCATION: (169)..(169)
<223> OTHER INFORMATION: Ile, Leu or Val
<220> FEATURE:
<221> NAME/KEY: VARIANT
<222> LOCATION: (172)..(172)
<223> OTHER INFORMATION: Ser or Thr
<220> FEATURE:
<221> NAME/KEY: VARIANT
<222> LOCATION: (175)..(175)
<223> OTHER INFORMATION: Arg, Lys or His
<220> FEATURE:
<221> NAME/KEY: VARIANT
<222> LOCATION: (176)..(176)
<223> OTHER INFORMATION: Ile, Leu or Val
<220> FEATURE:
<221> NAME/KEY: VARIANT
<222> LOCATION: (179)..(179)
<223> OTHER INFORMATION: Arg, Lys or His
<220> FEATURE:
<221> NAME/KEY: VARIANT
<222> LOCATION: (182)..(182)
<223> OTHER INFORMATION: Ile, Leu or Val
<220> FEATURE:
<221> NAME/KEY: VARIANT
<222> LOCATION: (185)..(185)
<223> OTHER INFORMATION: Asp or Glu
<220> FEATURE:
<221> NAME/KEY: VARIANT
<222> LOCATION: (191)..(191)
<223> OTHER INFORMATION: Ile, Leu or Val
<220> FEATURE:
<221> NAME/KEY: VARIANT
<222> LOCATION: (192)..(192)
<223> OTHER INFORMATION: Arg, Lys or His
<220> FEATURE:
<221> NAME/KEY: VARIANT
<222> LOCATION: (193)..(193)
<223> OTHER INFORMATION: Asp or Glu
<220> FEATURE:
<221> NAME/KEY: VARIANT
<222> LOCATION: (194)..(194)
<223> OTHER INFORMATION: Arg, Lys or His
<220> FEATURE:
<221> NAME/KEY: VARIANT
<222> LOCATION: (197)..(198)
<223> OTHER INFORMATION: Asp or Glu
<220> FEATURE:
<221> NAME/KEY: VARIANT
<222> LOCATION: (200)..(200)
<223> OTHER INFORMATION: Ile, Leu or Val
<220> FEATURE:
<221> NAME/KEY: VARIANT
```

```
<222> LOCATION: (201)..(202)
<223> OTHER INFORMATION: Asp or Glu
<220> FEATURE:
<221> NAME/KEY: VARIANT
<222> LOCATION: (204)..(204)
<223> OTHER INFORMATION: Ile, Leu or Val
<220> FEATURE:
<221> NAME/KEY: VARIANT
<222> LOCATION: (206)..(206)
<223> OTHER INFORMATION: Ile, Leu or Val
<220> FEATURE:
<221> NAME/KEY: VARIANT
<222> LOCATION: (212)..(212)
<223> OTHER INFORMATION: Ser or Thr
<220> FEATURE:
<221> NAME/KEY: VARIANT
<222> LOCATION: (213)..(213)
<223> OTHER INFORMATION: Asp or Glu
<220> FEATURE:
<221> NAME/KEY: VARIANT
<222> LOCATION: (214)..(214)
<223> OTHER INFORMATION: Ile, Leu or Val
<220> FEATURE:
<221> NAME/KEY: VARIANT
<222> LOCATION: (217)..(217)
<223> OTHER INFORMATION: Arg, Lys or His
<220> FEATURE:
<221> NAME/KEY: VARIANT
<222> LOCATION: (220)..(220)
<223> OTHER INFORMATION: Ile, Leu or Val
<220> FEATURE:
<221> NAME/KEY: VARIANT
<222> LOCATION: (221)..(221)
<223> OTHER INFORMATION: Arg, Lys or His
<220> FEATURE:
<221> NAME/KEY: VARIANT
<222> LOCATION: (223)..(224)
<223> OTHER INFORMATION: Asp or Glu
<220> FEATURE:
<221> NAME/KEY: VARIANT
<222> LOCATION: (225)..(225)
<223> OTHER INFORMATION: Arg, Lys or His
<220> FEATURE:
<221> NAME/KEY: VARIANT
<222> LOCATION: (226)..(226)
<223> OTHER INFORMATION: Arg, Lys or His
<220> FEATURE:
<221> NAME/KEY: VARIANT
<222> LOCATION: (228)..(228)
<223> OTHER INFORMATION: Arg, Lys or His
<220> FEATURE:
<221> NAME/KEY: VARIANT
<222> LOCATION: (229)..(230)
<223> OTHER INFORMATION: Asp or Glu
<220> FEATURE:
<221> NAME/KEY: VARIANT
<222> LOCATION: (231)..(231)
<223> OTHER INFORMATION: Ile, Leu or Val
<220> FEATURE:
<221> NAME/KEY: VARIANT
<222> LOCATION: (233)..(233)
<223> OTHER INFORMATION: Asp or Glu
<220> FEATURE:
<221> NAME/KEY: VARIANT
<222> LOCATION: (236)..(236)
<223> OTHER INFORMATION: Ile, Leu or Val
<220> FEATURE:
<221> NAME/KEY: VARIANT
<222> LOCATION: (242)..(242)
<223> OTHER INFORMATION: Arg, Lys or His
<220> FEATURE:
<221> NAME/KEY: VARIANT
<222> LOCATION: (243)..(243)
<223> OTHER INFORMATION: Ile, Leu or Val
<220> FEATURE:
<221> NAME/KEY: VARIANT
<222> LOCATION: (245)..(245)
<223> OTHER INFORMATION: Asp or Glu
<220> FEATURE:
```

```
<221> NAME/KEY: VARIANT
<222> LOCATION: (246)..(246)
<223> OTHER INFORMATION: Ile, Leu or Val
<220> FEATURE:
<221> NAME/KEY: VARIANT
<222> LOCATION: (249)..(249)
<223> OTHER INFORMATION: Ile, Leu or Val
<220> FEATURE:
<221> NAME/KEY: VARIANT
<222> LOCATION: (251)..(251)
<223> OTHER INFORMATION: Asp or Glu
<220> FEATURE:
<221> NAME/KEY: VARIANT
<222> LOCATION: (252)..(252)
<223> OTHER INFORMATION: Ile, Leu or Val
<220> FEATURE:
<221> NAME/KEY: VARIANT
<222> LOCATION: (254)..(254)
<223> OTHER INFORMATION: Ser or Thr
<220> FEATURE:
<221> NAME/KEY: VARIANT
<222> LOCATION: (257)..(257)
<223> OTHER INFORMATION: Arg, Lys or His
<220> FEATURE:
<221> NAME/KEY: VARIANT
<222> LOCATION: (259)..(259)
<223> OTHER INFORMATION: Ile, Leu or Val
<220> FEATURE:
<221> NAME/KEY: VARIANT
<222> LOCATION: (260)..(260)
<223> OTHER INFORMATION: Asp or Glu
<220> FEATURE:
<221> NAME/KEY: VARIANT
<222> LOCATION: (262)..(262)
<223> OTHER INFORMATION: Ile, Leu or Val
<220> FEATURE:
<221> NAME/KEY: VARIANT
<222> LOCATION: (263)..(263)
<223> OTHER INFORMATION: Arg, Lys or His
<220> FEATURE:
<221> NAME/KEY: VARIANT
<222> LOCATION: (264)..(264)
<223> OTHER INFORMATION: Asp or Glu
<220> FEATURE:
<221> NAME/KEY: VARIANT
<222> LOCATION: (265)..(265)
<223> OTHER INFORMATION: Arg, Lys or His
<220> FEATURE:
<221> NAME/KEY: VARIANT
<222> LOCATION: (266)..(266)
<223> OTHER INFORMATION: Asp or Glu
<220> FEATURE:
<221> NAME/KEY: VARIANT
<222> LOCATION: (270)..(270)
<223> OTHER INFORMATION: Ile, Leu or Val
<220> FEATURE:
<221> NAME/KEY: VARIANT
<222> LOCATION: (272)..(272)
<223> OTHER INFORMATION: Arg, Lys or His
<220> FEATURE:
<221> NAME/KEY: VARIANT
<222> LOCATION: (275)..(276)
<223> OTHER INFORMATION: Arg, Lys or His
<220> FEATURE:
<221> NAME/KEY: VARIANT
<222> LOCATION: (277)..(277)
<223> OTHER INFORMATION: Ile, Leu or Val
<220> FEATURE:
<221> NAME/KEY: VARIANT
<222> LOCATION: (278)..(278)
<223> OTHER INFORMATION: Arg, Lys or His
<220> FEATURE:
<221> NAME/KEY: VARIANT
<222> LOCATION: (279)..(279)
<223> OTHER INFORMATION: Asp or Glu
<220> FEATURE:
<221> NAME/KEY: VARIANT
<222> LOCATION: (283)..(283)
<223> OTHER INFORMATION: Ile, Leu or Val
```

-continued

```
<220> FEATURE:
<221> NAME/KEY: VARIANT
<222> LOCATION: (284)..(284)
<223> OTHER INFORMATION: Ser or Thr
<220> FEATURE:
<221> NAME/KEY: VARIANT
<222> LOCATION: (286)..(286)
<223> OTHER INFORMATION: Arg, Lys or His
<220> FEATURE:
<221> NAME/KEY: VARIANT
<222> LOCATION: (287)..(287)
<223> OTHER INFORMATION: Ile, Leu or Val
<220> FEATURE:
<221> NAME/KEY: VARIANT
<222> LOCATION: (290)..(290)
<223> OTHER INFORMATION: Asp or Glu
<220> FEATURE:
<221> NAME/KEY: VARIANT
<222> LOCATION: (292)..(292)
<223> OTHER INFORMATION: Ile, Leu or Val
<220> FEATURE:
<221> NAME/KEY: VARIANT
<222> LOCATION: (293)..(293)
<223> OTHER INFORMATION: Arg, Lys or His
<220> FEATURE:
<221> NAME/KEY: VARIANT
<222> LOCATION: (297)..(297)
<223> OTHER INFORMATION: Arg, Lys or His
<220> FEATURE:
<221> NAME/KEY: VARIANT
<222> LOCATION: (302)..(302)
<223> OTHER INFORMATION: Asp or Glu
<220> FEATURE:
<221> NAME/KEY: VARIANT
<222> LOCATION: (303)..(303)
<223> OTHER INFORMATION: Ile, Leu or Val
<220> FEATURE:
<221> NAME/KEY: VARIANT
<222> LOCATION: (305)..(305)
<223> OTHER INFORMATION: Arg, Lys or His
<220> FEATURE:
<221> NAME/KEY: VARIANT
<222> LOCATION: (309)..(309)
<223> OTHER INFORMATION: Ser or Thr
<220> FEATURE:
<221> NAME/KEY: VARIANT
<222> LOCATION: (310)..(310)
<223> OTHER INFORMATION: Ile, Leu or Val
<220> FEATURE:
<221> NAME/KEY: VARIANT
<222> LOCATION: (319)..(319)
<223> OTHER INFORMATION: Asp or Glu
<220> FEATURE:
<221> NAME/KEY: VARIANT
<222> LOCATION: (321)..(321)
<223> OTHER INFORMATION: Ser or Thr
<220> FEATURE:
<221> NAME/KEY: VARIANT
<222> LOCATION: (329)..(329)
<223> OTHER INFORMATION: Ile, Leu or Val
<220> FEATURE:
<221> NAME/KEY: VARIANT
<222> LOCATION: (331)..(331)
<223> OTHER INFORMATION: Arg, Lys or His
<220> FEATURE:
<221> NAME/KEY: VARIANT
<222> LOCATION: (333)..(333)
<223> OTHER INFORMATION: Arg, Lys or His
<220> FEATURE:
<221> NAME/KEY: VARIANT
<222> LOCATION: (336)..(336)
<223> OTHER INFORMATION: Arg, Lys or His
<220> FEATURE:
<221> NAME/KEY: VARIANT
<222> LOCATION: (338)..(338)
<223> OTHER INFORMATION: Arg, Lys or His
<220> FEATURE:
<221> NAME/KEY: VARIANT
<222> LOCATION: (341)..(341)
```

```
<223> OTHER INFORMATION: Asp or Glu
<220> FEATURE:
<221> NAME/KEY: VARIANT
<222> LOCATION: (342)..(342)
<223> OTHER INFORMATION: Ile, Leu or Val
<220> FEATURE:
<221> NAME/KEY: VARIANT
<222> LOCATION: (345)..(345)
<223> OTHER INFORMATION: Ile, Leu or Val
<220> FEATURE:
<221> NAME/KEY: VARIANT
<222> LOCATION: (347)..(347)
<223> OTHER INFORMATION: Asp or Glu
<220> FEATURE:
<221> NAME/KEY: VARIANT
<222> LOCATION: (349)..(350)
<223> OTHER INFORMATION: Ile, Leu or Val
<220> FEATURE:
<221> NAME/KEY: VARIANT
<222> LOCATION: (350)..(350)
<223> OTHER INFORMATION: Ile, Leu or Val
<220> FEATURE:
<221> NAME/KEY: VARIANT
<222> LOCATION: (351)..(351)
<223> OTHER INFORMATION: Asp or Glu
<220> FEATURE:
<221> NAME/KEY: VARIANT
<222> LOCATION: (355)..(355)
<223> OTHER INFORMATION: Asp or Glu
<220> FEATURE:
<221> NAME/KEY: VARIANT
<222> LOCATION: (356)..(356)
<223> OTHER INFORMATION: Arg, Lys or His
<220> FEATURE:
<221> NAME/KEY: VARIANT
<222> LOCATION: (357)..(357)
<223> OTHER INFORMATION: Ile, Leu or Val
<220> FEATURE:
<221> NAME/KEY: VARIANT
<222> LOCATION: (357)..(357)
<223> OTHER INFORMATION: Ile, Leu or Val
<220> FEATURE:
<221> NAME/KEY: VARIANT
<222> LOCATION: (359)..(359)
<223> OTHER INFORMATION: Asp or Glu
<220> FEATURE:
<221> NAME/KEY: VARIANT
<222> LOCATION: (361)..(362)
<223> OTHER INFORMATION: Arg, Lys or His
<220> FEATURE:
<221> NAME/KEY: VARIANT
<222> LOCATION: (364)..(364)
<223> OTHER INFORMATION: Ile, Leu or Val
<220> FEATURE:
<221> NAME/KEY: VARIANT
<222> LOCATION: (364)..(364)
<223> OTHER INFORMATION: Ile, Leu or Val
<220> FEATURE:
<221> NAME/KEY: VARIANT
<222> LOCATION: (366)..(366)
<223> OTHER INFORMATION: Asp or Glu
<220> FEATURE:
<221> NAME/KEY: VARIANT
<222> LOCATION: (367)..(367)
<223> OTHER INFORMATION: Ile, Leu or Val
<220> FEATURE:
<221> NAME/KEY: VARIANT
<222> LOCATION: (367)..(367)
<223> OTHER INFORMATION: Ile, Leu or Val
<220> FEATURE:
<221> NAME/KEY: VARIANT
<222> LOCATION: (368)..(368)
<223> OTHER INFORMATION: Ser or Thr
<220> FEATURE:
<221> NAME/KEY: VARIANT
<222> LOCATION: (369)..(370)
<223> OTHER INFORMATION: Xaa can be any naturally occurring amino acid

<400> SEQUENCE: 9
```

```
Met Asn Xaa Xaa Phe Glu Xaa Xaa Xaa Xaa Gly Ala Arg Ile
1               5                  10                  15

Gly Xaa Ala Xaa Leu Asp Ala Xaa Xaa Xaa Leu Asn Ala Xaa Leu
            20                  25                  30

Pro Met Ile Xaa Xaa Leu Gly Xaa Xaa Xaa Ala Trp Ala Xaa Xaa
            35                  40                  45

Pro Gly Xaa Xaa Cys Val Xaa Leu Arg Gly Asn Gly Ala Lys Ala Phe
    50                  55                  60

Cys Ala Gly Gly Xaa Val Xaa Xaa Leu Xaa Xaa Ala Cys Xaa Xaa Xaa
65                  70                  75                  80

Pro Gly Xaa Xaa Pro Pro Leu Ala Ala Xaa Phe Phe Ala Xaa Xaa Tyr
            85                  90                  95

Arg Leu Xaa Xaa Xaa Xaa His Xaa Tyr Pro Lys Pro Xaa Xaa Cys Trp
            100                 105                 110

Gly His Gly Xaa Val Xaa Gly Gly Gly Met Gly Leu Xaa Gln Gly Ala
        115                 120                 125

Xaa Xaa Arg Ile Val Thr Pro Xaa Xaa Arg Leu Ala Met Pro Glu Xaa
130                 135                 140

Xaa Ile Gly Leu Tyr Pro Asp Val Gly Ala Ser Trp Phe Leu Xaa Arg
145                 150                 155                 160

Xaa Pro Gly Xaa Leu Gly Leu Phe Xaa Gly Leu Xaa Gly Ala Xaa Xaa
            165                 170                 175

Asn Ala Xaa Asp Ala Xaa Asp Leu Xaa Leu Ala Asp Arg Phe Xaa Xaa
            180                 185                 190

Xaa Xaa Gln Gln Xaa Xaa Leu Xaa Xaa Xaa Leu Xaa Gln Xaa Asn Trp
            195                 200                 205

Gln Glu Gln Xaa Xaa Xaa Gln Leu Xaa Ser Leu Xaa Xaa Ala Xaa Xaa
        210                 215                 220

Xaa Xaa Ala Xaa Xaa Xaa Xaa Pro Xaa Ala Gln Xaa Leu Pro Arg Arg
225                 230                 235                 240

Gln Xaa Xaa Asp Xaa Xaa Leu Asp Xaa Ala Xaa Xaa Ala Xaa Ala Trp
            245                 250                 255

Xaa Ala Xaa Xaa Ala Xaa Xaa Xaa Xaa Asp Pro Leu Xaa Ala Xaa
            260                 265                 270

Ala Ala Xaa Xaa Xaa Xaa Xaa Gly Cys Pro Xaa Xaa Ala Xaa Xaa Val
    275                 280                 285

Trp Xaa Gln Xaa Xaa Arg Ala Arg Xaa Leu Ser Leu Ala Xaa Xaa Phe
    290                 295                 300

Xaa Met Glu Tyr Xaa Xaa Ser Leu Asn Cys Cys Arg His Pro Xaa Phe
305                 310                 315                 320

Xaa Glu Gly Val Arg Ala Arg Leu Xaa Asp Xaa Asp Xaa Gln Pro Xaa
            325                 330                 335

Trp Xaa Trp Pro Xaa Xaa Ala Gln Xaa Pro Xaa Ala Xaa Xaa Xaa Ala
        340                 345                 350

His Phe Xaa Xaa Xaa Trp Xaa Gly Xaa Xaa Pro Xaa Ala Xaa Xaa Xaa
        355                 360                 365

Xaa Xaa
    370

<210> SEQ ID NO 10
<211> LENGTH: 505
<212> TYPE: PRT
<213> ORGANISM: Artificial Sequence
<220> FEATURE:
```

```
<223> OTHER INFORMATION: General bacterial EC 3.1.2.4 malonyl-CoA
      hydrolase consensus sequence
<220> FEATURE:
<221> NAME/KEY: VARIANT
<222> LOCATION: (1)..(10)
<223> OTHER INFORMATION: Xaa can be any naturally occurring amino acid
      or absent
<220> FEATURE:
<221> NAME/KEY: VARIANT
<222> LOCATION: (11)..(11)
<223> OTHER INFORMATION: Xaa can be any naturally occurring amino acid
<220> FEATURE:
<221> NAME/KEY: VARIANT
<222> LOCATION: (12)..(23)
<223> OTHER INFORMATION: Xaa can be any naturally occurring amino acid
      or absent
<220> FEATURE:
<221> NAME/KEY: VARIANT
<222> LOCATION: (24)..(24)
<223> OTHER INFORMATION: Xaa can be any naturally occurring amino acid
<220> FEATURE:
<221> NAME/KEY: VARIANT
<222> LOCATION: (25)..(30)
<223> OTHER INFORMATION: Xaa can be any naturally occurring amino acid
      or absent
<220> FEATURE:
<221> NAME/KEY: VARIANT
<222> LOCATION: (32)..(32)
<223> OTHER INFORMATION: Xaa can be any naturally occurring amino acid
<220> FEATURE:
<221> NAME/KEY: VARIANT
<222> LOCATION: (34)..(35)
<223> OTHER INFORMATION: Xaa can be any naturally occurring amino acid
      or absent
<220> FEATURE:
<221> NAME/KEY: VARIANT
<222> LOCATION: (39)..(40)
<223> OTHER INFORMATION: Ile, Leu or Val
<220> FEATURE:
<221> NAME/KEY: VARIANT
<222> LOCATION: (42)..(42)
<223> OTHER INFORMATION: Ser or Thr
<220> FEATURE:
<221> NAME/KEY: VARIANT
<222> LOCATION: (43)..(43)
<223> OTHER INFORMATION: Ile, Leu or Val
<220> FEATURE:
<221> NAME/KEY: VARIANT
<222> LOCATION: (48)..(48)
<223> OTHER INFORMATION: Ile, Leu or Val
<220> FEATURE:
<221> NAME/KEY: VARIANT
<222> LOCATION: (52)..(52)
<223> OTHER INFORMATION: Ser or Thr
<220> FEATURE:
<221> NAME/KEY: VARIANT
<222> LOCATION: (57)..(57)
<223> OTHER INFORMATION: Arg, Lys or His
<220> FEATURE:
<221> NAME/KEY: VARIANT
<222> LOCATION: (63)..(63)
<223> OTHER INFORMATION: Ser or Thr
<220> FEATURE:
<221> NAME/KEY: VARIANT
<222> LOCATION: (67)..(67)
<223> OTHER INFORMATION: Ile, Leu or Val
<220> FEATURE:
<221> NAME/KEY: VARIANT
<222> LOCATION: (70)..(70)
<223> OTHER INFORMATION: Ile, Leu or Val
<220> FEATURE:
<221> NAME/KEY: VARIANT
<222> LOCATION: (73)..(73)
<223> OTHER INFORMATION: Arg, Lys or His
<220> FEATURE:
<221> NAME/KEY: VARIANT
<222> LOCATION: (74)..(74)
<223> OTHER INFORMATION: Ile, Leu or Val
<220> FEATURE:
```

```
<221> NAME/KEY: VARIANT
<222> LOCATION: (75)..(75)
<223> OTHER INFORMATION: Arg, Lys or His
<220> FEATURE:
<221> NAME/KEY: VARIANT
<222> LOCATION: (80)..(80)
<223> OTHER INFORMATION: Asp or Glu
<220> FEATURE:
<221> NAME/KEY: VARIANT
<222> LOCATION: (83)..(83)
<223> OTHER INFORMATION: Ile, Leu or Val
<220> FEATURE:
<221> NAME/KEY: VARIANT
<222> LOCATION: (86)..(87)
<223> OTHER INFORMATION: Ile, Leu or Val
<220> FEATURE:
<221> NAME/KEY: VARIANT
<222> LOCATION: (89)..(89)
<223> OTHER INFORMATION: Arg, Lys or His
<220> FEATURE:
<221> NAME/KEY: VARIANT
<222> LOCATION: (90)..(90)
<223> OTHER INFORMATION: Xaa can be any naturally occurring amino acid
      or absent
<220> FEATURE:
<221> NAME/KEY: VARIANT
<222> LOCATION: (95)..(95)
<223> OTHER INFORMATION: Arg, Lys or His
<220> FEATURE:
<221> NAME/KEY: VARIANT
<222> LOCATION: (102)..(102)
<223> OTHER INFORMATION: Asp or Glu
<220> FEATURE:
<221> NAME/KEY: VARIANT
<222> LOCATION: (103)..(103)
<223> OTHER INFORMATION: Ile, Leu or Val
<220> FEATURE:
<221> NAME/KEY: VARIANT
<222> LOCATION: (104)..(104)
<223> OTHER INFORMATION: Arg, Lys or His
<220> FEATURE:
<221> NAME/KEY: VARIANT
<222> LOCATION: (105)..(105)
<223> OTHER INFORMATION: Ser or Thr
<220> FEATURE:
<221> NAME/KEY: VARIANT
<222> LOCATION: (106)..(106)
<223> OTHER INFORMATION: Ile, Leu or Val
<220> FEATURE:
<221> NAME/KEY: VARIANT
<222> LOCATION: (108)..(108)
<223> OTHER INFORMATION: Asp or Glu
<220> FEATURE:
<221> NAME/KEY: VARIANT
<222> LOCATION: (116)..(116)
<223> OTHER INFORMATION: Xaa can be any naturally occurring amino acid
<220> FEATURE:
<221> NAME/KEY: VARIANT
<222> LOCATION: (127)..(127)
<223> OTHER INFORMATION: Asp or Glu
<220> FEATURE:
<221> NAME/KEY: VARIANT
<222> LOCATION: (128)..(128)
<223> OTHER INFORMATION: Xaa can be any naturally occurring amino acid
<220> FEATURE:
<221> NAME/KEY: VARIANT
<222> LOCATION: (128)..(128)
<223> OTHER INFORMATION: Ala, Asp, Arg, His, Lys, Ser, Thr, Asn, Glu,
      Tyr
<220> FEATURE:
<221> NAME/KEY: VARIANT
<222> LOCATION: (131)..(131)
<223> OTHER INFORMATION: Ile, Leu or Val
<220> FEATURE:
<221> NAME/KEY: VARIANT
<222> LOCATION: (132)..(132)
<223> OTHER INFORMATION: Asp or Glu
<220> FEATURE:
<221> NAME/KEY: VARIANT
```

```
<222> LOCATION: (135)..(135)
<223> OTHER INFORMATION: Ile, Leu or Val
<220> FEATURE:
<221> NAME/KEY: VARIANT
<222> LOCATION: (142)..(143)
<223> OTHER INFORMATION: Ile, Leu or Val
<220> FEATURE:
<221> NAME/KEY: VARIANT
<222> LOCATION: (150)..(150)
<223> OTHER INFORMATION: Ile, Leu or Val
<220> FEATURE:
<221> NAME/KEY: VARIANT
<222> LOCATION: (164)..(164)
<223> OTHER INFORMATION: Arg, Lys or His
<220> FEATURE:
<221> NAME/KEY: VARIANT
<222> LOCATION: (165)..(166)
<223> OTHER INFORMATION: Ile, Leu or Val
<220> FEATURE:
<221> NAME/KEY: VARIANT
<222> LOCATION: (170)..(170)
<223> OTHER INFORMATION: Ser or Thr
<220> FEATURE:
<221> NAME/KEY: VARIANT
<222> LOCATION: (171)..(171)
<223> OTHER INFORMATION: Arg, Lys or His
<220> FEATURE:
<221> NAME/KEY: VARIANT
<222> LOCATION: (193)..(193)
<223> OTHER INFORMATION: Arg, Lys or His
<220> FEATURE:
<221> NAME/KEY: VARIANT
<222> LOCATION: (195)..(200)
<223> OTHER INFORMATION: Xaa can be any naturally occurring amino acid
      or absent
<220> FEATURE:
<221> NAME/KEY: VARIANT
<222> LOCATION: (208)..(208)
<223> OTHER INFORMATION: Ile, Leu or Val
<220> FEATURE:
<221> NAME/KEY: VARIANT
<222> LOCATION: (211)..(211)
<223> OTHER INFORMATION: Ser or Thr
<220> FEATURE:
<221> NAME/KEY: VARIANT
<222> LOCATION: (215)..(215)
<223> OTHER INFORMATION: Ile, Leu or Val
<220> FEATURE:
<221> NAME/KEY: VARIANT
<222> LOCATION: (221)..(221)
<223> OTHER INFORMATION: Ile, Leu or Val
<220> FEATURE:
<221> NAME/KEY: VARIANT
<222> LOCATION: (223)..(223)
<223> OTHER INFORMATION: Ile, Leu or Val
<220> FEATURE:
<221> NAME/KEY: VARIANT
<222> LOCATION: (227)..(227)
<223> OTHER INFORMATION: Asp or Glu
<220> FEATURE:
<221> NAME/KEY: VARIANT
<222> LOCATION: (233)..(233)
<223> OTHER INFORMATION: Asp or Glu
<220> FEATURE:
<221> NAME/KEY: VARIANT
<222> LOCATION: (239)..(239)
<223> OTHER INFORMATION: Ile, Leu or Val
<220> FEATURE:
<221> NAME/KEY: VARIANT
<222> LOCATION: (242)..(242)
<223> OTHER INFORMATION: Ile, Leu or Val
<220> FEATURE:
<221> NAME/KEY: VARIANT
<222> LOCATION: (245)..(245)
<223> OTHER INFORMATION: Ile, Leu or Val
<220> FEATURE:
<221> NAME/KEY: VARIANT
<222> LOCATION: (252)..(252)
<223> OTHER INFORMATION: Asp or Glu
```

```
<220> FEATURE:
<221> NAME/KEY: VARIANT
<222> LOCATION: (253)..(253)
<223> OTHER INFORMATION: Ile, Leu or Val
<220> FEATURE:
<221> NAME/KEY: VARIANT
<222> LOCATION: (261)..(261)
<223> OTHER INFORMATION: Xaa can be any naturally occurring amino acid
<220> FEATURE:
<221> NAME/KEY: VARIANT
<222> LOCATION: (262)..(262)
<223> OTHER INFORMATION: Xaa can be any naturally occurring amino acid
      or absent
<220> FEATURE:
<221> NAME/KEY: VARIANT
<222> LOCATION: (263)..(263)
<223> OTHER INFORMATION: Xaa can be any naturally occurring amino acid
<220> FEATURE:
<221> NAME/KEY: VARIANT
<222> LOCATION: (265)..(265)
<223> OTHER INFORMATION: Ile, Leu or Val
<220> FEATURE:
<221> NAME/KEY: VARIANT
<222> LOCATION: (275)..(275)
<223> OTHER INFORMATION: Asp or Glu
<220> FEATURE:
<221> NAME/KEY: VARIANT
<222> LOCATION: (278)..(278)
<223> OTHER INFORMATION: Ile, Leu or Val
<220> FEATURE:
<221> NAME/KEY: VARIANT
<222> LOCATION: (281)..(284)
<223> OTHER INFORMATION: Xaa can be any naturally occurring amino acid
      or absent
<220> FEATURE:
<221> NAME/KEY: VARIANT
<222> LOCATION: (289)..(289)
<223> OTHER INFORMATION: Ile, Leu or Val
<220> FEATURE:
<221> NAME/KEY: VARIANT
<222> LOCATION: (296)..(298)
<223> OTHER INFORMATION: Xaa can be any naturally occurring amino acid
      or absent
<220> FEATURE:
<221> NAME/KEY: VARIANT
<222> LOCATION: (301)..(301)
<223> OTHER INFORMATION: Ile, Leu or Val
<220> FEATURE:
<221> NAME/KEY: VARIANT
<222> LOCATION: (306)..(306)
<223> OTHER INFORMATION: Xaa can be any naturally occurring amino acid
<220> FEATURE:
<221> NAME/KEY: VARIANT
<222> LOCATION: (308)..(308)
<223> OTHER INFORMATION: Ile, Leu or Val
<220> FEATURE:
<221> NAME/KEY: VARIANT
<222> LOCATION: (311)..(311)
<223> OTHER INFORMATION: Ile, Leu or Val
<220> FEATURE:
<221> NAME/KEY: VARIANT
<222> LOCATION: (313)..(314)
<223> OTHER INFORMATION: Xaa can be any naturally occurring amino acid
      or absent
<220> FEATURE:
<221> NAME/KEY: VARIANT
<222> LOCATION: (316)..(316)
<223> OTHER INFORMATION: Asp or Glu
<220> FEATURE:
<221> NAME/KEY: VARIANT
<222> LOCATION: (328)..(328)
<223> OTHER INFORMATION: Ile, Leu or Val
<220> FEATURE:
<221> NAME/KEY: VARIANT
<222> LOCATION: (332)..(332)
<223> OTHER INFORMATION: Ser or Thr
<220> FEATURE:
<221> NAME/KEY: VARIANT
<222> LOCATION: (334)..(334)
```

```
-continued

<223> OTHER INFORMATION: Ile, Leu or Val
<220> FEATURE:
<221> NAME/KEY: VARIANT
<222> LOCATION: (335)..(335)
<223> OTHER INFORMATION: Ser or Thr
<220> FEATURE:
<221> NAME/KEY: VARIANT
<222> LOCATION: (337)..(337)
<223> OTHER INFORMATION: Arg, Lys or His
<220> FEATURE:
<221> NAME/KEY: VARIANT
<222> LOCATION: (338)..(338)
<223> OTHER INFORMATION: Ile, Leu or Val
<220> FEATURE:
<221> NAME/KEY: VARIANT
<222> LOCATION: (350)..(350)
<223> OTHER INFORMATION: Ser or Thr
<220> FEATURE:
<221> NAME/KEY: VARIANT
<222> LOCATION: (351)..(351)
<223> OTHER INFORMATION: Ile, Leu or Val
<220> FEATURE:
<221> NAME/KEY: VARIANT
<222> LOCATION: (353)..(353)
<223> OTHER INFORMATION: Asp or Glu
<220> FEATURE:
<221> NAME/KEY: VARIANT
<222> LOCATION: (358)..(358)
<223> OTHER INFORMATION: Asp or Glu
<220> FEATURE:
<221> NAME/KEY: VARIANT
<222> LOCATION: (361)..(361)
<223> OTHER INFORMATION: Ile, Leu or Val
<220> FEATURE:
<221> NAME/KEY: VARIANT
<222> LOCATION: (367)..(368)
<223> OTHER INFORMATION: Arg, Lys or His
<220> FEATURE:
<221> NAME/KEY: VARIANT
<222> LOCATION: (369)..(372)
<223> OTHER INFORMATION: Xaa can be any naturally occurring amino acid
      or absent
<220> FEATURE:
<221> NAME/KEY: VARIANT
<222> LOCATION: (374)..(374)
<223> OTHER INFORMATION: Asp or Glu
<220> FEATURE:
<221> NAME/KEY: VARIANT
<222> LOCATION: (379)..(379)
<223> OTHER INFORMATION: Ile, Leu or Val
<220> FEATURE:
<221> NAME/KEY: VARIANT
<222> LOCATION: (380)..(380)
<223> OTHER INFORMATION: Arg, Lys or His
<220> FEATURE:
<221> NAME/KEY: VARIANT
<222> LOCATION: (383)..(384)
<223> OTHER INFORMATION: Ile, Leu or Val
<220> FEATURE:
<221> NAME/KEY: VARIANT
<222> LOCATION: (386)..(386)
<223> OTHER INFORMATION: Arg, Lys or His
<220> FEATURE:
<221> NAME/KEY: VARIANT
<222> LOCATION: (387)..(387)
<223> OTHER INFORMATION: Asp or Glu
<220> FEATURE:
<221> NAME/KEY: VARIANT
<222> LOCATION: (393)..(393)
<223> OTHER INFORMATION: Arg, Lys or His
<220> FEATURE:
<221> NAME/KEY: VARIANT
<222> LOCATION: (397)..(397)
<223> OTHER INFORMATION: Ile, Leu or Val
<220> FEATURE:
<221> NAME/KEY: VARIANT
<222> LOCATION: (400)..(400)
<223> OTHER INFORMATION: Ile, Leu or Val
<220> FEATURE:
```

```
<221> NAME/KEY: VARIANT
<222> LOCATION: (402)..(402)
<223> OTHER INFORMATION: Asp or Glu
<220> FEATURE:
<221> NAME/KEY: VARIANT
<222> LOCATION: (405)..(419)
<223> OTHER INFORMATION: Xaa can be any naturally occurring amino acid
      or absent
<220> FEATURE:
<221> NAME/KEY: VARIANT
<222> LOCATION: (420)..(420)
<223> OTHER INFORMATION: Ile, Leu or Val
<220> FEATURE:
<221> NAME/KEY: VARIANT
<222> LOCATION: (427)..(427)
<223> OTHER INFORMATION: Ile, Leu or Val
<220> FEATURE:
<221> NAME/KEY: VARIANT
<222> LOCATION: (431)..(431)
<223> OTHER INFORMATION: Xaa can be any naturally occurring amino acid
<220> FEATURE:
<221> NAME/KEY: VARIANT
<222> LOCATION: (433)..(434)
<223> OTHER INFORMATION: Xaa can be any naturally occurring amino acid
      or absent
<220> FEATURE:
<221> NAME/KEY: VARIANT
<222> LOCATION: (440)..(440)
<223> OTHER INFORMATION: Xaa can be any naturally occurring amino acid
<220> FEATURE:
<221> NAME/KEY: VARIANT
<222> LOCATION: (441)..(446)
<223> OTHER INFORMATION: Xaa can be any naturally occurring amino acid
      or absent
<220> FEATURE:
<221> NAME/KEY: VARIANT
<222> LOCATION: (447)..(448)
<223> OTHER INFORMATION: Xaa can be any naturally occurring amino acid
<220> FEATURE:
<221> NAME/KEY: VARIANT
<222> LOCATION: (449)..(505)
<223> OTHER INFORMATION: Xaa can be any naturally occurring amino acid
      or absent

<400> SEQUENCE: 10

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Met Xaa
            20                  25                  30

Met Xaa Xaa Thr Glu His Xaa Xaa Phe Xaa Xaa Ser Glu Asn Gly Xaa
        35                  40                  45

Ala Ser Ile Xaa Leu Asn Arg Pro Xaa Ala Leu Asn Ser Leu Xaa Tyr
    50                  55                  60

Asp Met Xaa Gln Pro Xaa Gly Gln Xaa Xaa Xaa Glu Trp Glu Asn Xaa
65                  70                  75                  80

Glu Arg Xaa Ala Leu Xaa Xaa Leu Xaa Xaa Gly Ala Gly Thr Xaa Gly
                85                  90                  95

Phe Cys Ala Gly Gly Xaa Xaa Xaa Xaa Xaa Tyr Xaa Ala Arg Ser Asn
            100                 105                 110

Glu Pro Gly Xaa Ala Leu Gln His Ala Glu Arg Phe Phe Glu Xaa Xaa
        115                 120                 125

Tyr Glu Xaa Xaa Thr Tyr Xaa Tyr Gln Tyr Lys Lys Pro Xaa Xaa Ala
    130                 135                 140

Cys Leu Asp Gly Ile Xaa Met Gly Gly Gly Val Gly Leu Thr Asn Gly
145                 150                 155                 160

Ala Lys Tyr Xaa Xaa Xaa Thr Glu Arg Xaa Xaa Trp Ala Met Pro Glu
                165                 170                 175
```

Met Asn Ile Gly Phe Phe Pro Asp Val Gly Ala Ala Tyr Phe Leu Asn
            180                 185                 190

Xaa Ala Xaa Xaa Xaa Xaa Xaa Pro Gly Tyr Leu Gly Arg Tyr Xaa
        195                 200                 205

Ala Leu Xaa Ala Ser Ile Xaa Lys Ala Ser Asp Val Xaa Phe Xaa Asn
210                 215                 220

Ala Ala Xaa Tyr Phe Met Thr Ser Xaa Ser Leu Pro Ala Phe Xaa Thr
225                 230                 235                 240

Glu Xaa Glu Ser Xaa Asn Trp His Lys Glu Asp Xaa Xaa His Thr His
                245                 250                 255

Leu Leu Lys Glu Xaa Xaa Xaa Val Xaa Arg Thr Phe Ala Thr Ala Pro
            260                 265                 270

Asn Leu Xaa Ser Glu Xaa Ala Pro Xaa Xaa Xaa Xaa Ser Leu Glu Glu
                275                 280                 285

Xaa Asn Ser His Phe Ala Phe Xaa Xaa Xaa Asp Thr Xaa Glu Glu Ile
        290                 295                 300

Trp Xaa Ala Xaa His Ser Xaa Glu Xaa Xaa Lys Xaa Gln Ser Ser Phe
305                 310                 315                 320

Ala Leu Lys Thr Lys Glu Thr Xaa Leu Ser Lys Xaa Pro Xaa Xaa Leu
                325                 330                 335

Xaa Xaa Thr Leu Lys Gln Phe Ile Asp Gly Arg Asp Lys Xaa Xaa Glu
            340                 345                 350

Xaa Cys Phe Ala Thr Xaa Leu Val Xaa Ala Lys Asn Phe Met Xaa Xaa
        355                 360                 365

Xaa Xaa Xaa Xaa Glu Xaa Phe Phe Glu Gly Xaa Xaa Ser Val Xaa Xaa
370                 375                 380

Asp Xaa Xaa Gln Asn Pro Asn Tyr Xaa Tyr Lys Gln Xaa Ser Asp Xaa
385                 390                 395                 400

Ser Xaa Glu Asp Xaa Xaa Xaa Xaa Xaa Xaa Xaa Xaa Xaa Xaa Xaa
                405                 410                 415

Xaa Xaa Xaa Xaa Asn Arg Phe Phe Asn Leu Xaa Asn Ala Gly Xaa His
            420                 425                 430

Xaa Xaa Pro Leu Ala Asp Leu Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa
        500                 505

<210> SEQ ID NO 11
<211> LENGTH: 6801
<212> TYPE: DNA
<213> ORGANISM: Artificial Sequence
<220> FEATURE:
<223> OTHER INFORMATION: Y1ACC codon optimized DNA sequence

<400> SEQUENCE: 11
atgagattgc agttgagaac cttgactaga aggttttctc tatggcttc tggttcttct       60 actccagatg ttgctccatt ggttgatcca aatattcata agggtttggc ctctcacttt    120
ttcggtttga actctgttca tactgctaag ccatctaagg tcaaagaatt tgttgcttct    180

```
catggtggtc ataccgttat caacaaagtt ttgattgcca caacggtat tgctgccgta      240 aaagaaatta ggtctgttag aaaatgggcc tacgaaactt ttggtgacga aagagctatt      300
tccttcactg ttatggctac acctgaagat ttggctgcta atgctgatta cattagaatg      360
gccgatcaat acgttgaagt tccaggtggt acaaacaaca acaattacgc taacgttgaa      420
ttgatcgttg atgtcgctga agatttggt gttgatgctg tttggctgg ttgggtcat      480 gcttctgaaa atccattatt gccagaatct ttggctgctt ctccaagaaa gatcgttttt      540
attggtccac caggtgctgc tatgagatca ttgggtgata agatttcttc taccatcgtt      600
gctcaacatg ctaaggttcc atgtattcca tggtctggta ctggtgttga tgaagttgtt      660
gttgataagt ccaccaactt ggtttccgtt tctgaagaag tttacactaa gggttgtact      720
actggtccaa acaaggttt ggaaaaggct aagcaaattg gtttcccagt tatgattaag      780
gcttctgaag gtggtggtgg taaaggtatt agaaaggttg aaagggaaga agatttcgaa      840
gctgcttacc atcaagttga aggtgaaatt ccaggttccc aattttcat tatgcaattg      900 gctggtaacg ccagacattt ggaagttcaa ttattggctg atcagtacgg caacaacatt      960
tctttgtttg gtagagattg ctccgttcaa agaaggcatc aaaagattat tgaagaagcc     1020
ccagttactg ttgctggtca acaaactttt actgctatgg aaaaagctgc cgtcagattg     1080
ggtaaattgg ttggttatgt ttctgccggt actgtcgaat acttgtactc tcatgaagat     1140
gacaagttct acttcttgga attgaaccca agattgcaag ttgaacatcc aactactgaa     1200
atggttaccg gtgttaattt gccagctgct caattgcaaa ttgctatggg tattccattg     1260
gacagaatca aggatattag gttgttctac ggtgttaacc cacataccac tactccaatt     1320
gatttcgatt tctctggtga agatgctgac aaaactcaaa gaaggccagt tccaagaggt     1380
catacaactg cttgtagaat tacttctgaa gatccaggtg aaggttttaa accatctggt     1440
ggtactatgc acgaattgaa ctttaggtcc tcttctaatg tttggggtta cttctctgtt     1500
ggtaatcaag gtggtatcca ctctttctct gattctcaat tcggtcatat tttcgccttt     1560
ggtgaaaaca gatccgcctc aagaaaacat atggttgttg ccttgaaaga attgtccatc     1620
agaggtgatt tcagaaccac tgttaatac ttgatcaaat tattggaaac cccagacttc     1680
gaggataaca ctattactac tggttggttg gacgagttga tctctaacaa attgactgct     1740
gaaagaccag attccttctt ggctgttgtt tgtggtgctg ctacaaaagc tcatagagct     1800
tcagaagatt ctatcgctac ttacatggct tctttggaaa aaggtcaagt tccagccaga     1860 gacatttga aaactttgtt cccagttgac ttcatctacg aaggtcaaag atacaagttt     1920
accgctacca gatcatccga agattcttac actttgttca tcaacggttc cagatgcgat     1980
attggtgtta gaccattgtc tgatggtggt attttgtgtt tggttggtgg tagatcccat     2040
aacgtttatt ggaagaaga agttggcgct accagattgt ctgttgattc taaaacttgc     2100
ttgttggaag tcgaaaacga tccaactcaa ttgagatcac catctccagg taagttggtt     2160
aagttcttgg ttgaaaacgg tgatcacgtt agagctaatc aaccatacgc tgaaatcgaa     2220
gtcatgaaga tgtacatgac tttgaccgct caagaagatg gtatcgttca attgatgaag     2280
caaccaggtt ctactattga agccggtgat attttggta ttttggcttt ggatgatcca     2340
tccaaggtca aacatgctaa accatttgaa ggtcagttgc cagaattggg tccaccaaca     2400
ttgtctggta acaaaccaca tcaaagatac gaacattgcc aaaacgtctt gcacaacatt     2460
ttgttgggtt cgataacca ggttgtcatg aagtctacat tgcaagaaat ggtcggtttg     2520
ttgagaaatc cagaattgcc atacttgcaa tgggctcatc aagtttcttc attgcataca     2580
```

```
agaatgtccg ctaagttgga tgctactttg gctggtttga ttgataaggc taaacaaagg   2640
ggtggtgaat ttccagctaa gcaattattg agagccttgg aaaaagaagc ttcatctggc   2700
gaagttgatg ctttgtttca acaaacattg gccccttgt ttgatttggc tagagaatat   2760
caagatggtt tggccatcca tgaattgcaa gttgctgctg gtttgttgca agcttattat   2820
gattctgaag ctagattctg cggtccaaac gttagagatg aagatgttat cttgaagttg   2880
agggaagaaa acagggactc tttgagaaaa gttgttatgg cccaattgtc ccattcaaga   2940
gttggtgcta aaaacaactt ggttttggct ttgttggatg agtacaaggt tgctgatcaa   3000
gctggtactg attctccagc ttctaatgtt catgttgcta atacttgag gccagtcttg   3060 agaaagattg tcgaattgga atcaagagct tccgctaagg tttctttgaa ggctagagaa   3120
attttgatcc aatgcgcttt gccatccttg aaagaaagaa ctgatcaatt ggaacacatc   3180
ttgagatcct ctgttgttga atcaagatac ggtgaagttg gtttggaaca tagaactcca   3240
agagctgaca tcttgaaaga agttgttgac tccaagtaca tcgtgttcga tgttttggct   3300
caattcttcg ctcatgatga tccatggata gttttggctg ctttggagtt gtatattaga   3360
agggcttgta aggcctactc cattttggat attaactacc accaagactc tgatttgcca   3420
ccagttattt cttggagatt cagattgcca actatgtcat ctgccttgta caactctgtt   3480
gtttcttctg gttctaagac tccaacttct ccatctgttt caagagctga ttctgtttcc   3540
gatttctctt acaccgttga aagagattct gctccagcta aactggtgc tatagttgct   3600 gttccacatt tggatgattt ggaagatgct ttgaccagag tcttggaaaa tttgccaaaa   3660
agaggtgctg gtttggctat ttctgttggt gcttctaaca aatcagctgc tgcttctgct   3720
agagatgctg ctgctgcagc tgcttcttct gttgatactg gtttgtctaa catctgcaac   3780
gttatgatcg gtagagttga tgaatccgat gatgatgata ccttgatcgc cagaatttcc   3840
caagttatcg aagatttcaa agaggacttc gaagcttgct ccttgagaag aattactttc   3900
tcattcggta actccagagg tacttaccca aagtactttta cttttagagg tccagcctat   3960
gaagaagatc caaccattag acatattgaa ccagctttgg cctttcaatt ggaattggct   4020
agattgtcta acttcgacat caagccagtt cataccgata acagaaacat ccatgtttac   4080
gaagctactg gtaagaatgc tgcttccgat aagagatttt tcaccagagg tatagttaga   4140
ccaggtagat tgagagaaaa catcccaaca tccgagtact gatttctga agctgataga   4200 ttgatgtccg atattttgga tgccttggaa gttattggta ctaccaactc tgatttgaac   4260
cacatcttca ttaacttctc cgctgttttt gctttgaagc cagaagaagt tgaagctgct   4320
tttggtggtt ttttggaaag attcggtaga agattgtgga gattgagagt tactggtgcc   4380
gaaattagaa tgatggtttc tgatccagaa actggttctg cttttccatt gagagctatg   4440
atcaacaacg tttccggtta cgttgtccaa tctgaattat acgctgaagc caagaatgat   4500
aagggtcaat ggatctttaa gtccttgggt aaaccaggtt caatgcatat gagatccatt   4560
aacactccat accctaccaa agaatggttg caacctaaaa gatacaaggc ccatttgatg   4620
ggtactacct actgttatga tttcccagag ttgttcagac agtccattga atctgattgg   4680
aaaaagtacg atggtaaggc tccagatgat ttgatgactt gcaacgaatt gatcttggac   4740
gaagattctg gtgaattgca agaagttaat agagaaccag gtgctaacaa cgttggtatg   4800
gttgcttgga atttgaagc taagactcca gaatatccaa ggggtagaag ttttatcgtt   4860
gttgccaacg atattaccctt ccagattggt tcttttggtc cagctgaaga tcaattcttc   4920
```

```
ttcaaggtta ctgaattggc cagaaagttg ggtattccaa gaatctactt gtctgctaat   4980
tccggtgcta gaattggtat tgctgatgaa ttggtcggta agtacaaagt tgcttggaat   5040
gacgaaactg atccatctaa gggtttcaag tacttgtact tcactccaga atcattggct   5100
accttgaaac cagatactgt tgttaccacc gaaattgaag aagaaggtcc aaacggcgtt   5160
gaaaagagac atgttattga ttacatcgtc ggtgaaaagg atggtttggg tgttgaatgt   5220
ttgagaggtt ctggtttaat tgctggtgct acttcaagag cttacaagga tattttcacc   5280
ttgaccttgg ttacctgtag atcagttggt attggtgctt acttggttag attgggtcaa   5340
agagccattc aaattgaagg tcagccaatt atcttgactg gtgctccagc tattaacaag   5400
ttgttgggta gagaagtcta ctcctctaac ttgcaattgg gtggtactca aatcatgtac   5460
aacaacggtg tttctcattt gaccgctaga gatgatttga acggtgttca taagatcatg   5520
cagtggttgt cttatattcc agcttcaaga ggtttgccag ttccagtttt gccacataag   5580
actgatgttt gggatagaga tgttaccttc caaccagtta gaggtgaaca atatgatgtc   5640
agatggttga tttctggtag gactttggaa gatggtgctt tgaatctggg tttgttcgat   5700
aaggactctt tccaagaaac tttatctggt tgggctaagg gtgttgttgt tggtagagct   5760
agattgggtg gtattccatt tggtgttatt ggtgttgaaa ctgccactgt tgataacact   5820
actccagctg atccagctaa tccagattct attgaaatgt ctacttccga agctggtcaa   5880
gtttggtatc caaattctgc tttcaagacc tcccaagcca ttaacgattt taatcatggt   5940
gaagccttgc cattgatgat tttggctaat tggagaggtt tttccggtgg tcaaagagat   6000
atgtacaacg aagttttgaa gtacggctcc tttattgtcg atgctttggt tgattacaag   6060
cagccaatta tggtttacat tccaccaact ggtgaattga ggtggttc ttgggttgtt   6120
gttgacccaa ctattaactc cgatatgatg gaaatgtacg ccgatgttga agtagaggt   6180
ggtgttttgg aaccagaagg tatggttggt attaagtaca aagagacaa gttgttagat   6240
accatggcca gattagatcc agagtactct tccttgaaaa aacaattgga agagtcccca   6300
gactccgaag aattgaaagt taagttgtcc gtcagggaaa agtctttgat gccaatctac   6360
caacaaatct ccgttcaatt tgctgacttg catgatagag ctggtagaat ggaagctaaa   6420
ggtgttatta gagaagcctt ggtttggaag gatgctagaa gattttttctt ttggaggatc   6480
agaagaaggt tggtcgagga atatttgatc accaagatca actccatttt gccatcttgt   6540
accagattgg aatgtttggc tagaatcaaa tcttggaagc cagctacttt ggatcaaggt   6600
tctgatagag gtgttgctga atggttttgac gaaaattctg atgctgttc tgccaggttg   6660
tctgaattga aaaagatgc ttctgctcag tccttcgctt cccaattgag aaaagataga   6720
caaggtacat tgcagggtat gaagcaagct ttggcttctt tgtctgaagc tgaaagagct   6780
gaattattga agggcttgta a                                            6801
```

<210> SEQ ID NO 12
<211> LENGTH: 7891
<212> TYPE: DNA
<213> ORGANISM: Artificial Sequence
<220> FEATURE:
<223> OTHER INFORMATION: Promoter study base plasmid

<400> SEQUENCE: 12

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
```

```
accacgcttt tcaattcaat tcatcatttt ttttttattc tttttttga tttcggtttc    240 tttgaaattt ttttgattcg gtaatctccg aacagaagga agaacgaagg aaggagcaca    300
gacttagatt ggtatatata cgcatatgta gtgttgaaga aacatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact attttgcaaag ggaagggatg   1140 ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta   1380
aatttttgtt aaatcagctc attttttaac caataggccg aaatcggcaa atcccttat   1440 aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt ttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcca ccgcggtggc ggccgcatag gccactagtg gatctgatat   2040
catcgatgaa ttcgagctcg ttttcgacac tggatggcgg cgttagtatc gaatcgacag   2100
cagtatagcg accagcattc acatacgatt gacgcatgat attactttct gcgcacttaa   2160
cttcgcatct gggcagatga tgtcgaggcg aaaaaaaata taaatcacgc taacatttga   2220
ttaaaataga acaactacaa tataaaaaaa ctatacaaat gacaagttct tgaaaacaag   2280 aatctttta ttgtcagtac tgattattcc tttgccctcg gacgagtgct ggggcgtcgg   2340
tttccactat cggcgagtac ttctacacag ccatcggtcc agacggccgc gcttctgcgg   2400
gcgatttgtg tacgcccgac agtcccggct ccggatcgga cgattgcgtc gcatcgaccc   2460
tgcgcccaag ctgcatcatc gaaattgccg tcaaccaagc tctgatagag ttggtcaaga   2520
```

```
ccaatgcgga gcatatacgc ccggagccgc ggcgatcctg caagctccgg atgcctccgc      2580
tcgaagtagc gcgtctgctg ctccatacaa gccaaccacg gcctccagaa gaagatgttg      2640
gcgacctcgt attgggaatc cccgaacatc gcctcgctcc agtcaatgac cgctgttatg      2700
cggccattgt ccgtcaggac attgttggag ccgaaatccg cgtgcacgag gtgccggact      2760
tcggggcagt cctcggccca aagcatcagc tcatcgagag cctgcgcgac ggacgcactg      2820
acggtgtcgt ccatcacagt ttgccagtga tacacatggg gatcagcaat cgcgcatatg      2880
aaatcacgcc atgtagtgta ttgaccgatt ccttgcggtc cgaatgggcc gaacccgctc      2940
gtctggctaa gatcggccgc agcgatcgca tccatggcct ccgcgaccgg ctgcagaaca      3000
gcgggcagtt cggtttcagg caggtcttgc aacgtgacac cctgtgcacg gcgggagatg      3060
caataggtca ggctctcgct gaattcccca atgtcaagca cttccggaat cgggagcgcg      3120
gccgatgcaa agtgccgata acataacga tctttgtaga aaccatcggc gcagctattt      3180
acccgcagga catatccacg ccctcctaca tcgaagctga aagcacgaga ttcttcgccc      3240
tccgagagct gcatcaggtc ggagacgctg tcgaactttt cgatcagaaa cttctcgaca      3300
gacgtcgcgg tgagttcagg cttttttacccc atggttgttt atgttcggat gtgatgtgag      3360
aactgtatcc tagcaagatt ttaaaaggaa gtatatgaaa aagaacctc agtggcaaat      3420 cctaaccttt tatatttctc tacagggggcg cggcgtgggg acaattcaac gcgtctgtga      3480
ggggagcgtt tccctgctcg caggtctgca gcgaggagcc gtaattttttg cttcgcgccg      3540 tgcggccatc aaaatgtatg gatgcaaatg attatacatg gggatgtatg ggctaaatgt      3600
acgggcgaca gtcacatcat gcccctgagc tgcgcacgtc aagactgtca aggagggtat      3660
tctgggcctc catgtcgctg gccgggtgac ccggcgggga cgaggcaagc taaacagatc      3720
tcccgggtag tttaaacaat gaatgtcacc tttgaagaaa gagccagttt acacggttac      3780
agaatcggta tcgcatcctt agacgcccca gcatccttga acgctttgtc cttaccaatg      3840
attgatgctt tacaagacag attgagagct tgggcagaag atgcagacat agcctgtgtc      3900
ttgttacgtg gtaatggttc taaagcattt tgcgcaggtg gtgacgttgt ccaattagct      3960
aagaaatgtt tggcctcccc aggtgaagcc cctgaattgg ctgaaagatt tttcgctaga      4020
agttacagat tagatcatta tttgcacaca tacccaaagc cttttgatatg ctgggctcat      4080 ggtcacgttt taggtggtgg tatgggtttg ttacaaggtg ctggtattag aatagtcacc      4140
ccatcttcaa gattggcaat gcctgaaatc tctattggtt tatttccaga tgttggtggt      4200 tcccattttct taagtagatt gcctggtaaa ttgggtttat ttttcggttt aaccgcttca      4260
ccattgaatg ccagagatgc tttggactta aacttggctg atagattctt gttagatact      4320
caacaagacg cattgatcga tggtttgatc caattgaact ggagagaaca accagatttg      4380
caattgcatt ccttgttaaa ggctttagaa caacaagcaa gaagtgaatt accagctgca      4440
caatggttgc ctagaagaga aagattagac gccttgttag atcaagctac tttaccattg      4500
tcttggcaag ccttagcttc attggaaaac gatgaagacg cattgttagc caaagccgct      4560
aagactatgt tgggtggttc acctttaaca ggtcatttgg tctggggtca aattagaaga      4620
gctagacact tatctttggc acaagtattt caaatggaat acggcatgtc attgaattgt      4680
tgcagacatc cagaatttgc agaaggtgta agagccagat taatcgataa agaccacgct      4740
ccacattggc actggcctga cgtaaaccaa gttcctgaag ccgttattgc agcccatttt      4800
gcaccattag atgaccaccc tttagctgat ttggcataag tttaaactca tgtaattagt      4860
tatgtcacgc ttacattcac gccctccccc cacatccgct ctaaccgaaa aggaaggagt      4920
```

```
tagacaaacct gaagtctagg tccctatttta ttttttttata gttatgttag tattaagaac    4980
gttatttata tttcaaattt ttcttttttt tctgtacaga cgcgtgtacg catgtaacat       5040
tatactgaaa accttgcttg agaaggtttt gggacgctcg aaggctttaa tttgcggcct       5100
ctagcagctt ttgttccctt tagtgagggt taatttcgag cttggcgtaa tcatggtcat       5160
agctgtttcc tgtgtgaaat tgttatccgc tcacaattcc acacaacata ggagccggaa       5220
gcataaagtg taaagcctgg ggtgcctaat gagtgaggta actcacatta attgcgttgc       5280
gctcactgcc cgctttccag tcgggaaacc tgtcgtgcca gctgcattaa tgaatcggcc       5340
aacgcgcggg gagaggcggt ttgcgtattg ggcgctcttc cgcttcctcg ctcactgact       5400
cgctgcgctc ggtcgttcgg ctgcggcgag cggtatcagc tcactcaaag gcggtaatac       5460
ggttatccac agaatcaggg gataacgcag gaaagaacat gtgagcaaaa ggccagcaaa       5520
aggccaggaa ccgtaaaaag gccgcgttgc tggcgttttt ccataggctc cgcccccctg       5580
acgagcatca caaaaatcga cgctcaagtc agaggtggcg aaacccgaca ggactataaa       5640
gataccaggc gttccccccct ggaagctccc tcgtgcgctc tcctgttccg accctgccgc      5700
ttaccggata cctgtccgcc tttctcccctt cgggaagcgt ggcgctttct caatgctcac     5760
gctgtaggta tctcagttcg gtgtaggtcg ttcgctccaa gctgggctgt gtgcacgaac       5820
cccccgttca gcccgaccgc tgcgccttat ccggtaacta tcgtcttgag tccaacccgg      5880
taagacacga cttatcgcca ctggcagcag ccactggtaa caggattagc agagcgaggt      5940
atgtaggcgg tgctacagag ttcttgaagt ggtggcctaa ctacggctac actagaagga      6000
cagtatttgg tatctgcgct ctgctgaagc cagttacctt cggaaaaaga gttggtagct      6060
cttgatccgg caaacaaacc accgctggta gcggtggttt ttttgtttgc aagcagcaga      6120
ttacgcgcag aaaaaaagga tctcaagaag atcctttgat cttttctacg gggtctgacg      6180
ctcagtggaa cgaaaactca cgttaaggga ttttggtcat gagattatca aaaaggatct      6240
tcacctagat ccttttaaat taaaaatgaa gttttaaatc aatctaaagt atatatgagt      6300
aaacttggtc tgacagttac caatgcttaa tcagtgaggc acctatctca gcgatctgtc      6360
tatttcgttc atccatagtt gcctgactgc ccgtcgtgta gataactacg atacgggagg      6420
gcttaccatc tggccccagt gctgcaatga taccgcgaga cccacgctca ccggctccag      6480
atttatcagc aataaaccag ccagccggaa gggccgagcg cagaagtggt cctgcaactt      6540
tatccgcctc catccagtct attaattgtt gccgggaagc tagagtaagt agttcgccag      6600
ttaatagttt gcgcaacgtt gttgccattg ctacaggcat cgtggtgtca cgctcgtcgt      6660
ttggtatggc ttcattcagc tccggttccc aacgatcaag gcgagttaca tgatccccca      6720
tgttgtgaaa aaaagcggtt agctccttcg gtcctccgat cgttgtcaga agtaagttgg      6780
ccgcagtgtt atcactcatg gttatggcag cactgcataa ttctcttact gtcatgccat      6840
ccgtaagatg cttttctgtg actggtgagt actcaaccaa gtcattctga atagtgta       6900
tgcggcgacc gagttgctct tgcccggcgt caatacggga taataccgcg ccacatagca      6960
gaactttaaa agtgctcatc attggaaaac gttcttcggg gcgaaaactc tcaaggatct      7020
taccgctgtt gagatccagt tcgatgtaac ccactcgtgc acccaactga tcttcagcat      7080
cttttacttt caccagcgtt tctgggtgag caaaaacagg aaggcaaaat gccgcaaaaa      7140
agggaataag ggcgacacgg aaatgttgaa tactcatact cttcctttt caatattatt       7200
gaagcattta tcagggttat tgtctcatga gcggatacat atttgaatgt atttagaaaa      7260
```

```
ataaacaaat aggggttccg cgcacatttc cccgaaaagt gccacctggg tccttttcat   7320
cacgtgctat aaaaataatt ataatttaaa tttttaata taaatatata aattaaaaat   7380
agaaagtaaa aaagaaatt aagaaaaaa tagttttgt tttccgaaga tgtaaaagac    7440
tctaggggga tcgccaacaa atactacctt ttatcttgct cttcctgctc tcaggtatta  7500
atgccgaatt gtttcatctt gtctgtgtag aagaccacac acgaaaatcc tgtgatttta  7560
cattttactt atcgttaatc gaatgtatat ctatttaatc tgcttttctt gtctaataaa  7620
tatatatgta aagtacgctt tttgttgaaa ttttttaaac ctttgtttat ttttttttct  7680
tcattccgta actcttctac cttctttatt tactttctaa aatccaaata caaaacataa  7740
aaataaataa acacagagta aattcccaaa ttattccatc attaaaagat acgaggcgcg  7800
tgtaagttac aggcaagcga tccgtcctaa gaaaccatta ttatcatgac attaacctat  7860
aaaaataggc gtatcacgag gcccttcgt c                                7891
```

<210> SEQ ID NO 13
<211> LENGTH: 60
<212> TYPE: DNA
<213> ORGANISM: Artificial Sequence
<220> FEATURE:
<223> OTHER INFORMATION: Primer

<400> SEQUENCE: 13
ccaatatata ataaaatatg gaggaatgcg atgctcagaa atacgctaaa atgtgcccaa      60

<210> SEQ ID NO 14
<211> LENGTH: 60
<212> TYPE: DNA
<213> ORGANISM: Artificial Sequence
<220> FEATURE:
<223> OTHER INFORMATION: Primer

<400> SEQUENCE: 14
tgcctggaga tccttactcg agttggatcc ttatttccat cttaagccat cgttaacttc      60

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
ttttactgat gcgtattctt tgaattttca aatagca                              37

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
tcaaagaata cgcatcagta aaaatttga tgga                                  34

<210> SEQ ID NO 17
<211> LENGTH: 41
<212> TYPE: DNA
<213> ORGANISM: Artificial Sequence
<220> FEATURE:
<223> OTHER INFORMATION: Primer

<400> SEQUENCE: 17
ttttactgat gtttattctt tgaattttca aatagcaact t          41

<210> SEQ ID NO 18
<211> LENGTH: 39
<212> TYPE: DNA
<213> ORGANISM: Artificial Sequence
<220> FEATURE:
<223> OTHER INFORMATION: Primer

<400> SEQUENCE: 18
tcaaagaata aacatcagta aaaatttga tggacttgg          39

<210> SEQ ID NO 19
<211> LENGTH: 39
<212> TYPE: DNA
<213> ORGANISM: Artificial Sequence
<220> FEATURE:
<223> OTHER INFORMATION: Primer

<400> SEQUENCE: 19
ttttactgat tcgtattctt tgaattttca aatagcaac          39

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
tcaaagaata cgaatcagta aaaatttga tggact          36

<210> SEQ ID NO 21
<211> LENGTH: 55
<212> TYPE: DNA
<213> ORGANISM: Artificial Sequence
<220> FEATURE:
<223> OTHER INFORMATION: Primer

<400> SEQUENCE: 21
ccaatatata ataaaatatg gaggaatgcg atgtctacaa cacataacgt ccctc          55

<210> SEQ ID NO 22
<211> LENGTH: 53
<212> TYPE: DNA
<213> ORGANISM: Artificial Sequence
<220> FEATURE:
<223> OTHER INFORMATION: Primer

<400> SEQUENCE: 22
tgcctggaga tccttactcg agttggatcc ttactcaaca ggtaaggcgc gag          53

<210> SEQ ID NO 23
<211> LENGTH: 61
<212> TYPE: DNA
<213> ORGANISM: Artificial Sequence
<220> FEATURE:
<223> OTHER INFORMATION: Primer

<400> SEQUENCE: 23
ctaattacat gactcgaggt cgacggtatc gttatttcca tcttaagcca tcgttaactt          60
c          61

<210> SEQ ID NO 24

```
<211> LENGTH: 67
<212> TYPE: DNA
<213> ORGANISM: Artificial Sequence
<220> FEATURE:
<223> OTHER INFORMATION: Primer

<400> SEQUENCE: 24
cattagaaag aaagcatagc aatctaatct aagtttaaaa caatgactac tcaaccccag    60
ctaaatg                                                              67

<210> SEQ ID NO 25
<211> LENGTH: 60
<212> TYPE: DNA
<213> ORGANISM: Artificial Sequence
<220> FEATURE:
<223> OTHER INFORMATION: Primer

<400> SEQUENCE: 25
gaaagcatag caatctaatc taagtttaaa acaatgaccg aacaagtctt attctcagta    60

<210> SEQ ID NO 26
<211> LENGTH: 59
<212> TYPE: DNA
<213> ORGANISM: Artificial Sequence
<220> FEATURE:
<223> OTHER INFORMATION: Primer

<400> SEQUENCE: 26
ctaattacat gactcgaggt cgacggtatc gttaagcgtt caacaaattg aaaaatctg     59

<210> SEQ ID NO 27
<211> LENGTH: 58
<212> TYPE: DNA
<213> ORGANISM: Artificial Sequence
<220> FEATURE:
<223> OTHER INFORMATION: Primer

<400> SEQUENCE: 27
gaaagcatag caatctaatc taagtttaaa acaatgaccg aacatgtatt attctcag      58

<210> SEQ ID NO 28
<211> LENGTH: 57
<212> TYPE: DNA
<213> ORGANISM: Artificial Sequence
<220> FEATURE:
<223> OTHER INFORMATION: Primer

<400> SEQUENCE: 28
ctaattacat gactcgaggt cgacggtatc gttaagcgtt taacaaattg aaaaatc       57

<210> SEQ ID NO 29
<211> LENGTH: 57
<212> TYPE: DNA
<213> ORGANISM: Artificial Sequence
<220> FEATURE:
<223> OTHER INFORMATION: Primer

<400> SEQUENCE: 29
gaaagcatag caatctaatc taagtttaaa acaatgagaa gatacatcag aggtggt       57

<210> SEQ ID NO 30
<211> LENGTH: 57
<212> TYPE: DNA
<213> ORGANISM: Artificial Sequence
<220> FEATURE:
<223> OTHER INFORMATION: Primer
```

<400> SEQUENCE: 30
ctaattacat gactcgaggt cgacggtatc gttatgcagc gttcaacaaa ttgaaaa          57

<210> SEQ ID NO 31
<211> LENGTH: 58
<212> TYPE: DNA
<213> ORGANISM: Artificial Sequence
<220> FEATURE:
<223> OTHER INFORMATION: Primer

<400> SEQUENCE: 31
gaaagcatag caatctaatc taagtttaaa acaatgaccg aacaagtctt attctcag        58

<210> SEQ ID NO 32
<211> LENGTH: 58
<212> TYPE: DNA
<213> ORGANISM: Artificial Sequence
<220> FEATURE:
<223> OTHER INFORMATION: Primer

<400> SEQUENCE: 32
ctaattacat gactcgaggt cgacggtatc gttaagcgtt caacaaattg aaaaatct       58

<210> SEQ ID NO 33
<211> LENGTH: 60
<212> TYPE: DNA
<213> ORGANISM: Artificial Sequence
<220> FEATURE:
<223> OTHER INFORMATION: Primer

<400> SEQUENCE: 33
gaaagcatag caatctaatc taagtttaaa acaatgaact tacaatttga agaaagacca     60

<210> SEQ ID NO 34
<211> LENGTH: 57
<212> TYPE: DNA
<213> ORGANISM: Artificial Sequence
<220> FEATURE:
<223> OTHER INFORMATION: Primer

<400> SEQUENCE: 34
ctaattacat gactcgaggt cgacggtatc gttacaaatc agctaaaggg tgttcac        57

<210> SEQ ID NO 35
<211> LENGTH: 59
<212> TYPE: DNA
<213> ORGANISM: Artificial Sequence
<220> FEATURE:
<223> OTHER INFORMATION: Primer

<400> SEQUENCE: 35
gaaagcatag caatctaatc taagtttaaa acaatgaact tacactttga agaattgac      59

<210> SEQ ID NO 36
<211> LENGTH: 57
<212> TYPE: DNA
<213> ORGANISM: Artificial Sequence
<220> FEATURE:
<223> OTHER INFORMATION: Primer

<400> SEQUENCE: 36
ctaattacat gactcgaggt cgacggtatc gttagtagtc agacaaatct gctaaag        57

<210> SEQ ID NO 37

```
<210> SEQ ID NO 37
<211> LENGTH: 59
<212> TYPE: DNA
<213> ORGANISM: Artificial Sequence
<220> FEATURE:
<223> OTHER INFORMATION: Primer

<400> SEQUENCE: 37
gaaagcatag caatctaatc taagtttaaa acaatgacaa tccactgtga agtattaac    59

<210> SEQ ID NO 38
<211> LENGTH: 55
<212> TYPE: DNA
<213> ORGANISM: Artificial Sequence
<220> FEATURE:
<223> OTHER INFORMATION: Primer

<400> SEQUENCE: 38
ctaattacat gactcgaggt cgacggtatc gttaaccaac gtcagccaaa gggtg        55

<210> SEQ ID NO 39
<211> LENGTH: 58
<212> TYPE: DNA
<213> ORGANISM: Artificial Sequence
<220> FEATURE:
<223> OTHER INFORMATION: Primer

<400> SEQUENCE: 39
gaaagcatag caatctaatc taagtttaaa acaatgaatg tcacctttga agaaagag     58

<210> SEQ ID NO 40
<211> LENGTH: 55
<212> TYPE: DNA
<213> ORGANISM: Artificial Sequence
<220> FEATURE:
<223> OTHER INFORMATION: Primer

<400> SEQUENCE: 40
ctaattacat gactcgaggt cgacggtatc gttatgccaa atcagctaaa gggtg        55

<210> SEQ ID NO 41
<211> LENGTH: 4431
<212> TYPE: DNA
<213> ORGANISM: Saccharomyces cerevisiae

<400> SEQUENCE: 41
cgaaacccta tgctctgttg ttcggatttg aaattttaaa actacattaa tgtgttagtt    60
tttctttctt tctttctttg tcttgacgtg atttggactt ctgtcttgca ttcgcgtcca   120
ttcatctgac ccaatattcc ttttggtttt gttatcctta taaaagaaa ggaagcttct    180
tagagggaaa aaaatgatga agagtaatgc caaaatataa ataaataat aaatatgaaa    240
atcattttct attttaata gaataagaag agcatcttaa gattacaatt tcaagaaata    300
gtttacacag tatatccaat aactccaata aactactttc ctatacaaat ttctatggtg   360
ggattaatag taaaacttct gtacttctct aattcaccaa gaaattaagg taaacatctg   420
gtaagcacta tccagctttt tgctattaca catatggctt ttctgcaatc atttcttccc   480
attttgtctc aagccgttag tcttgaaacc acaggcggag tagagttact tgatgcggta   540
ttttacatgc ctttttcac tgcaaaaaaa atgaaataca tatttacacg atttgcagga   600
cagtttacga tagtgagtat gcagaatagt taacacctt gttttatcct tttgtgtctt    660
aattatatga tataaaggcg cctggcaaat tcccgtttta agcttggt gagcgctagg     720
agtcactgcc aggtatcgtt tgaacacggc attagtcagg gaagtcataa cacagtcctt   780
```

```
tcccgcaatt ttcttttct attactcttg gcctcctcta gtacactcta tattttttta      840
tgcctcggta atgattttca tttttttttt tcccctagcg gatgactctt ttttttctt      900 agcgattggc attatcacat aatgaattat acattatata aagtaatgtg atttcttcga     960
agaatatact aaaaaatgag caggcaagat aaacgaaggc aaagatgaca gagcagaaag    1020
ccctagtaaa gcgtattaca aatgaaacca agattcagat tgcgatctct ttaaagggtg    1080
gtcccctagc gatagagcac tcgatcttcc cagaaaaaga ggcagaagca gtagcagaac    1140
aggccacaca atcgcaagtg attaacgtcc acacaggtat agggtttctg gaccatatga    1200
tacatgctct ggccaagcat tccggctggt cgctaatcgt tgagtgcatt ggtgacttac    1260
acatagacga ccatcacacc actgaagact gcgggattgc tctcggtcaa gcttttaaag    1320
aggccctact ggcgcgtgga gtaaaaaggt ttggatcagg atttgcgcct ttggatgagg    1380
cactttccag agcggtggta gatctttcga acaggccgta cgcagttgtc gaacttggtt    1440
tgcaaaggga gaaagtagga gatctctctt gcgagatgat cccgcatttt cttgaaagct    1500
ttgcagaggc tagcagaatt accctccacg ttgattgtct gcgaggcaag aatgatcatc    1560
accgtagtga gagtgcgttc aaggctcttg cggttgccat aagagaagcc acctcgccca    1620
atggtaccaa cgatgttccc tccaccaaag gtgttcttat gtagtgacac cgattattta    1680
aagctgcagc atacgatata tatacatgtg tatatatgta tacctatgaa tgtcagtaag    1740
tatgtatacg aacagtatga tactgaagat gacaaggtaa tgcatcattc tatacgtgtc    1800
attctgaacg aggcgcgctt tccttttttc ttttttgcttt ttcttttttt ttctcttgaa    1860
ctcgacggat ctatgcggtg tgaaataccg cacagatgcg taaggagaaa ataccgcatc    1920
aggaaattgt aaacgttaat attttgttaa aattcgcgtt aaattttgt taaatcagct    1980 cattttttaa ccaataggcc gatagcttca aaatgtttct actccttttt tactcttcca    2040
gattttctcg gactccgcgc atcgccgtac cacttcaaaa cacccaagca cagcatacta    2100
aatttcccct ctttcttcct ctagggtgtc gttaattacc cgtactaaag gtttggaaaa    2160
gaaaaaagag accgcctcgt ttcttttct tcgtcgaaaa aggcaataaa aattttttatc    2220 acgtttcttt ttcttgaaaa ttttttttttt gatttttttc tctttcgatg acctcccatt    2280
gatatttaag ttaataaacg gtcttcaatt tctcaagttt cagtttcatt tttcttgttc    2340
tattacaact ttttttactt cttgctcatt agaaagaaag catagcaatc taatctaagt    2400
ttaaaacaat gaatgtcacc tttgaagaaa gagccagttt acacggttac agaatcggta    2460
tcgcatcctt agacgcccca gcatccttga acgcttgtc cttaccaatg attgatgctt     2520
tacaagacag attgagagct tgggcagaag atgcagacat agcctgtgtc ttgttacgtg    2580
gtaatggttc taaagcattt tgcgcaggtg gtgacgttgt ccaattagct aagaaatgtt    2640
tggcctcccc aggtgaagcc cctgaattgg ctgaaagatt tttcgctaga agttacagat    2700
tagatcatta tttgcacaca tacccaaagc ctttgatatg ctgggctcat ggtcacgttt    2760
taggtggtgg tatgggtttg ttacaaggtg ctggtattag aatagtcacc ccatcttcaa    2820
gattggcaat gcctgaaatc tctattggtt tatttccaga tgttggtggt tcccatttct    2880
taagtagatt gcctggtaaa ttgggtttat ttttcggttt aaccgcttca ccattgaatg    2940
ccagagatgc tttggactta aacttggctg atagattctt gttagatact caacaagacg    3000
cattgatcga tggtttgatc caattgaact ggagagaaca accagatttg caattgcatt    3060
ccttgttaaa ggctttagaa caacaagcaa gaagtgaatt accagctgca caatggttgc    3120
```

| | |
|---|---|
| ctagaagaga aagattagac gccttgttag atcaagctac tttaccattg tcttggcaag | 3180 |
| ccttagcttc attggaaaac gatgaagacg cattgttagc caaagccgct aagactatgt | 3240 |
| tgggtggttc acctttaaca ggtcatttgg tctggggtca aattagaaga gctagacact | 3300 |
| tatctttggc acaagtattt caaatggaat acggcatgtc attgaattgt tgcagacatc | 3360 |
| cagaatttgc agaaggtgta agagccagat taatcgataa agaccacgct ccacattggc | 3420 |
| actggcctga cgtaaaccaa gttcctgaag ccgttattgc agcccatttt gcaccattag | 3480 |
| atgaccaccc tttagctgat tggcataac gataccgtcg acctcgagtc atgtaattag | 3540 |
| ttatgtcacg cttacattca cgccctcccc ccacatccgc tctaaccgaa aggaaggag | 3600 |
| ttagacaacc tgaagtctag gtccctattt attttttat agttatgtta gtattaagaa | 3660 |
| cgttatttat atttcaaatt tttctttttt ttctgtacag acgcgtgtac gcatgtaaca | 3720 |
| ttatactgaa aaccttgctt gagaaggttt tgggacgctc gaaggcttta atttgcggcc | 3780 |
| ataaagcagc cgctaccaaa cagacaagat tcagtatgta aggtaaatac ctttttgcac | 3840 |
| agttaaacta cccaaactta ttaaagcttg ataaattact gaaattccac ctttcagtta | 3900 |
| gattcaggcc tcatatagat tagatatagg gtacgtaaca ttctgtcaac caagttgttg | 3960 |
| gaatgaaagt ctaaaatgtc atctattcgg tagcactcat gttactagta tactgtcaca | 4020 |
| tgcggtgtaa cgtggggaca taaaacagac atcaaatata atggaagctg aaatgcaaag | 4080 |
| atcgataatg taataggaat gaaacatata aaacgaaagg agaagtaatg gtaatattag | 4140 |
| tatgtagaaa taccgattca attttgggga ttcttatatt ctcgagagaa tttctagtat | 4200 |
| aatctgtata cataatatta taggctttac caacaatgga atttcgacaa ttatcatatt | 4260 |
| attcaccaat taatcacaag ttggtaatga gtttgataac aagttacttt cttaacaacg | 4320 |
| ttagtatcgt caaaacactc ggttttactc gagcttgtag cacaataata ccgtgtagag | 4380 |
| ttctgtattg ttcttcttag tgcttgtata tgctcatccc gaccttccat t | 4431 |

<210> SEQ ID NO 42
<211> LENGTH: 5356
<212> TYPE: DNA
<213> ORGANISM: Saccharomyces cerevisiae

<400> SEQUENCE: 42

| | |
|---|---|
| accggagctt ggatatgata aacgaaatat tcttgaatcg tgagatcgcc tgttttcaaa | 60 |
| accgttggag gcagaaacaa ttttgtcaca agatgggcat tctaccccat ccttgctgta | 120 |
| ttattgtagt ctcgctttct tttatgctgg acaaatgaga ctactgcaca ttttttatacg | 180 |
| ttcttggttt tttttaaagg tgtggtttcg gcattatcct gccgcacgtt tcttggataa | 240 |
| ttcatcctga ttctctattt taaacgcttc agcctatcag gatttggttt tgatacatac | 300 |
| tgcaagagtg tatctcggga acagtcattt attccgcaac aaacttaatt gcggaacgcg | 360 |
| ttaggcgatt tctagcatat atcaaatacc gttcgcgatt tcttctgggt tcgtctcttt | 420 |
| tcttttaaat acttattaac gtactcaaac aactacactt cgttgtatct cagaatgaga | 480 |
| tccctcagta tgacaataca tcattctaaa cgttcgtaaa acacatatga aacaacttta | 540 |
| taacaaagcg aacaaatgg gcaacatgag atgaaactcc gcgtcccttta gctgaactac | 600 |
| ccaaacgtac gaatgcctga acaattagtt tagatccgag attccgcgct tccatcattt | 660 |
| agtataatcc atattttata taatatatag gataagtaac agcccgcgaa tcgaggagaa | 720 |
| cttctagtat atccacatac ctaatattat tgccttatta aaaatggaat cccaacaatt | 780 |
| acatcaaaat ccacattctc ttcaaaatca attgtcctgt acttccttgt tcatgtgtgt | 840 |

```
tcaaaaacgt tatatttata ggataattat actctatttc tcaacaagta attggttgtt    900
tggccgagcg gtctaaggcg cctgattcaa gaaatatctt gaccgcagtt aactgtggga    960
atactcaggt atcgtaagat gcaagagttc gaatctctta gcaaccatta ttttttttcct  1020
caacataacg agaacacaca ggggcgctat cgcacagaat caaattcgat gactggaaat   1080
tttttgttaa tttcagaggt cgcctgacgc atatacettt ttcaactgaa aaattgggag   1140
aaaaaggaaa ggtgagaggc cggaaccggc ttttcatata gaatagagaa gcgttcatga   1200
ctaaatgctt gcatcacaat acttgaagtt gacaatatta tttaaggacc tattgttttt   1260
tccaataggt ggttagcaat cgtcttactt tctaactttt cttacctttt acatttcagc   1320
aatatatata tatatttcaa ggatatacca ttctaatgtc tgcccctatg tctgcccta    1380
agaagatcgt cgttttgcca ggtgaccacg ttggtcaaga aatcacagcc gaagccatta   1440
aggttcttaa agctatttct gatgttcgtt ccaatgtcaa gttcgatttc gaaaatcatt   1500
taattggtgg tgctgctatc gatgctacag gtgtcccact tccagatgag gcgctggaag  1560
cctccaagaa ggttgatgcc gttttgttag gtgctgtggc tggtcctaaa tggggtaccg   1620
gtagtgttag acctgaacaa ggtttactaa aaatccgtaa agaacttcaa ttgtacgcca   1680
acttaagacc atgtaacttt gcatccgact ctcttttaga cttatctcca atcaagccac   1740
aatttgctaa aggtactgac ttcgttgttg tcagagaatt agtgggaggt atttactttg   1800
gtaagagaaa ggaagacgat ggtgatggtg tcgcttggga tagtgaacaa tacaccgttc   1860
cagaagtgca aagaatcaca agaatggccg ctttcatggc cctacaacat gagccaccat  1920
tgcctatttg gtccttggat aaagctaatc ttttggcctc ttcaagatta tggagaaaaa   1980
ctgtggagga aaccatcaag aacgaattcc ctacattgaa ggttcaacat caattgattg   2040
attctgccgc catgatccta gttaagaacc caacccacct aaatggtatt ataatcacca   2100
gcaacatgtt tggtgatatc atctccgatg aagcctccgt tatcccaggt tccttgggtt   2160
tgttgccatc tgcgtccttg gcctctttgc cagacaagaa caccgcattt ggtttgtacg   2220
aaccatgcca cggttctgct ccagatttgc caaagaataa ggttgaccct atcgccacta   2280
tcttgtctgc tgcaatgatg ttgaaattgt cattgaactt gcctgaagaa ggtaaggcca   2340
ttgaagatgc agttaaaaag gttttggatg caggtatcag aactggtgat ttaggtggtt   2400
ccaacagtac caccgaagtc ggtgatgctg tcgccgaaga agttaagaaa atccttgctt   2460
aaaaagattc tcttttttta tgatatttgt acataaactt tataaatgaa attcataata   2520
gaaacgacac gaaattacaa aatgaatat gttcataggg tagacgaaac tatatacgca    2580
atctacatac atttatcaag aaggagaaaa aggaggatag taaggaata caggtaagca    2640
aattgatact aatggctcaa cgtgataagg aaaaagaatt gcactttaac attaatattg   2700
acaaggagga gggcaccaca caaaaagtta ggtgtaacag aaaatcatga aactacgatt   2760
cctaatttga tattggagga ttttctctaa aaaaaaaaa atacaacaaa taaaaaacac    2820
tcaatgacct gaccatttga tggagtttaa gtcaataccct tcttgaagca tttcccataa  2880
tggtgaaagt tccctcaaga attttactct gtcagaaacg gcctatagct tcaaaatgtt   2940
tctactcctt ttttactctt ccagattttc tcggactccg cgcatcgccg taccacttca   3000
aaacacccaa gcacagcata ctaaatttcc cctctttctt cctctagggt gtcgttaatt   3060
acccgtacta aaggtttgga aaagaaaaaa gagaccgcct cgtttctttt tcttcgtcga   3120
aaaaggcaat aaaaattttt atcacgtttc ttttttcttga aatttttttt tttgattttt  3180
```

```
ttctctttcg atgacctccc attgatattt aagttaataa acggtcttca atttctcaag    3240
tttcagtttc attttttcttg ttctattaca actttttta cttcttgctc attagaaaga    3300
aagcatagca atctaatcta agtttaaaac aatgaatgtc acctttgaag aaagagccag    3360
tttacacggt tacagaatcg gtatcgcatc cttagacgcc ccagcatcct tgaacgcttt    3420
gtccttacca atgattgatg ctttacaaga cagattgaga gcttgggcag aagatgcaga    3480
catagcctgt gtcttgttac gtggtaatgg ttctaaagca ttttgcgcag gtggtgacgt    3540
tgtccaatta gctaagaaat gtttggcctc cccaggtgaa gcccctgaat tggctgaaag    3600
attttttcgct agaagttaca gattagatca ttatttgcac acatacccaa agcctttgat    3660
atgctgggct catggtcacg ttttaggtgg tggtatgggt ttgttacaag gtgctggtat    3720
tagaatagtc accccatctt caagattggc aatgcctgaa atctctattg gtttatttcc    3780
agatgttggt ggttcccatt tcttaagtag attgcctggt aaattgggtt tattttttcgg   3840
tttaaccgct tcaccattga atgccagaga tgctttggac ttaaacttgg ctgatagatt    3900
cttgttagat actcaacaag acgcattgat cgatggtttg atccaattga actggagaga    3960
acaaccagat ttgcaattgc attccttgtt aaaggcttta gaacaacaag caagaagtga    4020
attaccagct gcacaatggt tgcctagaag agaaagatta gacgccttgt tagatcaagc    4080
tactttacca ttgtcttggc aagccttagc ttcattggaa aacgatgaag acgcattgtt    4140
agccaaagcc gctaagacta tgttgggtgg ttcacctta acaggtcatt tggtctgggg    4200
tcaaattaga gagctagac acttatcttt ggcacaagta tttcaaatgg aatacggcat    4260
gtcattgaat tgttgcagac atccagaatt tgcagaaggt gtaagagcca gattaatcga    4320
taaagaccac gctccacatt ggcactggcc tgacgtaaac caagttcctg aagccgttat    4380
tgcagcccat tttgcaccat tagatgacca ccctttagct gatttggcat aacgataccg    4440
tcgacctcga gtcatgtaat tagttatgtc acgcttacat tcacgccctc cccccacatc    4500
cgctctaacc gaaaaggaag gagttagaca acctgaagtc taggtcccta ttttatttttt    4560
tatagttatg ttagtattaa gaacgttatt tatatttcaa atttttcttt tttttctgta    4620
cagacgcgtg tacgcatgta acattatact gaaaaccttg cttgagaagg ttttgggacg    4680
ctcgaaggct ttaatttgcg gccggaccaa ctatcatccg ctaattactg acattaccaa    4740
atgagatctg tgaatgggca agataaaaaa caaaaattga atgtttgac gttatgtaaa    4800
actattaatt ccttcgcttt cggcggtcac agaatttgcg tgtagctgac tcaaaagttg    4860
atactataat agctgccatt tatacctgtt agttatggcg atcgtttatc acgtcttgtt    4920
caatcaatat catttgttac tttatttgaa agtctgtatt actgcgccta ttgtcatccg    4980
taccaaagaa cgtcaaaaag aaacaagata ttttttgtgc ttacaccatt tatagatcac    5040
tgagcccaga atatcgctgg agctcagtgt aagtggcatg aacacaactc tgactgatcg    5100
cacatattgc cgttatcata aatactagtt gtacttgtca atgcgacgaa tggcatcatg    5160
cctattatta cgttcctctt tttccgtttc atgtttccag aatgctattg aatctaacac    5220
ttcaattata aaaagaata atccgcaat aattttaggc taattgttgt actgtcaagc     5280
gaacctaatg gttaaaattc agaggaacct tcgacgtagt ctgatcgcta cttctatatc    5340
ttatgttccc agtcaa                                                    5356
```

<210> SEQ ID NO 43
<211> LENGTH: 3492
<212> TYPE: DNA
<213> ORGANISM: Saccharomyces cerevisiae

<400> SEQUENCE: 43

```
aactcaatcg tgctaagcga caaactgaaa aggtatatca accagagatg aaatcggaaa      60
ttagcgggga tagcactctg aaacgtgttc aagtcacctt ccacgggaat ggtcgggtaa     120
ataaaaagaa aaagaaggtt cctccacgga agatggtat caagttccgt tgattgaaaa     180
tttttctttt caagcgatga ggttagcgaa gttgttcgaa caagcccaaa tatgtttaga     240
aggcagtacg aattgatacc ctgaactgtt actacatacc acagcttttc aattcaattc     300
atcatttttt ttttattctt ttttttgatt tcggtttctt tgaaattttt ttgattcggt     360
aatctccgaa cagaaggaag aacgaaggaa ggagcacaga cttagattgg tatatatacg     420
catatgtagt gttgaagaaa catgaaattg cccagtattc ttaacccaac tgcacagaac     480
aaaaacctgc aggaaacgaa gataaatcat gtcgaaagct acatataagg aacgtgctgc     540
tactcatcct agtcctgttg ctgccaagct atttaatatc atgcacgaaa agcaaacaaa     600
cttgtgtgct tcattggatg ttcgtaccac caaggaatta ctggagttag ttgaagcatt     660
aggtcccaaa atttgtttac taaaaacaca tgtggatatc ttgactgatt tttccatgga     720
gggcacagtt aagccgctaa aggcattatc cgccaagtac aattttttac tcttcgaaga     780
cagaaaattt gctgacattg gtaatacagt caaattgcag tactctgcgg gtgtatacag     840
aatagcagaa tgggcagaca ttacgaatgc acacggtgtg gtgggcccag gtattgttag     900
cggtttgaag caggcggcag aagaagtaac aaaggaacct agaggccttt tgatgttagc     960
agaattgtca tgcaagggct ccctatctac tggagaatat actaagggta ctgttgacat    1020
tgcgaagagc gacaaagatt tgttatcgg ctttattgct caaagagaca tgggtggaag    1080
agatgaaggt tacgattggt tgattatgac acccggtgtg ggtttagatg acaagggaga    1140
cgcattgggt caacagtata gaaccgtgga tgatgtggtc tctacaggat ctgacattat    1200
tattgttgga agaggactat ttgcaaaggg aagggatgct aagtagagg gtgaacgtta    1260
cagaaaagca ggctgggaag catatttgag aagatgcggc cagcaaaact aaaaaactgt    1320
attataagta aatgcatgta tactaaactc acaaattaga gcttcaattt aattatatca    1380
gttattaccc tatgcggtgt gaaataccgc acagatgcgt aaggagaaaa taccgcatca    1440
ggatagcttc aaaatgtttc tactcctttt ttactcttcc agattttctc ggactccgcg    1500
catcgccgta ccacttcaaa acacccaagc acagcatact aaatttcccc tctttcttcc    1560
tctagggtgt cgttaattac ccgtactaaa ggtttggaaa agaaaaaga gaccgcctcg    1620
tttcttttc ttcgtcgaaa aaggcaataa aaattttat cacgttttct tttcttgaaa    1680
atttttttt tgatttttt ctctttcgat gacctcccat tgatatttaa gttaataaac    1740
ggtcttcaat ttctcaagtt tcagtttcat tttttcttgtt ctattacaac tttttttact    1800
tcttgctcat tagaaagaaa gcatagcaat ctaatctaag tttaaaacaa tgaatgtcac    1860
ctttgaagaa agagccagtt tacacggtta cagaatcggt atcgcatcct tagacgcccc    1920
agcatccttg aacgctttgt ccttaccaat gattgatgct ttacaagaca gattgagagc    1980
ttgggcagaa gatgcagaca tagcctgtgt cttgttacgt ggtaatggtt ctaaagcatt    2040
ttgcgcaggt ggtgacgttg tccaattagc taagaaatgt ttggcctccc caggtgaagc    2100
ccctgaattg gctgaaagat ttttcgctag aagttacaga ttagatcatt atttgcacac    2160
atacccaaag cctttgatat gctgggctca tggtcacgtt ttaggtggtg gtatgggttt    2220
gttacaaggt gctggtatta gaatagtcac cccatcttca agattggcaa tgcctgaaat    2280
```

```
ctctattggt ttatttccag atgttggtgg ttcccatttc ttaagtagat tgcctggtaa    2340
attgggttta tttttcggtt taaccgcttc accattgaat gccagagatg ctttggactt    2400
aaacttggct gatagattct tgttagatac tcaacaagac gcattgatcg atggtttgat    2460
ccaattgaac tggagagaac aaccagattt gcaattgcat tccttgttaa aggctttaga    2520
acaacaagca agaagtgaat taccagctgc acaatggttg cctagaagag aaagattaga    2580
cgccttgtta gatcaagcta ctttaccatt gtcttggcaa gccttagctt cattggaaaa    2640
cgatgaagac gcattgttag ccaaagccgc taagactatg ttgggtggtt cacctttaac    2700
aggtcatttg gtctggggtc aaattagaag agctagacac ttatctttgg cacaagtatt    2760
tcaaatggaa tacggcatgt cattgaattg ttgcagacat ccagaatttg cagaaggtgt    2820
aagagccaga ttaatcgata aagaccacgc tccacattgg cactggcctg acgtaaacca    2880
agttcctgaa gccgttattg cagcccattt tgcaccatta gatgaccacc ctttagctga    2940
tttggcataa cgataccgtc gacctcgagt catgtaatta gttatgtcac gcttacattc    3000
acgccctccc cccacatccg ctctaaccga aaaggaagga gttagacaac ctgaagtcta    3060
ggtccctatt tattttttta tagttatgtt agtattaaga acgttattta tatttcaaat    3120
ttttcttttt tttctgtaca gacgcgtgta cgcatgtaac attatactga aaaccttgct    3180
tgagaaggtt ttgggacgct cgaaggcttt aatttgcggc cgtacaatca caaattaat    3240 cataatgttc atttatctat aatcaaacaa tgagaatata tactgaagtt tggtaggtta    3300
ttcttcagag atgcagtacg atatcaccaa cggtatgcag acacctatca aaacataaac    3360
ggattcatca tgaggtaaaa cgacttcctg ttcaacgctg agatcgtgat catgagaatc    3420
tccaccaaca aatgctgtga agacgcata tagtaaactg ccaccactca taagcagaag    3480
atttccactt at                                                        3492

<210> SEQ ID NO 44
<211> LENGTH: 1959
<212> TYPE: DNA
<213> ORGANISM: Artificial Sequence
<220> FEATURE:
<223> OTHER INFORMATION: SeACS(L641P) codon

<400> SEQUENCE: 44
atgtcccaaa ctcataagca cgctattcca gctaatattg ctgatagatg cttgatcaac      60
ccagaacaat acgaaactaa gtacaagcaa tccatcaacg atccagatac ttttttgggt     120
gaacaaggta agattttgga ttggattacc ccataccaaa aggtcaagaa tacttctttt     180
gctccaggta acgtttccat caaatggtat gaagatggta ctttgaactt ggctgctaac     240
tgtttggata gacacttgca agaaaacggt gatagaaccg ctattatttg ggaaggtgat     300
gatgcctctc aatccaaaca tatctcttac agagaattgc acagagatgt ctgtagattc     360
gctaacactt tgttggattt gggtattaag aagggtgacg ttgttgctat ctatatgcca     420
atggttcctg aagctgctgt tgctatgttg gcttgtgcta gaattggtgc tgttcattct     480
gttattttcg gtggttttc accagaagct gttgccggta gaattatcga ttcttcatcc     540
agattggtta tcaccgctga tgaaggtgtt agagctggta gatcaattcc attgaaaaag     600
aacgttgatg acgccttgaa gaacccaaat gttacttctg ttgaacacgt catcgttttg     660
aagagaaccg attctgatat tgactggcaa gaaggtagag atttgtggtg gagagatttg     720
attgaaaagg cttctccaga acatcaacca gaagcaatga acgctgaaga tcctttgttt     780
atcttgtaca cttctggttc tactggtaag ccaaaaggtg ttttacacac tactggtggt     840
```

-continued

```
tatttggttt acgctgctac tactttcaag tacgttttcg attatcatcc aggtgacatc    900
tattggtgta ctgctgatgt tggttgggtt actggtcatt cttatttgtt gtatggtcca    960
ttagcttgtg gtgctactac cttgatgttc gaaggtgttc caaattggcc aactccagct   1020
agaatgtgtc aagttgttga caaacaccaa gtcaacatct tgtatactgc tccaactgct   1080
attagagctt tgatggctga aggtgataag gctattgaag gtactgatag atcctccttg   1140
agaatcttgg gttctgttgg tgaacctatt aaccctgaag cttgggaatg gtactggaag   1200
aaaattggta agaaaagtg cccagttgtt gatacttggt ggcaaactga acaggtggt    1260
tttatgatta ctccattgcc aggtgctatt gaattgaaag ctggttctgc tactagacca   1320
ttttttggtg ttcaaccagc cttggttgat aatgaaggtc atccacaaga aggtgctact   1380
gaaggtaatt tggttattac tgattcttgg ccaggtcaag ctagaacttt gtttggtgat   1440
cacgaaagat tcgaacaaac ctactttttcc accttcaaga acatgtactt ttctggtgat   1500
ggtgctagaa gagatgaaga tggttactat tggattaccg gtagagttga tgatgtcttg   1560
aatgtttctg gtcacagatt gggtacagcc gaaattgaat ctgctttggt tgctcatcca   1620
aagattgctg aagcagcagt tgttggtatt ccacatgcta ttaagggtca agcaatctac   1680
gcttacgtta ccttgaatca tggtgaagaa ccatccccag aattatacgc tgaagttaga   1740
aactgggtca gaaaagaaat tggtccattg gctactccag atgttttaca ttggacagat   1800
tctttgccaa agaccagatc aggtaagatc atgagaagaa tcttgagaaa aattgctgcc   1860
ggtgatactt ctaacttggg tgataccctct actttggctg atccaggtgt tgttgaaaag   1920
ccattagaag aaaagcaagc cattgccatg ccatcttaa                          1959
```

<210> SEQ ID NO 45
<211> LENGTH: 367
<212> TYPE: PRT
<213> ORGANISM: Pseudomonas mendocina
<220> FEATURE:
<221> NAME/KEY: VARIANT
<222> LOCATION: (95)..(95)
<223> OTHER INFORMATION: Xaa can be any naturally occurring amino acid.

<400> SEQUENCE: 45

```
Met Asn Leu Gln Phe Glu Glu Arg Pro Ser Leu His Gly Tyr Arg Ile
1               5                   10                  15

Gly Ile Ala Ser Leu Asp Ala Glu Lys Ser Leu Asn Ala Leu Thr Leu
            20                  25                  30

Pro Met Ile Gln Ala Leu Asp Ala Arg Leu Gln Ala Trp Ala Glu Asp
        35                  40                  45

Pro Thr Ile Ala Cys Val Met Leu Arg Gly Asn Gly Pro Lys Ala Phe
    50                  55                  60

Cys Ala Gly Gly Asp Val Val Gln Leu Val Gln Gln Cys Arg Glu His
65                  70                  75                  80

Pro Gly Glu Val Pro Leu Ala Arg Arg Phe Phe Ala Asp Xaa Tyr
                85                  90                  95

Arg Leu Asp His Arg Ile His Ser Tyr Pro Lys Pro Phe Ile Cys Trp
            100                 105                 110

Ala His Gly His Val Leu Gly Gly Gly Met Gly Leu Met Gln Gly Ala
        115                 120                 125

Gly Val Arg Ile Val Thr Pro Ser Ser Arg Leu Gly Met Pro Glu Ile
    130                 135                 140

Asn Ile Gly Leu Tyr Pro Asp Val Gly Gly Ser Trp Phe Leu Ala Arg
```

```
                    145                 150                 155                 160
Leu Pro Gly Arg Leu Gly Leu Phe Leu Gly Leu Thr Ala Ala Ser Ile
                165                 170                 175

Asn Ala Arg Asp Ala Leu Asp Leu Asn Leu Ala Asp Arg Phe Leu Arg
            180                 185                 190

Asp Asp Gln Gln Asp Ala Leu Leu Glu Gly Leu Val Gln Leu Asn Trp
        195                 200                 205

Arg Glu Gln Pro Ala Ala Gln Leu His Ser Leu Leu Arg Ala Leu Glu
    210                 215                 220

Asn Glu Ala Arg Gly Glu Leu Pro Ala Ala Gln Trp Leu Pro Arg Arg
225                 230                 235                 240

Glu Arg Ile Asp Glu Leu Leu Asp Val Ala Asp Leu Pro Ala Ala Val
                245                 250                 255

Gln Ala Ile Ser Ala Leu Gln Gln Asp Asp Ala Leu Leu Ala Arg
                260                 265                 270

Ala Ala Lys Thr Leu Ala His Gly Cys Pro Leu Thr Ala His Leu Val
            275                 280                 285

Trp Gln Gln Ile Arg Arg Ala Arg His Leu Ser Leu Ala Glu Val Phe
        290                 295                 300

Arg Met Glu Tyr Ala Met Ser Leu Asn Cys Cys Arg His Pro Asp Phe
305                 310                 315                 320

Pro Glu Gly Val Arg Ala Arg Leu Ile Asp Lys Asp Gln Thr Pro His
                325                 330                 335

Trp His Trp Pro Asp Val Ala Ala Ile Pro Glu Ala Val Ile Glu Ala
                340                 345                 350

His Phe Ala Pro Ala Trp Glu Gly Glu His Pro Leu Ala Asp Leu
            355                 360                 365

<210> SEQ ID NO 46
<211> LENGTH: 351
<212> TYPE: PRT
<213> ORGANISM: Bacillus cereus
<220> FEATURE:
<221> NAME/KEY: VARIANT
<222> LOCATION: (91)..(91)
<223> OTHER INFORMATION: Xaa can be any naturally occurring amino acid.

<400> SEQUENCE: 46

Met Thr Glu His Val Leu Phe Ser Val Ser Glu Asn Gly Val Ala Ser
1               5                   10                  15

Ile Thr Leu Asn Arg Pro Lys Ala Leu Asn Ser Leu Ser Tyr Asp Met
                20                  25                  30

Leu Gln Pro Ile Gly Gln Lys Leu Lys Glu Trp Glu Asn Asp Glu Arg
            35                  40                  45

Ile Ala Leu Ile Val Leu Lys Gly Ala Gly Thr Lys Gly Phe Cys Ala
        50                  55                  60

Gly Gly Asp Ile Lys Thr Leu Tyr Glu Ala Arg Ser Asn Glu Ala Ala
65                  70                  75                  80

Leu Gln His Ala Glu Arg Phe Phe Glu Xaa Tyr Glu Ile Asp Thr
                85                  90                  95

Tyr Ile Tyr Gln Tyr Lys Lys Pro Ile Ile Ala Cys Leu Asp Gly Ile
            100                 105                 110

Val Met Gly Gly Gly Val Gly Leu Thr Asn Gly Ala Lys Tyr Arg Ile
        115                 120                 125

Val Thr Glu Arg Thr Lys Trp Ala Met Pro Glu Met Asn Ile Gly Phe
    130                 135                 140
```

```
Phe Pro Asp Val Gly Ala Ala Tyr Phe Leu Asn Lys Ala Pro Gly Tyr
145                 150                 155                 160

Ala Gly Arg Tyr Val Ala Leu Thr Ala Ser Ile Leu Lys Ala Ser Asp
            165                 170                 175

Val Leu Phe Ile Asn Ala Ala Asp Tyr Phe Ile Ala Ser Asp Ser Leu
        180                 185                 190

Pro Asn Phe Leu Thr Glu Leu Glu Ser Val Asn Trp Ser Lys Glu Asp
    195                 200                 205

Asp Val His Thr His Leu Lys Glu Val Ile Arg Thr Phe Ala Thr Ala
        210                 215                 220

Pro Thr Leu Glu Ser Glu Leu Ala Pro Ser Leu Glu Glu Ile Asn Ser
225                 230                 235                 240

His Phe Ala Phe Asp Thr Ile Glu Glu Ile Ile His Ser Leu Glu Lys
            245                 250                 255

Asp Gln Ser Ser Phe Ser Leu Lys Ala Lys Glu Thr Leu Leu Ser Lys
        260                 265                 270

Ser Pro Ile Ser Leu Lys Val Thr Leu Lys Gln Phe Ile Asp Gly Gln
    275                 280                 285

Asn Lys Ser Val Glu Glu Cys Phe Ala Thr Asp Leu Val Leu Ala Lys
290                 295                 300

Asn Phe Met Arg His Glu Asp Phe Phe Glu Gly Val Arg Ser Val Val
305                 310                 315                 320

Val Asp Lys Asp Gln Asn Pro Asn Tyr Lys Tyr Lys Gln Leu Ser Asp
            325                 330                 335

Val Ser Glu Glu Asp Val Asn Arg Phe Phe Asn Leu Leu Asn Ala
        340                 345                 350

<210> SEQ ID NO 47
<211> LENGTH: 360
<212> TYPE: PRT
<213> ORGANISM: Bacillus mycoides
<220> FEATURE:
<221> NAME/KEY: VARIANT
<222> LOCATION: (101)..(101)
<223> OTHER INFORMATION: Xaa can be any naturally occurring amino acid.

<400> SEQUENCE: 47

Met Arg Arg Tyr Ile Arg Gly Gly Phe Lys Met Thr Glu Asn Val Leu
1               5                   10                  15

Phe Ser Ile His Glu Asn Gly Val Ala Ser Ile Thr Leu Asn Arg Pro
            20                  25                  30

Lys Ala Leu Asn Ser Leu Ser Tyr Asp Met Leu His Pro Ile Gly Gln
        35                  40                  45

Lys Leu Lys Glu Trp Glu Lys Asp Asp Arg Ile Ala Val Val Ile Leu
    50                  55                  60

Lys Gly Ala Gly Thr Lys Gly Phe Cys Ala Gly Gly Asp Ile Lys Thr
65                  70                  75                  80

Leu Tyr Glu Ala Arg Ser Asn Glu Val Ala Leu Gln His Ala Glu His
            85                  90                  95

Phe Phe Glu Glu Xaa Tyr Glu Ile Asp Thr Tyr Ile Tyr His Tyr Pro
            100                 105                 110

Lys Pro Ile Ile Ala Cys Leu Asp Gly Ile Val Met Gly Gly Gly Val
        115                 120                 125

Gly Leu Thr Asn Gly Ala Lys Tyr Arg Ile Val Thr Asp Arg Thr Lys
    130                 135                 140
```

```
Trp Ala Met Pro Glu Met Asn Ile Gly Phe Phe Pro Asp Val Gly Ala
145                 150                 155                 160

Ala Tyr Phe Leu Asn Lys Ala Pro Gly Gln Thr Gly Arg Tyr Val Ala
            165                 170                 175

Leu Thr Ala Ser Val Leu Lys Ala Ala Asp Val Leu Tyr Ile Lys Ala
            180                 185                 190

Ala Asp His Tyr Met Pro Ser Glu Thr Leu Pro Thr Phe Leu Asp Ala
            195                 200                 205

Ile Glu Lys Val Asn Trp His Asp Gln Asn Ile His Ile Thr Leu Lys
            210                 215                 220

Glu Leu Ile Asn Lys Tyr Glu Thr Ala Pro Ser Val Glu Ser Glu Leu
225                 230                 235                 240

Val Ser Leu Leu Glu Glu Ile Asp Gln His Phe Ser Phe His Thr Val
            245                 250                 255

Glu Asp Ile Ile His Ser Leu Asp Asn Ala Asp Gly Ser Phe Ala Ser
            260                 265                 270

Lys Thr Lys Glu Thr Leu Leu Ser Lys Ser Pro Phe Ser Leu Lys Val
            275                 280                 285

Thr Leu Lys Gln Leu Ile Asp Gly Lys Glu Lys Ser Ile Glu Glu Cys
290                 295                 300

Phe Ala Thr Asp Leu Val Leu Ala Lys Asn Phe Met Arg His Glu Asp
305                 310                 315                 320

Phe Phe Glu Gly Val Arg Ser Val Val Val Asp Lys Asp Gln Asn Pro
            325                 330                 335

Lys Tyr Lys Tyr Lys Gln Leu Ser Asp Val Ser Asp Glu Asp Val Asn
            340                 345                 350

Arg Phe Phe Asn Leu Leu Asn Ala
            355                 360

<210> SEQ ID NO 48
<211> LENGTH: 370
<212> TYPE: PRT
<213> ORGANISM: Pseudomonas fluorescens
<220> FEATURE:
<221> NAME/KEY: VARIANT
<222> LOCATION: (95)..(95)
<223> OTHER INFORMATION: Xaa can be any naturally occurring amino acid.

<400> SEQUENCE: 48

Met Asn Leu His Phe Glu Glu Leu Thr Gly Ser Asp Gly Ala Arg Ile
1               5                   10                  15

Gly Ile Ala Ser Leu Asp Ala Glu Lys Ser Leu Asn Ala Leu Ser Leu
            20                  25                  30

Pro Met Ile Leu Ala Leu Gly Asp Arg Leu Asp Ala Trp Ala Lys Asp
            35                  40                  45

Pro Asn Ile Val Cys Val Leu Leu Arg Gly Asn Gly Pro Lys Ala Phe
50                  55                  60

Cys Ala Gly Gly Glu Val Arg Ser Leu Ala Leu Ala Cys Arg Glu Gln
65                  70                  75                  80

Pro Gly Glu Val Pro Ala Leu Ala Ala Gln Phe Phe Ala Ala Xaa Tyr
            85                  90                  95

Arg Leu Asp Tyr Arg Leu His Thr Phe Pro Lys Pro Leu Ile Cys Trp
            100                 105                 110

Gly His Gly Tyr Val Leu Gly Gly Met Gly Leu Leu Gln Ser Ala
            115                 120                 125

Ala Val Arg Ile Val Thr Pro Ser Ser Arg Leu Ala Met Pro Glu Ile
```

```
                130                 135                 140
Ser Ile Gly Leu Tyr Pro Asp Val Gly Ala Ser Trp Phe Leu Ser Arg
145                 150                 155                 160

Leu Pro Gly Lys Leu Gly Leu Phe Leu Gly Leu Thr Gly Ala His Val
                165                 170                 175

Asn Gly Arg Asp Ala Leu Asp Leu Gly Leu Ala Asp Arg Phe Leu Arg
                180                 185                 190

Asp Asp Gln Gln Asp Glu Leu Ile Glu Gly Leu Leu Gln Leu Asn Trp
                195                 200                 205

Gln Glu Gln Thr Ala Met Gln Leu Asn Ser Leu Phe Lys Ala Leu Ala
                210                 215                 220

Gln Glu Ala Val Asp Gln Leu Pro Glu Ala Gln Trp Leu Pro Arg Arg
225                 230                 235                 240

Ala Gln Ile Asp Glu Trp Leu Asp Val Gly Asp Val Arg Ser Ala Trp
                245                 250                 255

Arg Ala Leu Ser Gln Leu Arg Asp His Ala Asp Pro Leu Phe Ser Arg
                260                 265                 270

Ala Gly Lys Thr Leu Ser Glu Gly Cys Pro Leu Thr Ala His Leu Val
                275                 280                 285

Trp Glu Gln Ile Gln Arg Ala Arg His Leu Ser Leu Ala Gln Val Phe
                290                 295                 300

Gln Met Glu Tyr Thr Leu Ser Leu Asn Cys Cys Arg His Pro Glu Phe
305                 310                 315                 320

Ser Glu Gly Val Arg Ala Arg Leu Ile Asp Lys Asp Gln Thr Pro Arg
                325                 330                 335

Trp His Trp Pro Asp Val His Thr Leu Pro Asp Ala Val Val Gln Ala
                340                 345                 350

His Phe Asn Lys Ala Trp Glu Gly Arg His Pro Leu Ala Asp Leu Ser
                355                 360                 365

Asp Tyr
    370

<210> SEQ ID NO 49
<211> LENGTH: 351
<212> TYPE: PRT
<213> ORGANISM: Bacillus thuringiensis
<220> FEATURE:
<221> NAME/KEY: VARIANT
<222> LOCATION: (91)..(91)
<223> OTHER INFORMATION: Xaa can be any naturally occurring amino acid.

<400> SEQUENCE: 49

Met Thr Glu His Val Leu Phe Ser Val Ser Glu Asn Gly Val Ala Ser
1               5                   10                  15

Ile Thr Leu Asn Arg Pro Lys Ala Leu Asn Ser Leu Ser Tyr Asp Met
                20                  25                  30

Leu Gln Pro Ile Gly Gln Lys Leu Lys Glu Trp Glu His Asp Glu Arg
            35                  40                  45

Ile Ala Leu Ile Val Leu Lys Gly Ala Gly Thr Lys Gly Phe Cys Ala
        50                  55                  60

Gly Gly Asp Ile Lys Thr Leu Tyr Glu Ala Arg Ser Asn Glu Ala Ala
65                  70                  75                  80

Leu Gln His Ala Glu Arg Phe Phe Glu Glu Xaa Tyr Glu Ile Asp Thr
                85                  90                  95

Tyr Ile Tyr Gln Tyr Lys Lys Pro Ile Ile Ala Cys Leu Asp Gly Ile
                100                 105                 110
```

Val Met Gly Gly Val Gly Leu Thr Asn Gly Ala Lys Tyr Arg Ile
    115                 120                 125

Val Thr Glu Arg Thr Lys Trp Ala Met Pro Glu Met Asn Ile Gly Phe
    130                 135                 140

Phe Pro Asp Val Gly Ala Ala Tyr Phe Leu Asn Lys Ala Pro Gly Tyr
145                 150                 155                 160

Ala Gly Arg Tyr Val Ala Leu Thr Ala Ser Ile Leu Lys Ala Ala Asp
                165                 170                 175

Val Leu Phe Ile Asn Ala Ala Asp Tyr Phe Ile Ala Ser Asp Ser Leu
            180                 185                 190

Pro Asn Phe Leu Thr Glu Leu Glu Ser Val Asn Trp Pro Lys Lys Asp
        195                 200                 205

Asp Val His Thr His Leu Lys Glu Val Ile Arg Thr Phe Ala Thr Ala
    210                 215                 220

Pro Thr Leu Glu Ser Glu Leu Ala Pro Ser Leu Glu Ile Asn Ser
225                 230                 235                 240

His Phe Ala Phe Asp Thr Ile Glu Glu Ile Ile His Ser Leu Glu Lys
                245                 250                 255

Asp Gln Ser Ser Phe Ala Leu Lys Ala Lys Glu Thr Leu Leu Ser Lys
            260                 265                 270

Ser Pro Ile Ser Leu Lys Val Thr Leu Lys Gln Phe Ile Asp Gly Gln
        275                 280                 285

Asn Lys Ser Val Glu Glu Cys Phe Ala Thr Asp Leu Val Leu Ala Lys
    290                 295                 300

Asn Phe Met Arg His Glu Asp Phe Phe Glu Gly Val Arg Ser Val Val
305                 310                 315                 320

Val Asp Lys Asp Gln Asn Pro Asp Tyr Lys Tyr Lys Gln Leu Ser Asp
                325                 330                 335

Val Ser Glu Glu Asp Val Asn Arg Phe Phe Asn Leu Leu Asn Ala
            340                 345                 350

<210> SEQ ID NO 50
<211> LENGTH: 366
<212> TYPE: PRT
<213> ORGANISM: Pseudomonas fulva
<220> FEATURE:
<221> NAME/KEY: VARIANT
<222> LOCATION: (95)..(95)
<223> OTHER INFORMATION: Xaa can be any naturally occurring amino acid.

<400> SEQUENCE: 50

Met Asn Val Thr Phe Glu Glu Arg Ala Ser Leu His Gly Tyr Arg Ile
1               5                   10                  15

Gly Ile Ala Ser Leu Asp Ala Pro Ala Ser Leu Asn Ala Leu Ser Leu
            20                  25                  30

Pro Met Ile Asp Ala Leu Gln Asp Arg Leu Arg Ala Trp Ala Glu Asp
        35                  40                  45

Ala Asp Ile Ala Cys Val Leu Leu Arg Gly Asn Gly Ser Lys Ala Phe
    50                  55                  60

Cys Ala Gly Gly Asp Val Val Gln Leu Ala Lys Lys Cys Leu Ala Ser
65                  70                  75                  80

Pro Gly Glu Ala Pro Glu Leu Ala Glu Arg Phe Phe Ala Arg Xaa Tyr
                85                  90                  95

Arg Leu Asp His Tyr Leu His Tyr Pro Lys Pro Leu Ile Cys Trp
            100                 105                 110

```
Ala His Gly His Val Leu Gly Gly Met Gly Leu Leu Gln Gly Ala
        115                 120                 125

Gly Ile Arg Ile Val Thr Pro Ser Ser Arg Leu Ala Met Pro Glu Ile
130                 135                 140

Ser Ile Gly Leu Phe Pro Asp Val Gly Ser His Phe Leu Ser Arg
145                 150                 155                 160

Leu Pro Gly Lys Leu Gly Leu Phe Phe Gly Leu Thr Ala Ser Pro Leu
                165                 170                 175

Asn Ala Arg Asp Ala Leu Asp Leu Leu Ala Asp Arg Phe Leu Leu
                180                 185                 190

Asp Thr Gln Gln Asp Ala Leu Ile Asp Gly Leu Ile Gln Leu Asn Trp
                195                 200                 205

Arg Glu Gln Pro Asp Leu Gln Leu His Ser Leu Leu Lys Ala Leu Glu
        210                 215                 220

Gln Gln Ala Arg Ser Glu Leu Pro Ala Ala Gln Trp Leu Pro Arg Arg
225                 230                 235                 240

Glu Arg Leu Asp Ala Leu Leu Asp Gln Ala Thr Leu Pro Leu Ser Trp
                245                 250                 255

Gln Ala Leu Ala Ser Leu Glu Asn Asp Glu Asp Ala Leu Leu Ala Lys
                260                 265                 270

Ala Ala Lys Thr Met Leu Gly Gly Ser Pro Leu Thr Gly His Leu Val
                275                 280                 285

Trp Gly Gln Ile Arg Arg Ala Arg His Leu Ser Leu Ala Gln Val Phe
        290                 295                 300

Gln Met Glu Tyr Gly Met Ser Leu Asn Cys Cys Arg His Pro Glu Phe
305                 310                 315                 320

Ala Glu Gly Val Arg Ala Arg Leu Ile Asp Lys Asp His Ala Pro His
                325                 330                 335

Trp His Trp Pro Asp Val Asn Gln Val Pro Glu Gln Val Ile Ala Ala
                340                 345                 350

His Phe Ala Pro Leu Asp Asp His Pro Leu Ala Asp Leu Ala
                355                 360                 365

<210> SEQ ID NO 51
<211> LENGTH: 351
<212> TYPE: PRT
<213> ORGANISM: Bacillus cereus
<220> FEATURE:
<221> NAME/KEY: VARIANT
<222> LOCATION: (91)..(91)
<223> OTHER INFORMATION: Xaa can be any naturally occurring amino acid.

<400> SEQUENCE: 51

Met Thr Glu His Val Leu Phe Ser Val Ser Glu Asn Gly Val Ala Ser
1               5                   10                  15

Ile Thr Leu Asn Arg Pro Lys Ala Leu Asn Ser Leu Ser Tyr Glu Met
                20                  25                  30

Leu Gln Pro Ile Gly Lys Lys Leu Lys Glu Trp Glu Asn Asp Glu Gln
        35                  40                  45

Ile Ala Leu Ile Val Leu Lys Gly Ala Gly Thr Lys Gly Phe Cys Ala
50                  55                  60

Gly Gly Asp Ile Lys Thr Leu Tyr Glu Ala Arg Ser Asn Glu Ile Ala
65                  70                  75                  80

Leu Gln His Ala Glu Arg Phe Phe Glu Glu Xaa Tyr Glu Ile Asp Thr
                85                  90                  95

Tyr Ile Tyr Gln Tyr Lys Lys Pro Ile Ile Ala Cys Leu Asp Gly Ile
```

```
                  100                 105                 110
Val Met Gly Gly Val Gly Leu Thr Asn Gly Ala Lys Tyr Arg Ile
            115                 120                 125

Val Thr Glu Arg Thr Lys Trp Ala Met Pro Glu Met Asn Ile Gly Phe
130                 135                 140

Phe Pro Asp Val Gly Ala Ala Tyr Phe Leu Asn Lys Ala Pro Gly Phe
145                 150                 155                 160

Ala Gly Arg Tyr Val Ala Leu Thr Ala Ser Ile Leu Lys Ala Ser Asp
            165                 170                 175

Val Leu Phe Ile Asn Ala Ala Asp Tyr Phe Met Thr Ser Asp Ser Leu
            180                 185                 190

Pro Lys Phe Leu Thr Glu Leu Glu Ser Val Asn Trp His Lys Gly Asp
            195                 200                 205

Asp Val His Ile His Leu Lys Glu Val Ile Arg Thr Phe Ala Thr Thr
            210                 215                 220

Ser Asn Leu Glu Ser Glu Leu Ala Pro Leu Leu Glu Glu Ile Asn Ala
225                 230                 235                 240

His Phe Ala Phe Asp Thr Ile Glu Glu Ile Ile His Ser Leu Glu Lys
            245                 250                 255

Asp Gln Ser Ser Phe Ala Leu Lys Thr Lys Thr Leu Leu Ser Lys
            260                 265                 270

Ser Pro Ile Ser Leu Lys Val Thr Leu Lys Gln Phe Ile Asp Gly His
            275                 280                 285

Asp Lys Ser Val Glu Glu Cys Phe Ala Thr Asp Leu Val Leu Ala Lys
            290                 295                 300

Asn Phe Met Arg His Glu Asp Phe Phe Glu Gly Val Arg Ser Val Val
305                 310                 315                 320

Val Asp Lys Asp Gln Asn Pro Asn Tyr Lys Tyr Lys Gln Leu Ser Asp
            325                 330                 335

Val Ser Asp Glu Asp Val Asn Arg Phe Phe Asn Leu Leu Asn Ala
            340                 345                 350

<210> SEQ ID NO 52
<211> LENGTH: 351
<212> TYPE: PRT
<213> ORGANISM: Bacillus cereus
<220> FEATURE:
<221> NAME/KEY: VARIANT
<222> LOCATION: (91)..(91)
<223> OTHER INFORMATION: Xaa can be any naturally occurring amino acid.

<400> SEQUENCE: 52

Met Thr Glu Gln Val Leu Phe Ser Val Ser Glu Asn Gly Val Ala Thr
1               5                   10                  15

Ile Thr Leu Asn Arg Pro Lys Ala Leu Asn Ser Leu Ser Tyr Asp Met
            20                  25                  30

Leu Gln Pro Ile Gly Gln Lys Leu

```
Val Met Gly Gly Val Gly Leu Thr Asn Gly Ala Lys Tyr Arg Ile
        115                 120                 125

Val Thr Glu Arg Thr Lys Trp Ala Met Pro Glu Met Asn Ile Gly Phe
130                 135                 140

Phe Pro Asp Val Gly Ala Ala Tyr Phe Leu Asn Lys Ala Pro Gly Tyr
145                 150                 155                 160

Thr Gly Arg Phe Val Ala Leu Thr Ala Ser Ile Leu Lys Ala Ser Asp
                165                 170                 175

Val Leu Phe Ile Asn Ala Ala Asp Tyr Phe Met Thr Ser Asp Ser Leu
            180                 185                 190

Pro Glu Phe Leu Thr Glu Leu Glu Ser Val Asn Trp His Lys Glu Asp
        195                 200                 205

Asp Val His Thr Asn Leu Lys Glu Val Ile Arg Thr Phe Ala Thr Ala
    210                 215                 220

Pro Asn Leu Glu Ser Glu Leu Ala Pro Ser Leu Glu Val Ile Asn Ser
225                 230                 235                 240

His Phe Ala Phe Asp Thr Ile Glu Glu Ile Ile His Ser Leu Glu Lys
                245                 250                 255

Asp Glu Ser Ser Phe Ala Leu Lys Thr Lys Glu Ile Leu Leu Ser Lys
            260                 265                 270

Ser Pro Ile Ser Leu Lys Val Thr Leu Lys Gln Phe Ile Asp Gly Gln
        275                 280                 285

Asp Lys Ser Val Glu Glu Cys Phe Ala Thr Asp Leu Ile Leu Ala Lys
    290                 295                 300

Asn Phe Met Arg His Glu Asp Phe Phe Glu Gly Val Arg Ser Val Val
305                 310                 315                 320

Val Asp Lys Asp Gln Asn Pro Asn Tyr Lys Tyr Lys Gln Leu Ser Asp
                325                 330                 335

Val Ser Glu Glu Asp Val Asn Arg Phe Phe Asn Leu Leu Asn Ala
            340                 345                 350

<210> SEQ ID NO 53
<211> LENGTH: 309
<212> TYPE: PRT
<213> ORGANISM: Escherichia coli

<400> SEQUENCE: 53

Met Thr Gln Phe Ala Phe Val Phe Pro Gly Gln Gly Ser Gln Thr Val
1               5                   10                  15

Gly Met Leu Ala Asp Met Ala Ala Ser Tyr Pro Ile Val Glu Glu Thr
            20                  25                  30

Phe Ala Glu Ala Ser Ala Ala Leu Gly Tyr Asp Leu Trp Ala Leu Thr
        35                  40                  45

Gln Gln Gly Pro Ala Glu Glu Leu Asn Lys Thr Trp Gln Thr Gln Pro
    50                  55                  60

Ala Leu Leu Thr Ala Ser Val Ala Leu Tyr Arg Val Trp Gln Gln Gln
65                  70                  75                  80

Gly Gly Lys Ala Pro Ala Met Met Ala Gly His Ser Leu Gly Glu Tyr
                85                  90                  95

Ser Ala Leu Val Cys Ala Gly Val Ile Asp Phe Ala Asp Ala Val Arg
            100                 105                 110

Leu Val Glu Met Arg Gly Lys Phe Met Gln Glu Ala Val Pro Glu Gly
        115                 120                 125

Thr Gly Ala Met Ala Ala Ile Ile Gly Leu Asp Asp Ala Ser Ile Ala
```

```
                130                 135                 140
Lys Ala Cys Glu Glu Ala Ala Glu Gly Gln Val Val Ser Pro Val Asn
145                 150                 155                 160

Phe Asn Ser Pro Gly Gln Val Val Ile Ala Gly His Lys Glu Ala Val
                165                 170                 175

Glu Arg Ala Gly Ala Ala Cys Lys Ala Ala Gly Ala Lys Arg Ala Leu
                180                 185                 190

Pro Leu Pro Val Ser Val Pro Ser His Cys Ala Leu Met Lys Pro Ala
                195                 200                 205

Ala Asp Lys Leu Ala Val Glu Leu Ala Lys Ile Thr Phe Asn Ala Pro
                210                 215                 220

Thr Val Pro Val Val Asn Asn Val Asp Val Lys Cys Glu Thr Asn Gly
225                 230                 235                 240

Asp Ala Ile Arg Asp Ala Leu Val Arg Gln Leu Tyr Asn Pro Val Gln
                245                 250                 255

Trp Thr Lys Ser Val Glu Tyr Met Ala Ala Gln Gly Val Glu His Leu
                260                 265                 270

Tyr Glu Val Gly Pro Gly Lys Val Leu Thr Gly Leu Thr Lys Arg Ile
                275                 280                 285

Val Asp Thr Leu Thr Ala Ser Ala Leu Asn Glu Pro Ser Ala Met Ala
                290                 295                 300

Ala Ala Leu Glu Leu
305
```

RECOMBINANT HOST CELLS FOR THE PRODUCTION OF MALONATE

RELATED APPLICATIONS

The present application is a divisional of and claims priority to U.S. application Ser. No. 14/386,272 filed Sep. 18, 2014, which is a National Stage Application of PCT/US2013/029441 filed Mar. 6, 2013 and claims the benefit of U.S. Provisional Patent Application No. 61/607,479 filed Mar. 6, 2012 and U.S. Provisional Patent Application No. 61/619,112 filed Apr. 2, 2012, the entire disclosures of which are expressly incorporated herein by reference.

GOVERNMENT INTEREST

This invention was made with government support under grant no. DE-SC0006469 awarded by the Department of Energy. The government has certain rights in this invention.

BACKGROUND OF THE INVENTION

The long-term economic and environmental concerns associated with the petrochemical industry has provided the impetus for increased research, development, and commercialization of processes for conversion of carbon feedstocks into chemicals that can replace those derived from petroleum feedstocks. One approach is the development of biorefining processes to convert renewable feedstocks into products that can replace petroleum-derived chemicals. Two common goals in improving a biorefining process include achieving a lower cost of production and reducing carbon dioxide emissions.

Propanedioic acid ("malonate", CAS No. 141-82-2) is currently produced from non-renewable, petroleum feedstocks. Mono- or di-esterification of one or both carboxylic acid moieties of malonate with an alcohol (e.g. methanol or ethanol) yields the monoalkyl and dialkyl malonates, respectively. 2,2-dimethyl-1,3-dioxane-4,6-dione ("Meldrum's acid" CAS No. 2033-24-1) is produced from malonate using either acetone in acetic anhydride or isopropenyl acetate in acid.

Chemical synthesis is currently the preferred route for synthesis of malonate and malonate derived compounds. For example, dialkyl malonates are produced through either a hydrogen cyanide or carbon monoxide process. In the hydrogen cyanide process, sodium cyanide is reacted with sodium chloroacetate at elevated temperatures to produce sodium cyanoacetate, which is subsequently reacted with an alcohol/mineral acid mixture to produce the dialkyl malonate. Hildbrand et al. report yields of 75-85% (see "Malonic acid and Derivatives" In: Ullmann's Encyclopedia of Industrial Chemistry, Wiley-VCH, Weinheim, N.Y. (2002)). In the carbon monoxide process, dialkyl malonates (also referred to herein as diester malonates) are produced through cobalt-catalyzed alkoxycarbonylation of chloroacetates with carbon monoxide in the presence of an alcohol at elevated temperatures and pressures.

The existing, petrochemical-based production routes to the malonate and malonate-derived compounds are low yielding, environmentally damaging, dependent upon non-renewable feedstocks, and require expensive treatment of wastewater and exhaust gas. Thus, there remains a need for methods and materials for biocatalytic conversion of renewable feedstocks into malonate, purification of biosynthetic malonate, and subsequent preparation of downstream chemicals and products.

1. Summary of the Invention

The present invention provides recombinant host cells, materials, and methods for the biological production of malonate, methods for detecting the presence of malonate and determining the levels of malonate (referred to herein as "sensing malonate") in malonate producing host cells, and methods for screening host cells for increased malonate production. In addition, the present invention provides methods for the purification of biologically produced malonate, and the methods for converting malonate to other industrially important chemicals.

In a first aspect, the invention provides recombinant host cells comprising a heterologous nucleic acid encoding an acyl-CoA hydrolase that catalyzes conversion of malonyl-CoA to malonic acid, as illustrated here:

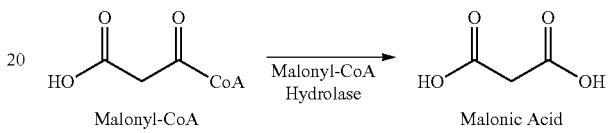

Malonyl-CoA → Malonic Acid

These recombinant host cells produce more malonate than counterpart cells that do not comprise such a heterologous hydrolase. In various embodiments, the host cells can produce at least 10 g/L malonate under appropriate fermentation conditions, and in various embodiments, productions levels can be as high as 50 g/L to 100 g/L or higher. In some embodiments, the heterologous nucleic acid encodes a mutated form of an endogenously expressed enzyme; thus, the present invention provides a variety of mutated acyl-CoA hydrolases, nucleic acids encoding them, and recombinant expression vectors comprising those nucleic acids. In other embodiments, the heterologous nucleic acid codes for the overexpression of an endogenous enzyme. Further, in some embodiments the heterologous nucleic acid encodes a wild-type or mutant enzyme of an acyl-CoA hydrolase heterologous to (not natively expressed in) the host cell. In some embodiments the host cell is a yeast cell. In other embodiments, the host cell is a bacterial cell.

Thus, in various embodiments, the heterologous nucleic acids provided by the invention encode a wild-type or mutated form of an acyl-CoA hydrolase. Non-limiting examples of acyl-CoA hydrolases encoded by the nucleic acids provided by the invention and suitable for malonyl-CoA hydrolysis include wild-type and modified enzymes selected from the group consisting of 3-hydroxyisobutyryl-CoA hydrolases (EC 3.1.2.4), 3-hydroxypropionyl-CoA hydrolases (EC 3.1.2.4), acetoacetyl-CoA hydrolases (EC 3.1.2.11), methylmalonyl-CoA hydrolases (EC 3.1.2.17), propionyl-CoA hydrolases (EC 3.1.2.18), succinyl-CoA hydrolases (EC 3.1.2.3), and malonyl-CoA:ACP transacylases (EC 2.3.1.39) mutated as provided herein to have malonyl-CoA hydrolase activity.

In various embodiments, the invention provides a malonyl-CoA hydrolase that is a mutant of a 3-hydroxyisobutyryl-CoA hydrolase (EC 3.1.2.4). Suitable 3-hydroxyisobutyryl-CoA hydrolases can be obtained from both eukaryotic and prokaryotic, including both Gram positive and Gram negative, organisms. In various embodiments, the 3-hydroxyisobutyryl-CoA hydrolase is obtained from a yeast strain, a *Bacillus* species, and a *Pseudomonas* species.

In additional embodiments, the invention provides a malonyl-CoA hydrolase that is a malonyl-CoA:ACP transacylase (EC 2.3.1.39) mutated as provided herein to have malonyl-CoA hydrolase activity, encoded by a prokaryote. In various embodiments, the prokaryote is a Gram-negative bacterium. In various embodiments of the invention, the Gram-negative bacterium is an *Escherichia*.

In a second aspect, the invention provides recombinant expression vectors encoding a wild-type or mutated acyl-CoA hydrolase that catalyzes conversion of malonyl-CoA to malonate. In some embodiments, the expression vector is a yeast expression vector; in other embodiments, the expression vector is a bacterial expression vector. In various embodiments, the bacterial expression vector is an *Escherichia coli* expression vector.

In a third aspect, the invention provides recombinant host cells suitable for the biosynthetic production of malonate at levels enabling its isolation and use as a starting material for chemical synthesis of other useful products. In some embodiments, the host cell is a eukaryote. In some embodiments, the host cell is a yeast cell. In various embodiments, the yeast is a *Candida, Cryptococcus, Hansenula, Issatchenkia, Kluyveromyces, Komagataella, Lipomyces, Pichia, Rhodosporidium, Rhodotorula, Saccharomyces* or *Yarrowia* species. In some embodiments, the eukaryotic host cell is a fungus. In some embodiments, the cell host is an algae.

In other embodiments, the host cell is a bacterial cell. In various embodiments, the host cell is a bacterial cell selected from the group consisting of *Bacillus, Clostridium, Corynebacterium, Escherichia, Pseudomonas*, and *Streptomyces*. In some embodiments, the host cell is an *E. coli* cell.

Generally, the recombinant host cells of the invention have been genetically modified for improved malonate yield, titer, and/or productivity. In various embodiments, the host cells have been modified for increased malonate biosynthesis through one or more host cell modifications selected from the group consisting of modifications that result in increased acetyl-CoA biosynthesis, increased malonyl-CoA biosynthesis, decreased malonyl-CoA utilization, decreased malonate catabolism, increased secretion of malonate into the fermentation broth, increased host cell tolerance to malonate in the fermentation broth, and/or increased host cell catabolism of carbon sources (e.g. acetate, alginate, ethanol, fatty acids, lignocellulosic biomass, methanol, pentose sugars, and syn gas).

In a fourth aspect, the invention provides methods for producing malonate in a recombinant host cell, which methods generally comprise culturing the recombinant host cell in fermentation broth under conditions that enable it to produce malonate. In some embodiments, the host cell has been engineered to express more or less of an endogenous enzyme that results in the production of more malonate than a corresponding cell that has not been so engineered. In some embodiments, the method comprises culturing a recombinant host cell expressing a heterologous (foreign or non-native) enzyme that results in the increased production of malonate. In some embodiments, the host cell used in the method comprises one or expression vectors comprising heterologous malonyl-CoA hydrolase enzymes. In some embodiments of these methods, the fermentation broth is supplemented with carbon sources promoting malonate production and selected from the group consisting of cellodextrins, 5 carbon sugars, 6 carbon sugars, carbon dioxide, ethanol, methanol, glycerol, acetate, and/or fatty acids.

In a fifth aspect, the invention provides biosensors comprising a malonate transcription factor and a promoter responsive to said transcription factor operably linked to a marker gene. The invention also provides methods for "sensing" malonate, malonate production, and malonate producing host cells and methods for screening for host cells with increased malonate production. In various embodiments, said methods comprise culturing a host cell expressing a malonate transcription factor and containing a promoter responsive to said transcription factor and operably linked to a marker gene, and selecting host cells with improved malonate production by screening for expression of the marker gene product and selecting those host cells that express higher levels of the marker gene product. In some embodiments, malonate is produced in one host cell, the fermentation broth from the first cell is contacted with (added to media containing) a second cell comprising a malonate transcription factor and a promoter responsive to said transcription factor operably linked to a marker gene, and host cells with improved malonate production are identified by identifying cells with the highest levels of expression of the marker gene product. In other embodiments, malonate is produced in a host cell comprising a malonate transcription factor and promoter responsive to malonate operably linked to a marker gene, and host cells with increased malonate production are screened for increased malonate production by screening for and identifying cells that express the highest levels of the marker gene product. In some embodiments, the transcription factor can bind malonate, which results in binding of the transcription factor to a cognate promoter and activation of the marker gene that is operably linked to the promoter. In some embodiments, the transcription factor is an MdcY transcription factor. In some embodiments, the method is practiced to screen or select for genetically modified host cells with improved malonate production relative to control cells.

In a sixth aspect, the invention provides purified malonate isolated from the fermentation broth of a host cell producing malonate, optionally a host cell of the invention. The invention also provides methods for purifying malonate from the fermentation broth of a host cell producing malonate, the methods generally comprising culturing a host cell in fermentation broth under conditions that enable the host cell to produce malonate, and purifying the malonate from the fermentation broth. In some embodiments of the invention, the concentration of malonate in the broth is increased by dewatering the fermentation broth during the purification process. In various embodiments of the invention, the dewatering is achieved by reverse osmosis processing, evaporation, or a combination of the two. In various embodiments, the purification is achieved by adding one or more of the following: a divalent cation, a monovalent cation, ammonium, a monosubstituted amine, a disubstituted amine, a trisubstituted amine, a cationic purification resin, or an acid. In various embodiments of the invention, these agents are added in conjunction with one or more organic solvents. In some embodiments of the invention, a hydrophobic solvent is used in a liquid-liquid extraction of the fermentation broth. In other embodiments, malonate is purified from the fermentation broth by reactive extraction or distillation with an acid catalyst and an alcohol.

In a seventh aspect, the invention provides methods of making compounds derived from malonate and compounds produced by such methods. The methods generally comprise reacting malonate with one or more substrates to produce a compound. In some embodiments of these methods, chemicals with established synthetic routes from malonate are produced using biologically derived malonate. In other embodiments of these methods, new synthetic routes for the production of useful chemicals are provided that are suitable for use with either a synthetically or biologically derived malonate. In some embodiments, monoalkyl malonate esters are synthesized from biologically derived malonate. In other embodiments, dialkyl malonate esters are synthesized from biologically derived malonate. In some embodiments, an acrylate is synthesized from malonate or malonic acid. In other embodiments, acrylate is synthesized from malonate monoesters or diesters. In other embodiments, dicarboxylic acids are produced from malonate. Illustrative dicarboxylic acids that can be produced in accordance with the methods of the invention include those selected from the group consisting of pentanedioic acid, hexanedioic acid, heptanedioic acid, octanedioic acid, nonanedioic acid, decanedioic acid, undecanedioic acid, dodecanedioic acid, and the corresponding monoalkyl and dialkyl esters of each. In other embodiments of the invention, dicarboxylic acids are produced from a malonate-derived compound. In other embodiments of the invention, ε-caprolactam is produced from malonate. In other embodiments of the invention, δ-valerolactam is produced from malonate.

These and other aspects and embodiments of the invention are illustrated in the accompanying drawings and described in more detail below.

DETAILED DESCRIPTION OF THE INVENTION

Figure 1:
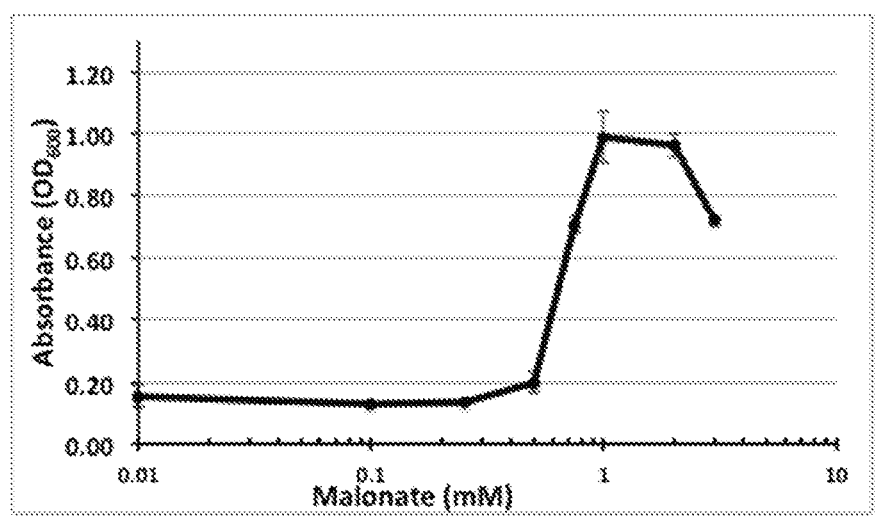
FIG. 1 shows a dose-response curve for an *E. coli* MdcY malonate biosensor of the invention that utilizes the promoter $P_{MdcL}$. The X-axis is the concentration of exogenous malonate added to the fermentation broth; the Y-axis is the cell culture density ($OD_{600}$) after 12 hours growth in medium with 25 μg/ml tetracycline. *E. coli* transformed with plasmid S14, comprising an MdcY transcription factor and a tetA gene under control of a $P_{MdcL}$ promoter, produced the tetracycline resistance protein TetA upon exogenous addition of malonate. The biosensor displayed malonate-dependent increases in tetracycline resistance as measured by the increase in $OD_{600}$ with the increase in concentration exogenously added malonate as described in additional detail in Example 21.

The present invention provides recombinant host cells, materials, and methods for the biological production of malonate, screening malonate producing host cells for improved malonate production, purification of biologically produced malonate, and the synthetic conversion of malonate to industrially important chemicals.

While the present invention is described herein with reference to aspects and specific embodiments thereof, those skilled in the art will recognize that various changes may be made and equivalents may be substituted without departing from the invention. The present invention is not limited to particular nucleic acids, expression vectors, enzymes, host microorganisms, or processes, as such may vary. The terminology used herein is for purposes of describing particular aspects and embodiments only, and is not to be construed as limiting. In addition, many modifications may be made to adapt a particular situation, material, composition of matter, process, process step or steps, in accordance with the invention. All such modifications are within the scope of the claims appended hereto.

All patents, patent applications, and publications cited herein are incorporated herein by reference in their entireties.

Section 1: Definitions

In this specification and in the claims that follow, reference will be made to a number of terms that shall be defined to have the following meanings.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

Amino acids in a protein coding sequence are identified herein by the following abbreviations and symbols. Specific amino acids are identified by a single-letter abbreviation, as follows: A is alanine, R is arginine, N is asparagine, D is aspartic acid, C is cysteine, Q is glutamine, E is glutamic acid, G is glycine, H is histidine, L is leucine, I is isoleucine, K is lysine, M is methionine, F is phenylalanine, P is proline, S is serine, T is threonine, W is tryptophan, Y is tyrosine, and V is valine. A dash (-) in a consensus sequence indicates that there is no amino acid at the specified position. A plus (+) in a consensus sequence indicates any amino acid may be present at the specified position. Thus, a plus in a consensus sequence herein indicates a position at which the amino acid is generally non-conserved; a homologous enzyme sequence, when aligned with the consensus sequence, can have any amino acid at the indicated "+" position. At positions in a consensus sequence where one of a subset of amino acids can be present, the following abbreviations are used: B represents that one of the amino acids R, K, or H is present at the indicated position; J represents that one of the amino acids D or E is present at the indicated position; 0 represents that one of the amino acids I, L, or V is present at the indicated position; U represents that one of the amino acids S or T is present at the indicated position; and $X_1$ represents that one of the amino acids A, D, R, H, K, S, T, N, Q, or Y (or a subset of those amino acids) is present at the indicated position. Illustrative subsets of $X_1$ include $X_1$ is A, D, K, S, T, N, or Y and $X_1$ is S or N. Specific amino acids in a protein coding sequence are identified by their respective single-letter abbreviation followed by the amino acid position in the protein coding sequence where 1 corresponds to the amino acid (typically methionine) at the N-terminus of the protein. For example, E124 in *S. cerevisiae* wild type EHD3 refers to the glutamic acid at position 124 from the EHD3 N-terminal methionine (i.e., M1). Amino acid substitutions (i.e., point mutations) are indicated by identifying the mutated (i.e., progeny) amino acid after the single-letter code and number in the parental protein coding sequence; for example, E124A in *S. cerevisiae* EHD3 refers to substitution of alanine for glutamic acid at position 124 in the EHD3 protein coding sequence. The mutation may also be identified in parentheticals, for example EHD3 (E124A). Multiple point mutations in the protein coding sequence are separated by a backslash (/); for example, EHD3 E124A/Y125A indicates that mutations E124A and Y125A are both present in the EHD3 protein coding sequence. The number of mutations introduced into some examples has been annotated by a dash followed by the number of mutations, preceeding the parenthetical identification of the mutation (e.g. A5W8H3-1 (E95Q)). The Uniprot IDs with and without the dash and number are used interchangeably herein (i.e. A5W8H3-1 (E95Q)=A5W8H3 (E95Q)).

As used herein, the term "express", when used in connection with a nucleic acid encoding an enzyme or an enzyme itself in a cell, means that the enzyme, which may be an endogenous or exogenous (heterologous) enzyme, is produced in the cell. The term "overexpress", in these contexts, means that the enzyme is produced at a higher level, i.e., enzyme levels are increased, as compared to the wild-type, in the case of an endogenous enzyme. Those skilled in the art appreciate that overexpression of an enzyme can be achieved by increasing the strength or changing the type of the promoter used to drive expression of a coding sequence, increasing the strength of the ribosome binding site or Kozak sequence, increasing the stability of the mRNA transcript, altering the codon usage, increasing the stability of the enzyme, and the like.

The terms "expression vector" or "vector" refer to a nucleic acid and/or a composition comprising a nucleic acid that can be introduced into a host cell, e.g., by transduction, transformation, or infection, such that the cell then produces ("expresses") nucleic acids and/or proteins other than those native to the cell, or in a manner not native to the cell, that are contained in or encoded by the nucleic acid so introduced. Thus, an "expression vector" contains nucleic acids (ordinarily DNA) to be expressed by the host cell. Optionally, the expression vector can be contained in materials to aid in achieving entry of the nucleic acid into the host cell, such as the materials associated with a virus, liposome, protein coating, or the like. Expression vectors suitable for use in various aspects and embodiments of the present invention include those into which a nucleic acid sequence can be, or has been, inserted, along with any preferred or required operational elements. Thus, an expression vector can be transferred into a host cell and, typically, replicated therein (although, one can also employ, in some embodiments, non-replicable vectors that provide for "transient" expression). In some embodiments, an expression vector that integrates into chromosomal, mitochondrial, or plastid DNA is employed. In other embodiments, an expression vector that replicates extrachromasomally is employed. Typical expression vectors include plasmids, and expression vectors typically contain the operational elements required for transcription of a nucleic acid in the vector. Such plasmids, as well as other expression vectors, are described herein or are well known to those of ordinary skill in the art.

The terms "ferment", "fermentative", and "fermentation" are used herein to describe culturing microbes under conditions to produce useful chemicals, including but not limited to conditions under which microbial growth, be it aerobic or anaerobic, occurs.

The term "heterologous" as used herein refers to a material that is non-native to a cell. For example, a nucleic acid is heterologous to a cell, and so is a "heterologous nucleic acid" with respect to that cell, if at least one of the following is true: (a) the nucleic acid is not naturally found in that cell (that is, it is an "exogenous" nucleic acid); (b) the nucleic acid is naturally found in a given host cell (that is, "endogenous to"), but the nucleic acid or the RNA or protein resulting from transcription and translation of this nucleic acid is produced or present in the host cell in an unnatural (e.g., greater or lesser than naturally present) amount; (c) the nucleic acid comprises a nucleotide sequence that encodes a protein endogenous to a host cell but differs in sequence from the endogenous nucleotide sequence that encodes that same protein (having the same or substantially the same amino acid sequence), typically resulting in the protein being produced in a greater amount in the cell, or in the case of an enzyme, producing a mutant version possessing altered (e.g. higher or lower or different) activity; and/or (d) the nucleic acid comprises two or more nucleotide sequences that are not found in the same relationship to each other in the cell. As another example, a protein is heterologous to a host cell if it is produced by translation of RNA or the corresponding RNA is produced by transcription of a heterologous nucleic acid; a protein is also heterologous to a host cell if it is a mutated version of an endogenous protein, and the mutation was introduced by genetic engineering.

The terms "host cell" and "host microorganism" are used interchangeably herein to refer to a living cell that can be (or has been) transformed via insertion of an expression vector. A host microorganism or cell as described herein may be a prokaryotic cell (e.g., a microorganism of the kingdom Eubacteria) or a eukaryotic cell. As will be appreciated by one of skill in the art, a prokaryotic cell lacks a membrane-bound nucleus, while a eukaryotic cell has a membrane-bound nucleus.

The terms "isolated" or "pure" refer to material that is substantially, e.g. greater than 50% or greater than 75%, or essentially, e.g. greater than 90%, 95%, 98% or 99%, free of components that normally accompany it in its native state, e.g. the state in which it is naturally found or the state in which it exists when it is first produced.

A carboxylic acid as described herein can be a salt, acid, base, or derivative depending on the structure, pH, and ions present. The terms "malonate" and "malonic acid" are used interchangeably herein. Malonic acid is also called propanedioic acid ($C_3H_4O_4$; CAS#141-82-2).

The term "malonate-derived compounds" as used herein refers to mono-alkyl malonate esters, including, for example and without limitation, mono-methyl malonate (also referred to as monomethyl malonate, CAS#16695-14-0), mono-ethyl malonate (also referred to as monoethyl malonate, CAS#1071-46-1), mono-propyl malonate, mono-butyl malonate, mono-tert-butyl malonate (CAS#40052-13-9), and the like; di-alkyl malonate esters, for example and without limitation, dimethyl malonate (CAS#108-59-8), diethyl malonate (CAS#105-53-3), dipropyl malonate (CAS#1117-19-7), dibutyl malonate (CAS#1190-39-2), and the like, and Meldrum's acid (CAS#2033-24-1). The malonate-derived compounds can be produced synthetically from malonate and are themselves valuable compounds but are also useful substrates in the chemical synthesis of a number of other valuable compounds.

As used herein, the term "nucleic acid" and variations thereof shall be generic to polydeoxyribonucleotides (containing 2-deoxy-D-ribose) and to polyribonucleotides (containing D-ribose). "Nucleic acid" can also refer to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. As used herein, the symbols for nucleotides and polynucleotides are those recommended by the IUPAC-IUB Commission of Biochemical Nomenclature (Biochem. 9:4022, 1970). A "nucleic acid" may also be referred to herein with respect to its sequence, the order in which different nucleotides occur in the nucleic acid, as the sequence of nucleotides in a nucleic acid typically defines its biological activity, e.g., as in the sequence of a coding region, the nucleic acid in a gene composed of a promoter and coding region, which encodes the product of a gene, which may be an RNA, e.g. a rRNA, tRNA, or mRNA, or a protein (where a gene encodes a protein, both the mRNA and the protein are "gene products" of that gene).

The term "operably linked" refers to a functional linkage between a nucleic acid expression control sequence (such as a promoter, ribosome-binding site, and transcription terminator) and a second nucleic acid sequence, the coding sequence or coding region, wherein the expression control sequence directs or otherwise regulates transcription and/or translation of the coding sequence.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used herein, "recombinant" refers to the alteration of genetic material by human intervention. Typically, recombinant refers to the manipulation of DNA or RNA in a cell or virus or expression vector by molecular biology (recombinant DNA technology) methods, including cloning and recombination. Recombinant can also refer to manipulation of DNA or RNA in a cell or virus by random or directed mutagenesis. A "recombinant" cell or nucleic acid can typically be described with reference to how it differs from a naturally occurring counterpart (the "wild-type"). In addition, any reference to a cell or nucleic acid that has been "engineered" or "modified" and variations of those terms, is intended to refer to a recombinant cell or nucleic acid.

As used herein, the term "transcription factor biosensor" refers to a system to detect a substance, e.g., malonate, by activating expression of a "marker" or "reporter" gene where reporter gene expression is mediated by a transcription factor that is capable of binding to a promoter and activating transcription upon binding of that substance, e.g., malonate. For example, malonate may bind to a transcription factor (e.g., MdcY) and activate transcription from a promoter (e.g., $P_{MdcL}$). A "malonate transcription factor" is a transcription factor that, when bound to malonate, can activate a promoter. Thus, MdcY is a malonate transcription factor.

The terms "transduce", "transform", "transfect", and variations thereof as used herein refers to the introduction of one or more nucleic acids into a cell. For practical purposes, the nucleic acid must be stably maintained or replicated by the cell for a sufficient period of time to enable the function(s) or product(s) it encodes to be expressed for the cell to be referred to as "transduced", "transformed", or "transfected". As will be appreciated by those of skill in the art, stable maintenance or replication of a nucleic acid may take place either by incorporation of the sequence of nucleic acids into the cellular chromosomal DNA, e.g., the genome, as occurs by chromosomal integration, or by replication extrachromosomally, as occurs with a freely-replicating plasmid. A virus can be stably maintained or replicated when it is "infective": when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

Section 2: Malonyl-CoA Hydrolase Enzymes

In accordance with one aspect of the invention, malonate is produced through the action of a malonyl-CoA hydrolase catalyzing the conversion of malonyl-CoA to malonate. To date, no wild-type malonyl-CoA hydrolase gene has been identified, although the presence of a small amount of malonate in the fermentation media of non-engineered strains indicates that a wild-type enzyme with this activity may exist. The present invention provides a number of genes that are counterparts to wild type genes that have been mutated to confer malonyl-CoA hydrolase activity. The host cell making the malonyl-CoA hydrolase is a recombinant host cell; in many embodiments, the host cell has been genetically modified to comprise heterologous nucleic acid(s) encoding malonyl-CoA hydrolase enzyme(s) catalyzing hydrolysis of malonyl-CoA to malonate. In some embodiments, the recombinant host cell is a eukaryote. In various embodiments, the eukaryote is a yeast strain selected from the non-limiting example genera: *Candida, Cryptococcus, Hansenula, Issatchenkia, Kluyveromyces, Komagataella, Lipomyces, Pichia, Rhodosporidium, Rhodotorula, Saccharomyces*, or *Yarrowia*. Those skilled in the art will recognize that these genera broadly encompass yeast, including those distinguished as oleaginous yeast. In some embodiments, the host cell is *Saccharomyces cerevisiae*. In other embodiments, the host cell is *Pichia kudriavzevii*. In other embodiments of the invention, the eukaryotic host cell is a fungus or algae. In yet other embodiments, the recombinant host cell is a prokaryote selected from the non-limited example genera: *Bacillus, Clostridium, Corynebacterium, Escherichia, Pseudomonas, Rhodobacter*, and *Streptomyces*. In some embodiments, the host cell is *E. coli*.

The present invention results in part from the discovery that various acyl-CoA hydrolases and transacylases can be engineered to have malonyl-CoA hydrolase activity and so be useful for biological production of malonate. Non-limiting examples of acyl-CoA hydrolases suitable for modification for malonyl-CoA hydrolysis include any of those from the group consisting of 3-hydroxyisobutyryl-CoA hydrolases (EC 3.1.2.4), 3-hydroxypropionyl-CoA hydrolases (EC 3.1.2.4), acetoacetyl-CoA hydrolases (EC 3.1.2.11), methylmalonyl-CoA hydrolases (EC 3.1.2.17), propionyl-CoA hydrolases (EC 3.1.2.18), succinyl-CoA hydrolases (EC 3.1.2.3), and malonyl-CoA:ACP transacylases (EC 2.3.1.39) mutated as provided herein to have malonyl-CoA hydrolase activity.

In some embodiments, the malonyl-CoA hydrolase used to produce malonate in accordance with the invention is a mutated *S. cerevisiae* EHD3 acyl-CoA hydrolase (see SEQ ID NO:1 for the wild-type EHD3 amino acid sequence). One such mutant with altered substrate specificity is the E124V mutant (see Rouhier, "Characterization of YDR036C from *Saccharomyces cerevisiae*." Dissertation, Miami University, Miami University and OhioLINK (2011)), which, while previously reported, was not reported to have malonyl-CoA hydrolase activity. In some embodiments of the invention, an *E. coli* host cell expressing the E124V mutant is used to produce malonate, which is then purified from the cell or fermentation broth. In other embodiments of the invention, a yeast cell expressing the E124V mutant is used to produce malonate in accordance with the invention. In yet another embodiment, an oleaginous yeast cell expressing the E124V mutant is used to produce malonate in accordance with the invention.

Prior attempts to produce the E124A mutant of EHD3 resulted in cell death upon induction of protein expression from a pET28a expression vector; the protein was unable to be purified (see Rouhier, supra). The present invention provides expression vectors for the E124A mutant that can be used in *E. coli* host cells, rendering them capable of producing malonate. These *E. coli* expression vectors are characterized in that, relative to the pET28a vector of Rouhier, the E124A mutant is produced at a lower, non-toxic, level. This is achieved, for example by employing expression vectors with a lower copy number or weaker promoter than used by Rouhier. One skilled in the art will also appreciate that translation can be modulated by the affinity of the ribosome binding site (RBS), or Kozak sequence, for the ribosome. Thus a weaker RBS or Kozak sequence can also be employed to reduce gene expression. Examples of lower copy number expression vectors include, but are not limited to pSC101 origin expression vectors, p15a origin expression vectors, and expression vectors that integrate into the chromosomal DNA. Examples of weaker promoters than the T7 promoter used by Rouhier include, but are not limited to the $P_{LacO1}$, $P_{TRC}$, and $P_{BAD}$ promoters. In some embodiments, the vector has a pSC101 origin of replication. In other embodiments, the promoter used for expression of the EHD3 E124A mutant coding sequence is the $P_{lacO1}$ promoter. Additionally, the present invention provides vectors for yeast host cells that code for the expression of the E124A mutant. The genetically modified *S. cerevisiae* EHD3 E124A expression vectors of the invention can be used in vivo for the production of malonate in *E. coli* and *S. cerevisiae*, and the methods of the invention provide means for the subsequent purification of malonate from fermentation broth of these strains, and the synthetic conversion of malonate into derivative small-molecule compounds.

The present invention also provides the E124S mutant of EHD3 for use as a malonyl-CoA hydrolase, vectors for expressing this mutant, and host cells that express this mutant and produce malonate (see Example 31). Wild-type *S. cerevisiae* EHD3 catalyzes the hydrolysis of 3-hydroxypropionyl-CoA (3HPA-CoA) and 3-hydroxyisobutyryl-CoA (3HIBA-CoA), and while this invention is not to be limited by theory, E124 is predicted to interact with the terminal hydroxyl moiety on 3HPA-CoA, stabilizing the substrate in the EHD3 active site (see Rouhier, supra). Certain aspects of this invention arise from the discovery that specific E124 point mutations increase enzyme hydrolysis of malonyl-CoA, producing malonate. Mutation of E124 to a nucleophilic amino acid (e.g., S or T), basic amino acid (e.g., H, K, or R), or amide amino acid (e.g., N or Q) improves the binding of malonyl-CoA in the EHD3 active site over 3-hydroxypropionyl-CoA and increases malonate production (relative to the unmutated counterpart enzyme). The E124S, E124T, E124N, E124Q, E124H, E124K, and E124R mutations also decrease production of byproducts (e.g., acetate, propionate, isobutyrate, and succinate) due to decreased hydrolysis of endogenous host cell acyl-CoA molecules. The E124S point mutation places a hydroxyl moiety in a position that promotes hydrogen bonding between the serine residue and the terminal carboxylate group of malonyl-CoA. The E124Q point mutation places the glutamine amide group in a position near the terminal carboxylate group of malonyl-CoA. The E124K point mutation places the lysine amine group in a position that promotes hydrogen bonding between the lysine residue and the terminal carboxylate group of malonyl-CoA. In contrast to the nucleophilic, amide, and basic E124 point mutations described above, mutations E124A and E124V remove the presence of a charged amino acid at position 124; these mutations both eliminate hydrogen bonding between the terminal carboxylate on malonate and the EHD3 124 amino acid sidechain and open the EHD3 active site to promiscuous activity, increasing undesirable byproduct formation and decreasing malonate production.

In some embodiments of the invention, an *E. coli* host cell expressing the E124S mutant is used to produce malonate. In other embodiments of the invention, a yeast host cell expressing the E124S mutant is used to produce malonate. In other embodiments, an oleaginous yeast host cell expressing the E124S mutant is used to produce malonate. In some embodiments of the invention, an *E. coli* host cell expressing the E124Q mutant is used to produce malonate. In other embodiments of the invention, a yeast host cell expressing the E124Q mutant is used to produce malonate. In other embodiments, an oleaginous yeast host cell expressing the E124Q mutant is used to produce malonate. In some embodiments of the invention, an *E. coli* host cell expressing the E124K mutant is used to produce malonate. In other embodiments of the invention, a yeast host cell expressing the E124K mutant is used to produce malonate. In other embodiments, an oleaginous yeast host cell expressing the E124K mutant is used to produce malonate. In some embodiments of the invention, an *E. coli* host cell expressing the E124H mutant is used to produce malonate. In other embodiments of the invention, a yeast host cell expressing the E124H mutant is used to produce malonate. In other embodiments of the invention, an oleaginous yeast host cell expressing the E124H mutant is used to produce malonate. In some embodiments of the invention, an *E. coli* host cell expressing the E124R mutant is used to produce malonate. In other embodiments of the invention, a yeast host cell expressing the E124R mutant is used to produce malonate. In other embodiments of the invention, an oleaginous yeast host cell expressing the E124R mutant is used to produce malonate. In other embodiments, a recombinant host cell expressing an EHD3 E124 nucleophilic amino acid point mutation (i.e., E124S or E124T) is used to produce malonate. In other embodiments, a recombinant host cell expressing an EHD3 E124 basic amino acid point mutation (i.e., E124H, E124K, or E124R) is used to produce malonate. In other embodiments, a recombinant host cell expressing an EHD3 E124 amide amino acid point mutation (i.e., E124N or E124Q) is used to produce malonate.

The present invention also provides a mutated EHD3 comprising a mutated active site, vectors for expressing the mutant, and host cells that express the mutant and produce malonate. Certain aspects of the present invention arose, in part, from the discovery that specific amino acids (i.e., F121, and F177) are important for acyl-CoA substrate binding, and introduction of specific point mutations increase malonyl-CoA hydrolysis and production of malonate. Introduction of mutation F121I or F121L increases malonyl-CoA access to the active site. Similarly, introduction of mutation F177I or F177L increases malonyl-CoA access to the active site. One or more point mutations at amino acid positions F121 or F177 can be introduced alone, or along with an E124 point mutation. In various embodiments, a F121 and/or F177 point mutation is introduced along with an E124 point mutation. In some embodiments, a recombinant host cell expressing an EHD3 F121I or F121L mutant is used to produce malonate. In other embodiments, a recombinant host cell expressing an EHD3 F177I or F178L mutant is used to produce malonate. In these embodiments, the recombinant host cell can be, without limitation, an *E. coli* or yeast, including but not limited to *S. cerevisiae* or other yeast, host cell.

The present invention also provides mutated EHD3 comprising a mutated mitochondrial targeting sequence, vectors for expressing the mutant, and host cells that express the mutant and produce malonate. In an *S. cerevisiae* host, wild-type EHD3 is localized in the mitochondria. Malonyl-CoA is found in both the mitochondria and the cytosol; EHD3 catalyzed hydrolysis of cytosolic malonyl-CoA requires localization of an EHD3 to the cytosol. Certain aspects of the present invention arose from the discovery that mutations of the EHD3 mitochondrial targeting sequence can increase production of malonate. The EHD3 amino acids important for mitochondrial targeting include R3, K7, K14, K18, and R22, and mutation of one or more of these basic amino acids to a hydrophobic amino acid (i.e., A or V) abrogates mitochondrial targeting. In some embodiments, a recombinant host comprising an EHD3 consisting of one or more mutations to A or V at amino acids selected from the group consisting of R3, K7, K14, K18, and R22 is used to produce malonate. In some embodiments, the recombinant host is a yeast strain. In other embodiments, the host is *S. cerevisiae*. In still further embodiments, the recombinant host cell contains one or more copies of an EHD3 with the mitochondrial targeting sequence unaltered (i.e., wild-type) and one or more copies of an EHD3 with the mitochondrial targeting sequence mutated. Additional examples of mitochondrial targeting sequences useful in this aspect of the invention are: WT COX4, SynA1, SynA2, Syn B1, and Syn B2, as outline for other applications by Allison & Schatz (Allison & Schatz (1986) PNAS 83:9011-9015). In further embodiments of the invention, peroxisomal targeting signal (e.g. PTS1, PTS2), most often containing a Ser-Lys-Leu motif, is fused to the C-terminus of the malonyl-CoA hydrolase to result in localization of this protein to the peroxisome.

Thus, in one aspect of the invention, the recombinant host cell comprises a heterologous nucleic acid encoding a mutant *S. cerevisiae* EHD3 that results in increased production of malonate relative to host cells not comprising the mutant EHD3. In some embodiments, the mutant EHD3 is heterologously expressed in *E. coli*. In other embodiments, the mutant EHD3 is heterologously expressed in *S. cerevisiae*. In other embodiments, the mutant EHD3 is heterologously expressed in an oleaginous yeast cell. In some embodiments, the mutant EHD3 contains a point mutation at position E124. In some embodiments, the point mutation at residue E124 is either E124A or E124V. In some embodiments, the point mutation at E124 is E124S or E124T. In some embodiments, the point mutation at E124 is E124S. In some embodiments, the point mutation at E124 is a basic amino acid selected from the group consisting of E124H, E124K, and E124R. In some embodiments, the point mutation at E124 is E124H. In some embodiments, the point mutation at E124 is E124K. In some embodiments, the point mutation at E124 is E124R. In some embodiments, the point mutation at residue E124 is E124N or E124Q. In some embodiments, the point mutation at residue E124 is E124Q. In some embodiments, one or more EHD3 amino acids selected from the group consisting of F121 and F177 are mutated to I or L. In some embodiments, one or more EHD3 amino acids selected from the group consisting of R3, K7, K14, K18, and R22 are mutated to either A or V.

In another aspect of the invention, an enzyme other than, or in addition to, EHD3 is utilized as a malonyl-CoA hydrolase to produce malonate in accordance with the invention. In some embodiments, *Haemophilus influenzae* YciA is heterologously expressed in a heterologous host to produce malonate in accordance with the invention (see Zhuang et al. *Biochemistry* 47: 2789-2796 (2008)). In other embodiments, the malonyl-CoA hydrolase is an acyl-CoA hydrolase endogenous to *Rattus norvegicus* (see Kovachy et al., *J. Biol. Chem.* 258:11415-11421 (1983)). In other embodiments, the malonyl-CoA hydrolase is the acyl-CoA hydrolase from brown adipose tissue mitochondrial protein fraction from *Mesocricetus auratus* (see Alexson et al., *J. Biol. Chem.* 263:13564-13571 (1988)).

Thus, in accordance with the invention acyl-CoA hydrolases other than, or in addition to, EHD3 (from *S. cerevisiae* or homologous enzymes from other organisms) can be used for biological synthesis of malonate in a recombinant host. In some embodiments, the recombinant host is *S. cerevisiae*. In other embodiments, the recombinant host is *E. coli*. In other embodiments, the recombinant host is a yeast other than *S. cerevisiae* as described in additional detail below. In various embodiments, the host is modified to express a mutated enzyme selected from the group consisting of *S. albicans* EHD3, *H. sapiens* HIBCH (UniProt:Q6NVY1), *A. thaliana* CHY1 (UniProt:Q9LKJ1), *R. norvegicus* HIBCH (UniProt:Q5XIE6), *M. musculus* HIBCH (UniProt:Q8QZS1), *G. gallus* HIBCH (UniProt:Q5ZJ60), *B. taurus* HIBCH (UniProt:Q2HJ73), *D. rerio* HIBCH (UniProt:Q58EB4), *B. cereus* Bch, *P. aeruginosa* Hich, *E. coli* YciA, *H. influenzae* YciA, *M. musculus* ACOT4, *M. musculus* ACOT8, *S. enterica* SARI_01218, *A. pernix* K1, *C. hutchinsonii* Chut02003666, *S. solfataricus* P2 SS02287, *S. acidocaldarius* DSM 639 Saci_0145, *P. aerophilum* str. IM2 PAE3404, *D. melanogaster* CG1635, *P. carbinolicus* DSM 2380 Pcar_1366, *A. dehalogenans* 2CP-C 110, *G. gallus* ACOT9, and *X. laevis* MGC114623.

Those of skill in the art will appreciate that one or multiple suitably mutated acyl-CoA hydrolases can be used in accordance with the invention to convert malonyl-CoA to malonate in a host cell. Moreover, acyl-CoA hydrolases other than those specifically disclosed herein can be utilized in mutated or heterologously expressed form, and it will be well understood to those skilled in the art in view of this disclosure how other appropriate enzymes can be identified, modified, and expressed to achieve the desired malonyl-CoA hydrolase activity as disclosed herein.

Consensus Sequences

Malonyl-CoA hydrolases of the invention include those that are homologous to consensus sequences provided by the invention. As noted above, any enzyme substantially homologous to an enzyme specifically described herein can be used in a host cell of the invention. One enzyme is homologous to another (the "reference enzyme") when it exhibits the same activity of interest and can be used for substantially similar purposes. Generally, homologous enzymes share substantial sequence identity. Sets of homologous enzymes generally possess one or more specific amino acids that are conserved across all members of the consensus sequence protein class.

The percent sequence identity of an enzyme relative to a consensus sequence is determined by aligning the enzyme sequence against the consensus sequence. Those skilled in the art will recognize that various sequence alignment algorithms are suitable for aligning an enzyme with a consensus sequence. See, for example, Needleman, S B, et al "A general method applicable to the search for similarities in the amino acid sequence of two proteins." *Journal of Molecular Biology* 48 (3): 443-53 (1970). Following alignment of the enzyme sequence relative to the consensus sequence, the percentage of positions where the enzyme possesses an amino acid (or dash) described by the same position in the consensus sequence determines the percent sequence identity. When a degenerate amino acid (i.e. B, J, O, U, "+") is present in a consensus sequence any of the amino acids described by the degenerate amino acid may be present in the enzyme at the aligned position for the enzyme to be identical to the consensus sequence at the aligned position. When a dash is present in a consensus sequence the enzyme must not have an amino acid present in the aligned position for the enzyme to be identical to the consensus sequence at the aligned position.

The present invention provides consensus sequences useful in identifying and constructing malonyl-CoA hydrolases of the invention. In various embodiments, these malonyl-CoA hydrolase consensus sequences contain active site amino acid residues believed to be necessary (although the invention is not to be limited by any theory of mechanism of action) for formation of an oxyanion hole responsible for stabilizing the enolate anion intermediate derived from a malonyl-CoA substrate as well as the amino acid residues important for malonyl-CoA binding, as described below. A malonyl-CoA hydrolase enzyme encompassed by a consensus sequence provided herein has an enzymatic activity that is identical, or essentially identical, or at least substantially similar with respect to ability to hydrolyze malonyl-CoA to that of one of the enzymes exemplified herein. A malonyl-CoA hydrolase enzyme may be found in nature or, more typically, is an engineered mutant of a wild-type enzyme modified in accordance with the invention to have malonyl-CoA hydrolase activity. A malonyl-CoA hydrolase enzyme may be identified or constructed from another enzyme by mutating the sequence of the other enzyme to create a sequence encompassed by a consensus sequence herein; if an enzyme shares substantial homology to a consensus sequence herein but has suboptimal, including no, malonyl-CoA hydrolase activity, then, in accordance with the invention, it is mutated to conform to a consensus sequence provided herein to provide a malonyl-CoA hydrolase of the invention.

The invention provides four malonyl-CoA hydrolase consensus sequences: (i) malonyl-CoA hydrolase based on EHD3 EC 3.1.2.4 (SEQ ID NO:7), (ii) malonyl-CoA hydrolase based on *Bacillus* EC 3.1.2.4 (SEQ ID NO:8), (iii) malonyl-CoA hydrolase based on *Pseudomonas* EC 3.1.2.4 (SEQ ID NO:9), and (iv) malonyl-CoA hydrolase based on both *Bacillus* and *Pseudomonas* EC 3.1.2.4 ((SEQ ID NO:10). The consensus sequences provide a sequence of amino acids in which each position identifies the amino acid (if a specific amino acid is identified) or a subset of amino acids (if a position is identified as variable) most likely to be found at a specified position in a malonyl-CoA hydrolase of that class. Those of skill in the art will recognize that fixed amino acids and conserved amino acids in these consensus sequences are identical to (in the case of fixed amino acids) or consistent with (in the case of conserved amino acids) with the wild-type sequence(s) on which the consensus sequence is based. A dash in a consensus sequences indicates that suitable enzymes for mutation in accordance with the invention can be found in nature that may have an additional amino acid at the location of the dash in the sequence, but typically no amino acid is present at the location of a dash.

Malonyl-CoA Hydrolase Consensus Sequence Based on EHD3 EC 3.1.2.4 Enzymes

The invention provides a malonyl-CoA hydrolase consensus sequence based on EHD3 EC 3.1.2.4 enzymes (SEQ ID NO:7), and in various embodiments, suitable malonyl-CoA hydrolases for use in the methods of the invention have at least 63% identity to this malonyl-CoA hydrolase consensus sequence. In various embodiments, enzymes suitable for mutation of the key glutamic acid residue to $X_1$ in accordance with the methods of the invention to confer malonyl-CoA hydrolase activity have 65%, 70%, 80%, 90%, or 95% or more identity to SEQ ID NO:7. Proteins having significant homology to this consensus sequence include UniProt ID: C5DE94 (63% identity), UniProt ID: Q6CJH2 (64% identity), UniProt ID: G2WAE2 (66% identity), UniProt ID: J8Q6P9 (66% identity), UniProt ID: G8C0H0 (68% identity), UniProt ID: C5DX08 (68% identity), UniProt ID: P28817 (69% identity), UniProt ID: A7TTD5 (69% identity), UniProt ID: J7S9J9 (70% identity), UniProt ID: Q6FM09 (71% identity), UniProt ID: I2H4L2 (71% identity), UniProt ID: H2AME2 (73% identity), UniProt ID: G8ZTJ4 (77% identity), UniProt ID: G0W4I8 (77% identity), UniProt ID: G0V818 (78% identity), and UniProt ID: J5S5X3 (79% identity). In some embodiments, a malonyl-CoA hydrolase with equal to or greater than 63% identity to the consenseus sequence SEQ ID NO:7 is expressed in a recombinant host cell and used to produce malonate in accordance with the invention.

In mutant and wild-type enzymes homologous to this consensus sequence (SEQ ID NO: 7), amino acids that are highly conserved are V101, R110, L114, R116, K119, L120, N121, A122, L123, L135, E137, Y138, K140, S141, S151, R156, C159, G161, G162, D163, V164, A168, F185, E188, Y189, S190, N192, A196, T197, K200, M206, G208, I209, T210, M211, G212, G213, G214, V215, G216, H220, P222, F223, R224, T227, E228, T230, M234, P235, E236, D238, I239, G240, F242, P243, D244, V245, F249, P252, Q263, Y267, L268, T271, G272, G277, G284, 5287, H288, Y289, L298, R301, L302, E304, E333, F334, L352, V354, 1355, F359, L374, F391, L399, K402, S403, S406, N417, D429, L430, T432, A433, E449, F450, K457, L458, K461, W468, L494, T502, Y506, P507, L514, P515, and K561. In various embodiments, malonyl-CoA hydrolase enzymes homologous to this consensus sequence (SEQ ID NO:7) contain at least 25% of these conserved amino acids, often a majority (greater than 50%) of these conserved amino acids, and sometimes all of these conserved amino acids.

Some amino acids in this consensus sequence (SEQ ID NO:7) are essential for activity and conserved across all members of the class. Malonyl-CoA hydrolase enzymes encompassed by the EHD3 EC 3.1.2.4 based consensus sequence contain six active site residues important for hydrolase activity: (i) three active site amino acid residues (G161, G162, G213) in the consensus sequence believed to be necessary (although the invention is not to be limited by any theory of mechanism of action) for formation of an oxyanion hole responsible for stabilizing the enolate anion intermediate derived from the malonyl-CoA substrate; (ii) two amino acid residues (E236, D244) of the consensus sequence necessary for acyl-CoA hydrolysis; and (iii) an amino acid residue at position 188 (of SEQ ID NO:7) believed to be necessary for malonyl-CoA substrate binding. Of these six residues, then, five are present in the consensus sequence (SEQ ID NO:7) and in all malonyl-CoA hydrolases encompassed by that sequence, and the sixth, at position 188 (amino acid $X_1$ in the consensus) is selected from the group consisting of polar or positively charged amino acids (R, H, K, S, T, N, Q, Y), as well as A and D, to provide a malonyl-CoA hydrolase of the invention capable of producing malonate in a recombinant host cell. The six essential residues from the consensus sequence sequence (G161, G162, G213, E236, D244, X₁188) correspond to G99, G100, G149, E172, D180, and E124 (typically mutated to X₁), respectively, in *S. cerevisiae* EHD3 used to illustrate the invention in example 31.

Malonyl-CoA Hydrolase Consensus Sequence Based on *Bacillus* EC 3.1.2.4 Enzymes

The invention provides a malonyl-CoA hydrolase consensus sequence (SEQ ID NO:8) based on *Bacillus* EC 3.1.2.4 enzymes, and in various embodiments, suitable malonyl-CoA hydrolases for use in the methods of the invention have at least 86% identity to this malonyl-CoA hydrolase consensus sequence. In various embodiments, enzymes suitable for mutation of the key glutamic acid residue to X₁ in accordance with the methods of the invention to confer malonyl-CoA hydrolase activity have 90%, or 95% or more identity to SEQ ID NO:8. Proteins having significant homology to this consensus sequence include UniProt ID: C2TX63 (92% identity), UniProt ID: C2UV40 (91% identity), UniProt ID: C2QBT2 (93% identity), UniProt ID: C2XTU0 (93% identity), UniProt ID: C2PVQ0 (93% identity), UniProt ID: C3A5N3 (93% identity), UniProt ID: C2SJV4 (93% identity), UniProt ID: C2Z7UI (92% identity), UniProt ID: C2VTI4 (97% identity), UniProt ID: B3Z9Y3 (97% identity), UniProt ID: B7JNH7 (97% identity), UniProt ID: Q63BK8 (97% identity), UniProt ID: B0Q3Q4 (97% identity), UniProt ID: B0AQX0 (97% identity), UniProt ID: B3YSW2 (97% identity), UniProt ID: C2NHG5 (97% identity), UniProt ID: B3ZIZ8 (97% identity), UniProt ID: C2QSV2 (97% identity), UniProt ID: C3C255 (97% identity), UniProt ID: B5UZZ1 (96% identity), UniProt ID: C2MKL7 (95% identity), UniProt ID: B9IZZ9 (95% identity), UniProt ID: F0PNG8 (95% identity), UniProt ID: Q738L0 (97% identity), UniProt ID: C2PEV7 (95% identity), UniProt ID: C2YRH7 (96% identity), UniProt ID: Q4MU30 (95% identity), UniProt ID: Q81DR3 (96% identity), UniProt ID: C2W7W8 (89% identity), and UniProt ID: A7GPH6 (86% identity). In various embodiments, a malonyl-CoA hydrolase with equal to or greater than 86% identity to the consenseus sequence SEQ ID NO:8 is expressed in a recombinant host cell and used to produce malonate in accordance with the invention. Sequences for B9IZZ9 (SEQ ID NO:46), C3ALI3 (SEQ ID NO:47), F0PNG8 (SEQ ID NO:49), Q63BK8 (SEQ ID NO:51), and Q81DR3 (SEQ ID NO:52) containing X₁ at the position of the key glutamic acid residue that is mutated in accordance with the invention to confer malonyl-CoA hydrolase activity are provided in the sequence listing.

In mutant and wildtype enzymes homologous to this consensus sequence (SEQ ID NO:8) amino acids that are highly conserved are M1, T2, E3, V5, L6, F7, S8, G13, V14, A15, I17, T18, L19, N20, R21, P22, K23, A24, L25, N26, S27, L28, S29, Y30, M32, L33, I36, G37, K39, L40, K41, E42, W43, E44, I49, I52, V53, L54, K55, G56, A57, G58, K60, G61, F62, C63, A64, G65, G66, D67, I68, K69, T70, L71, Y72, E73, A74, R75, S76, N77, E78, A80, L81, Q82, A84, E85, F87, F88, E90, E91, Y92, I94, D95, T96, Y99, Y101, K103, P104, I105, I106, A107, C108, L109, D110, G111, I112, V113, M114, G115, G116, G117, VI 18, G119, L120, T121, N122, G123, A124, R127, I128, V129, T130, T133, K134, W135, A136, M137, P138, E139, M140, N141, I142, G143, F144, F145, P146, D147, V148, G149, A150, A151, Y152, F153, L154, N155, A157, P158, G159, G162, V165, A166, L167, A169, L172, K173, A174, D176, V177, L178, I180, A182, A183, D184, L192, F195, L196, W204, V210, L214, K215, I231, E236, H241, F242, E248, I250, I251, S253, L254, E255, F261, L269, L270, S271, K272, S273, P274, S276, L277, K278, V279, T280, L281, K282, Q283, G287, K290, S291, E293, C295, F296, A297, T298, D299, L300, L302, A303, K304, N305, F306, M307, R308, H309, D311, F312, F313, E314, G315, V316, R317, S318, V320, D322, K323, D324, Q325, N326, P327, Y329, K330, Y331, D336, V337, V342, N343, F345, F346, L348, and L349. In various embodiments, malonyl-CoA hydrolase enzymes homologous to this consensus sequence (SEQ ID NO:8) contain at least 25% of these conserved amino acids, often a majority (greater than 50%) of these conserved amino acids, and sometimes all of these conserved amino acids.

Some amino acids in this consensus sequence (SEQ ID NO:8) are essential for activity and conserved across all members of the class. Malonyl-CoA hydrolase enzymes encompassed by the *Bacillus* EC 3.1.2.4 based consensus sequence contain six active site residues important for hydrolase activity: (i) three active site amino acid residues (G65, G66, G116) of the consensus sequence believed to be necessary (although the invention is not to be limited by any theory of mechanism of action) for formation of an oxyanion hole responsible for stabilizing the enolate anion intermediate derived from the malonyl-CoA substrate; (ii) two amino acid residues (E139, D147) of the consensus sequence necessary for acyl-CoA hydrolysis; and (iii) a mutated amino acid (X₁91) (of SEQ ID NO:8) believed to be necessary for malonyl-CoA substrate binding. Of these six residues, then, five are present in the consensus sequence (SEQ ID NO:8) and in all malonyl-CoA hydrolases encompassed by that sequence, and the sixth, X₁91 is necessary to provide a malonyl-CoA hydrolase of the invention capable of producing malonate in a recombinant host cell. The six essential residues from the consensus sequence sequence (G65, G66, G116, E139, D147, X₁91) correspond to G65, G66, G116, E139, D147, and E91 (typically mutated to X₁), respectively, in *Bacillus thuringiensis* subsp. finitimus (strain YBT-020) F0PNG8 used to illustrate the invention in example 31 (See SEQ ID NO: 49 containing mutation E91S).

Non-limiting examples of enzymes suitable for malonyl-CoA hydrolysis homologous to the consensus sequence (SEQ ID NO:8) and encoded by cloned or synthesized nucleic acids provided by the invention include mutant enzymes containing at least one mutation illustrated by the group of mutant enzymes consisting of *Bacillus cereus* (strain Q1) B9IZZ9 (E91S), B9IZZ9 (E91A), B9IZZ9 (E91H), B9IZZ9 (E91K), B9IZZ9 (E91R), B9IZZ9 (E91Q), B9IZZ9 (E91T), B9IZZ9 (E91N), B9IZZ9 (E91Y), B9IZZ9 (E91D); *Bacillus thuringiensis* subsp. finitimus (strain YBT-020) F0PNG8 (E91S), F0PNG8 (E91A), F0PNG8 (E91H), F0PNG8 (E91K), F0PNG8 (E91R), F0PNG8 (E91Q), F0PNG8 (E91T), F0PNG8 (E91N), F0PNG8 (E91Y), F0PNG8 (E91D); *Bacillus cereus* (strain ATCC 14579/DSM 31) Q81DR3, Q81DR3 (E91S), Q81DR3 (E91A), Q81DR3 (E91H), Q81DR3 (E91K), Q81DR3 (E91R), Q81DR3 (E91Q), Q81DR3 (E91T), Q81DR3 (E91N), Q81DR3 (E91Y), Q81DR3 (E91D); *Bacillus cereus* (strain ZK/E33L) Q63BK8, Q63BK8 (E91S), Q63BK8 (E91A), Q63BK8 (E91H), Q63BK8 (E91K), Q63BK8 (E91R), Q63BK8 (E91Q), Q63BK8 (E91T), Q63BK8 (E91N), Q63BK8 (E91Y), Q63BK8 (E91D).

Malonyl-CoA Hydrolase Consensus Sequence Based on *Pseudomonas* EC 3.1.2.4 Enzymes The invention provides a malonyl-CoA hydrolase consensus sequence based on *Pseudomonas* EC 3.1.2.4 enzymes (SEQ ID NO:9), and in various embodiments, suitable malonyl-CoA hydrolases for use in the methods of the invention have at least 75% identity to this malonyl-CoA hydrolase consensus sequence. In various embodiments, enzymes suitable for mutation of the key glutamic acid residue to $X_1$ in accordance with the invention to confer malonyl-CoA hydrolase activity have 80%, 90%, or 95% or more identity to SEQ ID NO:9. Proteins having significant homology to this consensus sequence include: UniProt ID: F5KBQ4 (80% identity), UniProt ID: A6VAN3 (81% identity), UniProt ID: A4XS22 (81% identity), UniProt ID: F6AA82 (75% identity), UniProt ID: E2XN63 (84% identity), UniProt ID: F2KE35 (85% identity), UniProt ID: C3KDS5 (83% identity), UniProt ID: F8G3B7 (86% identity), UniProt ID: G8PYD2 (85% identity), UniProt ID: Q4KGS1 (82% identity), UniProt ID: Q3KGL5 (85% identity), UniProt ID: B0KV51 (86% identity), UniProt ID: B1J4J2 (86% identity), UniProt ID: A5W8H3 (86% identity), UniProt ID: Q88N06 (86% identity), UniProt ID: Q1I5T5 (84% identity), UniProt ID: F8H1A4 (77% identity), UniProt ID: A4VIV7 (77% identity), and UniProt ID: Q915I5 (81% identity). In some embodiments, a malonyl-CoA hydrolase with equal to or greater than 75% identity to the conseneus sequence SEQ ID NO:9 is expressed in a recombinant host cell and used to produce malonate in accordance with the invention. Sequences for A4XS22 (SEQ ID NO:45), F6AA82 (SEQ ID NO:50), and E2XN63 (SEQ ID NO:48), each containing $X_1$ at the position of the key glutamic acid residue that is mutated in accordance with the invention, are included in the sequence listing.

Highly conserved amino acids in this consensus sequence (SEQ ID NO:9) are M1, E6, G13, R15, I16, A19, L21, D22, A23, L27, N28, A29, L30, L32, P33, M34, I35, L38, W45, A46, C53, V54, L56, R57, G58, N59, G60, K62, A63, F64, C65, A66, G67, G68, V70, L73, C77, P81, G82, P85, L87, A88, F91, F92, Y96, R97, L98, H103, P106, K107, P108, C111, W112, H114, G115, V117, G119, G120, G121, M122, G123, L124, Q126, R131, I132, V133, T134, P135, R138, L139, M141, P142, E143, I146, G147, L148, D151, V152, G153, S155, F157, L158, R160, P162, G163, L165, G166, L167, F168, L171, N177, D180, A181, D183, L184, L186, A187, D188, R189, Q195, Q196, L199, L203, Q205, N207, W208, E210, Q215, L216, S218, L219, A222, P232, L237, R239, R240, D244, L247, D248, A258, D267, L269, G280, P282, V288, W289, Q291, R294, R296, L298, S299, L300, E307, Y308, S311, L312, N313, C314, R316, H317, P318, F320, E322, G323, V324, R325, A326, R327, L328, D330, D332, P335, W337, W339, P346, A352, H353, and F354. In various embodiments, malonyl-CoA hydrolase enzymes homologous to this consensus sequence (SEQ ID NO:9) contain at least 25% of these conserved amino acids, often a majority (greater than 50%) of these conserved amino acids, and sometimes all of these conserved amino acids.

Some amino acids in this consensus sequence (SEQ ID NO:9) are essential for activity and conserved across all members of the class. Malonyl-CoA hydrolase enzymes encompassed by the Pseudomonas EC 3.1.2.4 based consensus sequence contain six conserved active site residues necessary for hydrolase activity (i) three active site amino acid residues (G67, G68, G120) of the consensus sequence believed to be necessary (although the invention is not to be limited by any theory of mechanism of action) for formation of an oxyanion hole responsible for stabilizing the enolate anion intermediate derived from an acyl-CoA substrate; (ii) two amino acid residues (E143, D151) of the consensus sequence believed to be necessary for acyl-CoA hydrolysis; and (iii) amino acid $X_1$95 (of SEQ ID NO:9) is believed to be necessary for malonyl-CoA substrate binding. Of these six residues, then, five are present in the consensus sequence (SEQ ID NO:9) and in all malonyl-CoA hydrolases encompassed by that sequence, and the sixth, $X_1$95 is necessary to provide a malonyl-CoA hydrolase of the invention capable of producing malonate in a recombinant host cell. In various embodiments of the invention, the key wild-type glutamic acid residue (E95) is (has been) mutated to a polar or positively charged amino acid (i.e. R, H, K, S, T, N, Q, Y), or A or D, to produce $X_1$95 and provide a malonyl-CoA hydrolase of the invention capable of producing malonate in a recombinant host cell. In some embodiments of the invention, amino acid E95 is (has been mutated to) an amino acid selected from the group consisting of K, S, T, N, Y, A, and D. In some embodiments of the invention, amino acid E95 is S or N. The six essential residues from the consensus sequence sequence (G67, G68, G120, E143, D151, $X_1$95) correspond to G67, G68, G120, E143, D151, and E95 (typically mutated to $X_1$), respectively, in Pseudomonas fulva (12-X) F6AA82-2 used to illustrate the invention in example 31 (see SEQ ID NO:50 containing mutations E95S/Q348A).

Non-limiting examples of enzymes suitable for malonyl-CoA hydrolysis homologous to the consensus sequence (SEQ ID NO:9) and encoded by cloned or synthesized nucleic acids provided by the invention include mutant enzymes containing at least one mutation illustrated by the group of mutant enzymes consisting of Pseudomonas fulva (strain 12-X) F6AA82 (E95S), F6AA82 (E95N), F6AA82 (E95A), F6AA82 (E95H), F6AA82 (E95K), F6AA82 (E95R), F6AA82 (E95Q), F6AA82 (E95D), F6AA82 (E95T), F6AA82 (E95Y) as demonstrated in example 43; Pseudomonas fluorescens WH6 E2XN63 (E95S), E2XN63 (E95N), E2XN63 (E95A), E2XN63 (E95H), E2XN63 (E95K), E2XN63 (E95R), E2XN63 (E95Q), E2XN63 (E95D), E2XN63 (E95T), E2XN63 (E95Y); Pseudomonas mendocina (strain ymp) A4XS22 (E95S), A4XS22 (E95N), A4XS22 (E95A), A4XS22 (E95H), A4XS22 (E95K), A4XS22 (E95R), A4XS22 (E95Q), A4XS22 (E95D), A4XS22 (E95T), E2XN63 (E95Y).

In various embodiments of the invention the malonyl-CoA hydrolase is F6AA82 (E95S) from Pseudomonas fulva (strain 12-X), E2XN63 (E95S) from Pseudomonas fluorescens WH6, A4XS22 (E95S) from Pseudomonas mendocina (strain ymp), as illustrated in Example 31.

As illustrated in Example 43, F6AA82 E95$X_1$ mutations resulted in malonyl-CoA hydrolase activity. F6AA82 proteins containing mutations E95S, E95Y, E95T, E95N, E96K, E95A, and E95D produced significantly (t-test, p<0.05) more malonate than the wild type F6AA82 protein. F6AA82 proteins containing these mutations are suitable for use as malonyl-CoA hydrolases and production of malonate. Of the F6AA82 enzymes containing an $X_1$ mutation conferring malonyl-CoA hydrolase activity, mutations E95S or E95N are preferred. Of the F6AA82 enzymes containing an $X_1$ mutation conferring malonyl-CoA hydrolase activity, mutations E95A, E95T, E95K, E95Y and E95D are suitable. In various embodiments of the invention the malonyl-CoA hydrolase is F6AA82 (E95S). In other embodiments of the invention the malonyl-CoA hydrolase is F6AA82 (E95N). F6AA82 proteins containing mutations E95H, E95Q, or E95R did not result in increased malonate production under test conditions employed as described in the examples.

Where an enzyme with substantial homology to a consensus sequence herein has suboptimal or no malonyl-CoA hydrolase activity, then, in accordance with the invention, it can be mutated to conform to a consensus sequence provided herein to provide a malonyl-CoA hydrolase of the invention. For example, protein A5W8H3 shows 86% identity to malonyl-CoA hydrolase consensus SEQ ID NO:9 but does not exhibit malonyl-CoA hydrolase activity (example 31). One or more amino acids that differ between A5W8H3 and consensus SEQ ID NO:9 may be mutated to introduce malonyl-CoA hydrolase activity. Specifically A5W8H3 mutations T2N, C5F, V7J, L8B, G10U, D12B, P24J, A26U, N31U, Q41B, A72B, A740, Q75J, S83J, S90B, A94J, F100B, A101B, N129U, A159U, F1690, P175B, G185J, G192B, A198J, A213J, N217B, Q224J, C228B, A229J, W2360, H241Q, E242B, Q245J, A2520, R261A, Q264J, D272B, G274A, Q275B, Y297B, Q302J, Q305B, M3100, N333B, A347J, A355J, A3570, and/or G368U may be used to impart malonyl-CoA hydrolase activity.

Malonyl-CoA Hydrolase Consensus Sequence Based on Bacterial EC 3.1.2.4 Enzymes

Despite *Bacillus* and *Pseudomonas* being evolutionarily distant (i.e. *Bacillus* is Gram-positive and *Pseudomonas* is Gram-negative), there is significant sequence conservation between the *Bacillus* EC 3.1.2.4 and *Pseudomonas* EC 3.1.2.4 enzymes. The present invention provides a malonyl-CoA hydrolase consensus sequence based on these bacterial EC 3.1.2.4 acyl-CoA hydrolases (SEQ ID NO:10). Malonyl-CoA hydrolase enzymes encompassed by this consensus sequence typically possess at least 25% (or a majority or all) of the highly conserved amino acids from this sequence, which conserved amino acids are selected from the group consisting of L53, L59, N60, L62, M66, L88, F97, C98, A99, G100, G101, F124, F125, Y129, K140, P141, G148, G152, G153, G154, G156, L157, T167, M174, P175, E176, I179, G180, D184, V185, G186, L191, L210, D219, A226, P333, N364, F375, E377, D385, and P390. A suitable malonyl-CoA hydrolase of the invention homologous to this consensus sequence includes the active site amino acids necessary for malonyl-CoA hydrolysis (G100, G101, G153, E176, and D184) of the consensus sequence, as well as a $X_1 128$, where the key wild-type glutamic acid residue (E128) is (has been) mutated to a polar or charged amino acid (i.e. R, H, K, S, T, N, Q, Y), or D or A, and is capable of producing malonate in a recombinant host cell.

Malonyl-CoA Hydrolases Based on Malonyl-CoA:ACP Transacylases

In yet other embodiments of the invention, the malonyl-CoA hydrolase is a mutated malonyl-CoA:ACP transacylase (EC 2.3.1.39). The invention provides an *E. coli* FabD sequence (SEQ ID NO:53), and in various embodiments, suitable malonyl-CoA hydrolases for use in the methods of the invention have at least 50%, 60%, 70%, 80%, 90%, 95%, or more sequence identity when aligned relative to SEQ ID NO:53 and contain one or more of the following amino acid mutations at the aligned positions: S92C, H201N, R117D, R117E, R117N, R117Y, R117G, R117H, Q11D, Q11E, Q11N, Q11Y, Q11G, Q11H, L93A, L93V, L93I, L93F, L93S, L93G.

In some embodiments of this invention the malonyl-CoA hydrolase is a mutated *E. coli* FabD malonyl-CoA:ACP transacylase (see SEQ ID NO:53 for wild type sequence) with one or more mutation selected from the group consisting of S92C, H201N, R117D, R117E, R117N, R117Y, R117G, R117H, Q11D, Q11E, Q11N, Q11Y, Q11G, Q11H, L93A, L93V, L93I, L93F, L93S, L93G. Example 35 illustrates recombinant yeast cells expressing a mutated *E. coli* FabD enzyme containing one of the following combinations of mutations S92C/L91V/R117H, L91I/R117Y/A246E, Q80L/L91S/R117G, and L91I/R117Y, and producing malonate at levels higher than wild type yeast without a mutated FabD enzyme.

Section 3: Expression Vectors

In various aspects of the present invention, the recombinant host cell has been modified by "genetic engineering" to produce a recombinant malonyl-CoA hydrolase enzyme and malonate. The host cell is typically engineered via recombinant DNA technology to express heterologous nucleic acids that encode a malonyl-CoA hydrolase, which is either a, mutated version of a naturally occurring acyl-CoA hydrolase or transacylase or a non-naturally occurring malonyl-CoA hydrolase prepared in accordance with one of the consensus sequences provided herein or is a naturally occurring acyl-CoA hydrolase with malonyl-CoA hydrolase activity that is either overexpressed in the cell in which it naturally occurs or is heterologously expressed in a cell in which it does not naturally occur.

Nucleic acid constructs of the present invention include expression vectors that comprise nucleic acids encoding one or more malonyl-CoA hydrolase enzymes. The nucleic acids encoding the enzymes are operably linked to promoters and optionally other control sequences such that the subject enzymes are expressed in a host cell containing the expression vector when cultured under suitable conditions. The promoters and control sequences employed depend on the host cell selected for the production of malonate. Thus, the invention provides not only expression vectors but also nucleic acid constructs useful in the construction of expression vectors. Methods for designing and making nucleic acid constructs and expression vectors generally are well known to those skilled in the art and so are only briefly reviewed herein.

Nucleic acids encoding the malonyl-CoA hydrolase enzymes can be prepared by any suitable method known to those of ordinary skill in the art, including, for example, direct chemical synthesis and cloning. Further, nucleic acid sequences for use in the invention can be obtained from commercial vendors that provide de novo synthesis of the nucleic acids.

A nucleic acid encoding the desired enzyme can be incorporated into an expression vector by known methods that include, for example, the use of restriction enzymes to cleave specific sites in an expression vector, e.g., plasmid, thereby producing an expression vector of the invention. Some restriction enzymes produce single stranded ends that may be annealed to a nucleic acid sequence having, or synthesized to have, a terminus with a sequence complementary to the ends of the cleaved expression vector. The ends are then covalently linked using an appropriate enzyme, e.g., DNA ligase. DNA linkers may be used to facilitate linking of nucleic acids sequences into an expression vector.

A set of individual nucleic acid sequences can also be combined by utilizing polymerase chain reaction (PCR)-based methods known to those of skill in the art. For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual nucleic acid sequences may be joined and subsequently transduced into a host cell simultaneously. Thus, expression of each of the plurality of nucleic acid sequences is effected.

A typical expression vector contains the desired nucleic acid sequence preceded and optionally followed by one or more control sequences or regulatory regions, including a promoter and, when the gene product is a protein, ribosome binding site, e.g., a nucleotide sequence that is generally 3-9 nucleotides in length and generally located 3-11 nucleotides upstream of the initiation codon that precede the coding sequence, which is followed by a transcription terminator in the case of E. coli or other prokaryotic hosts. See Shine et al., Nature 254:34 (1975) and Steitz, in Biological Regulation and Development: Gene Expression (ed. R. F. Goldberger), vol. 1, p. 349 (1979) Plenum Publishing, N.Y. In the case of eukaryotic hosts like yeast a typical expression vector contains the desired nucleic acid coding sequence preceded by one or more regulatory regions, along with a Kozak sequence to initiate translation and followed by a terminator. See Kozak, Nature 308:241-246 (1984).

Regulatory regions or control sequences include, for example, those regions that contain a promoter and an operator. A promoter is operably linked to the desired nucleic acid coding sequence, thereby initiating transcription of the nucleic acid sequence via an RNA polymerase. An operator is a sequence of nucleic acids adjacent to the promoter, which contains a protein-binding domain where a transcription factor can bind. Transcription factors activate or repress transcription initation from a promoter. In this way, control of transcription is accomplished, based upon the particular regulatory regions used and the presence or absence of the corresponding transcription factor. Non-limiting examples for prokaryotic expression include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Non-limiting examples of promoters to use for eukaryotic expression include pTDH3, pTEF1 (as illustrated in Example 31), pTEF2, pRNR2, pRPL18B, pREV1, pGAL1, pGAL10, pGAPDH, pCUP1, pMET3, pPGK1, pPYK1, pHXT7, pPDC1, pFBA1, pTDH2, pPGI1, pPDC1, pTPI1, pENO2, pADH1, and pADH2. As described in Example 44, the promoters for the genes HSP150, PGK1, PHO5, SCT1, PRB1, TPI1, ACH1, HXK2, ACO1, JEN1, MDH2, PDX1, CIT1, ALD4, ADH1, TDH3, ADH2, and SDH1 from S. cerevisiae strain BY4741 were demonstrated to be useful for the production malonic acid in accordance with the invention. As will be appreciated by those of ordinary skill in the art, a variety of expression vectors and components thereof may be used in the present invention.

Although any suitable expression vector may be used to incorporate the desired sequences, readily available expression vectors include, without limitation: plasmids, such as pESC, pTEF, p414CYC1, p414GALS, pSC101, pBR322, pBBR1MCS-3, pUR, pEX, pMR100, pCR4, pBAD24, pUC19, pRS series; and bacteriophages, such as M13 phage and λ phage. Of course, such expression vectors may only be suitable for particular host cells or for expression of particular malonyl-CoA hydrolases. One of ordinary skill in the art, however, can readily determine through routine experimentation whether any particular expression vector is suited for any given host cell or protein. For example, the expression vector can be introduced into the host cell, which is then monitored for viability and expression of the sequences contained in the vector. In addition, reference may be made to the relevant texts and literature, which describe expression vectors and their suitability to any particular host cell. In addition to the use of expression vectors, strains are built where expression cassettes are directly integrated into the host genome.

The expression vectors are introduced or transferred, e.g. by transduction, transfection, or transformation, into the host cell. Such methods for introducing expression vectors into host cells are well known to those of ordinary skill in the art. For example, one method for transforming E. coli with an expression vector involves a calcium chloride treatment wherein the expression vector is introduced via a calcium precipitate.

For identifying whether a nucleic acid has been successfully introduced or into a host cell, a variety of methods are available. For example, a culture of potentially transformed host cells may be separated, using a suitable dilution, into individual cells and thereafter individually grown and tested for expression of a desired gene product of a gene contained in the introduced nucleic acid. For example, an often-used practice involves the selection of cells based upon antibiotic resistance that has been conferred by antibiotic resistance-conferring genes in the expression vector, such as the beta lactamase (amp), aminoglycoside phosphotransferase (neo), and hygromycin phosphotransferase (hyg, hph, hpt) genes.

Typically, a host cell of the invention will have been transformed with at least one expression vector. When only a single expression vector is used, the vector will typically contain a malonyl-CoA hydrolase gene. Once the host cell has been transformed with the expression vector, the host cell is cultured in a suitable medium containing a carbon source, such as a sugar (e.g., glucose). As the host cell is cultured, expression of the enzyme(s) for producing malonate occurs. Once expressed, the enzyme(s) catalyzes the hydrolysis of the thioester bond of malonyl-CoA, thus releasing malonate and CoA.

If a host cell of the invention is to include more than one heterologous gene, the multiple genes can be expressed from one or more vectors. For example, a single expression vector can comprise one, two, or more genes encoding one, two, or more malonyl-CoA hydrolase enzyme(s) and/or other proteins providing some useful function, e.g. improved malonate yield, titer, and/or productivity. The heterologous genes can be contained in a vector replicated episomally or in a vector integrated into the host cell genome, and where more than one vector is employed, then all vectors may replicate episomally (extrachromasomally), or all vectors may integrate, or some may integrate and some may replicate episomally. Chromosomal integration is typically used for cells that will undergo sustained propagation, e.g., cells used for production of malonate for industrial applications. Example 45 illustrates the benefits of genomic integration of a malonyl-CoA hydrolase gene provided by the invention; in that example, a single integrated copy of the gene is shown to result in higher malonic acid titers than achieved when the same gene was expressed from a plasmid. This example also serves to demonstrate modulation of malonic acid production as provided by the invention, as an increase in the number of copies of the malonyl-CoA hydrolase encoding gene per cell results in an increase of malonic acid in the fermentation media. While a "gene" is generally composed of a single promoter and a single coding sequence, in certain host cells, two or more coding sequences may be controlled by one promoter in an operon. In some embodiments, a two or three operon system is used.

In some embodiments, the coding sequences employed have been modified, relative to some reference sequence, to reflect the codon preference of a selected host cell. Codon usage tables for numerous organisms are readily available and can be used to guide sequence design. The use of prevalent codons of a given host organism generally improves translation of the target sequence in the host cell.

As one non-limiting example, in some embodiments the subject nucleic acid sequences will be modified for yeast codon preference (see, for example, Bennetzen et al., *J. Biol. Chem.* 257: 3026-3031 (1982)). In some embodiments, the nucleotide sequences will be modified for *E. coli* codon preference (see, for example, Nakamura et al., *Nucleic Acids Res.* 28:292 (2000)). In other embodiments, the nucleotide sequences are modified to include codons optimized for *S. cerevisiae* codon preference (see Example 42).

Nucleic acids can be prepared by a variety of routine recombinant techniques. Briefly, the subject nucleic acids can be prepared from genomic DNA fragments, cDNAs, and RNAs, all of which can be extracted directly from a cell or recombinantly produced by various amplification processes including but not limited to PCR and rt-PCR. Subject nucleic acids can also be prepared by a direct chemical synthesis.

The nucleic acid transcription levels in a host microorganism can be increased (or decreased) using numerous techniques. For example, the copy number of the nucleic acid can be increased through use of higher copy number expression vectors comprising the nucleic acid sequence, or through integration of multiple copies of the desired nucleic acid into the host microorganism's genome, as demonstrated in Example 45. Non-limiting examples of integrating a desired nucleic acid sequence onto the host chromosome include recA-mediated recombination, lambda phage recombinase-mediated recombination and transposon insertion. Nucleic acid transcript levels can be increased by changing the order of the coding regions on a polycistronic mRNA or breaking up a polycistronic operon into multiple poly- or mono-cistronic operons each with its own promoter. RNA levels can be increased (or decreased) by increasing (or decreasing) the strength of the promoter to which the protein-coding region is operably linked. Illustrative techniques for plasmid design and assembly to afford malonate production are provided in Examples 1, 3, 31, and 35.

The translation level of a desired polypeptide sequence in a host microorganism can also be increased in a number of ways. Non-limiting examples include increasing the mRNA stability, modifying the ribosome binding site (or Kozak) sequence, modifying the distance or sequence between the ribosome binding site (or Kozak sequence) and the start codon of the nucleic acid sequence coding for the desired polypeptide, modifying the intercistronic region located 5' to the start codon of the nucleic acid sequence coding for the desired polypeptide, stabilizing the 3'-end of the mRNA transcript, modifying the codon usage of the polypeptide, altering expression of low-use/rare codon tRNAs used in the biosynthesis of the polypeptide. Determination of preferred codons and low-use/rare codon tRNAs can be based on a sequence analysis of genes derived from the host microorganism.

The polypeptide half-life, or stability, can be increased through mutation of the nucleic acid sequence coding for the desired polypeptide, resulting in modification of the desired polypeptide sequence relative to the control polypeptide sequence. When the modified polypeptide is an enzyme, the activity of the enzyme in a host may be altered due to increased solubility in the host cell, improved function at the desired pH, removal of a domain inhibiting enzyme activity, improved kinetic parameters (lower Km or higher Kcat values) for the desired substrate, removal of allosteric regulation by an intracellular metabolite, and the like. Altered/modified enzymes can also be isolated through random mutagenesis of an enzyme, such that the altered/modified enzyme can be expressed from an episomal vector or from a recombinant gene integrated into the genome of a host microorganism.

Section 4: Recombinant Host Cells

In one aspect, the invention provides recombinant host cells suitable for biological production of malonate. Any suitable host cell may be used in practice of the methods of the present invention. In some embodiments, the host cell is a recombinant host microorganism in which nucleic acid molecules have been inserted, deleted or modified (i.e., mutated; e.g., by insertion, deletion, substitution, and/or inversion of nucleotides), either to produce malonate, or to increase yield, titer, and/or productivity of malonate relative to a "control cell" or "reference cell". A "control cell" can be used for comparative purposes, and is typically a wild-type or recombinant parental cell that does not contain one or more of the modification(s) made to the host cell of interest.

In an important embodiment, the present invention provides recombinant yeast cells suitable for the production of malonate at levels sufficient for subsequent purification and use as described herein. Yeast host cells are excellent host cells for construction of recombinant metabolic pathways comprising heterologous enzymes catalyzing production of small molecule products. There are established molecular biology techniques and nucleic acids encoding genetic elements necessary for construction of yeast expression vectors, including, but not limited to, promoters, origins of replication, antibiotic resistance markers, auxotrophic markers, terminators, and the like. Second, techniques for integration of nucleic acids into the yeast chromosome are well established. Yeast also offers a number of advantages as an industrial fermentation host. Yeast can tolerate high concentrations of organic acids and maintain cell viability at low pH and can grow under both aerobic and anaerobic culture conditions, and there are established fermentation broths and fermentation protocols. The ability of a strain to propagate and/or produce desired product under low pH provides a number of advantages with regard to the present invention. First, this characteristic provides tolerance to the environment created by the production of malonic acid. Second, from a process standpoint, the ability to maintain a low pH environment limits the number of organisms that are able to contaminate and spoil a batch. Third, this characteristic also eliminates or at least reduces the need to add additional acid to facilitate purification of malonic acid by some methods provided by the invention (see Example 37).

In some embodiments of the invention, the recombinant host cell comprising a heterologous nucleic acid encoding a malonyl-CoA hydrolase is a eukaryote. In various embodiments, the eukaryote is a yeast selected from the non-limiting list of genera; *Candida, Cryptococcus, Hansenula, Issatchenki, Kluyveromyces, Komagataella, Lipomyces, Pichia, Rhodosporidium, Rhodotorula, Saccharomyces* or *Yarrowia* species. In various embodiments, the yeast is of a species selected from the group consisting of *Candida albicans, Candida ethanolica, Candida krusei, Candida methanosorbosa, Candida sonorensis, Candida tropicalis, Cryptococcus curvatus, Hansenula polymorpha, Issatchenkia orientalis, Kluyveromyces lactis, Kluyveromyces marxianus, Kluyveromyces thermotolerans, Komagataella pastoris, Lipomyces starkeyi, Pichia angusta, Pichia deserticola, Pichia galeiformis, Pichia kodamae, Pichia kudriavzevii, Pichia membranaefaciens, Pichia methanolica, Pichia pastoris, Pichia salictaria, Pichia stipitis, Pichia thermotoler-* ans, *Pichia trehalophila, Rhodosporidium toruloides, Rhodotorula glutinis, Rhodotorula graminis, Saccharomyces bayanus, Saccharomyces boulardi, Saccharomyces cerevisiae, Saccharomyces kluyveri,* and *Yarrowia lipolytica*. One skilled in the art will recognize that this list encompasses yeast in the broadest sense, including both oleaginous and non-oleaginous strains. Examples 46 and 47 illustrate the use of *Pichia* kudriavzevii strain Y-134 in accordance with the invention.

Alternative recombinant host cells are provided by the invention for biological production of malonate. Illustrative examples include eukaryotic, prokaryotic, and archaea cells. Illustrative examples of eukaryotic cells include, but are not limited to: *Aspergillus niger, Aspergillus oryzae, Crypthecodinium cohnii, Cunninghamella japonica, Entomophthora coronata, Mortierella alpina, Mucor circinelloides, Neurospora crassa, Pythium ultimum, Schizochytrium limacinum, Thraustochytrium aureum, Trichoderma reesei* and *Xanthophyllomyces dendrorhous*. In general, if a eukaryotic cell is used, a non-pathogenic strain is employed. Illustrative examples of non-pathogenic strains include, but are not limited to: *Pichia pastoris* and *Saccharomyces cerevisiae*. In addition, certain strains, including *Saccharomyces cerevisiae*, have been designated by the Food and Drug Administration as Generally Regarded As Safe (or GRAS) and so can be conveniently employed in various embodiments of the methods of the invention.

Illustrative examples of recombinant prokaryotic host cells provided by the invention include, but are not limited to, *Bacillus subtilis, Brevibacterium ammoniagenes, Clostridium beigerinckii, Enterobacter sakazakii, Lactobacillus acidophilus, Lactococcus lactis, Mesorhizobium loti, Pseudomonas aeruginosa, Pseudomonas putida, Rhodobacter capsulatus, Rhodobacter sphaeroides, Salmonella enterica, Salmonella typhi, Salmonella typhimurium, Shigella flexneri, Staphylococcus aureus, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis,* and *Streptomyces vinaceus*. Certain of these cells, including *Bacillus subtilis, Lactobacillus acidophilus*, have been designated by the Food and Drug Administration as Generally Regarded As Safe (or GRAS) and so are employed in various embodiments of the methods of the invention. While desirable from public safety and regulatory standpoints, GRAS status does not impact the ability of a host strain to be used in the practice of this invention; hence, non-GRAS and even pathogenic organisms are included in the list of illustrative host strains suitable for use in the practice of this invention.

*Escherichia coli* is also an excellent prokaryotic host cell for metabolic pathway construction, and *E. coli* is also well utilized in industrial fermentation of small-molecule products. Unlike most wild type yeast strains, wild type *E. coli* can catabolize both pentose and hexose sugars as carbon sources. *E. coli* also has a shorter doubling time relative to yeast, enabling experiments to be conducted more rapidly. The present invention provides a wide variety of *E. coli* host cells suitable for the production of malonate as described herein. In various embodiments of the methods of the invention, the recombinant host cell comprising a heterologous nucleic acid encoding a malonyl-CoA hydrolase is an *E. coli* cell.

Section 5: Additional Modifications and Fermentation Conditions for Improved Malonate Production In other aspects of the invention, increased malonate yield, titer, and/or productivity is achieved by employing host cells provided by the invention that have been genetically modified in ways other than, or in addition to, introduction of a heterologous malonyl-CoA hydrolase and/or by employing fermentation conditions provided by certain methods of the invention. In brief, the recombinant host cell of the invention comprise genetic modifications that increase acetyl-CoA biosynthesis, increase malonyl-CoA biosynthesis, decrease malonate catabolism, increase secretion of malonate from the host cell, increase host cell tolerance to malonate, and increase catabolism of various carbon sources.

Genetic Modifications and Fermentation Conditions that Increase Acetyl-CoA Biosynthesis In accordance with the invention, increased malonate titer, yield, and/or productivity can be achieved by genetic modifications that increase acetyl-CoA biosynthesis, and the invention provides enzymes that increase acetyl-CoA biosynthesis, vectors for expressing enzymes that increase acetyl-CoA biosynthesis, host cells expressing enzymes that increase acetyl-CoA biosynthesis and increase malonate titer, yield, and/or productivity, and methods relating thereto. As described above, malonate is produced by hydrolysis of malonyl-CoA, which, can be produced from acetyl-CoA; thus, increases in acetyl-CoA biosynthesis can improve malonate production.

One route by which acetyl-CoA is produced is by an acetyl-CoA synthetase (EC 6.2.1.1), which catalyzes the formation of acetyl-CoA from acetate and coenzyme A (CoA). The invention provides recombinant host cells suitable for producing malonate in accordance with the methods of the invention comprising one or more heterologous acetyl-CoA synthetase (ACS) enzymes that increase malonate titer, yield, and/or productivity relative to a host cell not comprising a heterologous acetyl-CoA synthetase. Non-limiting examples of suitable ACS enzymes are *S. cerevisiae* ACS1 (GenBank: AAC04979.1) and ACS2 (GenBank: CAA97725.1). In some embodiments, a recombinant host cell comprising *S. cerevisiae* acetyl-CoA synthetase ACS1 and/or ACS2 is used to increase malonate titer, yield, and/or productivity. In other embodiments, a recombinant host cell comprising an acetyl-CoA synthetase selected from the group consisting of *Salmonella enterica* Acs, *Escherichia coli* AcsA, and *Bacillus subtilis* AcsA is used to increase malonate yield, titer, and/or productivity. Those skilled in the art appreciate that other acetyl-CoA synthetases can be expressed in a recombinant host cell producing malonate in accordance with the invention to increase malonate yield, titer, and/or productivity. This modification is illustrated in Examples 9 and 46.

A second route through which acetyl-CoA is produced is by a pyruvate dehydrogenase complex, which catalyzes the formation of acetyl-CoA from pyruvate. The invention provides recombinant host cells suitable for producing malonate in accordance with the methods of the invention that comprise one or more heterologous pyruvate dehydrogenase complex enzymes that increase malonate titer, yield, and/or productivity relative to a host cell not comprising a heterologous pyruvate dehydrogenase complex enzyme. Non-limiting examples of suitable pyruvate dehydrogenase complex enzymes include *S. cerevisiae* PDA1, PDB1, LAT1, LPD1, and PDX1. In some embodiments of the invention, malonate yield, titer, and/or productivity are increased in a recombinant host cell used to produce malonate by expressing one or more pyruvate dehydrogenase enzymes selected from the group consisting of *S. cerevisiae* PDA1, PDB1, LAT1, LPD1, and PDX1. Those skilled in the art appreciate that other pyruvate dehydrogenase enzymes can be expressed in a recombinant host cell producing malonate in accordance with the invention to increase malonate yield, titer, and/or productivity. This modification is illustrated in Example 10.

A third route through which acetyl-CoA is produced is by a heterologous ethanol catabolic pathway comprising enzymes catalyzing the conversion of ethanol to acetyl-CoA. Compared to malonate, ethanol is a less expensive chemical, and host cells producing malonate and expressing an ethanol catabolic pathway can convert ethanol to malonate. An alcohol dehydrogenase (EC 1.1.1.1) catalyzes conversion of ethanol to acetaldehyde. Non-limiting examples of suitable alcohol dehydrogenase enzymes include those selected from the group consisting of *S. cerevisiae* ADH2, *E. coli* AdhP, *H. sapiens* ADH1A, *H. sapiens* ADH1B, and *H. sapiens* ADH1C. In addition to the alcohol dehydrogenase, an ethanol catabolic pathway also comprises either an acetaldehyde dehydrogenase (acylating; EC 1.2.1.10), or an aldehyde dehydrogenase (EC 1.2.1.3) and an acetyl-CoA synthetase (EC 6.2.1.1). An acetaldehyde dehydrogenase (acylating) catalyzes the conversion of acetaldehyde to acetyl-CoA, an aldehyde dehydrogenase catalyzes the conversion of acetaldehyde to acetate, and an acetyl-CoA synthase, as described above, catalyzes the formation of acetyl-CoA from acetate and CoA. Non-limiting examples of suitable acetaldehyde dehydrogenases (acylating) include those selected from the group consisting of *E. coli* MhpF, *E. coli* AdhE, *Pseudomonas* sp CF600 DmpF, and *Pseudomonas putida* TodL. Non-limiting examples of aldehyde dehydrogenases include *S. cerevisiae* ALD2, ALD3, ALD4, ALD5, and ALD6; and *H. sapiens* ALD1, ALD2, ALD4, and ALD10. Non-limiting examples of acetyl-CoA synthetase enzymes include *S. cerevisiae* ACS1, *S. cerevisiae* ACS2, and *E. coli* Acs.

The present invention provides recombinant host cells suitable for producing malonate in accordance with the methods of the invention comprising one or more heterologous ethanol catabolic pathway enzymes that increase malonate yield, titer, and/or productivity relative to host cells not comprising the heterologous ethanol catabolic pathway enzyme(s). In some embodiments, the heterologous ethanol catabolic pathway enzymes are an ethanol dehydrogenase and an acetaldehyde dehydrogenase (acylating). In some embodiments, the heterologous ethanol catabolic pathway enzymes are *S. cerevisiae* ADH2 ethanol dehydrogenase and *E. coli* MhpF acetaldehyde dehydrogenase (acylating). In some embodiments, a heterologous *S. cerevisiae* ADH2 and *E. coli* MhpF are expressed in recombinant *E. coli* expressing a heterologous *S. cerevisiae* EHD3 malonyl-CoA hydrolase. In other embodiments, a heterologous *S. cerevisiae* ADH2 and *E. coli* MhpF are expressed in recombinant *S. cerevisiae* expressing a heterologous *S. cerevisiae* EHD3 malonyl-CoA hydrolase. In other embodiments, a heterologous *S. cerevisiae* ADH2 and *E. coli* MhpF are expressed in a recombinant oleaginous yeast expressing a heterologous *S. cerevisiae* EHD3 malonyl-CoA hydrolase. In other embodiments, the heterologous ethanol catabolic pathway enzymes are *S. cerevisiae* ADH2 ethanol dehydrogenase and *Pseudomonas* sp. CF600 DmpF acetaldehyde dehydrogenase (acylating). In some embodiments, a heterologous *S. cerevisiae* ADH2 and *Pseudomonas* sp. CF600 DmpF are expressed in recombinant *E. coli* expressing a heterologous *S. cerevisiae* EHD3 malonyl-CoA hydrolase. In some embodiments, a heterologous *S. cerevisiae* ADH2 and *Pseudomonas* sp. CF600 DmpF are expressed in recombinant *S. cerevisiae* expressing a *S. cerevisiae* EHD3 malonyl-CoA hydrolase. In some embodiments, a heterologous *S. cerevisiae* ADH2 and *Pseudomonas* sp. CF600 DmpF are expressed in a recombinant oleaginous yeast expressing a heterologous *S. cerevisiae* EHD3 malonyl-CoA hydrolase. In other embodiments, the heterologous ethanol catabolic pathway enzymes are *S. cerevisiae* ADH2 ethanol dehydrogenase and *Pseudomonas putida* TodL acetaldehyde dehydrogenase (acylating). In some embodiments, a heterologous *S. cerevisiae* ADH2 and *Pseudomonas putida* TodL are expressed in recombinant *E. coli* expressing a heterologous *S. cerevisiae* EHD3 malonyl-CoA hydrolase. In some embodiments, a heterologous *S. cerevisiae* ADH2 and *Pseudomonas putida* TodL are expressed in recombinant *S. cerevisiae* expressing a heterologous *S. cerevisiae* EHD3 malonyl-CoA hydrolase. In some embodiments, a heterologous *S. cerevisiae* ADH2 and *Pseudomonas putida* TodL are expressed in a recombinant oleaginous yeast expressing a heterologous *S. cerevisiae* EHD3 malonyl-CoA hydrolase. In other embodiments, the heterologous ethanol catabolic pathway enzymes are one or more alcohol dehydrogenase selected from the group containing *S. cerevisiae* ADH2, *E. coli* AdhP, *H. sapiens* ADH1A, *H. sapiens* ADH1B, and/or *H. sapiens* ADH1C and one or more acetaldehyde dehydrogenase (acylating) selected from the group containing *E. coli* MhpF, *E. coli* AdhE, *Pseudomonas* sp CF600 DmpF, and *Pseudomonas putida* TodL. Those skilled in the art appreciate that other alcohol dehydrogenase enzymes and acetaldehyde dehydrogenase (acylating) enzymes can be expressed in a recombinant host cell suitable for producing malonate in accordance with the methods of the invention to increase malonate yield, titer, and/or productivity.

In other embodiments, the heterologous ethanol catabolic pathway enzymes are an ethanol dehydrogenase, an aldehyde dehydrogenase, and an acetyl-CoA synthetase. In some embodiments, the heterologous ethanol catabolic pathway enzymes are a *S. cerevisiae* ALD2 alcohol dehydrogenase, a *S. cerevisiae* ALD2 aldehyde dehydrogenase, and a *S. cerevisiae* ACS1 acetyl-CoA synthetase. In other embodiments, the heterologous ethanol catabolic pathway enzymes are a *S. cerevisiae* ALD2 alcohol dehydrogenase, a *S. cerevisiae* ALD2 aldehyde dehydrogenase, and a *S. cerevisiae* ACS2 acetyl-CoA synthetase. In other embodiments, the heterologous ethanol catabolic pathway enzymes are a *S. cerevisiae* ALD2 alcohol dehydrogenase, a *S. cerevisiae* ALD6 aldehyde dehydrogenase, and a *S. cerevisiae* ACS1 acetyl-CoA synthetase. In other embodiments, the heterologous ethanol catabolic pathway enzymes are a *S. cerevisiae* ALD2 alcohol dehydrogenase, a *S. cerevisiae* ALD6 aldehyde dehydrogenase, and a *S. cerevisiae* ACS2 acetyl-CoA synthetase. In other embodiments, the heterologous ethanol catabolic pathway enzymes are one or more alcohol dehydrogenases selected from the group containing *S. cerevisiae* ADH2, *E. coli* AdhP, *H. sapiens* ADH1A, *H. sapiens* ADH1B, and/or *H. sapiens* ADH1C, one or more aldehyde dehydrogenases selected from the group containing *S. cerevisiae* ALD2, *S. cerevisiae* ALD3, *S. cerevisiae* ALD4, *S. cerevisiae* ALD5, *S. cerevisiae* ALD6, *H. sapiens H. sapiens* ALD1, *H. sapiens* ALD2, *H. sapiens* ALD4, and/or *H. sapiens* ALD10, and one or more acetyl-CoA synthetases selected from the group containing *S. cerevisiae* ACS1, *S. cerevisiae* ACS2, and/or *E. coli* Acs.

In some embodiments, recombinant host cells suitable for producing malonate according to the methods of the invention comprise a heterologous ethanol catabolic pathway enzyme and convert endogenously produced ethanol into acetyl-CoA and increase malonate yield, titer, and/or productivity. In other embodiments, ethanol is exogenously added to the fermentation broth and recombinant host cells suitable for producing malonate according to the methods of the invention comprise a heterologous ethanol catabolic pathway enzyme and convert exogenously added ethanol into acetyl-CoA and increase malonate yield, titer, and/or productivity. When exogenously added to the fermentation broth, ethanol is added to obtain a minimal concentration of 1% ethanol volume/volume, and is typically added to the fermentation broth to obtain a concentration between between 1-15% volume/volume. Ethanol catabolism for improving malonate production in accordance with the invention is illustrated in Example 11.

Increased cytosolic pools of acetyl-CoA is a fourth route to increase malonate biosynthesis; in numerous plant and animal cells, but not *S. cerevisiae*, ATP citrate lyase (EC 2.3.3.8) is the primary enzyme responsible for cytosolic acetyl-CoA biosynthesis. In more detail, acetyl-CoA in the mitochondrion is condensed with oxaloacetate to form citrate through the activity of citrate synthase. Subsequently, citrate is transported from the mitochondrion into the cytosol where ATP citrate lyase catalyzes the formation of acetyl-CoA, oxaloacetate, and ADP. While *S. cerevisiae* does not contain a native ATP citrate lyase, suitable heterologous ATP citrate lyase enzymes have been described in oleaginous yeast strains (see, for example, Boulton et al., *J. Gen. Microbiol.* 127:169-176 (1981)). The present invention provides recombinant host cells comprising one or more heterologous nucleic oleaginous yeast ATP citrate lyase enzymes. Non-limiting examples of oleaginous yeast ATP citrate lyase enzymes include those selected from the group of oleaginous yeasts consisting of *Candida curvata, Cryptococcus albidus, Lipomyces lipofer, Rhodospiridium toruloides, Rhodotorula glutanis, Trichosporon cutaneum, Yarrowia lipolytica*, and the like. In various embodiments, the recombinant host cell comprises a heterologous nucleic acid encoding an ATP citrate lyase. In various embodiments, the ATP citrate lyase is from an organism selected from the group consisting of *Candida curvata, Cryptococcus albidus, Lipomyces lipofer, Rhodospiridium toruloides, Rhodotorula glutanis, Trichosporon cutaneum, Yarrowia lipolytica*. This modification is illustrated in Example 12.

Acetyl-CoA biosynthesis can also be increased in accordance with the invention by altering expression of one or more nucleic acids encoding proteins affecting fatty acid storage or catabolism. The present invention provides host cells comprising genetic modifications of one or more nucleic acids encoding proteins affecting fatty acid storage and catabolism. In *Saccharomyces cerevisiae*, these proteins include SNF2, IRA2, PRE9, PHO90, SPT21, PDX1, ANT1, FOX3, PAS1, PAS3, ARE1, ARE2, DGA1, LRO1, ACL1, MAE1, GLC3, GLG1, GLG2, PAT1, and PEX11. This modification is illustrated in Example 13.

In some embodiments of the invention, the host cell comprises genetic modifications affecting expression and/or activity of proteins involved in fatty acid catabolism. For example, most host cells will naturally degrade fatty acids, hydroxy fatty acids and many diacids through beta-oxidation pathways. Beta-oxidation occurs, in most cases, by activating free fatty acid groups to CoA thioesters with acyl-CoA ligases. The acyl-CoA intermediate is further oxidized and degraded—proceeding through a 2,3 enoyl-CoA, 3-hydroxyacyl-CoA, and 3-ketoacyl-CoA—and subsequent cleavage results in production of acetyl-CoA and an acyl-CoA shortened by two carbons relative to the initial substrate. The enzymatic activities required for beta-oxidation are known. The present invention provides host cells that possess increased catabolic pathway activity for medium (C4-C8)- and long (>C8)-chain fatty acids, hydroxyl fatty acids, and diacids compared to control host cells. For example, in yeast (e.g., *Saccharomyces cerevisiae*), beta-oxidation occurs in the peroxisome; examplary, non-limiting, nucleic acid products affecting peroxisomal beta-oxidation are *Saccharomyces cerevisiae* PAT1 and PEX11. In some embodiments of the invention, a host cell modified for increased expression of PAT1 and/or PEX11 is provided for use in the methods herein for the production of malonate. This modification is illustrated in Example 14.

Genetic Modifications and Fermentation Conditions that Increase Malonyl-CoA Biosynthesis In accordance with the invention, increased malonate titer, yield, and/or productivity can be achieved through increased malonyl-CoA biosynthesis, and the invention provides host cells, vectors, enzymes, and methods relating thereto. Malonyl-CoA is produced in host cells through the activity of an acetyl-CoA carboxylase (EC 6.4.1.2) catalyzing the formation of malonyl-CoA from acetyl-CoA and carbon dioxide. The invention provides recombinant host cells for producing malonate that express a heterologous acetyl-CoA carboxylase (ACC). In some embodiments, the host cell is a *S. cerevisiae* cell comprising a heterologous *S. cerevisiae* acetyl-CoA carboxylase ACC1 or an enzyme homologous thereto. In some embodiments, the host cell modified for heterologous expression of an ACC such as *S. cerevisiae* ACC1 is further modified to eliminate ACC1 post-translational regulation by genetic modification of *S. cerevisiae* SNF1 protein kinase or an enzyme homologous thereto. The invention also provides a recombinant host cell suitable for producing malonate in accordance with the invention that is an *E. coli* cell that comprises a heterologous nucleic acid coding for expression of *E. coli* acetyl-CoA carboxylase complex proteins AccA, AccB, AccC and AccD or one or more enzymes homologous thereto. In accordance with the invention, additional acetyl-CoA carboxylases can be heterologously expressed to increase malonyl-CoA and malonate biosynthesis. This modification is illustrated in Example 15.

In various embodiments of the invention, expression of BirA, biotin-[acetylCoA carboxylase] holoenzyme synthetase, is coexpressed with *E. coli* acetyl-CoA carboxylase complex proteins AccA, AccB, AccC and AccD to enhance the activity of the ACC complex and result in an increase in malonyl-CoA and malonate production. In various embodiments of the invention, *S. cerevisiae* ACC1 is further modified to eliminate ACC1 post-translational regulation by introducing serine to alanine mutations at any, all, or any combination of the following residues; S10, S233, S430, S1114, S1145, S1148, S1157, S1159, S1162, S1163, S1169. In some embodiments of the invention, the acetyl-CoA carboxylase used is from *Yarrowia lipolytica* CLIB122, herein referred to as Y1ACC. Example 42 illustrates how the inclusion of this enzyme in a malonate-producing host strain provided by the invention results in a doubling of the titer of malonate from that host after 120 hours of fermentation, relative to the same host fermented without this enzyme. In additional embodiments of the invention, this enzyme is coexpressed with a biotin-[acetyl-CoA carboxylase] holoenzyme synthetase, also derived from this organism (BPL1). In additional embodiments of the invention, the acetyl-CoA carboxylases and biotin-[acetylCoA carboxylase] holoenzyme synthetase encoding genes are dtsR1 accBC and derived from *Corynebacterium glutamicum*. In additional embodiments of the invention, these genes are derived from a yeast strain including, but not limited to those of the genera, *Candida*, *Pichia*, or any of the other yeast herein. In various embodiments of the invention, the host cell producing malonate expresses any combination of these acetyl-CoA carboxylases and biotin-[acetyl-CoA carboxylase] holoenzyme synthetase enzymes.

In some embodiments of the invention, a host cell suitable for producing malonate according to the methods of the invention comprises genetic modifications affecting expression and/or activity of proteins involved in fatty acid biosynthesis. Malonyl-CoA is naturally a substrate in the biosynthesis of fatty acids, and diversion of malonyl-CoA to fatty acid production decreases the ability for the host cell to produce malonate. The invention provides recombinant host cells for producing malonate that express a heterologous fatty acid synthase (FAS) multienzyme complex. Temperature sensitive mutations of *S. cerevisiae* fatty acid synthase complex are known (see, Knobling et al., *Eur. J. Biochem.*, 59:415-421 (1975)). Expression of a heterologous, temperature sensitive fatty acid synthase complex allows diversion of malonyl-CoA to fatty acid biosynthesis to be controlled by the temperature at which the host cell is cultured. In some embodiments, the host cell is a *S. cerevisiae* cell comprising *S. cerevisiae* fatty acid synthases FAS1 and FAS2 or enzymes homologous thereto. In some embodiments of the invention, FAS 1 and FAS2 enzymes are temperature-sensitive FAS1 or FAS2 enzymes.

In addition to genetic modification of the host cell, fatty acid biosynthesis can be decreased through addition of a FAS inhibitor to the cell culture media. For example, the FAS inhibitor cerulenin forms a covalent bond with the active site cysteine C1305 in the *S. cerevisiae* ketoacyl synthase domain of the FAS complex, inhibiting enzyme activity (Johansson et al., PNAS, 105:12803-12808 (2008)). Cerulenin is not only effective in inhibiting *S. cerevisiae* FAS activity, but is generally an inhibitor of FAS complexes containing a Cys-His-His or Cys-His-Asn catalytic triad in the ketoacyl synthase domain. In some embodiments, cerulenin is added to the fermentation broth to a final concentration between 5 mg/l and 100 mg/l to inhibit fatty acid biosynthesis and increase malonate production in recombinant host cells producing malonate in accordance with the methods of the invention. In various embodiments of a method of the invention, a FAS inhibitor is added to fermentation broth containing recombinant host cells producing malonate. In some embodiments of a method of the invention, the FAS inhibitor is cerulenin, as illustrated in Example 16. In some embodiments of the method of the invention, cerulenin is supplemented in the fermentation broth at a concentration between 5 mg/l and 100 mg/l. In other embodiments of a method of the invention, the fatty acid synthase complex inhibitor is selected from a group consisting of platensimycin, thiolactomycin, and triclosan.

One of the substrates for acetyl-CoA carboxylase is carbon dioxide, and increasing the carbon dioxide partial pressure in the fermentation broth promotes formation of malonyl-CoA. The fermentation broth should contain a minimum dissolved carbon dioxide pressure of 0.01 atmospheres, and an increase in dissolved carbon dioxide partial pressure above this threshold is desirable. The fermentation broth should typically contain between 0.1 and 1 atmospheres dissolved carbon dioxide partial pressure. The dissolved carbon dioxide partial pressure in the fermentation broth may be increased to above saturating conditions, or above 1 atmosphere dissolved carbon dioxide. In some embodiments of a method of the invention, the dissolved carbon dioxide partial pressure in the fermentation broth is increased to between 0.1 and 1 atmospheres. In some embodiments of the method of the invention, carbon dioxide partial pressure is increased through addition of carbonates or bicarbonates to fermentation broth. For example, and without limitation, calcium carbonate can be added to the fermentation broth to increase dissolved carbon dioxide partial pressure. In other embodiments of the method of the invention, the fermentation is run in a pressurized vessel that contains carbon dioxide at above atmospheric pressure. In other embodiments of the method of the invention, carbon dioxide gas is sparged into the fermentation broth. The gas mixture being sparged may contain other gases if the added components do not interfere with host cell growth or malonate production. It may be advantageous to co-localize the source of the carbon dioxide gas with the malonate fermentation. For example, and without limitation, gaseous carbon dioxide resulting from various fermentation processes (e.g., ethanol, isobutanol, 3-hydroxypropionate, etc.), chemical processes (e.g., downstream malonate synthetic chemistry), or energy generation (e.g., coal or natural gas powerplants) may be pumped into fermentation broth from malonate producing host cells to increase the carbon dioxide partial pressure, as illustrated in Example 17.

Genetic Modifications that Decrease Malonate Catabolism

In accordance with the invention, increased malonate titer, yield, and/or productivity can be achieved by decreasing malonate catabolism, and the invention provides host cells, vectors, enzymes, and methods relating thereto. One metabolic pathway by which malonate is catabolized in a host cell is through the activity of an acyl-CoA synthetase catalyzing the conversion malonate and Coenzyme A to malonyl-CoA. In some embodiments of the invention, a recombinant host cell suitable for producing malonate in accordance with the methods of the invention comprises a genetic modification resulting in the deletion, attenuation, or modification of one or more nucleic acids encoding for an acyl-CoA synthetase. In some embodiments of the invention, the recombinant host cell is yeast and the one or more acyl-CoA synthetases are selected from the group consisting of FAA1, FAA2, FAA3, FAA4, LSC1, and LSC2. In other embodiments of the invention, the recombinant host cell is *E. coli* and the one or more acyl-CoA synthetases are selected from the group consisting of FadD, FadK, FadI, SucC, SucD, and YahF. This aspect of the invention is illustrated in Example 18.

Genetic Modifications that Increase Malonate Secretion from the Host Cell

In accordance with the invention, increased malonate titer, yield, and/or productivity can be achieved by increasing malonate transport into the fermentation broth, and the invention provides host cells, materials, and methods relating thereto. In some embodiments of the invention, the recombinant host cell suitable for use in the methods of the invention is a *S. cerevisiae* cell that comprises a heterologous nucleic acid coding for expression of an *S. cerevisiae* transport protein selected from the group consisting of PDR5, PDR10, PDR11, PDR12, PDR15 and PDR18. In some embodiments of the invention, the recombinant host cell suitable for producing malonate in accordance with the methods of the invention is an *E. coli* cell that comprises a heterologous nucleic acid coding for expression of *E. coli* DcuC. This aspect of the invention is illustrated in Example 19.

Genetic Modifications that Increase Host Cell Tolerance to Malonate

In accordance with the invention, increased malonate titer, yield, and/or productivity can be achieved by increasing host cell tolerance to malonate, and the invention provides host cells, materials, and methods relating thereto. High concentrations of malonate can competitively inhibit succinate dehydrogenase (EC 1.3.5.1) activity (see Slater, *Methods Enzymol.* 10:48-57 (1967)). The present invention is based, in part, on the discovery that mutant succinate dehydrogenase enzymes exhibit a lower competitive inhibition by malonate. For example *S. cerevisiae* succinate dehydrogenase SDH1 residues E300, R331, and R442 are important for substrate (e.g., succinate) recognition. Increasing the size of the SDH1 active site decreases competitive inhibition by malonate while still allowing the enzyme to maintain activity toward the native substrate, succinate. In specific, introduction of one or more mutations selected from the group consisting of E300D, R331K or R331H, and R442K and R442H decreases competitive inhibition of SDH1 by malonate. In some embodiments, a recombinant host cell expressing an SDH1 with point mutation R300D is used to produce malonate in accordance with the invention. In other embodiments, a recombinant host cell expressing an SDH1 with point mutation R331K or R331H is used to produce malonate in accordance with the invention. In other embodiments, a recombinant host cell expressing an SDH1 with point mutation R442K or R442H is used to produce malonate in accordance with the invention. This aspect of the invention is illustrated in Example 20.

Genetic Modifications that Increase Catabolism of Various Carbon Sources

In the methods of the invention, carbon feedstocks are utilized for production of malonate. Suitable carbon sources include, without limitation, those selected from the group consisting of purified sugars (e.g., dextrose, sucrose, xylose, arabinose, lactose, etc.); plant-derived, mixed sugars (e.g., sugarcane, sweet sorghum, molasses, cornstarch, potato starch, beet sugar, wheat, etc.), plant oils, fatty acids, glycerol, cellulosic biomass, alginate, ethanol, carbon dioxide, methanol, and synthetic gas ("syn gas"). A given host cell may catabolize a particular feedstock efficiently or inefficiently. If a host cell inefficiently catabolizes a feedstock, then one can modify the host cell to enhance or create a catabolic pathway for that feedstock. For example, Example 47 shows production of malonate, in accordance with the invention, from a number of different carbon sources using *Pichia kudriavzevii* as the host strain. While this organism does not catabolize sucrose under the conditions tested, the invention provides the introduction of a sucrose invertase (beta-fructofuranosidase, EC 3.2.1.26) to facilitate the use of this carbon source. Example 30 also demonstrates the production of malonic acid in accordance with the methods of the invention using a variety of carbon sources. Additional embodiments of the invention include the use of methanol catabolizing host strains. In some embodiments, the host is a yeast strain. In some embodiments, the host is selected from the *Komagataella pastoris, Pichia methanolica,* or *Pichia pastoris*.

The invention provides host cells comprising genetic modifications that increase malonate titer, yield, and/or productivity through the increased ability to catabolize non-native carbon sources. Wild type *S. cerevisiae* cells are unable to catabolize pentose sugars, lignocellulosic biomass, or alginate feedstocks. In some embodiments, the invention provides a an *S. cerevisiae* cell comprising a heterologous nucleic acid encoding enzymes enabling catabolism of pentose sugars useful in production of malonate as described herein. In other embodiments, the heterologous nucleic acid encodes enzymes enabling catabolism of lignocellulosic feedstocks. In yet other embodiments of the invention, the heterologous nucleic acid encodes enzymes increasing catabolism of alginate feedstocks.

Those skilled in the art will recognize that the individual manipulations to increase malonate production from a given host cell can be used in virtually unlimited combination and often confer simulatious benefits resulting in a much higher malonate output than a single manipulations and in cases, the sum of the individual manipulations. Thus, the invention encompasses not only the single manipulations described herein, it also is embodied by any combination of these perterbuations resulting in the increase of malonic acid produced the host strain.

Section 6: Detecting Malonate Producing Host Cells and Screening Host Cells for Improved Malonate Production The present invention also provides a transcription factor biosensor system that can be used for the accurate sensing of malonate in liquid media. In many applications, this system is used to detect malonate produced within a host cell by sensing the presence of malonate in the fermentation media containing the malonate producing host cell. "Accurate sensing" refers to detecting the presence of and/or directly or indirectly determining the concentration of malonate; therefore, by accurately sensing malonate, this aspect of the invention has application in strain improvement, i.e., for increasing malonate production in host cells. In this system, malonate binds to a protein moiety present on a transcription factor. Binding of malonate to the malonate binding moiety results in either binding of the transcription factor to the promoter that is activated by the transcription factor, or in some embodiments, results in derepression of the promoter by the malonate-bound transcription factor.

Any number of transcription factors that bind to malonate, or are activated to bind to a promoter in response to a signal generated by binding of malonate to a binding moiety, are suitable for use in this system.

In some embodiments, the transcription factor can bind malonate, which results in binding of the transcription factor to a cognate promoter and activation of a gene that is operably linked to the promoter. Non-limiting examples of transcription factors that bind malonate include the transcription factors *Acinetobacter calcoaceticus* MdcY (SEQ ID NO:3), *Rhizobium leguminosarum* MatR (SEQ ID NO:4), *Klebsiella pneumoniae* MauR (SEQ ID NO:5), and homologs thereof.

In some embodiments, a transcription factor used in the invention is an MdcY transcription factor. An MdcY transcription factor can directly bind malonate and regulate transcription mediated by promoters such as $P_{MdcL}$. MdcY and MdcY-responsive promoters are known in the art (see, e.g., Koo et al., *J Bacteriol.* 182:6382-6390 (2000)).

An example of an MdcY polypeptide sequence from *Acinetobacter calcoaceticus* is provided in SEQ ID NO:3. MdcY polypeptides that can be employed in accordance with the invention include variants and homologs of the MdcY polypeptide sequence set forth in SEQ ID NO:3. Thus, a MdcY transcription factor polypeptide may have an amino acid sequence that has at least 60% identity, typically at least 75%, 90%, 95%, 99% or greater amino acid sequence identity, preferably over a region of at least 100 or more amino acids, or at least 200 or more amino acids, or over the length of the entire polypeptide, to an amino acid sequence of SEQ ID NO:3. One of skill in the art understands in view of this disclosure that variants can also be employed, e.g., using the known sequences as guidance for selecting amino acid substitutions that will not result in loss of function.

In some embodiments, the MdcY transcription factor for use in the invention is naturally present in a host cell. In other embodiments, a host cell is genetically modified to express a foreign transcription factor by introducing a heterologous nucleic acid encoding the malonate transcription factor into the host cell. In some embodiments, the genetically modified host cell comprising a heterologous nucleic acid encoding the malonate transcription factor is an E. coli host cell.

The MdcY transcription factor can bind to a number of promoters and activate expression of a gene operably linked to the promoter. An example of a MdcY-responsive promoter suitable for use in accordance with the invention is provided in SEQ ID NO:6. In some embodiments, an MdcY-responsive promoter for use in the invention, typically comprise an operator sequence ATTGTATACAAT. In some embodiments, the promoter is at least 75% identical to the promoter sequence shown in SEQ ID NO:6. In some embodiments, the promoter comprises a subsequence of SEQ ID NO:6 comprising 10, 20, 25, 30, 35, or more, contiguous nucleotides of SEQ ID NO:6.

Thus, in one aspect, the present invention provides a method for accurately sensing malonate. In some embodiments, the sensing step comprises detecting, e.g., measuring the amount of a gene product of a reporter or marker gene (e.g. a fluorescent reporter gene). In some embodiments, the gene product of the reporter gene influences the growth rate of a host cell comprising the components of a malonate transcription factor biosensor of the invention. In some embodiments, the gene product of the reporter gene causes the modified host cell to become resistant or sensitive to a compound. For example, in some embodiments, the reporter gene is an antibiotic resistance gene (e.g. a tetA gene) where the presence of malonate in the culture medium induces antibiotic resistance such that the host cell exhibits improved growth in the presence of malonate when the antibiotic is present, as illustrated in Example 21. In some embodiments, a host cell that comprises the components of a transcription factor biosensor of the invention is a host cell that is capable of producing malonate. Example 36 illustrates practice of this aspect of the invention using both antibiotic resistance (tetA) and a colorimetric signal (lacZ) as outputs that are correlated to malonic acid concentration, produced in accordance with other aspects of the invention, in fermentation media.

Generally, then, the present invention provides for a method for screening or selecting a host cell that produces malonate comprising: (a) providing a modified host cell of the present invention, (b) culturing the host cell, and (c) screening or selecting the host cell based on the expression of the reporter gene by the host cell.

In some embodiments of the present invention, the method for screening or selecting a host cell that produces malonate comprises: (a) providing a plurality of modified host cells of the present invention wherein the modified host cells of different modification are in separate cultures, (b) culturing each separate culture of host cell, (c) screening or selecting the host cell based the expression of the reporter gene by the host cell, and (d) comparing the expression of the reporter genes of the separate cultures. In some embodiments of the present invention, step (d) comprises identifying one or more cultures, and/or the corresponding host cell, that have an increased expression of the gene product of the reporter gene. It will be recognized by those skilled in the art that these cultures arise from a single transformant and represent a clonal population.

In some embodiments, the method of the invention is a method for selecting a host cell that produces malonate, wherein the selection is a positive selection. In a positive selection, the selecting step selects for host cells that have a higher expression of a reporter gene that increases the probability of remaining viable and doubling, and thus have a higher probability of remaining viable and doubling. For example, host cells producing malonate will remain viable and propagate at a rate faster than host cells not that do not produce malonate. Similarly, host cells with increased malonate production as compared to a control strain will propogate at a rate faster than the control strain.

In some embodiments of the present invention, the method for selecting an E. coli host cell that produces malonate comprises: (a) providing a plurality of modified E. coli host cells of the present invention wherein the modified host cells of different modification are in separate cultures, (b) culturing each separate culture of host cell, (c) positively selecting the host cell based the expression of the reporter gene by the host cell, and (d) comparing the expression of the reporter genes of the separate cultures.

In other embodiments of the present invention, the method for selecting an E. coli host cell that produces malonate comprises: (a) providing a plurality of modified E. coli host cells of the present invention wherein the modified host cells of different modification are in the same culture, (b) culturing the heterogenous mixture of modified host cells in growth medium containing a positive selecting agent such that the host cells exhibiting a higher production of malonate than the plurality of host cells will propogate at a rate faster than host cells exhiting lower production of malonate and (d) isolating the host cells exhibiting the highest production of malonate.

Section 7: Malonate Purification

In a sixth aspect, the invention provides methods for purifying malonate from fermentation broth, the methods comprising: (a) culturing a host cell under conditions suitable for production of malonate, (b) and recovering (i.e., purifying) the malonate from fermentation broth. The invention also provides purified malonate produced in accordance with the methods of the invention. Biosynthesized malonate can be produced intracellularly and/or secreted into the culture medium. Intracellulary produced malonate is typically secreted into the culture medium using a membrane transporter, as described above. Malonate not secreted can be removed from the host cell by chemical, enzymatic, or mechnanical cell lysis. Malonate can be recovered from the cells, from the fermentation broth, or both. If the cell is engineered to secrete malonate, one can opt to recover the malonate only from the fermentation broth or one can opt to recover it both from the media and from the cell (i.e., by lysing the cell). If the cell is not engineered to secrete malonate one can lyse the host cell to isolate the malonate therein.

The present invention provides methods to isolate malonate produced biologically. As used herein, "isolate", "purify", and "recover" are used to refer to separation of the malonate from other substances present. "Isolation", "purification", or "recovery" as used in this context is intended to convey a preparation of malonate that is enriched in malonate relative to the cell or fermentation broth that produced it but that may or may not be substantially (i.e., more than 50%) pure on a weight/weight (w/w) basis. Isolating malonate in accordance with these methods involves separating the malonate produced from at least part or all of the fermentation medium, host cells, and parts thereof, from which malonate is produced. Malonate may be purified, i.e., to more than 50% purity on a w/w basis, in accordance with the invention from the fermentation broth and/or from the producing cell in which any naturally occurring or recombinant host cell (e.g., *E. coli, S. cerevisiae*, oleaginous yeast, and the like) producing malonate is grown, i.e., the host cell is not limited to a recombinant host cell of the invention. The isolated malonate may be free or essentially free of impurities from the host cells. The malonate is isolated or purified to a degree such that any impurities present do not interfere in the subsequent use of the malonate. For example, if the subsequent use is as an industrial chemical, such as a chemical to be used in a polymerization reaction, then the malonate is essentially free of impurities when any remaining impurities would not interfere with the use of the malonate in a polymerization reaction. Typically malonate used for polymerization reactions has a purity of at least 95% w/w or higher. If the malonate is to be used as a fuel, such as a fuel to be used in a combustion reaction, then the compound is essentially free of impurities when any impurities remaining would not interfere with the use of the malonate as a fuel. If the malonate is used as an animal feed, then the malonate is essentially free of impurities when any impurities remaining would not interfere with the use of the material as animal feed. When malonate is used as an animal feed, one may opt to recover the biomass containing malonate from the fermentation broth and use the biomass as animal feed.

In some embodiments of the purification methods of invention, the fermentation broth is concentrated to increase the working concentration of malonate and decrease the volume of liquid that requires processing. In various embodiments of the purification methods of the invention, this concentration is achieved by evaporation, including vacuum and heat, reverse osmosis, "high pass" membrane dewatering, and/or thin film evaporation.

In some embodiments, the purification methods of the invention comprise the step of recovering the malonate produced, wherein the recovering step is concurrent or subsequent to the culturing step. In some embodiments, the malonate is purified from the fermentation broth and the host cells. In other embodiments, the host cells are separated from the fermentation broth, lysed, and then malonate is recovered from the host cells. In other embodiments, the host cells are lysed in the fermentation broth and malonate is recovered from the lysed cells and fermentation broth. One method for recovering malonate from the fermentation broth provided by the invention is precipitation of malonate with a cation. In some embodiments this is a monovalent cation, in other embodiments it is a divalent cation. Typically the cation is added to the fermentation broth (or lysate) as a salt. For example, precipitation of calcium malonate from an aqueous solution, which may be fermentation broth or a cell lysate or a mixture of both, containing malonate in accordance with the invention is accomplished by the addition of a calcium salt (Weiner, *Org. Synth.* 18:50 (1938); Weiner, *Org. Synth. Coll.* 2:376 (1943)). Various calcium salts (e.g., calcium hydroxide, calcium carbonate, calcium chloride) can be used in accordance with the invention to precipitate malonate from fermentation broth.

A calcium malonate salt forms when the when two malonate carboxylic acids are unprotonated and calcium is present in the fermentation broth. Calcium malonate is insoluble in aqueous solutions, e.g., fermentation broth, will precipitate, and can then be recovered from the fermentation broth. The $pK_a$ values of the two malonate carboxylic acid moieties are 2.83 and 5.69; thus, when the fermentation broth pH is below 5.7, calcium malonate does not form and malonate remains dissolved in the fermentation broth. When the fermentation broth pH is above 5.7, calcium malonate can form and will precipitate from the fermentation broth. Carboxylic acids are weak acids, and the accumulation of malonate in the fermentation broth will decrease the pH, and if the pH falls below 5.7 the addition of calcium cations does not result in the formation of calcium malonate. One method of the invention to purify malonate from fermentation broth is to add a calcium salt where the calcium salt anion is a base (i.e., calcium carbonate and calcium hydroxide) and addition of the calcium salt raises and/or maintains the fermentation broth pH above 5.7. In some embodiments of a method of the invention, calcium hydroxide is added to the fermentation broth to reach/maintain a pH between 5.69 and 7.5 and precipitate calcium malonate. In a second embodiment of a method of the invention, calcium carbonate is added to the fermentation medium to reach/maintain a pH between 5.69 and 7.5 and precipitate calcium malonate. In a third embodiment of the invention, calcium chloride is added to the fermentation broth when the fermentation broth pH is between 5.69 and 7.5 and precipitate calcium malonate. In accordance with the methods of the invention, other calcium salts can be added to the fermentation broth to precipitate malonate. Addition of calcium carbonate has the additional advantage of increasing the carbon dioxide partial pressure in the fermentation broth, promoting formation of malonyl-CoA through the activity of acetyl-CoA carboxylase, described above. Example 23 illustrates this aspect of the invention by describing the purification of malonate using a calcium salt.

One may add the calcium salt at the beginning of the fermentation (i.e., before substantial malonate has accumulated), during the fermentation, or at the end of the fermentation. In some embodiments, calcium carbonate or calcium hydroxide is added to the fermentation broth before the host cells have begun producing malonate. In other embodiments, calcium carbonate or calcium hydroxide is added to the fermentation broth before malonate concentrations exceed 5, 10, 15, 20, 25, 30, 40, or 50 g/l. In other embodiments, calcium carbonate or calcium hydroxide is added the fermentation broth at the end of the fermentation. One may choose to recover the calcium malonate precipitate from the fermentation broth concurrent or subsequent to the fermentation.

Because calcium malonate monohydrate solubility decreases with increasing temperature, recovery of malonate from the fermentation broth may be increased by raising the temperature to between 50° C. and 100° C. during the recovery step. In some embodiments of the method of the invention, a calcium salt (i.e., calcium carbonate, calcium hydroxide, and/or calcium chloride) is added to fermentation broth, the temperature is increased to between 50° C. and 100° C., and malonate is recoved from the fermentation broth. In additional embodiments of the invention, the temperature is increased above 100° C. However, thermal decomposition of malonic acid can occur at temperatures of about 100° C., accordingly, increasing the temperature to or above 100° C. may negatively impact yield.

In some embodiments of the invention, malonate is purified from the production media by precipitation with a monovalent cation. Typically the monovalent cation is added to the fermentation broth (or lysate) as a salt. For example, precipitation of sodium malonate from an aqueous solution, which may be fermentation broth or a cell lysate or a mixture of both, containing malonate in accordance with the invention is accomplished by the addition of a sodium salt. Various sodium salts (e.g., sodium hydroxide, sodium carbonate, sodium chloride) can be used in accordance with the invention to precipitate malonate from fermentation broth. A sodium malonate salt forms when the when two malonate carboxylic acids are unprotonated and sodium is present in the fermentation broth. Sodium malonate is soluble in aqueous solutions, e.g., fermentation broth, but can be forced out of solution by increasing the pH of the media above the higher pKa of malonic acid (5.69); see Example 32. Additional precipitation of the sodium malonate is achieved by increasing the concentration of the ions by evaporation of the solvent (water). As with the aspects of the invention associated with calcium malonate precipitation, the addition of sodium salts containing a base (e.g. sodium hydroxide or sodium carbonate) can be used to maintain the pH of the fermentation broth above 5.7, thus facilitating precipitation of the sodium salt. Separation of the precipitate from the fermentation broth provides purified malonate in accordance with the invention.

Another method of the invention for isolating malonate from the fermentation broth is through reactive extraction with an aliphatic primary, secondary, or tertiary amine or a primary, secondary, or tertiary alcohol. This method arises in part from the discovery that both primary alcohols and tertiary amines are highly effective agents for the selective removal of malonate from fermentation broth as is illustrated in Examples 24-26, 36-41. In some embodiments of the invention, malonate is purified from the fermentation broth by reactive extraction with trioctylamine in organic solvent. In other embodiments of in the invention, malonate is purified from the fermentation broth using a tertiary amine selected from the group consisting of triethylamine, tripropylamine, tributylamine, tripentylamine, trihexylamine, triheptylamine, trinonylamine, and tridecylamine. In additional embodiments of the invention, the amine compound is ammonia. In yet other embodiments, it is a dialkylamine including, but not limited to diethylamine, dipropylamine, diisopropylamine, dibutylamine, dipentylamine, dihexylamine, diheptylamine, dioctylamine, dinonylamine, didecylamine. Example 33 demonstrates the isolation of malonate from fermentation broth using diethylamine. In various embodiments of the invention the amino compound is added in conjunction with an organic solvent or mixture of solvents including, but not limited to: pentanol, hexanol, heptanol, octanol, nonanol, decanol, hexane, decane, kerosene, ethers, ethylacetate or any combination thereof. In various embodiments, the solvent is a branched or unbranched, alkane, alcohol, diol, ester, ether, diether, or lactone containing four to twenty carbons In various embodiments, addition of solvents facilitates the transfer of amino compounds to the aqueous phase and the amine-coordinated malonates to the organic phase, thus improving purification.

A number of parameters can be adjusted in accordance with the invention to improve malonate extraction. Length of alkyl groups, ionic strength of the fermentation broth, pH, molar equivalents of trialkylamines, temperature, and cosolvent each have an impact on the extraction efficiency of trialkyamines. The impact of alkyl group length is illustrated in example 36. Tripropyl-, trihexyl-, and trioctyl-amine are each capable of isolating malonic acid from the aqueous phase and solubilizing it into the 1-octanol organic phase in accordance with the invention. The extraction efficiency of trioctylamine>trihexylamine>tripropylamine, indicating the longer of these chain lengths is the preferable embodiment (for high-yield) of the invention at low pH, with a 1-octanol cosolvent.

As with salt precipitation, pH has an impact on malonic acid extraction from an aqueous phase when using trialkylamines. Trialkylamine extraction has the highest efficiency when both acid moieties are carboxylated. Example 37 shows the extraction efficiencies of trioctylamine over a range of pH values. The highest level of extraction occurs at pH 1.5 and diminishes as pH is increased. Above the second pKa of malonic acid (5.69) there is virtually no extraction. While the invention provides malonate extraction from an aqueous phase using trialkylamines without limitation on pH, embodiments at pH of 2.0 or lower are preferred for maximum efficiency. In some embodiments of the invention, host cell growth and production of malonate at a low pH, as illustrate by Example 48, facilitates protonation of malonate to enhance extraction with trialkylamines. In other embodiments of the invention, exogenous acid is added to facilitate this protonation.

In various embodiments of the invention, different concentrations of trialkylamine are used. As reported in Example 38, linear relationship between extraction efficiency and trioctylamine:malonic acid mol fraction was observed; specifically the linear relationship existed between trioctylamine:malonic acid mol fractions of 0 to 1. Above 1 molar ratio, 100% of the malonic acid was extracted into the organic phase. Thus, to maximize extraction efficiency the amount of trialkylamine in the organic phase must be equimolar to the amount of malonic acid in the aqueous phase (e.g., fermentation broth). Ideally a greater than equimolar amount of trialkylamine will be added to the organic phase to compensate for decreased extraction efficiencies due to other organic acids and anions in the fermentation broth.

As illustrated in Example 39, trialkylamine extraction efficiency of malonic acid is negatively impacted by increasing the ionic strength (salt concentration) of the aqueous phase. Desalting of various ions can be achieved through a number of methods, including: addition of other agents to generate an insoluble salt, pH adjustment, and/or passage through various membranes.

In various embodiments of the invention, the reactive extraction is Fischer esterification of malonate at one or both carboxylic acids with an alcohol in the presence of an acid catalyst to result in the formation of monoalkyl and dialkyl malonate esters, respectively. For example, diethyl malonate can be produced by Fischer esterification of malonate using ethanol. The monoalkyl and dialkyl malonate esters have low solubility in aqueous solutions and low volatility, enabling the malonate esters to be separated from water and other volatile components in the fermentation broth by distillation. In various embodiments of the invention, separation of the esters is achieved by phase partitioning into an organic solvent. In general, a primary or secondary aliphatic alcohol is suitable for Fischer esterification with malonate; for example, and without limitation, the alcohol may be selected from the group consisting of methanol (CAS#67-56-1), ethanol (CAS#64-17-5), 1-propanol (CAS#71-23-8), 1-butanol (CAS#71-36-3), isopropanol (CAS#67-64-0) and isobutanol (CAS#78-83-1), among others. A number of acid catalysts are suitable for Fischer esterification of an alcohol with malonate; for example, and without limitation, the acid catalyst may be selected from the group consisting of sulfuric acid, tofic acid, scandium(III) triflate, N,N'-dicyclohexylcarbodiimide and tetrabutyl ammonium tribromide. In various embodiments of the invention, malonate is purified from fermentation broth by reactive distillation using ethanol to convert malonate to diethyl malonate. In other embodiments of the invention, malonate is purified from the fermentation broth by reactive distillation using methanol to convert malonate to dimethyl malonate. In various embodiments of the invention, the acid catalyst is sulfuric acid.

As is illustrated in Examples 41 Fischer esterification to ethanol using sulfuric acid as a catalyst can result in >99% purification of malonic acid from an aqueous phase. In various embodiments of the invention, the excess ethanol used in this process is recovered under reduced pressure and recycled for use in subsequent fermentation batches. In various other embodiments of the invention, the catalyst is matrix based (e.g. amberlite resins) and is recovered, recharged, and reused in subsequent batches.

The economics of malonate purification by Fischer esterification can be improved in accordance with the invention by co-localization of the malonate biorefinery with an alcohol biorefinery or chemical refinery (used herein to refer to production of alcohol from renewable or petroleum feedstocks using synthetic chemistry and not a fermentation process). In some embodiments of the invention, a malonate biorefinery is co-localized with an alcohol biorefinery or chemical refinery to reduce the cost of monoalkyl or dialkyl malonate ester synthesis. In some embodiments of the invention, the alcohol resulting from the biorefinery or chemical refinery is of lower purity than typically sold and distributed for fuel and/or chemical applications.

In other embodiments, the method of the invention for isolating malonate from the fermentation broth involves liquid-liquid extraction using an organic solvent. The $pK_a$ values of the two malonate carboxylic acid moieties are 2.83 and 5.69; thus, when the pH of the media is reduced below 2.8, greater than 50% of the molecules are not ionize. The affinity of these species is higher for organic solvent than for the aqueous fermentation broth. The separation of these molecules into the organic phase serves to drive the equilibrium toward the protonated species and thus progressively into the organic solvent. In some embodiments of the invention, the acid pH of the broth is the result of fermentation conditions. In other embodiments of the invention, the pH is lowered to the appropriate acidity by the addition of an acid. In various embodiments of the invention, the solvent is selected from, but not limited to, the group consisting of ethylacetate, dichloromethane, dichloroethane, decane, dodecane, hexanes, octanol, pentanol, or mixtures of thereof. In some embodiments of the invention, host cell growth and production of malonate at a low pH facilitates protonation of malonate to enhance solubility of the malonate in the organic solvent. In other embodiments of the invention, exogenous acid is added to facilitate this protonation. In some embodiments of the invention, the solvent is removed (wholly or partially) by vacuum distillation. In various embodiments of the invention, the concentrated malonic acid is esterified to an alcohol, as described elsewhere, and the ester purified by distillation.

In additional embodiments of the invention, malonate is removed from the fermentation broth by binding to an ion exchange resin. In various embodiments of the invention, the resin is selected from, but not limited to, the following: Lewatit® VP OC 1065, Lewatit® MP-64 chloride form, Toyopearl®, Dowex® 66 free base, Amberlite® IRA-67 free base, Amberlite® IRA-96 free base, Amberjet® 4200 chloride form, Lewatit® MonoPlus M 500 chloride form, Dowex® 1X8 chloride form, Amberlyst A26 hydroxide form, Amberlite® IRA958 chloride form. In various embodiments of the invention, malonic acid is eluted from the resin using a pH or salt gradient. In additional embodiments of the invention, one or more of these resins is used to remove impurities from the concentrated malonic acid While the purification methods of the present invention can be used as single-step purification methods for purification of malonate from the fermentation broth, two or more purification methods can be used in series in accordance with the invention. For example, and without limitation, precipitation of malonate with calcium hydroxide may be followed by Fischer esterification of malonate with ethanol and further purification of the resulting diethyl malonate using distillation.

Section 8: Chemistry for Using Malonate to Synthesize Other Chemicals

Malonate is a chemical precursor in a large number of important industrial reactions. The present invention enables, for the first time, the use of biologically derived malonate in these reactions. In any known reaction that utilizes malonate as a reactant, biologically derived malonate can be used. In any reaction using a monoalkyl malonate, dialkyl malonate, or Meldrum's acid, biologically derived malonate can be used following conversion to the appropriate substrate for the reaction. Furthermore, the invention provides new chemical synthesis methods in which malonate is used as a starting material. For these reactions, one can use malonate derived from any means, including biological production of malonate through enzyme catalyzed oxidation of malonate semialdehyde, synthetic oxidation of biologically- or synthetically-derived 3-hydroxypropionate, or synthetic oxidation of biologically- or synthetically-derived 1,3-propanediol.

Thus, in addition to providing biologically derived malonate for use in known chemical reactions, the invention provides new methods for using malonate and malonate-derived compounds to produce other useful compounds.

The invention arises in part from the fact that malonate and malonate-derived compounds can be used as substrates in the synthesis of acrylates (i.e., acrylate, methyl acrylate, ethyl acrylate, propyl acrylate, and butyl acrylate) by reaction with formaldehyde. The acrylates represent billions of dollars per year in sales and are used in products as wide ranging as diapers to shampoo to films and coatings. The invention provides two basic syntheses for production of an acrylate by reacting malonate or malonate-diesters with formaldehyde. In one method, malonate-diester is reacted with formaldehyde in the presence of an appropriate base (e.g. diethylamine) to produce the diester of 2-methylenemalonate. Subsequent saponification of the esters and heating results in the production of one part acrylate, one part $CO_2$, and two parts alcohol. The composition of the ester portion of the malonate diester, the base, and the solvent used can vary widely. For example, and without limitation, dimethyl, diethyl, dipropyl, dibutyl, diisopropyl, or dihexyl esters can be utilized. Similarly, the base used can be one of many. In various embodiments, the base is a tri-substituted amine. Non-limiting examples of tri-substituted amines suitable for use according the methods of the invention include those selected from the group containing piperidine, trimethylamine, triethylamine, tripropylamine, triisopropylamine, tributylamine, or longer chain trialkylamine. In some embodiments of this aspect of the invention, diethyl malonate is reacted with formaldehyde in pyrrolidine to form acrylate in a Knoevenagel condensation and subsequently saponified and heated to yield one part acrylate, one part CO$_2$, and two parts ethanol. In other embodiments of the method of the invention, dimethyl malonate is reacted with formaldehyde in diethylamine to form dimethyl 2-methylenemalonate which is subsequently converted to acrylate, CO$_2$, and methanol.

In other embodiments, a magnesium salt catalyzes the condensation of a malonate-diester with formaldehyde to form a diester 2-methylenemalonate which is then worked up in the described manner. For example, and without limitation, magnesium-silicate is a suitable magnesium salt for this reaction. In some embodiments, diethyl-malonate is reacted with formaldehyde in the presence of a magnesium-silicate catalyst to form diethyl 2-methylenemalonate. In other embodiments, diisopropyl malonate is reacted with formaldehyde in the presence of a magnesium-silicate catalyst to form diisopropyl 2-methylenemalonate. A general scheme using a malonate mono-ester is illustrated here:

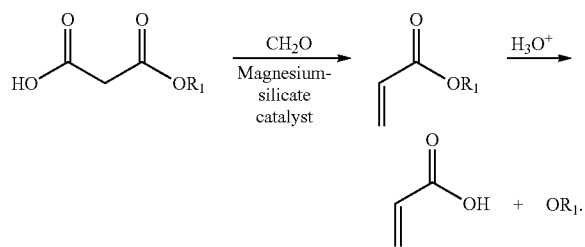

In this case, R$_1$ is selected from the non-limiting examples: H, CH$_3$, CH$_3$CH$_2$, CH$_3$(CH$_2$)$_2$, CH$_3$(CH$_2$)$_3$, (CH$_3$)$_2$CH$_2$, or (CH$_3$)$_2$CH$_2$CH$_2$.

In another embodiment, a Doebner modification of the Knoevenagel condensation is employed and malonate is reacted with formaldehyde in pyridine to produce acrylate. Example 28 illustrates the production of acrylate from malonate in accordance with this embodiment of the invention. In other embodiments, monomethyl malonate is reacted with formaldehyde in pyridine to form methyl acrylate. In the scheme illustrated here, a malonate mono-ester serves as the starting material in a Doebner modification of the Knoevenagel condensation

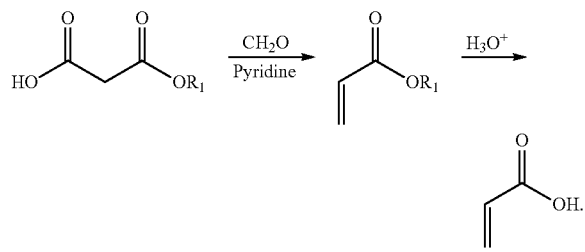

R$_1$ is selected from the non-limiting examples: H, CH$_3$, CH$_3$CH$_2$, CH$_3$(CH$_2$)$_2$, CH$_3$(CH$_2$)$_3$, (CH$_3$)$_2$CH$_2$, or (CH$_3$)$_2$CH$_2$CH$_2$. In other embodiments, monoethyl malonate is reacted with formaldehyde in pyridine to form ethyl acrylate.

In additional embodiments of the invention, malonate and malonate-derived compounds can be used as substrates in the synthesis of unsaturated dicarboxylic acids through reaction with various substrates, including, but not limited to, aldehydes, alkyl halides, dialdehydes, alkyl dihalides, terminal olefins, and combinations of the above (i.e., difunctional substrates). In the case of reaction of malonate or malonate-derived compound with an aldehyde, an alkene is formed that can be subsequently hydrogenated to yield the saturated product. Generally, malonate and malonate-derived compounds can be used to synthesize C5-C12 straight chain, saturated or unsaturated diacids (i.e., pentanedioic acid (CAS 110-94-1), hexanedioic acid (CAS 124-04-9), heptanedioic acid (CAS 111-16-0), octanedioic acid (CAS 505-48-6), nonanedioic acid (CAS 123-99-9), decanedioic acid (CAS 111-20-6), undecanedioic acid (CAS 1852-04-6), dodecanedioic acid (CAS 693-23-2)) and their corresponding dialkyl esters. In various embodiments of the invention, malonate is used as a substrate in the chemical synthesis of a C5-C12 straight chain, saturated diacid. In various embodiments of the invention, malonate or a malonate-derived compound is used as a substrate in the chemical synthesis of pentanedioic acid, hexanedioic acid, heptanedioic acid, octanedioic acid, nonanedioic acid, decanedioic acid, undecanedioic acid, or dodecanedioic acid.

In other embodiments of the invention, or a compound derived from malonate provided by, or not provided by, the invention is used as a substrate in the chemical synthesis of pentanedioic acid. Pentanedioic acid can be formed in accordance with the invention through reaction of synthetically derived diethyl malonate and formaldehyde (see Ahluwalia et al., "Organic reaction mechanisms," 2nd ed. Alpha Science International: Harrow (2005) pgs 340-341); synthetically derived diethyl malonate and dichloromethane (see Perkin et al., J Am Chem Soc 59:990-995 (1891)); and synthetically derived Meldrum's acid and formaldehyde (see Hedge et al., J. Org. Chem. 26:3166-3170 (1961)).

In other embodiments of the invention, malonate or a malonate-derived compound is used as a substrate in the chemical synthesis of hexanedioic acid. Hexane dioic acid is one of two compounds used to produce Nylon 6,6 and represents billions of dollars in annual raw material sales. Nylon 6,6 is use in a wide range of durable consumer goods including, carpet, airbags for automobiles, and rope. Hexanedioic acid can be formed in accordance with the invention through reaction of magnesium-chelated malonate monoesters and 1,2-dichloroethane. Alkylation of dichloroethane and dimethyl malonate has been described (U.S. Pat. No. 6,262,298); however the undesired product dimethyl cyclopropane-1,1-dicarboxylate is the only product reported at 99.3% purity and 83% theoretical yield. Formation of cyclopropane-1,1-dicarboxylate results from intramolecular alkylation following the initial alkylation of 1,2-dichloroethane. In contrast, the present invention provides materials and methods for using a magnesium-chelated malonate monoester that does not allow the undesired intramolecular alkylation to the cylopropane. A magnesium-chelated malonate monoester reacts with 1,2-dichloroethane through decarboxylation-facilitated enolate generation; the second intramolecular reaction (i.e., to the cyclopropane dicarboxylate) is unable to proceed following decarboxylation. An examplary catalyst for use in accordance with this embodiment of the invention is magnesium-silicate. Those skilled in the art appreciate that various dihaloalkanes (e.g. 1,3-dihalopropane, 1,2-dihalopropane) can also be used with a magnesium-chelated malonate monoester to form a dicarboxylic acid product and that those halide groups can be I, Cl, Br, or F. For example, and without limitation, a 1,3-dihalopropane can be reacted with a magnesium-chelated malonate monoester to produce heptanedioic acid.

The invention also provides methods for production of hexanedioic acid by reaction of malonate and malonate-derived compounds with ethanedial. The formation of alkenoic acids by Knoevenagel reaction of malonate-diesters and aliphatic mono-aldehydes is known (see, for example, Rao et al., *J Am Oil Chem Soc*, 70:297-299 (1993); and, Zhang et al., *Synth Comm*, 40:3093-3100 (2010)). The present invention arises in part from the discovery that a dialdhyde can be reacted with a malonate-derived compound to produce the corresponding tetraester 1,3-diene-1,1,4,4-tetracarboxylate. For example, reaction of diethyl malonate with ethanedial yields tetraethyl buta-1,3-diene-1,1,4,4-tetracarboxylate; similarly, the reaction of malonate with ethanedial (glyoxal) yields hexa-2,4-dienedioic acid. Hydrolysis of the ester groups, when desired, proceeds through addition of acid to the reaction mixture. Decarboxylation to form the unsaturated dicarboxylic acid (i.e., hexa-2,4-dienedioic acid) is thermally induced, and subsequent hydrogenation of the unsaturated dicarboxylic acid yields hexanedioic acid. In some embodiments of the invention, diethyl malonate and ethanedial are condensed to yield the dialkylated bis-malonate ethyl ester; subsequent saponification to hydrolyze the ester groups followed by thermally-induced decarboxylation yields the unsaturated dicarboxylic acid. Hydrogenation of the unsaturated dicarboxylic acid yields hexanedioic acid. This process is summarized in the following reaction scheme, in which the alkyl groups ($R_1$ and $R_2$) are chosen from the non-limiting examples: H, $CH_3$, $CH_3CH_2$, $CH_3(CH_2)_2$, $CH_3(CH_2)_3$, $(CH_3)_2CH_2$, or $(CH_3)_2CH_2CH_2$.

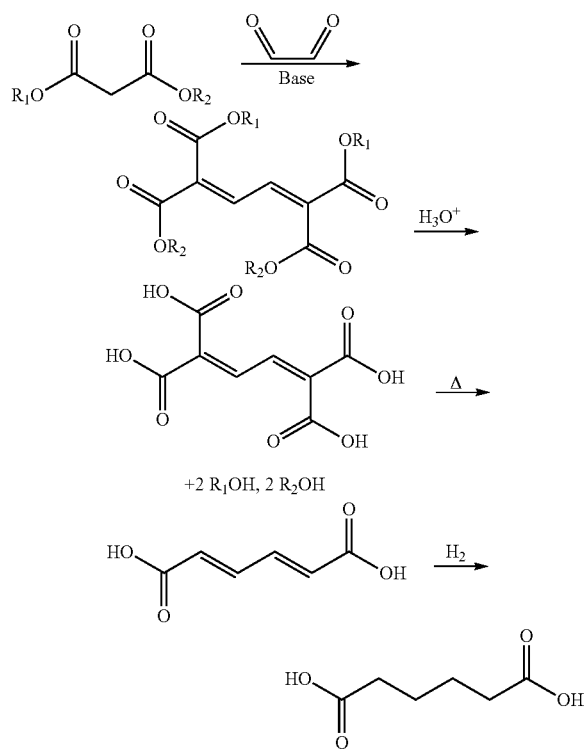

Those skilled in the art appreciate that Knoevenagel condensation of various dialdehydes and malonate-derived compound can be used according to the methods of the invention to synthesize saturated and unsaturated (with the alkenes at the 2 and n−2 positions) dicarboxylic acids. For example, and without limitation, propanedial can be used to synthesize heptanedicarboxylic acid, butane-1-4-dial is used to synthesize octanedicarboxylic acid, and pentane-1,5-dial can be used to synthesize nonanedicarboxylic acid.

In other embodiments of the invention, a malonate or a malonate-derived compound is used as a substrate in the chemical synthesis of heptanedioic acid. In addition to the dihaloalkane and dialdehyde routes to heptanedioic acid described above, the invention also provides methods for synthesis of heptanedioic acid through reaction of prop-2-enal (acrolein), which may or may not be derived from malonate as provided by the invention, and malonate. Michael addition of malonate to prop-2-enal yields a 2-(3-oxopropyl)malonic acid, and subsequent condensation to the aldehyde moiety with another molecule of malonate produces hex-1-ene-1,1,6,6-tetracarboxylic acid. Thermally induced decarboxylation followed by hydrogenation yields heptanedioic acid.

In another method of the invention, malonate is used as a substrate in the chemical synthesis of a lactam or lactone. In one embodiment, synthetic conversion of diethyl malonate to ☐elta-valerolactam though the following steps; Diethyl malonate is produced by Fischer esterification of malonate with ethanol. Michael addition of diethyl malonate to acrylonitrile affords diethyl 2-(2-cyanoethyl) malonate. Hydrogenation of the nitrile moiety of diethyl 2-(2-cyanoethyl) malonate yields an amino acid that is lactamized under mild conditions to yield to ethyl 2-oxopiperidine-3-carboxylate. Saponification of the ester moiety of ethyl 2-oxopiperidine-3-carboxylate followed by heating results in decarboxylation to afford delta-valerolactam. This non-limiting example is illustrated here:

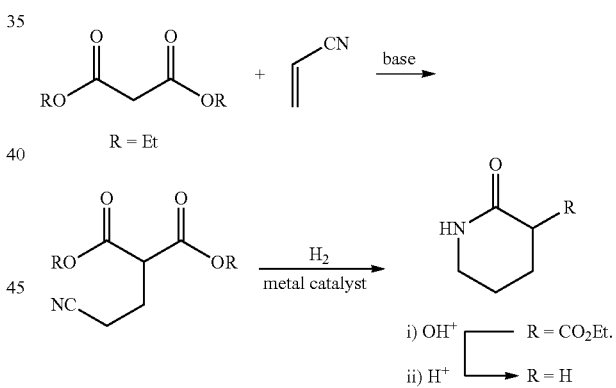

In another method of the invention, mono-ethyl malonate is used as a substrate in the chemical synthesis of ethyl acetate. Heating of the mono-ethyl malonate results in thermally induced decarboxylation to form ethyl acetate. In some embodiments, mono-ethyl malonate is used to synthesize ethyl acetate. One skilled in the art will recognize that there are a number of established methods for making mono-alkyl malonates from the malonic acid provided by the invention.

In another method of the invention, a mono-alkyl malonate (e.g. mono-methyl malonate, mono-ethyl malonate, mono-propyl malonate, mono-butyl malonate, mono-isobutyl malonate) is used as a substrate in the chemical synthesis of 3-hydroxypropionate or its related alkyl esters. Borane will chemoselectively reduce the free carboxylic acid moiety of the mono-alkyl malonate and produce the corresponding alkyl 3-hydroxypropionate. Alkyl 3-hydroxypropionates are themselves valuable products. The ester can also be hydrolyzed to yield 3-hydroxypropionate. 3-hydroxypropionate can in turn be dehydrated to acrylic acid, a valuable commodity chemical describe in more detail herein. In some embodiments, a mono-alkly malonate is used to synthesize 3-hydroxypropionate. In some embodiments, the mono-alkyl malonate is mono-methyl malonate. In some embodiments, the mono-alkyl malonate is mono-ethyl malonate.

In another method of the invention, malonate is used to synthesize a dialkylated 1,3-dicarbonyl compound. In various embodiments, malonate is used as a substrate in the chemical synthesis of a compound selected from the group consisting of diethyl 2,2-dimethylmalonate, diethyl 2,2-diethylmalonate, diethyl 2,2-dipropylmalonate, diethyl 2,2-dibutylmalonate, dimethyl 2,2-dimethylmalonate, dimethyl 2,2-diethylmalonate, dimethyl 2,2-dipropylmalonate, and dimethyl 2,2-dibutylmalonate. Synthesis of dialkylated 1,3-dicarbonyl compounds can be formed in accordance with the invention from synthetically derived dialkyl malonates using alkyl halides (see Gatterman et al., "The practical methods of organic chemistry" 3rd ed, The Macmillan Company: New York, pgs. 189-191 (1916)).

In other embodiments of the invention, the malonic acid or malonate-derived compound provided by the invention is reacted with urea to form barbituric acid, the core structure of approximate fifty related pharmaceuticals currently on the market, including phenobarbital.

In some embodiments of the synthetic methods of the invention, a highly purified malonate preparation is used for the synthetic reaction and/or associated downstream applications; in other embodiments, a less purified malonate is used. In still other cases, a crude lysate or other relatively unpurified malonate can be used for the synthetic reaction and/or downstream applications. For most synthetic chemistry reactions, malonate purity greater than 90% w/w is typically desired. In cases where malonate is used for polymerization reactions even greater purity (i.e., 95% w/w or higher) may be desired. In other applications, however, one may employ a much less pure preparation of malonate. For example, malonate is useful as an animal foodstock, and for this purpose, one may employ the producing cells themselves or a crude lysate of them.

In another embodiment of the invention, malonate (produced by any means) is reacted with glutarate-semialdehyde (which can also be produced from malonate) to yield hept-2-enedioic acid. This is an additional example of a Knoevenagel condensation and can be conducted with the broad array of solvent and catalytic reagents associated with this reaction. Hept-2-enedioic acid is then reduced using catalytic hydrogenation to yield heptanedioic acid (pimelic acid). Pimelic acid has a wide variety of uses, including as a monomer in Nylon 5,7; as a fermentation media supplement used to enhance biotin biosynthesis; and as a plasticizer. Prior art methods for pimelic acid synthesis are costly and low yielding. The invention provides a new chemical synthesis for this important compound that may be derived from malonic acid as provided by the invention.

In other embodiments of the invention, vapor or liquid phase hydrogenation is used to convert dialkylmalonates into 1,3-propanediol. Due to the reactive nature of the number two carbon of malonate and malonate esters, polysubstituted derivatives of various compounds can be produced using the malonate provided by the invention. In some embodiments, neopentylglycol (2,2-dimethylpropane-1,3-diol), an important component of some polyesters, is produced by first generating 2,2-dimethyl-dialkyl malonate. This can compound can be produced using a variety of bases as catalysts and a methyl halide as the source of the methyl group. The subsequent hydrogenation of the ester groups results in the production neopentylglycol and the cognate alcohols from the ester groups. This represents a novel route to this important industrial compound. Furthermore, due to the highly reactive nature of the number two carbon of malonate and malonate derived compounds, other alkylhalides can be employed to result in new compounds with the potential for novel properties when incorporated into polymers.

The invention, having been described in detail, is illustrated by the following examples, which should not be construed as limiting the invention, given its diverse aspects, embodiments, and applications.

EXAMPLES

Example 1: Construction of Recombinant Nucleic Acids Encoding Wild-Type EHD3 and EHD3 Mutants E124S, E124A, E124A/E308V, and E124V Malonyl-CoA Hydrolases and Expression Vectors for Production of Malonate in E. coli The present invention provides methods for producing malonate in an *E. coli* host, as well as *E. coli* host cells that produce malonate and express an EHD3 mutant enzyme, including but not limited to E124S, E124A, and E124V. This example describes the construction of protein coding sequences for EHD3 and the mutant EHD3 proteins useful in the invention, expression vectors containing those coding sequences, and host cells comprising those expression vectors. The nucleic acid encoding wild type *S. cerevisiae* EHD3 was amplified by PCR from Baker's yeast using primer pair A93/A94. Point mutation E124A was introduced using primer pairs A93/A96 and A95/A94, mutation E124V was introduced using primer pairs A93/A98 and A97/A94, and mutation E124S was introduced using primer pairs A93/A100 and A99/A94. The resulting nucleic acids were cloned into an *E. coli* expression vector containing the pSC101 origin of replication, a chloramphenicol resistance cassette, and a $P_{LacO1}$ promoter using standard techniques. The resulting vectors were transformed into an *E. coli* DH10b host and plated on Luria-Bertani (LB) agar plates containing 50 μg/ml chloramphenicol ($Cm^{50}$) and 2% w/v glucose. Individual colonies were then inoculated into 3 ml LB media in 48-well plates; following 6 hours growth, plasmids were isolated and the EHD3 protein-coding region sequenced. When sequencing plasmids derived from clones of EHD3 (E124A), it was discovered that a second, point mutation, E308V, stabilized the EHD3 (124A) clone; the presence of an uncharged valine residue likely stabilizes protein folding. The EHD3 (E124A, E308V) strain was also used for malonate production (see Example 2). Primers A93-A100 are SEQ ID NO:13-20, respectively.

Example 2: In Vivo Production of Malonate in E. coli Using EHD3 Mutants E124S and E124a/E308V This example describes the host cells and culture conditions resulting in the in vivo production of malonate using a heterologous EHD3 malonyl-CoA hydrolase in an *E. coli* host cell. *E. coli* strain K12 was transformed with vectors containing wild-type EHD3, EHD3 (E124A), EHD2 (E124V), EHD3 (E124S), EHD3 (E124A, E308V) or an empty vector negative control. Transformants were streaked on LB agar plates (Cm$^{50}$, 2% glucose). Following overnight growth at 37° C., individual colonies were inoculated into 3 ml LB (Cm$^{50}$, 2% glucose) in a 48-well plate. Cultures were incubated on a plate shaker at 37° C. for 6 hours, at which point each culture was inoculated 1% v/v into M9 minimal medium supplemented with Cm$^{50}$ and a mixed carbon source (0.5% glycerol, 0.05% glucose, 0.2% lactose) in a 48-well plate. Cultures were incubated on a plate shaker at 30° C., and a 500 µL sample of the fermentation broth was removed for analysis after 48 hours incubation.

Samples were centrifuged (×6000 g, 1 min) and the supernatant analyzed for malonate quantification. Chemical standards were prepared in 20 µM of water. The separation of malonate was conducted on a Shimadzu Prominence XR UPLC connected to a refractive index detector and UV detector monitoring 210 nm. Product separation was performed on a Bio-Rad Aminex HPX-87 h Fermentation Monitoring column. The UPLC was programmed to run isocratically using 5 mM $H_2SO_4$ as the eluant with a flow rate of 600 µL per minute. 10 µL were injected per sample, and the sample plate temperature was held at 4° C. Malonate standards began eluting at ~19.8 minutes. Addition of the standard to samples containing malonate demonstrated a proportional increase in malonate peak area, confirming malonate production. Malonate concentrations (mg/l) were calculated by comparison to a standard curve prepared from authentic malonate.

For cultures harboring the empty vector control, no peak was observed at the same retention time as the malonate standard, and the integrated peak area was below the detection limit of the instrument (i.e., no malonate production was observed). Malonate production was observed in samples harboring wild-type EHD3, EHD3 (E124A), EHD3 (E124V), EHD3 (E124S), and EHD3 (E124A, E308V); malonate concentrations were (mean±std dev; n=3): Wild-type EHD3, 6.0±0.2 mg/l, EHD3 (E124A), 7.6±0.7 mg/l, EHD3 (E124V), 0.28±0.03 mg/l, EHD3 (E124S), 82.3±7.8 mg/l, and EHD3 (E124A/E308V), 8.35±2.5 mg/l. EHD3 (E124V) resulted in decreased production of malonate relative to the wild-type protein, likely due to both poor malonyl-CoA substrate binding and high promiscuous activity toward other, endogenous acyl-CoA molecules. Similarly, EHD3 (E124A) yielded only a minor increase in malonate production relative to wild-type EHD3. EHD3 mutant E124S resulted in a significant (p<0.05, t-test) increase in malonate production over wild-type EHD3, EHD3 (E124A), and EHD (E124V), demonstrating the importance of E124S in increasing malonyl-CoA substrate binding and malonate production.

Example 3: Construction of Additional EHD3 E124 Mutants and Expression Vectors for In Vivo Production of Malonate in E. coli Example 1 describes the construction of E. coli expression vectors for wild-type EHD3 and a subset of E124 mutations, specifically E124A, E124V, E124S, and E124A/E308V, and Example 2 describes their use to produce malonate in E. coli cells. This example describes construction of E. coli expression vectors for all EHD3 E124 point mutations, i.e., E124G, E124T, E124C, E124L, E124I, E124M, E124P, E124Y, E124W, E124D, E124N, E124Q, E124H, E124K, E124R, and E124F. These EHD3 mutants were constructed using an E. coli vector with pSC101 origin and P$_{LacO1}$ origin of replication, as described in Example 1. The forward PCR primer comprises nucleic acid sequence (5'-aattttttactgatNNNtattctttgaattttcaaatagc-3'), where sequence "NNN" is the three nucleotides encoding the desired E124 amino acid point mutation; likewise, the reverse PCR primer comprises nucleic acid sequence (5'-ttcaaagaataaNNNatcagtaaaaaatttgatggacttg-3'), where sequence "NNN" is complementary to the three nucleotides encoding the desired E124 amino acid point mutation. The forward PCR primer was used in conjuction with PCR primer A94 (SEQ ID NO:14), and the reverse PCR primer was used in conjuction with PCR primer A93 (SEQ ID NO:13) to produce two overlapping EHD3 gene fragments containing the desired point mutation. Amplification of the two EHD3 gene fragments with primers A93 and A94 yielded the full length EHD3 gene containing the desired point mutation. The expression vectors were constructed using standard cloning protocols and transformed into E. coli DH10b and were subsequently isolated as described in Example 1 and verified by sequencing.

Example 4: In Vivo Production of Malonate in Recombinant E. coli Using EHD3 E124 Mutants This example describes fermentation of a set of E. coli host cells, each member of the set containing one of the 19 possible EHD3 E124 amino acid substitutions and determination of malonate levels produced. Specific E124 point mutations should theoretically improve malonyl-CoA binding and malonate production relative to wild-type; in particular, point mutations E124T, E124N, E124Q, E124H, E124K, and E124R should improve malonate production, theoretically due to introducing amino acids containing functional groups that improve interaction with the terminal carboxylic acid moiety of malonate. Point mutations E124S, E124Q, and E124K have side-chains that are located in the EHD3 binding pocket in positions that should theoretically best coordinate malonate binding. Malonate production is performed and quantified substantially as described in Example 2.

Example 5: Construction of YciA Malonyl-CoA Hydrolase Expression Vectors for In Vivo Production of Malonate in E. coli This example describes the use of E. coli YciA for the production of malonate in E. coli in accordance with the invention. Wild type E. coli acyl-CoA YciA is PCR amplified from the host genome using primers A120 (SEQ ID NO:21) and A121 (SEQ ID NO:22). The resulting nucleic acid is cloned behind the P$_{LacO1}$ promoter on an E. coli expression plasmid containing a pSC101 origin of replication and an ampicillin resistant gene. The control vector comprises an empty vector without the yciA gene insertion behind the P$_{LacO1}$ promoter. As described in Example 1, individual colonies are cultured, their plasmid isolated, and the coding region of the YciA gene insert sequenced.

Example 6: In Vivo Production of Malonate in Recombinant E. coli Using Heterologous YciA This example describes the host cells and culture conditions resulting in in vivo production of malonate using an expression vector encoding a heterologous YciA malonyl-CoA hydrolase as described in Example 5 in an E. coli host cell. Wild type E. coli strain K12 is transformed with vectors containing E. coli YciA; wild-type E. coli harboring an empty vector serves as a negative control. Malonate production is performed and quantified as described in Example 2.

Example 7: Construction of Engineered EHD3 Malonyl-CoA Hydrolase Expression Vectors for In Vivo Production of Malonate in Yeast The present invention also provides expression vectors, host cells, and methods for in vivo production of malonate in a yeast cell. Yeast cells can, in general, tolerate higher concentrations of organic acids in the fermentation broth and possess better-established industrial fermentation protocols than E. coli.

The yeast expression vectors described in this example were generated in part from use of the E. coli expression vectors described in Examples 1 and 3 as PCR templates for the EHD3 genes. The yeast expression vectors contain a 2-micron origin of replication, ura3 auxotrophic marker, and TEF promoter; the vectors also contain a puc origin of replication and an ampicillin or chloramphenicol resistance cassette for vector propogation in E. coli. The plasmids were transformed into either a S. cerevisiae BY4741 or BY4742 background, both derivatives of the S288C parental strain.

Additional mutations can be introduced into the EHD3 coding sequence to abrogate mitochondrial targeting. The basic amino acids R3, K7, K14, K18, and R22 in the EHD3 coding sequence are important for mitochondrial targeting, and mutation of any one or more of them to A or V decreases mitochondrial EHD3 expression and increases cytosolic EHD3 expression. Mutations are introduced by PCR amplification of an EHD3 template with forward and reverse primers containing the desired point mutation. Mutations are introduced using primers matching the EHD3 gene with the exception that the nucleotide sequence at the position of the desired amino acid point mutations is altered to "gyt" (where y is either a cysteine or thymine nucleotide in a mixed population of oligonucleotide PCR primers). The gene fragments are first cloned into an E. coli expression vector harboring a pSC101 origin of replication, $p_{LacO1}$ promoter, and chloramphenicol resistance marker, and the vector sequences confirmed as described in Example 1; following isolation of the desired mutant, the EHD3 gene is amplified and cloned into a yeast expression vector.

Example 8: In Vivo Production of Malonate in Recombinant Yeast Using Engineered EHD3 Malonyl-CoA Hydrolase S. cerevisiae BY4742 host cells are transformed with a yeast expression vector prepared substantially as described in Example 7 harboring heterologous EHD3 or an empty vector negative control plasmid using standard protocols. Transformants are streaked on synthetic complete dropout medium (SD) agar plates lacking uracil and cultured at 30° C.; individual colonies are grown overnight in 3 mL SD media overnight at 30° C. and subsequently diluted 1% v/v into 3 ml of SD lacking uracil. Strains are cultured at 30° C. for 72 hours; 500 µl aliquots are sampled at 24, 48, and 72 hour timepoints for quantification of malonate production and $OD_{600}$. The TEF promoter is a constitutive promoter.

Example 9: Increasing Malonate Biosynthesis in Engineered Yeast Through Expression of Heterologous Acetyl-CoA Synthetase In addition to the methods, vectors, and host cells for expression of a heterologous malonyl-CoA hydrolase and in vivo production of malonate, as illustrated in Examples 1-8, the invention also provides methods and host cells for improved titer, yield, and/or productivity of malonate. In one aspect, malonate production is improved by increasing the biosynthesis of acetyl-CoA. This example describes heterologous expression of acetyl-CoA synthetase enzymes in a recombinant S. cerevisiae host comprising a malonyl-CoA hydrolase pathway and resulting improvement in malonate production. The five acetyl-CoA synthetase proteins illustrated are S. cerevisiae ACS1 and ACS2, E. coli AcsA, Salmonella enterica Acs, and Bacillus subtilis AcsA. All genes are PCR amplified from their respective hosts and cloned into a yeast expression vector harboring a 2-micron origin of replication, ura3 auxotrophic marker, and TEF promoter; the vectors also contain a puc origin of replication and ampicillin resistance cassette for vector propogation in E. coli.

Example 10: Increasing Malonate Biosynthesis in Engineered Yeast Through Expression of Heterologous Pyruvate Dehydrogenase While Example 9 describes increased acetyl-CoA biosynthesis through expression of heterologous acetyl-CoA synthetases, this example describes increased acetyl-CoA biosynthesis through expression of heterologous pyruvate dehydrogenase enzymes. In specific, S. cerevisiae pyruvate dehydrogenase enzymes PDA1, PDB1, LAT1, LPD1, and PDX1 are heterologously expressed in recombinant S. cerevisiae comprising a malonyl-CoA hydrolase pathway. The genes are all PCR amplified from the S. cerevisiae chromosome and cloned into a yeast expression vector harboring a 2-micron origin of replication, ura3 auxotrophic marker, and TEF promoter; the vectors also contain a puc origin of replication and ampicillin resistance cassette for vector propogation in E. coli.

Example 11: Increasing Malonate Biosynthesis in E. coli and S. cerevisiae by Heterologous Expression of an Ethanol Catabolic Pathway This example describes a third route to increase acetyl-CoA biosynthesis: heterologous expression of an ethanol catabolic pathway. An ethanol catabolic pathway comprises two or three enzymes. An alcohol dehydrogenase and an acetaldehyde dehydrogenase (acylating), or an alcohol dehydrogenase, acetaldehyde dehydrogenase (non-acylating), and an acetyl-CoA synthetase. The alcohol dehydrogenase enzymes S. cerevisiae ADH2, E. coli AdhP, and H. sapiens ADH1A, H. sapiens ADH1B, and H. sapiens ADH1C are combinatorially cloned with with an acetaldehyde dehydrogenase (acylating) or aldehyde dehydrogenase and acetyl-CoA synthetase. The acetaldehyde dehydrogenase (acylating) enzymes E. coli MhpF, E. coli AdhE, Pseudomonas sp CF600 DmpF, and Pseudomonas putida TodL are also all cloned combinatorially. In ethanol catabolic pathways utilizing an acetaldehyde dehydrogenase (non-acylating) S. cerevisiae ALD2, ALD3, ALD4, ALD5, and ALD6 are used. Acetyl-CoA synthetase enzymes used are S. cerevisiae ACS1 and ACS2, and E. coli Acs. All genes are PCR amplified from genomic DNA.

For E. coli host cells, the ethanol catabolic pathway is expressed from a vector backbone harboring p15a origin of replication, ampicillin resistance marker, and $P_{lacO1}$ promoter. All combinations of all two and three gene pathways are constructed as single operons. E. coli K12 is co-transformed with an EHD3 expression plasmid and an ethanol catabolic pathway plasmid and streaked on LB agar plates ($Cm^{50}$, $Cb^{50}$, 2% w/v glucose). Control strains harbor empty vector. Production cultures and analysis thereof are conducted as described in Example 2, with the notable exception of the addition of the second antibiotic require to maintain the second plasmid.

*S. cerevisiae* fermentations can be conducted using identical ethanol concentrations as the *E. coli* experiments. The yeast expression vectors harbor a 2-micron origin, ura3 auxotrophic marker, and CUP promoter, and all combinations of the ethanol catabolic pathways are constructed on this vector backbone; a plasmid absent an ethanol catabolic pathway serves as a negative control. An ethanol catabolic pathway plasmid is transformed into recombinant *S. cerevisiae* BY4742 comprising an engineered EHD3 malonyl-CoA hydrolase pathway on a yeast chromosome. All fermentations are conducted at 30° C. in SD media without uracil. Ethanol catabolic pathway expression is induced with 100 µM copper sulfate after 12 or 24 hours growth. 500 µl aliquots are sampled at 24, 48, and 72 hours for quantification of ethanol, acetaldehyde, acetate, and malonate concentrations; $OD_{600}$ measurements of cell density are also recorded at each timepoint. In addition to malonate titer, ethanol consumption is calculated.

Example 12: Increasing Malonate Biosynthesis in *S. cerevisiae* by Heterologous Expression of an ATP Citrate Lyase This example describes a fourth approach to increase acetyl-CoA biosynthesis and improve malonate production in recombinant *S. cerevisiae*. ATP citrate lyase (EC 2.3.3.8) catalyzes the formation of acetyl-CoA, oxaloacetate, and ADP in the cytosol from citrate. ATP citrate lyase enzymes from the oleaginous yeasts *Candida curvata*, *Cryptococcus albidus*, *Lipomyces lipofer*, *Rhodospiridium toruloides*, *Rhodotorula glutanis*, *Trichosporon cutaneum*, *Yarrowia lipolytica*, are PCR amplified from genomic DNA and cloned into a yeast expression vector behind a CUP promoter; the expression vector contains a 2-micron origin and leu2d auxotrophic marker. A plasmid absent an ATP citrate lyase enzyme serves as a negative control.

An ATP citrate lyase pathway plasmid is transformed into recombinant *S. cerevisiae* BY4742 comprising an engineered EHD3 malonyl-CoA hydrolase pathway on a yeast chromosome. All experiments are conducted at 30° C. in SD media without uracil. ATP citrate lyase pathway expression is induced with 100 µM copper sulfate after 12 or 24 hours growth. Some cultures are also supplemented with 0.5, 1, 2.5, or 5 g/l citrate to provide an additional demonstration of pathway activity. 500 µl aliquots are sampled at 24, 48, and 72 hours for quantification of citrate (where applicable) and malonate concentrations; $OD_{600}$ measurements of cell density are also recorded at each timepoint. In addition to malonate titer, citrate consumption can be calculated.

Example 13: Increasing Malonate Biosynthesis in Recombinant Yeast Through Modification of Host Cell Fatty Acid Storage This example describes a fifth approach to increase acetyl-CoA biosynthesis and improve malonate production in recombinant *S. cerevisiae*. Fatty acid biosynthesis pathways compete with malonate production for acetyl-CoA and malonyl-CoA, and altering host cell fatty acid anabolism can increase malonate production. The present invention provides host cells comprising genetic modifications of one or more nucleic acids encoding proteins affecting fatty acid storage and catabolism. In *Saccharomyces cerevisiae*, the proteins SNF2, IRA2, PRE9, PHO90, SPT21, PDX1, ANT1, FOX3, EHD3, PAS1, PAS3, ARE1, ARE2, DGA1, LRO1, ACL1, MAE1, GLC3, GLG1, GLG2, PAT1, and PEX11 are knocked out individually and combinatorially and the resulting strains cultured for malonate production. All *S. cerevisiae* strains constructed comprise an engineered EHD3 malonyl-CoA hydrolase pathway for production of malonate. Fermentations are performed as described in Example 8, and malonate is quantified as described in Example 2.

Example 14: Increasing Malonate Biosynthesis in Recombinant Yeast Through Increased Beta-Oxidase Activity This example describes a sixth approach to increase acetyl-CoA biosynthesis and improve malonate production in recombinant *S. cerevisiae*. In addition to decreasing host cell fatty acid anabolism, increasing host cell fatty acid catabolism can increase malonate production. The present invention provides host cells modified for increased expression of PAT1 and/or PEX11. PAT1 and PEX11 are PCR amplified from genomic *S. cerevisiae* DNA and cloned into a yeast expression vector behind a CUP promoter; the expression vector contains a 2-micron origin and leu2d auxotrophic marker. A plasmid without a beta-peroxidase enzyme serves as a negative control.

A beta-oxidase pathway plasmid is transformed into recombinant *S. cerevisiae* BY4742 comprising an engineered EHD3 malonyl-CoA hydrolase pathway on a yeast chromosome. The engineered malonyl-CoA hydrolase is integrated onto the chromosome using standard recombination methods. The resulting strain serves as a base to test subsequent modifications and their impact on malonate production. All experiments are conducted at 30° C. in SD media without uracil. Pathway expression is induced with 100 copper sulfate after 12 or 24 hours growth. Some cultures are also supplemented with 0.5, 1, 2.5, or 5 g/l palmitic acid to provide an additional demonstration of pathway activity. 500 µl aliquots are sampled at 24, 48, and 72 hours for quantification of palmitic acid (where applicable) and malonate concentrations; $OD_{600}$ measurements of cell density are also recorded at each timepoint. In addition to malonate titer, palmitic acid consumption can be calculated.

Example 15: Improving Malonate Biosynthesis in Engineered Yeast Through Increased Acetyl-CoA Carboxylase Activity In addition to the methods, vectors, and host cells for expression of a heterologous malonyl-CoA hydrolase and in vivo production of malonate, the invention also provides methods and host cells for improved titer, yield, and/or productivity of malonate. In one aspect, malonate production is improved by increasing the biosynthesis of malonyl-CoA. Malonyl-CoA is the penultimate intermediate in the biosynthesis of malonate from acetyl-CoA, and in *S. cerevisiae*, this reaction is catalyzed by acetyl-CoA carboxylase (ACC1).

Malonyl-CoA biosynthesis is increased by overexpression of *S. cerevisiae* ACC1. Toward this end, the ACC1 gene is cloned using standard methods behind the CUP promoter on an *S. cerevisiae* expression plasmid containing a 2-micron origin of replication and ura3 auxotrophic marker. The control vector comprises an empty vector. *S. cerevisiae* host strains are engineered with chromosomal deletions of ACC1 and SNF1 protein kinase responsible for ACC1 phosphoregulation; chromosomal deletions are constructed both independently and in combination. Host cells harboring expression plasmids or control plasmids are grown as described in Example 8 and malonate production quantified as described in Example 2.

Example 16: Improving Malonate Biosynthesis in Host Cells Through Supplementation of the Fermentation Broth with Cerulenin In this example, malonate production in a recombinant host cell expressing an EHD3-derived malonyl-CoA hydrolase is improved by supplementation of the fermentation broth with cerulenin. The malonate production plasmid A4, comprising S. cerevisiae EHD3 (E124S) under control of a $P_{LacO1}$ promoter, is transformed into an E. coli K12 host.

Individual colonies are inoculated into 3 ml LB medium ($Cm^{50}$, 2% w/v glucose) in 48-well plates and cultured for 6 hours at 37° C. on a plate shaker. Strains are then subcultured 1%-v/v into 3 mL of M9 minimal medium ($Cm^{50}$, 0.5% w/v glycerol, 0.05% w/v glucose, 0.2% w/v lactose) and cultured at 30° C. on a plate shaker. Following 6 hours growth, one half of the cultures are supplemented with 10 mg/l cerulenin. After 48 hours growth, malonate concentration in the supernatant is measured as described in Example 2.

Example 17: Improving Malonate Biosynthesis in Engineered Yeast Through Supplementation of Fermentation Broth with Carbon Dioxide In this example, fermentation conditions are modified to increase the biosynthesis of malonyl-CoA. Enzymatic conversion of acetyl-CoA to malonyl-CoA by the enzyme acetyl-CoA carboxylase requires a stoichiometric amount of carbon dioxide, and supplementation of the growth media with carbon dioxide increases malonate production. Carbon dioxide is added to the growth media as either solid calcium carbonate or gaseous carbon dioxide.

Recombinant yeast cells harboring a malonyl-CoA biosynthetic pathway are grown in a defined minimal medium supplemented with between 0.1-10 g/l calcium carbonate. Control cultures are not supplemented with calcium carbon. Malonate production is quantified as described in Example 2 over the course of 48 hours growth.

Example 18: Improving Malonate Biosynthesis in Engineered Yeast Through Decreased Malonate Catabolism In this example, malonate production is increased by eliminating endogenous malonate catabolism in the host cell. S. cerevisiae contains multiple acyl-CoA synthetases, including FAA1, FAA2, FAA3, FAA4, LSC1, and LSC2; by deletion or modification of the nucleic acids on the host genome encoding these proteins, catabolism of malonate in the growth media can be decreased.

Malonyl-CoA knockout strains are constructed of each of the yeast acyl-CoA synthetases. The resulting strains are then cultured in a defined medium supplemented with 1-5 g/l sodium malonate. The malonate concentration in the fermentation broth is monitored over the course of 48 hours and quantified as described in Example 2. Strains with multiple knockouts can be constructed following similar procedures.

Example 19: Improving Malonate Biosynthesis in Engineered Yeast Through Improved Malonate Secretion from the Host Cell In this example, malonate production is improved by increasing secretion of malonate from the host cell. This is accomplished by overexpression of one or more of each of the S. cerevisiae pleiotropic resistant pumps, namely PDR5, PDR10, PDR11, PDR12, PDR15 and PDR18.

Example 20: Improving Malonate Biosynthesis in Engineered Yeast Through Decreased Succinate Dehydrogenase Competitive Inhibition by Malonate In this example, competitive inhibition of S. cerevisiae succinate dehydrogenase SDH1 is decreased, enabling higher titers of malonate to be achieved. First, the S. cerevisiae is genetically modified for deletion of the native, chromosomal copy of succinate dehydrogenase (SDH1) using standard methods. The resulting strain is grown anaerobically to facilitate growth in absence of SDH1 protein. The SDH1 deletion strain is subsequently transformed with a vector harboring a genetically modified SDH expression cassette containing an E300D, R331K, R331H, R442K, R442H mutation, or a combination of these mutations. These mutant SDH genes are cloned behind a constitutive TEF promoter on a yeast backbone harboring 2-micron origin and ura3 auxotrophic marker. Vectors are subsequently transformed into S. cerevisiae strain encoding malonyl-CoA hydrolase on the chromosome and the resulting strains grown in SD media lacking uracil. The transformed strains are cultured for malonate production as described in Example 8 and malonate is quantified as described in Example 2 to quantify the impact of these SDH mutations on malonate production.

Example 21: MdcY Malonate Transcription Factor Biosensor Using Exogenously Added Malonate Plasmid S14 was used to demonstrate biosensor response to exogenously added malonate in an E. coli host cell. S14 employs the malonate responsive transcription factor, MdcY (SEQ ID NO:3), and the MdcY-responsive promoter, $P_{MdcL}$ (SEQ ID NO:6) derived from Acinetobacter calcoaceticus. This biosensor of the invention was constructed using an E. coli vector backbone with ampicillin resistance marker and ColE1 origin of replication; the tetA tetracycline resistance gene was placed under control of the $P_{MdcL}$ promoter. Transformation of plasmid S14 into an E. coli host resulted in a strain expressing the tetA gene product following supplementation of the fermentation broth with malonate, and the strain exhibits a malonate-dependent increase in tetracycline resistance.

Nucleic acids encoding for MdcY and TetA gene products, $P_{MdcL}$ promoter, and the E. coli vector backbone were synthetically produced; the biosensor vectors were than constructed by PCR amplification of the nucleic acids and subsequent cloning into the E. coli vector backbone. The plasmids were transformed into chemically competent E. coli DH10b and the resulting clones plated on LB agar plates containing 50 µg/ml carbenicillin ($Cb^{50}$). Individual colonies were grown overnight in 3 ml LB medium supplemented with antibiotic and the sequences of the purified plasmid were verified.

E. coli strain K12 was co-transformed with plasmids S14 and individual colonies isolated from LB agar plates ($Cb^{50}$). Colonies were grown in 25 ml LB broth ($Cb^{50}$) until reaching an optical density at 600 nm ($OD_{600}$) of approximately 0.50, at which point in time cell stocks were prepared and stored at −80° C.; cell stocks were 0.5 ml cell culture and 0.5 ml of a 50% v/v glycerol solution.

All biosensor demonstrations were performed with malonate. An aliquot of biosensor cell stock was thawed and used to inoculate 50 ml of LB medium ($Cb^{50}$) in a 250 ml, baffled Erlenmeyer flask. Cultures were incubated for 2 hours at 37° C.; subsequently, 0.6 ml biosensor culture was added to 48-well plates prepared with 2.3 ml LB medium ($Cb^{50}$) supplemented with tetracycline and malonate acid at the desired concentration (n=4). Plates were than grown at 30° C. on an orbital titer plate shaker. Following 12 hours incubation, 200 µl samples were taken for $OD_{600}$ measurement.

Biosensor cultures harboring S14 displayed a dose-dependent response for malonate (FIG. 1). The dynamic range (the maximum difference in $OD_{600}$ values between the fully induced samples and those samples absent malonate supplementation) was 1.2 $OD_{600}$ units, indicating the MdcY-$P_{MdcL}$, based biosensor was highly responsive to exogenously added malonate. An increase in $OD_{600}$ was observed between between 0.5-1 mM exogenously added malonate, providing a suitable range over which malonate can be quantified using this method.

Example 22. MdcY Malonate Transcription Factor Biosensor to Detect Biologically Produced Malonate in Fermentation Broth In this example, a malonate transcription factor biosensor was used to detect the production of malonate from a yeast strain engineered as described in other aspects of the invention.

Malonic acid was produced using a genetically engineered yeast strain as follows. *S. cerevisiae* BY4741 yeast cells harboring a vector for expression of malonyl-CoA hydrolase comprising a CYC1 terminator, an ampicillin resistance cassette, a PMB1 origin of replication, a CEN/ARS origin of replication, and a URA3 selection marker was used for fermentation. The F0PNG8-1 malonyl-CoA hydrolase (from *Bacillus thuringiensis* subsp. finitimus strain YBT-020; UniProt ID F0PNG8, with E91S mutation) and the F6AA82-2 malonyl-CoA hydrolase (from *Pseudomonas fulva* strain 12-X; UniProt ID F6AA82, with E95S and Q348A mutations) were each expressed from this plasmid under control of the TEF1 promoter. The culture medium described in Example 30 was used with 20 g/L glucose as a carbon source. Production was performed as follows. Two ml of culture medium in a 48-well plate was inoculated with 20 µl of a starter culture of the producer strain, in quadruplicate. The plate was covered with a breathable membrane, incubated on a plate shaker at 30° C., and sampled for HPLC and biosensor analysis of product accumulated after 142 h of growth. Cells and cell debris were removed from the culture media by centrifugation and filtered through 0.45 micron membrane prior to analysis by HPLC or biosensor.

*E. coli* cells harboring either plasmid pS14, encoding a tetracycline resistance gene (tetA) under expression control of the malonic acid-responsive $P_{mdcl}$ promoter, or plasmid pS27, encoding a lacZ gene under expression control of the malonic acid-responsive $P_{mdcl}$. promoter, were used as biosensor indicator strains. The vector pS27 was constructed in the same manner as described for pS14 in Example 21, with the lacZ gene, encoding a beta-galactosidase, inserted in place of the tetA gene. Biosensor strains were prepared as described in Example 21.

Yeast spent media obtained from 96-well production plates were added to 96-well plates containing 120 ul of biosensor cell culture. For the TetA (pS14) biosensor, 10 ul of tetracycline stock solution (to provide a range of 20-35 ug/ml) were added to each well. For both the TetA (pS14) and lacZ (pS27) biosensor, the remaining volume of each well was filled with LB medium ($Cb^{50}$) to a final volume of 600 ul and grown as previously described. Samples (200 ul) were collected to 96 well plates after 2 h for S27 cultures and after 5-8 h for S14 cultures, and OD600 was measured. An ortho-nitrophenyl-β-galactoside (ONPG) assay was performed on samples from S27 (beta-galactosidase reporter) biosensor plates as follows. Cells were diluted 1:4 in 25 ul lysis buffer and subsequently 90 ul of ONPG stock solution (10 mg/ml in deionized water) were added to each well. Contents of each well were completely mixed and left at 30° C. for 4-16 hours. Optical densities were measured at 420 nm.

A dose-dependent response to malonate was observed. Specific malonic acid concentrations were also measured by HPLC, as described in Example 2, and quantified by comparison to a standard curve. Linear regression analyses between the quantifiable output of the biosensor, OD420 (for pS27) or OD600 (for pS14) and specific malonic acid concentrations measured by HPLC were calculated to have coefficients of determination ($R^2$) of 0.88492 plotting 37 OD420 samples and 0.89755 plotting 18 OD600 samples.

One skilled in the art will recognize that these very high coefficients of determination are indicative of the correlation between biosensor output and malonate concentration in the culture media. This aspect of the invention provides a tremendous advantage in both cost and time with regard to screening differential outputs in biological malonate production. Dilution of culture media used to challenge the biosensor can facilitate the extension of the dynamic response range of the sensor from zero to full solution saturation of malonate. The use of a plate based screen enables the screening of 96 samples in a few minutes in comparison to a time requirement of 2-20 minutes or more per sample for HPLC analysis. The savings in capital investment and solvent usage and disposal engendered by limiting or replacing HPLC altogether are also substantial.

Example 23. Precipitation of Malonate from Fermentation Broth by Addition of Calcium Hydroxide, Calcium Carbonate, and Calcium Chloride In this example, malonic acid was purified from the fermentation broth by precipitation with a divalent cation, specifically calcium. The purification methods were demonstrated using synthetic metabolites exogenously added to the fermentation broth. A yeast culture of *S. cerevisiae* BY4741 was grown in 0.5 L of synthetic complete media for 72 h at 30° C., 200 rpm. After 72 h, 25 ml aliquots of whole-cell fermentation broth were used to dissolve 0, 0.5, 1, 5, 10, 25, 50, 75, 100 g/l equivalents of malonic acid. Each 25 ml sample was divided into five-5 ml aliquots, and the pH of one aliquot of each concentration was adjusted to 5.5, 6.0, 6.5, 7.0, or 7.5. All samples were then centrifuged (×6000 rcf, 5 min, 25° C.), and the supernatants were transferred to separate tube. HPLC analysis showed malonic acid only in the supernatant fraction. Next, calcium chloride, a representative divalent cation, was employed for precipitating malonic acid from the clarified supernatant fraction by addition in equimolar equivalents to 0.5, 1, 5, 10, 25, 50, 75, 100 g/l of malonic acid of each sample at 25° C. The malonate concentration remaining in the supernatant and precipitate was then measured by HPLC as described in Example 2. At concentrations below 5 g/L, the extraction efficiency was 10% or less. It was also negligible once the pH was lowered to 5.5. However, at higher concentrations and pH values from 6-7.5 this method was quite effective at purifying malonate. The respective extraction efficiencies (percent isolated from fermentation broth) for this method at 100 g/L, 75 g/L, 50 g/l, 25 g/L, and 10 g/L are as follows: pH 7.5=89.8%, 88.5%, 83.3%, 70.1%, and 66.4%; pH 7.0=88.0%, 86.9%, 81.8%, 71.5%, and 63.9%; pH 6.5=80.5%, 79.0%, 75.8%, 65.0%, and 59.0%; pH 6.0=54.4%, 55.0%, 52.8%, 43.0%, 34.9%.

These results demonstrate that this method of the invention purified the malonic acid from the fermentation broth, separating it from both yeast cells and other dissolved chemicals.

Example 24: Purification of Biologically Derived Malonate from Fermentation Broth by Reactive Extraction with Ethanol and Methanol In this example, endogenously produced malonate from cultures of S. cerevisiae harboring a malonate biosynthesis pathway is purified from fermentation broth by reactive extractionb. The host cells are first removed from 50 mL of fermentation broth by centrifugation (×6000 rcf, 5 min). Formation of the diethyl and dimethyl ester in the fermentation broth is performed using methods adapted from: Gatterman L. and Babsinian VS. "The practical methods of organic chemistry" 3rd ed, The Macmillan Company: New York, pg. 161-162 (1916). In brief, sodium chloride is added to the fermentation broth; subsequently, ethanol and sulfuric acid are added leading to formation of the diethyl malonate ester.

Example 25: Reactive Extraction of Malonate from Fermentation Broth Using Tertiary Amines Yeast fermentation broth is prepared as described in Example 23. Malonic acid is exogenously added to the fermentation broth to a final concentration of 50 g/l. The solution pH is adjusted to a value<4.0 by addition of an acid.

Three solutions of tertiary amines (TA) are prepared using 1-octanol as a diluent at 0.25, 0.5, and 0.75 mol-TA/kg 1-octanol. Tertiary amines used are triethylamine, tripropylamine, tributylamine, tripentylamine, trihexylamine, triheptylamine, trinonylamine, and tridecylamine.

An equal volume of organic solvent containing the amine and diluent are mixed with a fermentation broth containing malonate. The reaction is stirred at 1000 rpm, 25° C., for 2 hours; subsequently, the two phases are separated by centrifugation (×6000 rcf, 10 min). Malonate concentration in each phase can be measured by HPLC as described in Example 2.

Example 26: Reactive Distillation of Malonate from Fermentation Broth Using Methanol and Ethanol This example describes reactive distillation of malonate from fermentation broth using methanol and ethanol; a cationic exchange resin, Amberlyst-15, is used as the solid catalyst. The resin is dried in a vacuum oven for 6 hours at 70 degrees C. before use. The assembly consists of a glass column packed with ceramic attached to a collection container. Esterification takes place in a reactor connected to the bottom of the column. A condenser is placed at the top of the column for the condensation of low volatile vapors. The esterification reactor is fed with the fermentation broth and the ion-exchange resin, Amberlyst-15 (2% w/w), is added as a catalyst. Sufficient heat is applied to the reactor to vaporize the reaction mixture, and either methanol or ethanol is added to the reactor once the desired temperature is achieved. Samples are withdrawn from the drain valves of the esterification reactor and collection container. After completion of the reaction, volumes and masses of final reaction mixtures from the esterification reactor and collection containers are measured. Malonate consumption and product formation are measured as described in Example 2.

Example 27: Synthetic Conversion of Malonate to Dimethyl Malonate and Diethyl Malonate Biologically derived malonate is produced from recombinant S. cerevisiae in 1 L culture flasks as follows: strains are streaked on synthetic complete dropout medium (SD) agar plates lacking uracil and cultured at 30° C.; individual colonies are grown overnight in 3 mL SD media overnight at 30° C. and subsequently diluted 1% v/v into 500 ml of SD lacking uracil. Strains are cultured at 30° C. for 72 hours. The resulting fermentation broth is centrifuged (×6000 g, 10 min) and the supernatant separated from the cell pellet. Malonate is precipitated from the fermentation broth using calcium chloride (Refer to Example 23). The resulting calcium malonate is then converted to diethyl malonate by adding excess ethanol and equimolar sulfuric acid to catalyse a Fischer esterification.

Figure 2:
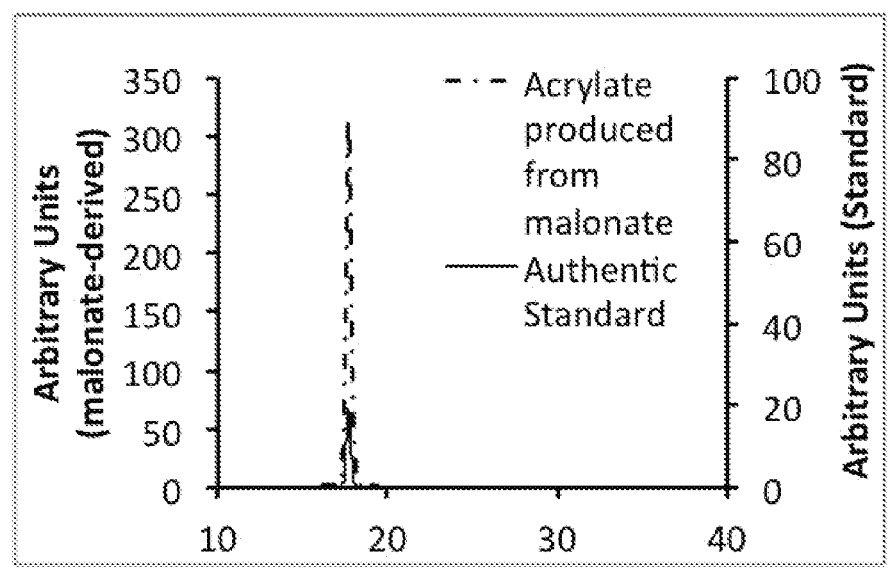
FIG. 2 is an HPLC chromatogram trace showing separation and detection of acrylic acid production from malonate according to the methods of the invention as described in Example 28. The X-axis shows elution of acrylic acid at approximately 17.5 minutes, and the Y-axis shows arbitrary units derived from detection of acrylic acid via a UV detector monitoring 210 nm. Acrylic acid produced from malonate according to the methods of the invention (dashed line) exhibited the same retention time as an authentic acrylic acid standard (solid line).

Example 28: Production of Acrylate from Malonate and Formaldehyde by Doebner Modification of the Knoevenagel Condensation Acrylate was produced in accordance with the invention through the condensation of malonic acid with paraformaldehyde in pyridine. The reaction was conducted in a 3-necked round bottom flask with a magnetic stirrer. Fifteen ml pyridine and 15 ml toluene were added to the flask, and 10 g powdered malonic acid were added in 5 equal parts; subsequently, 1.1 equivalents (3.2 g) of paraformaldehyde was added to the reaction vessel over a thirty minute period. The mixture was stirred vigorously to promote solubilization of the components. The temperature of the reaction was started at 0° C. and then increased over the course of several hours to 50° C. until the formation of carbon dioxide, evidenced by the formation of bubbles, was observed. After 2 hours of heating at 50° C., the flask was allowed to return to room temperature and an aliquot of the reaction was diluted 100-fold in water and analyzed by HPLC using the method described in Example 2. The sample of malonate-derived acylic acid co-eluted with an authentic standard at an elution time of approximately 17.5 minutes (see FIG. 2).

While the Doebner modification of the Knoevenagel reaction has been used to produce many compounds, its use in acrylate production is novel and important. Over a billion kilograms of acrylic acid are used annually to make wide a range of products from diapers to films and coatings. It is currently sourced largely from petroleum and production using the method described in this invention provides a partially or optionally fully renewable route to this commodity chemical, depending on the source of paraformaldehyde. In addition, malonic acid produced through the methods of this invention will be substantially less expensive than its petroleum derived counterpart. This facilitates production of sustainable or partially sustainable acrylic acid at a cost competitive with the incumbent petrochemical route.

Example 29: Production of Pentanedioic Acid from Malonate and Formaldehyde

Biologically derived malonate is produced from recombinant *S. cerevisiae* in one L culture flasks as described in Example 8. The resulting fermentation broth is centrifuged (×6000 g, 10 min) and the supernatant separated from the cell pellet. Malonate is precipitated from the fermentation broth using calcium chloride and converted to diethyl malonate. The biologically derived diethyl malonate is then reacted with formaldehyde in pyridine and worked up to the desired acid according to literature methods (Hedge et al. (1961) JOC 26:3166-3170).

Example 30: Bio-Catalytic Production of Malonate from Various Carbon Sources In accordance with the invention, *S. cerevisiae* BY4741 yeast cells harboring a malonyl-CoA hydrolase expression vector comprising a CYC1 terminator, an ampicillin resistance gene, a PMB1 origin of replication, a CEN/ARS origin of replication, and a URA3 selection marker were grown in yeast fermentation media comprising 5 g/L ammonium sulfate, 1 g/L monopotassium phosphate, 0.5 g/L magnesium sulfate, 0.1 g/L sodium chloride, 0.1 g/L calcium chloride, 2 mg/L inositol, 0.5 mg/L boric acid, 0.4 mg/L calcium pentothenate, 0.4 mg/L niacin, 0.4 mg/L pyridoxine hydrochloride, 0.4 mg/L thiamine HCl, 0.4 mg/L zinc sulfate, 0.4 mg/L manganese sulfate, 0.2 mg/L p-aminobenzoic acid, 0.2 mg/L riboflavin, 0.2 mg/L sodium molybdate, 0.2 mg/L ferric chloride, 0.1 mg/L potassium iodide, 40 µg/L copper sulfate, 2 µg/L folic acid, 2 µg/L biotin, 10 mg/L adenine, 50 mg/L L-arginine HCl, 80 mg/L L-aspartic acid, 20 mg/L L-histidine HCl, 50 mg/L L-isoleucine, 100 mg/L L-leucine, 50 mg/L L-lysine HCl, 20 mg/L methionine, 50 mg/L L-phenylalanine, 100 mg/L L-threonine, 50 mg/L L-tryptophan, 50 mg/L L-tyrosine, and 140 mg/L L-valine (the base media). In different fermentations, each of the following was used as a sole carbon source: 20 g/L glucose, 2% v/v ethanol, or 2% v/v glycerol. [0227] In this example, the F0PNG8-1 malonyl-CoA hydrolase (from *Bacillus thuringiensis* subsp. finitimus strain YBT-020; UniProt ID F0PNG8, with E91S mutation) was used under control of the TEF promoter. One and one-half ml of base media supplemented with 2% of the carbon source in a 48-well plate was inoculated with 50 µl of a saturated culture of the producer strain for culture in triplicate. The culture plate was covered with a breathable membrane, incubated on a plate shaker at 30° C., and sampled for HPLC analysis of product accumulation after 138 h of growth.

HPLC analysis of malonate accumulation was conducted as described in Example 2. The results were as follows: glucose as carbon source: 4.8 mM+/−0.2 mM (standard deviation) malonate; ethanol as carbon source: 7.5 mM+/−0.8 mM malonate; and glycerol as carbon source: 1.7 mM+/−0.1 mM malonate. These results show that the carbon sources tested were all suitable for use in production of malonate in accordance with the invention.

Example 31: Construction and Expression of Recombinant Plasmid Vectors Encoding Various Malonyl-CoA Hydrolases, and their Use in the Production of Malonate in Yeast Nucleic acids encoding various malonyl-CoA hydrolases provided by the invention were amplified by PCR from plasmids using the primers listed as follows: EHD3 (E124S) primers Y1-11_A13-R (SEQ ID NO:23)/Y1-11_A13-F (SEQ ID NO:24); B9IZZ9-1 primers YO012 (SEQ ID NO:25)/YO013 (SEQ ID NO:26); F0PNG8-1 primers YO014 (SEQ ID NO:27)/YO015 (SEQ ID NO:28); C3ALI3-1 primers Y0018 (SEQ ID NO:29)/YO019 (SEQ ID NO:30); Q81DR3-1 primers YO020 (SEQ ID NO:31)/YO021 (SEQ ID NO:32); A4XS22-1 primers YO024 (SEQ ID NO:33)/Y0025 (SEQ ID NO:34); E2XN63-1 primers YO026 (SEQ ID NO:35)/YO027 (SEQ ID NO:36); A5W8H3-1 primers YO028 (SEQ ID NO:37)/YO029 (SEQ ID NO:38); and F6AA82-1 primers YO030 (SEQ ID NO:39)/YO031 (SEQ ID NO:40). The purified PCR products were cloned downstream of the TEF1 promoter and upstream of the CYC1 terminator in a shuttle vector containing an ampicillin resistance cassette, a PMB1 origin of replication, a CEN/ARS origin of replication and a URA3 selection marker. The resulting plasmids were transformed into *E. coli* competent host cells and selected on LB agar plates containing $Cb^{50}$. Following overnight incubation at 37° C., individual colonies were inoculated in 2 ml of LB-$Cb^{50}$ in a 48-well plate and grown for 5 h at 37° C. on a shaker before the plasmids were isolated and confirmed by sequencing. Upon sequencing the construct containing protein F6AA82 (E95S), an unintended point mutation, Q348A, was found; this mutation was attributed to an error during PCR amplification. The resulting protein, F6AA82 (E95S/Q348A), is also referred to as F6AA82-2 herein. The Q348A point mutation was not shown to be necessary to obtain protein activity.

*S. cerevisiae* BY4741 cells were used as host for the vectors for expression of the various malonyl-CoA hydrolases. The plasmid vectors were individually introduced into the yeast host cells using standard procedures. Transformants were selected on agar plates of the media described in Example 30, containing 2% glucose as the carbon source.

The eight hydrolase-expressing *S. cerevisiae* strains were cultured as described in Example 22 and analyzed by HPLC as described in Example 2. The relative concentrations of malonate in the fermentation media were as follows (expressed as integrated area under the malonate peak; mean±S.D.; n=4): *S. cerevisiae* BY4741 (negative control) 48,865±9,345; EHD3 (E124S) 94,721±8,115; B9IZZ9 (E91S) 261,717±38,012; F0PNG8 (E91S) 216,654±31,145; F6AA82 (E95S/Q348A) 212,096±29,338; E2XN63 (E95S) 198,046±35,084; Q81DR3 (E91S) 193,665±37,898; Q63BK8 (E91S) 167,477±8,110; and A5W8H3 (E95S) 52,047±9,042. The identifiers are the Uniprot ID (http://www.uniprot.org/) followed by the mutation provided by the invention to result in malonate production. No malonate was detected in samples consisting of medium not inoculated with yeast cells.

In additional examples, C3ALI3 from *Bacillus mycoides* and A4XS22 from *Pseudomonas medocina* (strain ymp) containing E101S and E95S mutations, respectively, were utilized as malonyl-CoA hydrolases. Because the media conditions were varied slightly by buffering to pH 4.0, F0PNG8-1 and F6AA82-1 were included for comparison; all other fermentation, sampling, and analytical conditions were as described above. The results were as follows: C3ALI3 (E101 S) 10±1 mM, A4XS22 (E95S) 7±1 mM, F0PNG8 (E91S) 11±2 mM, and F6AA82 (E95S/Q348A) 23±2 mM malonate. In the absence of a malonyl-CoA hydrolase protein, *S. cerevisiae* cells did not produce detectable concentrations of malonate.

This example demonstrates, in accordance with the invention, malonate can be produced in a yeast host cell expressing an enzyme containing an $X_1$ mutation conferring malonyl-CoA hydrolase activity. The E to S active site mutations common to all the mutant hydrolases used in this example can be utilized in other members of these enzyme classes to provide similar results.

Example 32: Precipitation of Malonic Acid from Cells and Fermentation Broth Using a Monovalent Cation In this example, malonic acid was purified from the fermentation broth by precipitation with a monovalent cation. The monovalent cation was sodium. The purification methods were demonstrated using synthetic malonic acid exogenously added to fermentation broth. A culture of S. cerevisiae BY4741 was grown up, prepared and seeded with malonic acids as described in example 23. Next, sodium chloride, a representative monovalent cation, was employed for precipitating malonic acid from the clarified supernatant fraction. Either 2 or 4 molar equivalents (as compared to malonate concentration) of sodium chloride was added to the supernatant fraction of each sample at 25° C. The malonate concentration remaining in the supernatant and precipitate was then measured by HPLC as described in Example 2. The concentration of malonate remaining in the media seeded with 100 g/L malonate and treated two molar equivalents of sodium chloride varied by pH as follows: pH 5.5=103%, pH 6.0=96%, pH 6.5=71%, pH 7.0=74%, pH 7.5=86%. The concentration of malonate remaining in the media seeded with 100 g/L malonate and treated four molar equivalents of sodium chloride varied by pH as follows: pH 5.5=92%, pH 6.0=86%, pH 6.5=66%, pH 7.0=81%, pH 7.5=86%.

Example 33: Purification of Malonate from Cells and Fermentation Broth Using Diethyl Amine In this example, malonic acid was purified from the fermentation broth by addition of diethyl amine. The purification method was demonstrated using commercially obtained malonic acid exogenously added to the fermentation broth. Yeast fermentation media was prepared and known quantities of malonic acid added as described in a previous example. Diethyl amine, a representative di-substituted amine, was employed for purifying malonic acid from the clarified supernatant fraction. Between 0.5 and 100 g/l of diethyl amine was added to the supernatant fraction of each sample at 25° C. The metabolite concentration remaining in the supernatant and precipitate was then measured as previously described via HPLC, as described in Example 2. The concentration of malonate remaining in the media seeded with 100 g/L malonate treated with 4 equivalents of diethylamine per equivalent of malonate varied by pH as follows: pH 5.5=100%, pH 6.0=86%, pH 6.5=65%, pH 7.0 67%, pH 7.5=57%.

Example 34: Synthesis of Pimelic Acid

This example describes the synthesis of pimelic acid via the condensation of glutarate semialdehyde with malonate and catalytic hydrogenation. In a 250 ml round bottom flask, 10 grams of glutarate semialdehyde are dissolved in 40 ml of pyridine. Nine grams of malonic acid are added, and the mixture is heated, with stirring at 80° C. for 5 hours. The pyridine is removed using rotoevaporation, and the resulting material, containing the intermediate hept-2-en-1-7-dioic acid, is redissolved in hexanol. A Pd/C catalyst is added and the resulting mixture is stirred under a hydrogen atmosphere for 24 h. The catalyst is removed by filtration through Celite; the solvent is removed under reduced pressure; and the resulting pimelic acid is purified using by silica gel flash chromatography.

Pimelic acid is a key component of Nylon 5,7, which is used in fermentation to supplement biotin auxotrophy as well as in the production of several plastics. Prior art methods for pimelic acid synthesis are costly and low yielding. The invention provides a new chemical synthesis for this important compound that may be derived from malonic acid as provided by the invention.

Example 35: Construction and Expression of Recombinant Vectors Encoding Additional Malonyl-CoA Hydrolases, and Production of Malonate in Yeast In this example, E. coli malonyl-CoA:ACP transacylate FabD (SEQ ID NO:53) was mutated to contain one or more of the following amino acid changes at the indicated positions S92C, H201N, R117D, R117E, R117N, R117Y, R117G, R117H, Q11D, Q11E, Q11N, Q11Y, Q11G, Q11H, L93A, L93V, L93I, L93F, L93S, L93G and was employed as a malonyl-CoA hydrolase in S. cerevisiae. The nucleic acid encoding E. coli FabD was PCR amplified from E. coli strain K12 using primer F1 (5'-ATGACGCAATTTGCATTTGT-GTTCCC-3') and F2 (5'-TTAAAGCTCGAGCGCCGCT-3'). The amplified gene was then mutated using standard methods and inserted into a shuttle expression plasmid under the control of the TEF1 promoter and upstream of the CYC1 terminator. This vector contains an ampicillin resistance cassette, a PMB1 origin of replication, a CEN/ARS origin of replication, and a URA3 selection marker. The individual mutational combinations assayed are listed with the results below.

Individual colonies were inoculated into 1 ml of the media described in Example 30 containing 2% glucose as a carbon source. The cultures were incubated on a shaker at 30° C. for 24 h, and 20 μl of these cultures were used to inoculate production cultures of 2 ml of the same media. The production cultures were covered with a breathable membrane, incubated with shaking at 30° C. and sampled for HPLC analysis of product accumulation after 96 h and 168 h of growth.

No malonate was detected in samples consisting of medium not inoculated with yeast cells. Wild type yeast produced less than 0.1 mM malonate following 168 h fermentation. Expressing any of the four FabD variants produced malonate at levels higher then cells not expressing these proteins. Malonate accumulation after 96 and 168 h of fermentation using various engineered FabD malonyl-CoA-ACP transacylase enzymes expressed in S. cerevisiae were as follows: FabD S92C/L93V/R117H 96 h=1.01 mM, 168 h=2.49 mM; FabD L93I/R117Y 96 h=1.47 mM, 168 h=2.48 mM; FabD L93S/R117G 96 h=1.11 mM, 168 h=2.89 mM; FabD L93I/R117Y 96 h=1.64 mM, 168 h=3.47 mM.

Example 36: Reactive Extraction of Malonic Acid from Water with Trialkylamines in 1-Octanol In this example malonic acid was purified from water by reactive extraction with three trialkylamines; tripropylamine, trihexylamine, and trioctylamine. The purification method was demonstrated using authentic malonic acid added to distilled water. Maionic acid was added to water to a final concentration of 100 g/l; the pH of the solution was approximately 1.5.

250 ul of the aqueous malonic acid solution was mixed with 250 ul of an organic phase consisting of 25% v/v trialkylamine and 75% v/v 1-octanol. One sample was prepared without addition of the organic phase; this sample provided a measurement of the initial concentration malonic acid in each sample. Samples were mixed by inversion for 18 hours, centrifuged (×18,000 g) for 1 minute, and the aqueous phase sampled for analysis of malonic acid concentration by HPLC.

For HPLC analysis of malonic acid in the aqueous phase we employed a Shimadzu XR HPLC system equipped with a UV detector. 5 µl of each sample was injected into the system and separated with an Aminex HPX-87 h fermentation-monitoring column (Bio-Rad, Hercules, Calif.). The mobile phase was de-ionized water (pH 1.95 with sulfuric acid), flow rate was 0.6 ml/min, oven temperature was 50C and, the UV detector monitored 210 nm. Samples containing were monitored for malonic acid elution at ~10 minutes post injection.

33±2.6% of the malonic acid was extracted with tripropylamine, 73±4.4% of the malonic acid was extracted with trihexylamine, and 89±11.9% of the malonic acid was extracted with trioctylamine (n=3). Therefore, long chain length trialkylamines are preferred over short-chain length trialkylamines to increase extraction efficiency. Of the trialkylamines used in this example, trioctylamine is preferred to the shorter-chain length trihexylamine and tripropylamine.

Example 37: Decreasing Aqueous Phase pH to Increase Reactive Extraction of Malonic Acid Using Trialkylamines In this example malonic acid was purified from water at different pH values by reactive extraction with trioctylamine in 1-octanol. A stock solution of 100 g/l malonic acid was first prepared in water. The stock solution was then separated into working samples that were adjusted to the desired pH. Because addition of base diluted the malonic acid concentration at each pH value both malonic acid concentration before and after reactive extraction were taken. Calculation of the difference in malonate concentration between the pre- and post-extracted samples provided the percent yield at each pH value tested.

The reactive extraction was performed as follows. 250 ul of the aqueous malonic acid solution was mixed with 250 ul of an organic phase consisting of 25% v/v trioctylamine and 75% v/v 1-octanol. All samples were mixed by inversion for 18 hours, centrifuged (×18,000 g) for 1 minute, and the aqueous phase sampled for analysis of malonic acid concentration by HPLC as described in Example #36.

The extraction efficiencies at each pH were as follows; pH 1.5, 70%; pH 2.26, 57%; pH 2.93, 45%; pH 4.05, 30%; pH 4.62, 23%; pH 5.0, 15%; pH 5.5, 5%; pH 6.0, 0%; and pH 7.0, 3%.

Extraction efficiency decreased with increasing pH, and the highest extraction efficiency was achieved at pH 1.5. Above pH 6.0 extraction efficiencies were negligible. Thus, it is preferred that the pH of the fermentation broth be below 2.0 when extracting malonic acid using a trialkylamine.

Example 38: Increasing Trialkylamine Concentration in an Organic Phase to Increase Reactive Extraction of Malonic Acid from an Aqueous Solution In this example malonic acid was purified from water using a trialkylamine/1-octanol organic phase overlay containing different concentrations trioctylamine. The purification method was demonstrated using synthetic malonic acid added to distilled water to a final concentration of 100 WI; the pH of the solution was approximately 1.5.

250 ul of the aqueous malonic acid solution was mixed with 250 ul of an organic phase consisting of the indicated amount of trialkylamine (expressed as the mol fraction relative to malonic acid in the aqueous phase) in 1-octanol. One sample was prepared without addition of the organic phase and was used to provide the measurement of the initial malonic acid concentration in the aqueous phase.

Samples were mixed by inversion for 18 hours, centrifuged (×18,000 g) for 1 minute, and the aqueous phase sampled for analysis of malonic acid concentration by HPLC as described in Example #36.

A linear relationship between extraction efficiency and trioctylamine:malonate mol fraction was observed; specifically the linear relationship existed between trioctylamine:malonic acid mol fractions of 0 to 1. Above 1 molar ratio, 100% of the malonic acid was extracted into the organic phase. Thus, the amount of trialkylamine in the organic phase must be equimolar to the amount of malonic acid in the aqueous phase (e.g., fermentation broth) to maximize extraction yield. Ideally a greater than equimolar amount of trialkylamine will be added to the organic phase to compensate for decreased extraction efficiencies due to other organic acids and anions in the fermentation broth.

Example 39: Increasing Malonic Acid Reactive Extraction Yield from Aqueous Solutions at Different Ionic Strengths by Using Equimolar Amounts of Trioctylamine in 1-Octanol In this example malonic acid was purified from water at different ionic strengths by reactive extraction with trioctylamine; by increasing the molar ration of trioctylamine in the organic phase to malonic acid in the aqueous phase to 1:1 we were able to improve the malonic acid extraction efficiency.

Malonic acid was added to water to a final concentration of 100 g/l. The ionic strength was adjusted to the indicated concentration by addition of sodium chloride. The final pH of all samples following addition of malonic acid and sodium chloride was approximately pH 1.5.

250 ul of the aqueous malonic acid solution was mixed with 250 ul of an organic phase consisting of trioctylamine in 1-octanol. The trioctylamine volumes were calculated such that the triocytylamine:malonic acid molar ratio was as indicated; the remainder of the volume was 1-octanol. One sample was prepared without addition of the organic phase; this sample provided a measurement of the initial malonic acid concentration. Samples were mixed by inversion for 18 hours at 18° C., centrifuged (×18,000 g) for 1 minute, and the aqueous phase sampled for analysis of malonic acid concentration by HPLC as described in Example 36.

Ionic strength (mM concentration) impacted the extraction of malonic acid using 0.59, 1.07, 1.61, and 2.14 molar equivalents of trioctylamine as follows; at an ionic strength of 0, 63.5%, 98.6%, 99.5%, and 99.4% of malonic acid was recovered respectively; at an ionic strength of 75, 60.3%, 91.3%, 93.7%, and 93.6% of malonic acid was recovered respectively; at an ionic strength of 150, 55.9%, 85.8%, 89.5%, and 89.1% of malonic acid was recovered respectively; at an ionic strength of 225, 52.4%, 83.5%, 86.0%, and 85.9% of malonic acid was recovered respectively; at an ionic strength of 300, 46.5%, 79.4%, 83.1%, and 82.6% of malonic acid was recovered respectively; at an ionic strength of 375, 44.3%, 76.7%, 79.9%, and 80.1% of malonic acid was recovered respectively; at an ionic strength of 450, 43.3%, 72.8%, 77.0%, and 78.1% of malonic acid was recovered respectively; at an ionic strength of 500, 43.1%, 72.2%, 75.1%, and 76.6% of malonic acid was recovered respectively.

Increasing the trioctylamine:malonic acid molar ratio to 1:1 increased the malonic acid extraction efficiency from the aqueous solution at all ionic concentrations tested. No meaningful improvements in malonic acid extraction efficiency were obtained by increasing the trioctylamine:malonic acid molar ratio above 1:1. When extracting malonic acid from aqueous solutions it is preferable to use a trioctylamine:malonic acid molar ratio of at least 1:1, and if there are no other organic acids a molar ratio of exactly 1:1 is preferred. If contaminating organic acids are present, a molar ratio higher than 1:1 may be preferred in order to improve the malonic acid extraction efficiencies.

Example 40: Increasing Malonic Acid Back Extraction Yields from Trialkylamine/1-Octanol Organic Phase by Increasing Ionic Strength of Aqueous Phase In this example we demonstrate methods to back extract malonic acid from an organic phase consisting of a trioctylamine in 1-octanol and into an aqueous phase.

Malonic acid was added to water to a final concentration of 100 g/l and extracted into an organic phase consisting of trioctylamine (used at a 1:1 molar ratio to malonic acid) dissolved in 1-octanol. 10 ml of aqueous solution was extracted into 10 ml of organic phase at 18° C. for 18 hours. The organic phase was then separated by centrifugation (×4000 g, 5 min). The aqueous phase was also sampled to quantify the non-extracted malonic acid concentration.

250 ul organic phase were then mixed with 250 ul aqueous solutions at the given ionic strength sodium chloride or sodium hydroxide. Samples were mixed by inversion at 18° C. for 18 hours. The samples were than centrifuged (×18,000 g, 1 min) and the aqueous phase sampled for analysis of malonic acid concentration by HPLC as described for Example 36.

The data presented below was normalized to the malonic acid concentration that was back-extracted into distilled water. Addition of either 0.5 molar sodium chloride or sodium hydroxide increased the yields of the back extraction reaction over 25-fold. Addition of sodium chloride above 1.5 M decreased back extraction yields; however, with sodium hydroxide back extraction yields continued to improve with further addition of sodium hydroxide. Back extraction yields would be further increased by running back extraction reactions at an elevated temperature (i.e. above 18° C.). Milimolar concentration of NaCl and fold improvement: 0 mM, 1; 0.5 mM, 27.3; 1 mM, 43.1; 1.5 mM, 74.5; 2 mM, 63.4; 2.5 mM, 66.5; 3 mM, 69.4; 3.5 mM, 63.7; 4 mM, 57.8; 4.5 mM, 53.3; and 5 mM, 45.2. Milimolar concentrations of NaOH and fold improvement: 0 mM, 1; 0.5 mM, 33.6; 1 mM, 46.5; 1.5 mM, 57.5; 2 mM, 52.7; 2.5 mM, 56.4; 3 mM, 62.6; 3.5 mM, 58.2; 4 mM, 68.5; 4.5 mM, 67; 5 mM, 74.2.

Example 41: Purification of Malonic Acid from Aqueous Solution by Esterification and Subsequent Phase Separation In this example we demonstrated esterification of malonic acid and ethanol to form diethyl malonate and subsequent phase separation of the diethyl malonate into a hexane organic phase.

500 µl aqueous solutions containing malonic acid at 100 g/l concentration, ethanol at the indicated concentration, and sulfuric acid at the indicated concentration were prepared. Malonic acid and ethanol were the substrates for forming diethyl malonate; sulfuric acid was added as the catalyst. An organic overlay of 250 µl hexane was added to each of the samples, they were mixed by inversion for 18 hours at 25° C. and atmospheric pressure, centrifuged (×18,000 g) for 1 minute, and the aqueous phase sampled for analysis of malonic acid concentration by HPLC as described in Example 36.

Consumption of malonic acid was measured by the decrease in malonic acid concentration in the aqueous phase. The baseline malonic acid concentration (i.e. 100% unreacted malonic acid) in the aqueous phase was established from a sample containing 0% v/v ethanol and 0% v/v sulfuric acid.

The addition of both ethanol and sulfuric acid to the reaction mixture was necessary to catalyze malonic acid esterification. The most preferable reaction conditions, as measured by percent consumption of malonic acid, were achieved at high ethanol and sulfuric acid concentrations. Namely, greater than 40% v/v ethanol (7.14 molar ratio to malonic acid) and greater than 10% v/v sulfuric acid (1.94 molar ratio to malonic acid) were necessary to catalyze near complete consumption of malonic acid. The results of this demonstration are as follows: esterification reactions were conducted with 5, 10, 20, 30, 40, and 50% (V/V) ethanol. The malonic acid remaining in the aqueous phase was as follows: with 5% (V/V) sulfuric acid 78.9%, 61.6%, 43.2%, 43.2%, 28.2%, and 16.6%; 10% (V/V) sulfuric acid 83.5%, 70.3%, 49.5%, 28.6%, 16.6%, and 8.5%; 5% (V/V) sulfuric acid 71.8%, 53.2%, 28.1%, 11.8%, 4.4%, and 0.6%, respectively. The no acid control showed 95.1%, 93.2%, 85.8%, 69.1%, 63.0%, and 87.3% malonate remaining in the respective solutions with ethanol. The addition of acid with no ethanol present resulting in the following concentrations of malonic acid remaining in the aqueous phase: 96.1%, 92.7%, and 84.4% for 5, 10, and 20% (V/V) sulfuric acid, respectively.

Example 42: Improving Malonate Biosynthesis in Engineered Yeast Through Increased Acetyl-CoA Carboxylase Activity In addition to the methods, vectors, and host cells for expression of a heterologous malonyl-CoA hydrolase and in vivo production of malonate, the invention also provides methods and host cells for improved titer, yield, and/or productivity of malonate. In one aspect, malonate production is improved by increasing the biosynthesis of malonyl-CoA. Malonyl-CoA is the penultimate intermediate in the biosynthesis of malonate from acetyl-CoA, and in S. cerevisiae, this reaction is catalyzed by acetyl-CoA carboxylase (ACC1).

In this example, the ACC from the yeast Yarrowia lipolytica CLIB122 (NCBI Reference Sequence: XP_501721) was back-translated to a DNA sequence using standard codon optimization tables for expression in S. cerevisiae. The resulting in the Y1ACC DNA sequence is included below as SEQ ID NO:11.

DNA encoding 50 nucleotide of upstream S. cerevisiae FAA1 homolog followed by 300 base pairs of the S. cerevisae TEF1 promoter sequence followed by the Y1ACC sequence (SEQ ID NO:11) and finally 50 nucleotides of downstream S. cerevisiae FAA1 were synthesized as a single piece of DNA from oligonucleotides using standard protocols and amplified by PCR. The resulting, flanked, Y1ACC PCR product and a linear DNA construct containing the selectable URA3 gene and flanking FAA1 homologous sequences, to direct recombination into the FAA1 site on the chromosome, were co-transformed into BY4741 containing 2 copies of malonyl-CoA hydrolase F6AA82-2 provided by the invention (strain LYM004), using a standard lithium acetate transformation procedure, and selected for by plating on Synthetic Defined medium containing 2% glucose (SD) and lacking uracil (-Ura) plates. Clones and corresponding genomic DNA were isolated and verified by PCR to contain the Y1ACC integration into FAA1.

For in vivo malonate production, one individual colony for each transformant picked was inoculated in a 50 µl aliquot of SD-Ura medium in a 96-well plate. LYM004 was grown for comparison of yeast lacking expression of a heterologous Y1ACC. The plate was incubated on a shaker at 30° C. for approximately 4 h and 25 µl of these pre-cultures were used to inoculate fermentation plates. In this example, 2 ml of SD medium in 48-well plates was used for the fermentation. The fermentation plates were covered with a breathable membrane, incubated on a plate shaker at 30° C. and sampled for HPLC analysis of product accumulation after 72 and 120 h of fermentation. HPLC analysis of malonate accumulation in the fermentation broth was conducted as described in example 36.

No malonate was detected in samples consisting of medium only. LYM004 expressing Y1ACC produced 1.94 and 2.43-fold more malonate at 72 and 120 h, respectively, than LYM004 alone. The highest concentration of malonate measured in the fermentation media were observed in samples collected after 120 h of fermentation.

Example 43: Production of Malonate in *S. cerevisiae* Using Engineered F6AA82 Malonyl-CoA Hydrolase In this example all twenty proteogenic amino acid point mutations were introduced at position E95 in protein F6AA82 (Q348A). Amino acid position 95 was believed to interact with the terminus of malonyl-CoA, and mutation of E95 would introduce malonyl-CoA hydrolase activity into the protein.

F6AA82 (Q348A) mutants at position 95 (i.e., all amino acids) were constructed using standard methods and cloned into a yeast plasmid containing a uracil auxotrophic marker, CEN/ARS origin of replication, TEF promoter and CYC terminator. The F6AA82 mutants were cloned behind the TEF promoter and directly upstream of the CYC terminator. All plasmids contained an ampicillin resistance marker and ColE1 origin for propagation of the plasmid in *E. coli*.

Plasmids were transformed into *S. cerevisiae* using a lithium acetate procedure and transformants were selected on SD-Uracil agar plates at 30° C. Twelve colonies of each mutant were inoculated into pre-cultures of 500 µl SD-Ura medium in a 96-well plate and were incubated~0.16 h with shaking at 30° C. A 5 µl aliquot of these pre-cultures was used to inoculate 96-well production plates containing 500 µl RD4-Ura (1×YNB, 3×SC supplement, 2% glucose, 75 mM succinic acid buffer pH 4.0, uracil dropout) media. The production plates were incubated at 30° C. with shaking for 3 days before sampling the fermentation broth. The samples were clarified by centrifugation and filtered on a 0.45 µm membrane prior to HPLC analysis. HPLC analysis of malonate accumulation in the fermentation broth was conducted as described in example 36.

The production from each F6AA82 mutant (containing mutation Q348A in addition to the described E95 mutations), under these conditions, was as follows: F6AA82 (E95N) 8.03±0.14 mM, F6AA82 (E95S) 4.18±0.61 mM, F6AA82 (E95Y) 3.87±0.30 mM, F6AA82 (E95A) 2.33±0.50 mM, F6AA82 (E95K) 1.65±0.23 mM, F6AA82 (E95T) 1.16±0.62 mM, F6AA82 (E95D) 0.75±0.27 mM, F6AA82 (E95F) 0.17±0.13 mM, F6AA82 (E95Y) 0.11±0.32 mM, F6AA82 (E95L) 0.11±0.12 mM, F6AA82 (E95G) 0.00±0.01 mM, F6AA82 (E95P) −0.31±0.78 mM, F6AA82 (E95R) −0.32±0.69 mM, F6AA82 (E95) −0.32±0.40 mM, F6AA82 (E95W) −0.34±0.73 mM, F6AA82 (E95Q) −0.37±0.74 mM, F6AA82 (E95N) −0.53±0.70 mM, F6AA82 (E95C) −0.57±0.69 mM, F6AA82 (E95I) −0.64±0.81 mM, and F6AA82 (E95M) −0.77±0.79 mM. Negative concentrations of malonate were due to the production titers falling below the detectable level of the HPLC and indicate the absence of malonate production.

F6AA82 (Q348A) proteins containing mutations E95S, E95Y, E95T, E95N, E96K, E95V, and E95D produced significantly (t-test, p<0.05) more malonate than the F6AA82 (Q348A) protein. F6AA82 proteins containing these mutations are suitable for the hydrolysis of malonyl-CoA and production of malonate. F6AA82 mutations E95S and E95N are preferred for the hydrolysis of malonyl-CoA and production malonate.

E95Y, E95T, E95K, E95V, and E95D produced significantly (t-test, p<0.05) more malonate than the wild type F6AA82 protein. F6AA82 proteins containing these mutations are suitable for the hydrolysis of malonyl-CoA and production of malonate.

Example 44: Impact of Promoter Selection on the Production of Malonate in *S. cerevisiae*

In this example, an expression plasmid backbone comprising a CEN/ARS origin of replication, a PMB1 origin of replication, an ampicillin resistance marker, an URA3 marker and an hph marker was amplified from plasmid Y20. The malonyl-CoA hydrolase F6AA82-2 flanked by the CYC1 terminator was amplified by PCR from plasmid Y1-F6AA82-2 and assembled with the backbone using standard techniques. The resulting plasmid, pPLIB0-Q9I, was used as a backbone for cloning of the different promoters selected.

Ninety-six reference genes were selected from *S. cerevisiae* strain BY4741. Promoter sequences to these genes were generated by PCR amplifying, using *S. cerevisiae* strain BY4741 genomic DNA as template, nucleic acid fragments corresponding to approximately 750 base pairs immediately upstream of their open reading frame, including the start codon of the gene of interest. Using standard cloning techniques, these promoter sequences were cloned immediately upstream of F6AA82-2 (Start codon at 3739 in SEQ ID NO:12) in pPLIB0-Q9I. The resulting plasmids were propagated in *E. coli* and the presence of the desired promoter was verified by sequencing.

The plasmids described above were used to transform *S. cerevisiae* BY4741 using standard lithium acetate procedures. Transformants were selected on agar plates of CSM medium without uracil at 30° C. One transformant harboring each plasmid was inoculated in a pre-culture plate consisting of 300 ul of RD-Ura medium (2×YNB, 3×SC-U, 2% glucose) in a 96-well plate. The pre-culture plate was incubated at 30° C. approximately 20 h with shaking, and 30 µl of these pre-cultures was used to inoculate production plates consisting of 1.8 ml of RD4-Ura medium (2×YNB, 3×SC-U, 2% glucose, 75 mM succinate buffer pH 4.0) in 48-well culture plates (1 production well for each pre-culture). The plates were incubated at 30° C. with shaking for 144 h before sampling the fermentation broth. The samples were clarified by centrifugation and filtered on a 0.45 μm membrane prior to HPLC analysis.

HPLC analysis of malonate accumulation in the fermentation broth was conducted as described in example 36. Millimolar malonate concentration in the fermentation broth after 144 h of fermentation with different promoters driving expression of F6AA82-2 are as follows: HSP150 8.8; PGK1 8.6; PHO5 8.5; SCT1 7.8; PRB1 7.6; TPI1 7.1; ACH1 7; HXK2 6.9; ACO1 6.9; JEN1 6.9; MDH2 6.8; PDX1 6.6; CIT1 6.6; ALD4 6.6; ADH1 6.5; TDH3 6.4; ADH2 6.4; SDH1 6.4; TDH1 6.1; MLS1 6.1; RPN6 6; GLK1 5.9; POT1 5.8; HSP26 5.8; FBA1 5.7; LPD1 5.7; CYC1 5.5; COX5a 5.5; TEF1 5.5; SHH4 5.5; GND2 5.5; TPS1 5.5; MDH1 5.4; PDC1 5.4; HXK1 5.3; TDH2 5.3; IDH2 5.3; DDR2 5.2; SLT2 5.2; ENO2 5.1; COX6 5; CHO1 4.9; PHO3 4.9; PFK1 4.9; ACS1 4.9; GUT2 4.8; PHM7 4.8; CIT2 4.7; ACS2 4.7; ALD2 4.5; IDH1 4.5; IDP2 4.5; FBP1 4.3; PHO12 4.3; PDC5 4.2; PFY1 4.1; GDH1 4.1; PEX13 4.1; ICT1 4.1; YSA1 4; KGD2 3.9; GIM5 3.9; GAP1 3.9; DBP5 3.8; STE5 3.7; B102 3.7; PDC6 3.6; HXT5 3.6; REG1 3.6; TPS3 3.5; BIOS 3.3; PHO8 3.3; IRC7 3.2; GPM1 3.2; ALAI 3.1; KGD1 3.1; MIG1 3.1; YKT6 2.9; SNO4 2.8; ARA1 2.8; PDR10 2.7; YBR139W 2.3; ERR2 2.2; CRC1 1.9; TSL1 1.3; ENO1 1.2; PFK2 1.1; RPL6A 1.1 As many of these promoters are unnamed, the letter number code in front of each number indicates the gene immediately downstream of the cloned promoter, in S. cerevisiae strain BY4741.

This example demonstrates that a wide variety of promoters can be used to control expression of a malonyl-CoA hydrolase to produce malonate in vivo in yeast. Furthermore, 40 different promoters resulted in titers of at least 5 mM malonate, and 7 promoters resulted in production of at least 7 mM in this experiment.

Example 45: Integration of a Malonyl-CoA Hydrolase Encoding Gene to the S. cerevisiae Genome for the Production of Malonate In this example, S. cerevisiae strain BY4741 is used as a host strain, for the genomic integration of the malonyl-CoA hydrolase afforded by the invention. Three sites on the S. cerevisiae genome were chosen for integration of the synthetic nucleic acid constructs in this strain and the three linear nucleic acids cassettes to be integrated each carried unique homology sites to target integration and a unique selectable marker encoded upstream of the malonyl-CoA hydrolase. In all three cases nucleic acid encoding the malonyl-CoA hydrolase F6AA82 (E95S/Q348A) flanked by the TEF1 promoter and the CYC1 terminator was utilized as the expression portion of the cassette.

In two cases the solo long terminal repeats YPRCdelta15 and YORWdelta22, non-coding DNA of the chromosome, were targeted for integration. In the third case, a malonyl-CoA hydrolase cassette provided by the invention (F6AA82 (E95S/Q348A)) was integrated in place of the BUD21 gene. The sequences of these linear insertion cassettes are included below as SEQ ID NO:41, SEQ ID NO:42, and SEQ ID NO:43. The unique integration sites and selectable markers are YPRCdelta15 (HIS3), YORWdelta22 (LEU2), and BUD21 (URA3), respectively.

These nucleic acid cassettes were constructed and transformed into S. cerevisiae BY4741 using standard protocols. Transformants were selected on agar plates made of SC medium with appropriate amino acid dropouts at 30° C. Several transformants for each construction were re-streaked on selective agar plates. Transformants were then screened and verified by production of malonate and by PCR. The following strains resulted from these integrations: LYM002 contains 1 copy of F6AA82 (E95S/Q348A) integrated at YPRCdelta15 (HIS3); LYM004 carries 2 copies of F6AA82 (E95S/Q348A), one at YPRCdelta15 (HIS3) the second at YORWdelta22 (LEU2); LYM007 is derived from LYM004 and has a third copy of F6AA82 (E95S/Q348A) integrated at the BUD21 locus.

For fermentation and malonate production, S. cerevisiae BY4741 carrying plasmid Y1-F6AA82 (E95S/Q348A) served as a positive control. Pre-cultures of 500 μl of RD4 medium in a 96-well plate were incubated 16-20 h with shaking at 30° C. A 5 μl aliquot of these pre-cultures was used to inoculate 96-well production plates containing 500 μl of RD4 medium (1×YNB, 3×SC supplement, 2% glucose, 75 mM succinic acid buffer pH 4.0). The production plates were incubated at 30° C. with shaking for 120 h before sampling of the fermentation broth. The samples were prepared and analyzed by HPLC as described in Example 36.

A standard curve established with an authentic standard was used to determine malonate concentration in the fermentation broth. The malonic acid production levels from these fermentations were as follows S. cerevisiae BY4741+ Y1-F6AA82 (E95S/Q348A), 2.6±0.4 mM; LYM002, 3.2±0.2 mM; LYM004, 4.6±0.2 mM; LYM007, 7.7±0.3 mM.

This example illustrates the benefits of genomic integration of a malonyl-CoA hydrolase encoding gene provided by the invention in that a single integrated copy of the gene results in higher malonic acid titers than the same gene expressed from a plasmid. This example also serves to demonstrate modulation of malonic acid by the invention via the number of malonyl-CoA hydrolase encoding genes are present in the cell.

Example 46: Expression of Acetyl-CoA Synthetases for Increased Production of Malonate from an Engineered Host Cell Acetyl-CoA synthetases (ACSs) are common to many organisms. These enzymes produce acetyl-CoA using acetate and adenosine triphosphate (ATP) as substrates. In accordance with this invention, these enzymes can be used to convert acetate from any source, including endogenous metabolism, feedstock hydrolysis, or by feeding, into acetyl-CoA, the penultimate precursor in malonyl-CoA biosynthesis. By increasing acetyl-CoA levels, one can increase malonyl-CoA, and hence, malonate, in host cells provided by the invention.

An illustrative ACS suitable for this purpose can be obtained from the bacteria Salmonella enterica. To express the S. enterica ACS (SeACS) in S. cerevisiae, the amino acid sequence was back-translated to a DNA sequence using codon optimization tables, and one residue determined to be involved in decreasing enzymatic activity was mutated (L641P). The resulting codon optimized DNA sequence provided by the invention is SEQ ID NO:44.

Nucleic acids encoding the SeACS1 (L641P) were synthesized de novo from oligonucleotides and inserted into a yeast plasmid, Y1, under the control of the TEF1 promoter from S. cererivisiae using standard protocols. This plasmid also contains a CEN/ARS origin and a gene for conferring uracil prototrophy. Clones of LYM004 containing this plasmid were selected by plating on SD-uracil plates and verified to contain the SeACS1(L641P) gene by sequencing.

LYM004 was used as host for the expression of the SeACS1(L641P) acetyl-CoA synthetase. For in vivo malonate production, one individual colony for each transformant picked was inoculated in a 50 µl aliquot of SD-Ura medium in a 96-well plate. LYM004 was grown for comparison of yeast lacking expression of a heterologous SeACS1(L641P), but containing a Y1 empty vector. The plate was incubated on a shaker at 30° C. for approximately 48 h, and 50 µl of these pre-cultures were used to inoculate fermentation plates. In this example, 500 uL of RD4U medium in 96-well plates were used for the fermentation. The fermentation plates were covered with a breathable membrane, incubated on a plate shaker at 30° C., and sampled for HPLC analysis of product accumulation after 120 h of fermentation. HPLC analysis was conducted as described in Example 36.

No malonate was detected in samples consisting of medium not inoculated with yeast cells. Under the conditions tested, LYM004 expressing SeACS1 produced 1.86-fold more (5.5±0.62 mM) malonate at 120 h than LYM004 with an empty Y1 control alone, thus illustrating the improvements in malonate production provided by this embodiment of the invention.

Example 47: Utilization of Different Carbon Sources for Production of Malonate Using a Modified Strain of *Pichia* Kudriavzevii Strain LPK3003 was derived from *Pichia* kudriavzevii strain Y-134 (obtained from the USDA Agricultural Research Services, Peoria, Ill.) by genomic integration of a nucleic acid cassette encoding the hph hygromycin phosphotransferase (conferring resistance to hygromycin B) driven by the PkTEF1 promoter, and the F6AA82 (E95S/Q348A) malonyl-CoA hydrolase driven by the PkTDH1 promoter.

Seed cultures of LPK3003 were grown for 16-20 h in YPD medium with shaking at 30° C. This seed culture was used to inoculate 1.1×YNB, which was then aliquoted at 450 per well in a 96-well plate. 50 µl of solutions of various carbon sources (glucose, sucrose, ethanol, glycerol or acetate from sodium acetate) were added to each well (in triplicate) to a final concentration of 2% (w/v). The plate was incubated at 30° C. with shaking for 115 h and the fermentation broth was sampled. Samples were prepared and analyzed by HPLC as described in Example 36.

In this example, there was little or no growth observed for sucrose or acetate carbon sources, and malonate accumulation was negligible in these samples. As described above, host cells can be modified to confer or enhance sucrose and/or acetate catabolism by introducing a sucrose invertase and/or acetyl-CoA synthase (ACS), respectively. The other carbon sources tested in this example resulted in malonate accumulation (average replicates±S.D.): 4.6±0.5 mM from glucose, 5.38±0.05 mM from glycerol and 3.7±0.3 mM from ethanol.

These results demonstrate that a variety of carbon sources can be used to produce malonate from an engineered *Pichia* kudriavzevii strain expressing a malonate-CoA hydrolase. Notably, glycerol provided the highest titers in this example.

Example 48: Bio-Reactor Based Production of Malonate

In this example, yeast strain LYM004 (see Example 45 for construction details) was grown in fed-batch control in a 0.5 L bioreactor. A single colony of LYM004 was isolated from a SC plate and cultured in 5 mL of RD4 media (see Example 43 for recipe). The culture was maintained at 30° C. overnight, shaking at 200 rpm. The 4 mL of culture was used to inoculate 50 mL of fresh RD4 media in a 250 mL non-baffled flask and grown overnight at 30° C., 200 rpm. The time zero OD 600 nm absorbance was 0.304. After overnight growth (16 h), this culture was used to inoculate 1 L of RD4 media. This culture was split into 2 separate 500 mL aliquots and added to two separate bioreactors. Both fermentations were maintained at 30° C., with a single impeller run at 400 rpm, and sparge rate of 1 vessel volumes per minute (VVM) using compressed air. The cultures were grown overnight (21 h) to allow for glucose consumption prior to starting the fed-batch phase. The feed (recipe below) was delivered for 2 s, every 980 s. 0.5 mL samples were taken daily and analyzed for production of malonic acid. After 4 days, the cultures had accumulated 34 mM of malonic acid and reached an OD 600 nm of 16.2. After 9 days, the cultures had accumulated 116 mM of malonic acid and reached an OD 600 nm of 52.1.

The batch feed media consisted of 17 g/L Difco YNB; 50 g/L ammonium sulfate; 49.8 g/L Synthetic Complete (SC) supplement lacking histidine, methionine, and leucine; 2.57 g/L methionine; 8.85 g/L succinic acid, and 20 g/L glucose; the pH o was adjusted to 4.0.

This protocol was repeated a strain, LYM007, that expressed 3 copies of a malonyl-CoA hydrolase (see Example 45). In this example, a single impeller was run at 700 rpm and the composition of the feed was as follows: 68 g/L YNB (Sigma), 16.6 g/L SC-his-met-leu (Sunrise Science), 1.284 g/L methionine, 75 mM succinate buffer (pH 4.0), 400 g/L glucose. The feed rate used was cycle 5 s on every 980 s. 0.2 mL samples were taken daily and analyzed for production of malonic acid, acetic acid, succinic acid, pyruvic acid via HPLC. Growth was monitored by measuring optical density at 600 nm (OD600). The OD600 and malonate concentration from each time point was as follows: 18 h, OD=6.9, 3.2 mM; 45 h, OD=13.8, 14.0 mM; 69 h, OD=16.6, 24.2 mM; 88.5 h OD=24.4, 31.1 mM; 111.8 h, OD=36.9, 47.8 mM.

In a comparative example, LPK3003 (see Example 47) was grown in fed-batch control in a 0.5 L fermenter. A single colony of LPK3003 was isolated from a YPD plate and cultured in 5 mL of YPD media. The culture was grown at 30° C. overnight, shaking at 200 rpm. The 5 mL of culture was used to inoculate 50 mL of fresh minimal media, containing 6.8 g/L YNB (Difco) and 2 g/L glucose and grown overnight at 30° C., 200 rpm. This culture was then used to inoculate 500 mL of 6.8 g/L YNB (Difco) media, 2 g/L glucose and grown in a 1 liter fermenter. Temperature was maintained at 30° C., a single impeller was run at 700 rpm, and sparge rate was set to 1 vessel volumes per minute (VVM) using compressed air. The cultures were grown overnight for 21 h to allow for glucose consumption prior to starting the fed-batch phase. A feed, containing 68 g/L YNB and 400 g/L of glucose was initiated by setting the fermenter feed to cycle on every 980 s for 5 s. 200 uL samples were taken daily and analyzed for growth (OD600) and production of malonic acid (as described in Example 36). Foaming was controlled by addition of 200 uL of antifoam at every sampling interval. pH was measured and adjusted to 4.5 with 10N NaOH at every sampling interval. Production of malonic acid continued beyond 111 h, accumulating 36.4 mM of malonic acid. Importantly, this is the first demonstration of production without addition of amino acids, uracil, or adenine. The OD600, malonate concentration, and pH from each time point was as follows: 18 h, OD=2.1, 0.7 mM, pH=2.3; 45 h, OD=12.2, 8.8 mM, pH=2.0; 69 h, OD=12.8, 18.1 mM, pH=2.0; 88.5 h, OD=27.6, 22.9 mM, pH=2.7; 111.8 h, OD=40.1, 36.4 mM, pH=2.4; 194 h, OD=60.6, 94 mM, pH=3.3.

While the titer of malonate was higher from LYM007, the conditions under which LPK3003 can be grown (minimal media, low pH) and the fact that it contains only a single copy of F6AA82-2 malonyl-CoA hydrolase make this a superior strain for additional engineering efforts.

Pursuant to 37 C.F.R. 1.821(c), a sequence listing was submitted on Sep. 6, 2017 via EFS-Web as an ASCII compliant text file named LYGOS-0002-03-01-US-e_Seq-Listing, that was created on Sep. 5, 2017 and having a size of 143 kilobytes. The contents of the aforementioned file are hereby incorporated by reference in their entirety.

The invention claimed is:

1. A recombinant *Escherichia coli* cell comprising the heterologous malonyl-CoA hydrolase of SEQ ID: 50, wherein $X_1$ is N.

2. A recombinant *Escherichia coli* cell comprising a heterologous malonyl-CoA hydrolase, wherein said heterologous malonyl-CoA hydrolase an enzyme with an amino sequence that has at least 75% identity to consensus sequence SEQ ID NO:9 and is identical to SEQ ID NO:9 at positions corresponding to G67, G68, G120, E143, and D151; and wherein $X_1$ is N.

3. The recombinant *Escherichia coli* cell of claim 2 wherein said enzyme further comprises at least 25% of the amino acids M1, E6, G13, R15, I16, A19, L21, D22, A23, L27, N28, A29, L30, L32, P33, M34, I35, L38, W45, A46, C53, V54, L56, R57, G58, N59, G60, K62, A63, F64, C65, A66, V70, L73, C77, P81, G82, P85, L87, A88, F91, F92, Y96, R97, L98, H103, P106, K107, P108, C111, W112, H114, G115, V117, G119, G121, M122, G123, L124, Q126, R131, I132, V133, T134, P135, R138, L139, M141, P142, I146, G147, L148, V152, G153, S155, F157, L158, R160, P162, G163, L165, G166, L167, F168, L171, N177, D180, A181, D183, L184, L186, A187, D188, R189, Q195, Q196, L199, L203, Q205, N207, W208, E210, Q215, L216, S218, L219, A222, P232, L237, R239, R240, D244, L247, D248, A258, D267, L269, G280, P282, V288, W289, Q291, R294, R296, L298, S299, L300, E307, Y308, S311, L312, N313, C314, R316, H317, P318, F320, E322, G323, V324, R325, A326, R327, L328, D330, D332, P335, W337, W339, P346, A352, H353, and F354.

4. The recombinant *Escherichia coli* cell of claim 2 wherein said enzyme further comprises at least 50% of the amino acids M1, E6, G13, R15, I16, A19, L21, D22, A23, L27, N28, A29, L30, L32, P33, M34, I35, L38, W45, A46, C53, V54, L56, R57, G58, N59, G60, K62, A63, F64, C65, A66, V70, L73, C77, P81, G82, P85, L87, A88, F91, F92, Y96, R97, L98, H103, P106, K107, P108, C111, W112, H114, G115, V117, G119, G121, M122, G123, L124, Q126, R131, I132, V133, T134, P135, R138, L139, M141, P142, I146, G147, L148, V152, G153, S155, F157, L158, R160, P162, G163, L165, G166, L167, F168, L171, N177, D180, A181, D183, L184, L186, A187, D188, R189, Q195, Q196, L199, L203, Q205, N207, W208, E210, Q215, L216, S218, L219, A222, P232, L237, R239, R240, D244, L247, D248, A258, D267, L269, G280, P282, V288, W289, Q291, R294, R296, L298, S299, L300, E307, Y308, S311, L312, N313, C314, R316, H317, P318, F320, E322, G323, V324, R325, A326, R327, L328, D330, D332, P335, W337, W339, P346, A352, H353, and F354.

5. The recombinant *Escherichia coli* cell of claim 2 wherein said enzyme further comprises the amino acids M1, E6, G13, R15, I16, A19, L21, D22, A23, L27, N28, A29, L30, L32, P33, M34, I35, L38, W45, A46, C53, V54, L56, R57, G58, N59, G60, K62, A63, F64, C65, A66, V70, L73, C77, P81, G82, P85, L87, A88, F91, F92, Y96, R97, L98, H103, P106, K107, P108, C111, W112, H114, G115, V117, G119, G121, M122, G123, L124, Q126, R131, I132, V133, T134, P135, R138, L139, M141, P142, I146, G147, L148, V152, G153, S155, F157, L158, R160, P162, G163, L165, G166, L167, F168, L171, N177, D180, A181, D183, L184, L186, A187, D188, R189, Q195, Q196, L199, L203, Q205, N207, W208, E210, Q215, L216, S218, L219, A222, P232, L237, R239, R240, D244, L247, D248, A258, D267, L269, G280, P282, V288, W289, Q291, R294, R296, L298, S299, L300, E307, Y308, S311, L312, N313, C314, R316, H317, P318, F320, E322, G323, V324, R325, A326, R327, L328, D330, D332, P335, W337, W339, P346, A352, H353, and F354.

* * * * *